US006468758B1

(12) United States Patent
Benson et al.

(10) Patent No.: US 6,468,758 B1
(45) Date of Patent: Oct. 22, 2002

(54) COMPOSITIONS AND METHODS FOR OVARIAN CANCER THERAPY AND DIAGNOSIS

(75) Inventors: Darin R. Benson; Michael J. Lodes, both of Seattle; Jennifer L. Mitcham, Redmond; Gordon E. King, Seattle, all of WA (US)

(73) Assignee: Corixa Corporation, Seattle, WA (US)

(*) Notice: Subject to any disclaimer, the term of this patent is extended or adjusted under 35 U.S.C. 154(b) by 0 days.

(21) Appl. No.: 09/397,787

(22) Filed: Sep. 16, 1999

Related U.S. Application Data

(63) Continuation-in-part of application No. 09/246,429, filed on Feb. 8, 1999, which is a continuation-in-part of application No. 09/159,320, filed on Sep. 23, 1998, now abandoned.

(51) Int. Cl.[7] .................... G01N 33/574; C12Q 1/68; C07H 21/04
(52) U.S. Cl. .................... 435/7.23; 435/6; 536/24.31
(58) Field of Search .................... 536/23.2, 24.31; 530/358; 435/6, 7.1, 233, 7.23

(56) References Cited

FOREIGN PATENT DOCUMENTS

| WO | WO 94/21287 | 9/1994 |
|----|-------------|--------|
| WO | WO 94/23728 | 10/1994 |
| WO | WO 95/11986 | 5/1995 |
| WO | WO 95/19783 | 7/1995 |
| WO | WO 97/02280 | 1/1997 |
| WO | WO 97/25426 | 7/1997 |
| WO | WO 97/34921 | 9/1997 |

OTHER PUBLICATIONS

Bugg et al. Expression of a mutant DNA topoisomerase II in CCRF–CEM human leukemic cells selected for resistance to teniposide vol. 88 pp. 7654–7658 Sep. 1991.*

Database EMBL Nucleotide And Protein Sequences, Accession No. AA490863, Aug. 15, 1997.

Liang et al., "Differential Display and Cloning of Messenger RNAs from Human Breast Cancer versus Mammary Epithelial Cells," *Cancer Research* 52:6966–6968, 1992.

Porter–Jordan and Lippman, "Overview of the Biological Markers of Breast Cancer," *Breast Cancer* 8(1):73–100, 1994.

Schlom et al., "Strategies for the Development of Recombinant Vaccines for the Immunotherapy of Breast Cancer," *Breast Cancer Research and Treatment* 38(1):27–39, 1996.

Watson and Fleming, "Isolation of Differentially Expressed Sequence Tags from Human Breast Cancer," *Cancer Research* 54:4598–4602, 1994.

Yee et al., "Isolation of Tyrosinase–Specific CD8+ and Cd4+ T Cell clones from the Peripheral Blood of Melanoma Patients Following In Vitro Stimulation with Recombinant Vaccinia Virus," *The Journal of Immunology* 157:4079–4086, 1996.

* cited by examiner

Primary Examiner—John S. Brusca
Assistant Examiner—Margorie A. Moran
(74) Attorney, Agent, or Firm—Seed Intellectual Property Law Group PLLC

(57) ABSTRACT

Compositions and methods for the therapy and diagnosis of cancer, such as ovarian cancer, are disclosed. Compositions may comprise one or more ovarian carcinoma proteins, immunogenic portions thereof, polynucleotides that encode such portions or antibodies or immune system cells specific for such proteins. Such compositions may be used, for example, for the prevention and treatment of diseases such as ovarian cancer. Methods are further provided for identifying tumor antigens that are secreted from ovarian carcinomas and/or other tumors. Polypeptides and polynucleotides as provided herein may further be used for the diagnosis and monitoring of ovarian cancer.

3 Claims, 32 Drawing Sheets

OV2

AMINO ACID SEQUENCE

MAELTALESLIEMGFPRGRAEKALALTGNQGIEAAMDWLMEHEDDPDVDEPLETPLGHILGREPT
SSEQGGLEGSGSAAGEGKPALSEEERQEQTKRMLELVAQKQREREEREEREALERERQRRRQGQE
LSAARQRLQEDEMRRAAEERRREK

NUCLEOTIDE SEQUENCE (5')

GAATTCAAGC CTCCTTCTCG TCACACACCA GGTCCCCGCG GAAGCCGCGG TGTCGGCGCC
ATGGCGGAGC TGACGGCTCT TGAGAGTCTC ATCGAGATGG GCTTCCCCAG GGGACGCGCG
GAGAAGGCTC TGGCCCTCAC AGGGAACCAG GGCATCGAGG CTGCGATGGA CTGGCTGATG
GAGCACGAAG ACGACCCCGA TGTGGACGAG CCTTTAGAGA CTCCCCTTGG ACATATCCTG
GGACGGGAGC CCACTTCCTC AGAGCAAGGC GGCCTTGAAG GATCTGGTTC TGCTGCCGGA
GAAGGCAAAC CCGCTTTGAG TGAAGAGGAA AGACAGGAAC AAACTAAGAG GATGTTGGAG
CTGGTGGCCC AGAAGCAGCG GGAGCGTGAA GAAAGAGAGG AACGGGAGGC ATTGGAACGG
GAACGGCAGC GCAGGAGACA AGGGCAAGAG TTGTCAGCAG CACGACAGCG GCTACAGGAA
GATGAGATGC GCCGGGCTGC TGAGGAGAGG CGGAGGGAAA AGGC

AMINO ACID SEQUENCE

MPKRKAEGDAKGDKAKVKDEPQRRSARLSAKPAPPKPEPKPKKAPAKKGEKVPKGKKGKADAG
KEGNNPAENGDAKTDQAQKAEGAGDAK

NUCLEOTIDE SEQUENCE

GAATTCAAGC GAGAACGACC CCCGGACCGA CCAAAGCCCG CGCGCCGCTG CATCCCGCGT
CCAGCACCTA CGTCCCGCTG CCGTCGCCGC CGCCACCATG CCCAAGAGAA AGGCTGAAGG
GGATGCTAAG GGAGATAAAG CAAAGGTGAA GGACGAACCA CAGAGAAGAT CCGCGAGGTT
GTCTGCTAAA CCTGCTCCTC CAAAGCCAGA GCCCAAGCCT AAAAAGGCCC CTGCAAAGAA
GGGAGAGAAG GTACCCAAAG GGAAAAAGGG AAAAGCTGAT GCTGGCAAGG AGGGGAATAA
CCCTGCAGAA AATGGAGATG CCAAAACAGA CCAGGCACAG AAAGCTGAAG GTGCTGGAGA
TGCCAAGTGA AGTGTGTGCA TTTTTGATAA CTGTGTACTT CTGGTGACTG TACAGTTTGA
AATACTATTT TTTATCAAGT TTTATAAAAA TGCAGAATTT TGGTTTACTT T

AMINO ACID SEQUENCE

MPKRKVSSAEGAAKEEPKRRSARLSAKPPAKVEAKPKKAAAKDKSSDKKVQTKGKRGAKGKQA
EVANQETKEDLPAENGETKTEESPASDEAGEKEAKSD

NUCLEOTIDE SEQUENCE

GAATTCAAGC GAGGAGTGGC AGCGGCAAGG CAGCCCAGTT TCGCGAAGGC TGTCGGCGCG
CCGCGGCCCG CAGGCACCCG GCACGCGCCT TCCCCGCAGG CACCCGGCAC GCGCCTTCCC
CGCCGCCACG ATGCCCAAGA GGAAGGTCAG CTCCGCCGAA GGCGCCGCCA AGGAAGAGCC
CAAGAGGAGA TCGGCGCGGT TGTCAGCTAA ACCTCCTGCA AAAGTGGAAG CGAAGCCGAA
AAAGGCAGCA GCGAAGGATA AATCTTCAGA CAAAAAAGTG CAAACAAAAG GGAAAAGGGG
AGCAAAGGGA AAACAGGCCG AAGTGGCTAA CCAAGAAACT AAAGAAGACT TACCTGCGGA
AAACGGGGAA ACGAAGACTG AGGAGAGTCC AGCCTCTGAT GAAGCAGGAG AGAAAGAAGC
CAAGTCTGAT TAATAACCAT ATACCA

NUCLEOTIDE SEQUENCE

GAATTCAAGC GGAATTCCCT CCCCCTCCTT GTGCCTTCTT TGTATATAGG CTTCTCACGG
CGACCAATAA ACAGCTCCCA GTTTG

NUCLEOTIDE SEQUENCE

```
GAATTCAAGC CCGGGGCTGA AAACGGTGGC AGAAAGTGAG CAACTTAGGG AGACAGAAAG
AGCGCAGAAC TCGAAATTCC GAGGCAGAGA GAGCGGAGGG CAAGCCGTGG GTAGAAACGC
GCCGAGGCGA GGACGAAGGC CTTGGCCCGC GGAGACGCAG GCACCCGCGG AGAACGCTTC
GGATCCGTCA CGGTTTTGCC TCATTTGGAA GATATTACTT CGCCCCTGAA AA
```

NUCLEOTIDE SEQUENCE

GAATTCAAGC CCTGAAAGGA CCTTGGGTGG TAAAGCTGTA CTTGGTGGGA GTGAGGGCGT
GGGGAGGAAC CATGCAAATC GCCTTCCATG GTTTTTAAAT GCAGTAAATA ACATTTCTGG
ATGAGACTTG TTTCCAAAAT AAACCAGCTA TATCTGT

NUCLEOTIDE SEQUENCE

```
GAATTCAAGC GGGGAGCGGA GCGGGGCCGC CGGGGCCTCT CCAGGGCCGC AGCGGCAGCA
GTTGGGCCCC CCGCCCCGGC CGGCGGACCG AAGAACGCAG GAAGGGGGCC GGGGGGACCC
GCCCCCGGCC GGCCGCAGCC ATGAACTCCA ACGTGGAGAA CCTACCCCCG CACATCATCC
GCCTGGTGTA CAAGGAGGTG ACGACACTGA CCGCAGACCC ACCCGATGGC ATCAAGGTCT
TTCCCAACGA GGAGGACCTC ACCGACCTCC AGGTCACCAT CGAGGGCCCT GAGGGGACCC
CATATGCTGG AGGTCTGTTC CGCATGAAAC TCCTGCTGGG GAAGGACTTC CCTGCCTCCC
CACCCAAGGG CTACTTCCTG ACCAAGATCT TCCACCCGAA CGTGGGCGCC AATGGCGAGA
TCTGCGTCAA CGTGCTCAAG AGGGACTGGA CGGCTGAGCT GGGCATCCGA CACGTACTGC
TGACCATCAA GTGCCTGCTG ATCCACCCTA ACCCGAGTC TGCACTCAAC GAGGAGGCGG
GCCGCCTGCT CTTGGAGAAC TACGAGGAGT ATGCGGCTCG GGCCCGTCTG CTCACAGAGA
TCCACGGGGG CGCCGGCGGG CCCAGCGGCA GGGCCGAAGC CGGTCGGGCC CTGGCCAGTG
GCACTGAAGC TTCCTCCACC GACCCTGGGG CCCCAGGGGG CCCGGGAGGG GCTGAGGGTC
CCATGGCCAA GAAGCATGCT GGCGAGCSCG ATAAGAAGCT GGCGGCCAAC AAAAACACGG
ACAACAAGCG GGCGCTGCGG CGGCTGTAGT GGGCTCTCTT CCTCCTTCCA CCGTGACCCC
AACCTYTCCT GTCCCCTCCC TCCAACTCTG TCTYTAAGTT ATTTAAATTA TGGCTGGGGT
CGGGGAGGGT ACAGGGGGCA CTGGGACCTG GATTTGTTTT TCTAAATAAA GTTGGAAAAG
CA
```

NUCLEOTIDE SEQUENCE

```
GAATTCAAGC CTCATGCCTG TAATCCCAGC ACTTTGGAAG GCAGGAGCCA CCAAGCGCAG
CCATGATTTA TTAGATCACT TCTAAAAGCC CTCTCTCCAT CTCCAAGCCA GCAAGTGCTT
CTTTGCACCC CAGCTCTAAA ACAAAGCCCT TGGGGACACA ATCAAAGACA GTAGTTGCCA
AGAGGAATAG GGAGCATGGA AAGAAGGTGC TGGATGTGCA TACAGCTAAC CTGGTAACTC
CAAACTGGAT GAGCTCATTC CTTGAGACTG GAATTACAAA ATTGGAACAG CTCACTAATA
ATTGAAGATG ATTTGGGAAA ACCATTATCC TTCCTCAGGT TTTACAAGGT TTTTATGACT
CATTTATAAG GTCCTACAGC TAAAAAAAAT CATGCTGTAT TTCAGAGAAG TTTAACTTGA
AAATATTTTT TTCACTAATT AAAAATTCCC ATTATACCTT ATAGTTGCAA TTGTATCCTT
ATTGCTGAAA GATATCCATA CTACCTACCA CTTCTTTAAA ATTTAAAAAA TTCTATAAAT
AAAAAATATA ACAATTGCAA ATATGTAAAT AACTTCCAAC ATAAAACAAA ATTTATAGTA
ATTATAAGAA GTTCTTTTAT ACTAAAAATT AAGTTGTAAT TATGATAGAA ATAATCTGTA
AAAGGTATTT TTAGCAAAAT TTATTAATAC GGGTAGCAAT AATAATACCC AATTATATAT
GCATATTGTT TGTATTTTAG AACCTGTGAC AAATGAAAAT GGTTTTCCTA GATAAGAACG
AAACTGTGTT GGGTGGCTAA CAAGATYGAA ACTCATCTGA CTTTGAGAAA TAAATCAATT
TGGTTTGTTT ATTTAAAAAA AAAAAGCTT
```

NUCLEOTIDE SEQUENCE

```
GAATTCAAGC GAGGCATGGG CTGCCGCCCT TTCCACGGCT GGACCAGCCT TGTCTTACTG 60
GCCATGGCTG AAGACTACTG AAGGGAGGGA GAGGAGGGGA GCCAAGACAC TCATGCCACT 120
CTGGCTCTGA AGGGACAAAG GCTTCTGGCT TTTGCCCCCA GCCCCTTGGA TACCAGTAAT 180
TCAAACCTTC CTCATTTCAT CTCAGGTGTC TCCTTGCTGT CATCCCACAT AGCCCTGGGG 240
TGAATGTGAA TCCAGAGTCT ATTTTTCTAA ATAAATTGGA AAAAACAAAA AAAAAGCTT
```

NUCLEOTIDE SEQUENCE

GAATTCTTAC TGGGTTGGTG AAGATTCCAC ATACAAATTT TTTGAGGTTA TCCTCATTGA
TCCATTCCAT AAAGCTATCA GAAGAAATCC TGACACCCAG TGGATCACCA AACCAGTCCA
CAAGCACAGG GAGATGCGTG GGCTGACATC TGCAGGCCGA AAGAGCCGTG GCCTTGGAAA
GGGCCACAAG TTCCACCACA CTATTGGTGG CTCTCGCCGG GCAGCTTGGA GAAGGCGCAA
TACTCTCCAG CTCCACCGTT ACCGCTAATA TAAGTAAAGT TTGTAAAATT CATACTTAAT
AAACAATTTA GGACAGTCAA AAAAAAAAAA AAAGCTTG

NUCLEOTIDE SEQUENCE

GAATTCAAGC GCAGTACATG CTAAGACTTC ACCAGTCAAA GCGAACTACT ATACTCAATT
GATCCAATAA CTTGACCAAC GGAACAAGTT ACCCTAGGGA TAACAGCGCA ATCCTATTCT
AGAGTCCATA TCAACAATAG GGTTTACGAC CTCGATGTTG GATCAGGACA TCCCGATGGT
GCAGCCGCTA TTAAAGGTTC GTTTGTTCAA CGATTAAAGT CCTACGTGAT CTGAGTTCAG
ACCGGAGTAA TCCAGGTCGG TTTCTATCTA CTTCAAATTC CTCCCTGTAC GAAAGGACAA
GAGAAATAAG GCCTACTTCA CAAAGCGCCT TCCCCCGTAA ATGATATCAT CTCAACTTAG
TATTATACCC ACACCCACCC AAGAACAGGG TTTGTT

NUCLEOTIDE SEQUENCE

```
GAATTCAAGC GACGGCTACC TGGCTCCGGA GAATGGGTAT TTGATGGAGG CTGCGCCGGA
GTGAAGAGGT CGTCCTCTCC ATCTGCTGTG TTTGGACGCG TTCCTGCCCA GCCCCTTGCT
GTCATCCCCT CCCCCAACCT TGGCCACTTG AGTTTGTCCT CCAAGGGTAG GTGTCTCATT
TGTTCTGGCC CCTTGGATTT AAAAATAAAA TTAATTTCCT GTAAAAAAAA AAAAAAAGCT
T
```

NUCLEOTIDE SEQUENCE

GAATTCAAGC CTACACACCA AATCTGCTAG TTCCTTGATC TCCGACCTCT CAAGCTCTAG
AACTGCTAGA AATAAATTTC TATTTTTATA AGCT

NUCLEOTIDE SEQUENCE

GAATTCAAGC CCACGCTTCA CCACCAAGAG GCCCAACACC TTCTTCTAGG TGCAGGGCCC
TCGTCCGGGT GTGCCCCAAA TAAACTCAGG AACGCCCCGG T

NUCLEOTIDE SEQUENCE

GAATTCAAGC GCTGACAGAG ATACCTACAG ACGGAGTGCT GTGCCACCTG GTGCCGACAA
GAAAGCCGAG GCTGGGGCTG GGTCAGCAAC CGAATTCCAG TTTAGAGGCG GATTTGGTCG
TGGACGTGGT CAGCCACCTC AGTAAAATTG GAGAGGATTC TTTTGCATTG AATAAACT

Fig. 15

OVp2-2
CAAACAATAC TATCTTATAA AATAGTACTG TTGAATTATT CCAAGCCTCC CTAGGTTTGC TCTCAAATGT CATTTACAGA
TTGGGCTAAC GACCTAAAAT CTATATATAA AGACTTTCTG AAGAACTCTG TATTATAGCA ATACCAAACG AGTGCTGTGT
GTGCAAACAG TCTGGCGTTG CTTTTTATGT TGATATTTAT CCTAGAACAC TGAAAGAGAA TATGCCAGTG ATAACTCACT
TTAC

OVp2-13
TCAACCTCCT CCTCCAAGCC CTTTCTCAGT ACAAGCTTTC AATAAAGGGG CAAGTTGCAG TGCCCAAGGA TTTGACTATG
GCCTGGGAAA TAACAAACGT GACAGAGGAA CTATCTCAAC ATCTTCAAGA CCAGTGTCCA CATCAGGGAA GTCAGAGCTG
CCCTCTAAGC ACAGCAGGTC AGTTAAACCC GACGGGCATG TGAGCCGGAC TCCTGCTGAC CAGAAGAAGC CACGGGGGAC
A

OVp2-14
AAGCCAAAAT TCTAACCTGT ATCAGAGGAG TGAAATGCCC CGTGAATTGA GGCAACTGTA GATATTCGAA ATGCTTCTAA
AAAGGCTGTG AGGTTATGTC CTTTACTGCA TGTCATTGGT AGGTCATCTC AAAATGGCAC TCGAGCTTTG GAAGGGTGAG
AACTATTGCT AGATTTGGTA GGGGGTCTGC ATCTATGGGC CCGAGTCCTC CATCTCCACA AGCT

OVp2-20
ATCTGCTTTA AGTAACTACA TGAAATATCT CAAGCCCCAA GTAACTATAC CCAGAACCAG CACCAACCGA GGCTTCTGAA
CAAAAACAAC CTCACAAAGC AATTTACCCA GAAAGCAACA TTTCTAAGAC AGGAGACTGC CTCCTCCAAA TGGCTCACTC
CATTGAAAAA ACGCCATCTG CCAGAGGCAG ACACCAAATA AAAGGCACTT GGACATCAGG ATTTGTAAAA AAACAAGTAC

OVp2-21
AAGCGGATTT TTTTATACAA CCTTAGACCA CCTTCTTTAG CTTTAGGCGT CTGCGGTTGC CCTTGGATCT GTTCTCAATC
CTCAGTGTGT GTGGCAGCAT GTGATCATAG AGAGCTGGGC AAAGTTCACT TTCTCTTTGC TGACAGTCTC ACCTTTTCTC
ACTGGGAAGC TGCACAGGAG CCTTTGGGCT GGTTCAGCCC AGAGGCCCCT GTTCTCCTGC CTTCC

OVp2-25
ATGGCGCCCC GCGCCCGGAG GGCCCCTTCT GAGCGCCCCG GCCCCTCCCT CCGCGCTCCC CCTCCTCCCC GCGGCGCCCC
CGCCCCGCCC CGCCCCCGCC GAGACCCCGA CCCCGGCCCC ACGGGCGGAC ACTCGGCCGG GCAGCCGCGG GCCGAGCGCA
GCCGCTCCGC ACCGATGCGC CTGGTGGCAG ACTCCAAGTG GGACCGGCGG ACACGCAGCC TCGCGTGTCA GGGGAAGCTG
ATGGAGAA

OVp2-27
TGCCGGGGAG GCTGAACAGG AGGGTTAGGA ATAAAATCAG GGCTTAAGCA GAGCTGGTCC ATTCCTCAGT CCTCTCACGC
CCCTGTTTTC TGAGCACGGG CGTTCTGACT CAGTTTTAAC TTTGAATTTA GGAGATAACA CAACATTTGT TCCTTGCCCA
TTAAAAAAAA AAAAAAACAA GTAACTTTTT TTGCTCCAGC TGTACTCAAC CTGGTTGACT AATGCTCACT GTAGAGCTAG
AAAACCAA

OVp2-28
GAATAGGAAC TAAAATGTAA ATCTGTCTTA AACATCTGTG AAAAAGATGG TACTTTTGAC AACATTTATC TGCATGTCCA
GATCAGCAAT GAGTCGGCAA TTGACTTCTA CAGGAAGTTT GGCCTTTGAG ATTATTGAGA CAAAGAAGAA CTACTATAAG
AGGATAGAGC CCGCAGATGC TCATGTGCTG CAGAAAAACC TCAAAGTTCC TTCTGGTCAG AATGCAGATG TGCAAAAGAC
AGACAACT

*Fig. 16A*

OVp2-29

AAAAAGATGG TACTTTTGAC AACATTTATC TGCATGTCCA GATCAGCAAT GAGTCGGCAA TTGACTTCTA CAGGAAGTTT
GGCTTTGAGA TTATTGAGAC AAAGAAGAAC TACTATAAGA GGATAGAGCC CGCAGATGCT CATGTGCTGC AGAAAAACCT
CAAAGTTCCT TCTGGTCA

OVp2-31

AAGCCCGAGG GGCTGCAAGC CCGGGAGGGC CCCTGTAGGA GCCCAGCGCG TGGCGGGGAC TGCAGCAGGA ACTCCTGCCT
GGCGTGGCAT CGCGGGGCGC CCGCTGGGGA GACGCCACCC GTGTGTGACC CCTGTCCGGA GCGGATCCAG AACCACCCCC
GGACTCAACT GTGTGAGGTC CACACGGACT GTTGGCCGTG CCAACCAGGG ACTGGCGCTC CGACCTGCCC GAGGACCCCA
AAGC

OVp2-37

AAGCCTGTTT CAAACAAAAC CAAAAACCTA AGTAGAGCAT TACAGGCCTC TGTGGCTGCT GCGTTTCTGT AGAAAGCAAC
TTATTTTATT GACTTTTTTT TTTTAAGGAA AAGAAATAAA AAGACCCCAG CAAGCAAAAA CATTTAAAAA ATGATTTTTT
TTCCTCCTAC TTAAGTGGTT CTTTCTCCCT TTGCTCTACT TTTGGAGAAT GAACTTAACA TCCCGGCTTC TTTTGTTAAG
CCATAGCTGA CCTTAATCTG TGGTTAGTTT ATTAAAATAA TTAAAAATAC TTTCTAAGAA GAGATATTTT TGATATTAGG
ACTGATGTTG AAACATATAG GGGCAATTTA TAAAAAGGTA GTTAGAGAAA TATATTTTAG TGAACTATAA CCACAGAGCA
CAGATGACTC CCAATGAGCT GATCTGTCTT TAGGTTTCTC CCTTTCC

OVp2-38

TTGCCGAACC GCTTTCTTAC CCTCCGCACC CGTTAAGTTC TCCGGTCGGG CGGCAGTCTC TGAACACTTA GCCGCGCCAT
CCGGGGTCAC ACCGCCTGGA AGGAGGTGAC GGGGGCGGCG CGGGGCGCGG ACACTCCCCG CTGAGAGTCC GCCTGCCATG
GACTCGGAAT ATTACAGCGG CGACCAGTCA GATGATGGTG GTGCTACCCC AGTACAGGAT GAACGGGATT CAGGGTCAGA
CGGTGAGGAT GATGTAAATG AGCAACACTC CGGATCAGAC ACTGGAAGTG TAGAACGTCA TTCAGAGAAT GAAACTAGTG
ATCGAGAAGA TGGCCTCCCC AAAGGACATC ATGTGACAGA CTCTGAGAAC GATGAGCCCT TAAATCTTAA TGCTAGTGAC
TCTGAAAGTG AGGAGCTTCA CAGGCAAAAG GACAGCGACT CTGAATCTGA G

OVp2-40

AAACAATACT ATCTTATAAA ATAGTACTGT TGAATTATTC CAAGCCTCCC TAGGTTTGCT CTCAAATGTC ATTTACAGAT
TGGGCTAACG ACCTAGAATC TATATATAAA GACTTTCTGA AGAACTCTGT ATTATAGCAA TACCAAACGA GTGCTGTGTG
TGCAAACAGT CTGGCGTTGC TTTTTATGTT GATATTTATC CTAGAACACT GAAAGAGAAT ATGCCAGTGA TAACTCACTT
TACTTCAGTC ATTTCAACAC AGAAAATGCT TCTCTAGCAT TTTTCTTTTG TAGTGTTAAC ATTTTGAAAT TCATGTTTCA
GAGGCTTCAT CATCACAGAA TTTACTCTTG CTCCATGAAA AAAAATTAAA TACCTTCAGA GGAATATTTA AGTTGTAAAC
TATGAAACTT GAGAAATCCT CTTGAGATAA AAGGCTGCCA AATC

OVp2-42

GATCCAATTC CAACAATCTA TCTTATAAAA TAGACTGTTG AATTATTCCA AGCCTCCCTA GGTTTGCTCT CAAATGTCAT
TTACAGATTG GGCTAACGAC CTAAAATCTA TATATAAAGA CTTTCTGAAG AACTCTGTAT TATAGCAATA CCAAACGAGT
GCTGTGTGTG CAAACAGTCT GGCGTTGCTT TTTATGTTGA TATTTATCCT AGAACACTGA AGAGAATAT GCCAGTGATA
ACTCACTTTA CTTCAGTCAT TTCAACACAG AAAATGCTTC TCTAGCATTT TTCTTTTGTA GTGTTAACAT TTGAAATTC
ATGTTTCAGA GGCTTCATCA TCACAGAATT TACTCTTGCT CCATGAAAAA AAATTAAATA CCTTCAGAGG AATATTTAAG
TTGTAAACTA TGAAACTTGA GAAATCCTCT TGAGATAAAA GGCTGCCAAA T

OVp2-52

AAGCCGCGAG TGCTGTCTCC GCAGCCGCGC GGTAGACGGC CGCGTTCCAG CCCTGCTGGC GACCCCCGGA GTTGAGCCTG
CGAGTTGGGT GCGGGAACAC CGGCCCTGGG TGGCCGGGAA CCCTAAGGCC ACCACCGCGA TCCGCAGGTC AAACGTGACG
GGGCTCCCTC CTGGATAGGG TCGGTCGGGA AGTTGATGGA GACTCGACAG GCCTAAGTGT CCACCATC

*Fig. 16B*

OVp2-56

ATCCGCGGCC AACCAGAGCG CGCGCGCGGC ACAACCTCAT CCCAGGCTCG CGTGCGCAGC AGCTGGAGCA GATCCGCAGG
GACATCCGAG ACTTCCGGTC TAGCGCGGGG CTGGACAAAG TCATAGTGCT GTGGACGGCG AACACGGAGC GCTTCTGTGA
GGTGATTCCA GGCCTCAACG ACACAGCCGA GAACCTGCTG CGCACCATTG AGCTCGGTCT GGAGGTGTCG CCCTCCACGC
TCTTCGCCGT GGCCAGCATC CTGGAGGGCT GTGCCTTCCT CAATGGGTCT CCGCAGAACA CCCTGGTGCC CGGAGCTCTT
GAGCTCGCGT GGCAGCACCG GGTTTTTGTG GGCGGAGATG ACTTCAAGTC AGGCCAGACC AAAGTCAAGT CCGTGCTTGT
GGACTTCCTC ATTGGCTCCG GCCTCAAGAC CATGTCCATC GTGAGTTACA ACCACCTGGG CAACAACGAT GGGGAGAACC
CTATCGGCGC CATTGCAGTT CCGCTCTAAG GAGGTGTCCA AGAGCAACGT GGTGGACGAC ATGGTGCAGA GCAACCCAGT
GCTCTATACG CCCGGCGAAG AGCCTGACCA CTGCGTGGTC ATCAAGTATG TGCCGTACGT GGGTGACAGC AAGCGCGCGC
TGGATGAGTA TACCTCGGAG CTGATGCTGG GCGGAACCAA CACACTGGTG CTGCACAACA CGTGTGAGGA CTCGCTGCTG
GCCGCACCCA TCATGCTGGA CCTAGCGCTG CTGACCGAGC TGTGCCAGCG CGTGAGCTTC TGCACTGACA TGGACCCCGA
GCCGCAGACC TTCCACCCCG TGCTGTCCCT GCTCAGCTTC CTCTTCAAGG CGCCACTAGT GCCGCCCGGC AGCCGGTGG
TCAATGCGCT TTTCCGCCAG CGCAGCTGCA TCGAGAACAT CCTCAGGGCC TGCGTGGGGC TCCCGCCACA GAACCACATG
CTCCTGGAAC ACAAAATGGA GCGCCCAGGG CCCAGCCTCA AGCGAGTTGG ACCCGTGGCT GCCACCTACC CTATGTTGAA
CAAGAAAGGA CCGGTACCCG CTGCCACCAA TGGCTGCACC GGTGATGCCA ATGGGCATCT GCAAGAGGAG CCCCCAATGC
CCACCACCTG AGGCCCCGGT CACACAGTTT CTCGGCTCTT CCTCCCCGCT GCCCCCCACG ACCCTACCTT GAAGGCCCCC
ACAAATAAAG GCGCTGCCAC TCAAAAAAAA A

OVp2-60

AAGCACTGAC CCCACCCAGG ATCAAGGCTC ANGATGCAAT GACAAATAAC GCTACCACTA GGCAGAACTT GACCCGTGTG
TAGGAGGATA GTGGGAAAAG CACTTAGAGG CCGGGGTCAG TAACAACATC AGCCAACAGG GATGACCACG CCCGCTGGGC
TTCAGCATGG AGGTGAAACA AGCAGCCCTG GCTCCTGCCC TGCGGGCACC TCTGTCTGGG AGGGGCAGGA GGGGCTTC

OVp2-69

AAGCTCAGAG CCCACCCGGC ATGTACAACT GTGAAAGGCC TTGGAAAACT GGAGCGATGA GAGCGGTGAA TCGTGTTGGT
CTCATTGGAG ACCCGCAGAT TGGGAGATTC TGGAACCAGG ACGACCTTGC CCCTCACCTG CAGCAGAAGC CCCCGGAAAC
GCCCGGCCCC GACCCGGACC TGAGCCGCCT GGGGGCCCAA GGGAAGCTGA ACGCCCGGTG GGCTCCCGCG ATGGTTCT

OVp2-71

GATTCGAGAG AGGGAAATCT CACTTCCACC TTATTTTCAC TAAATTTTCT GAAACAGACA AAATGTGTAG TGTTGACAGG
GCCAATCTCC GTGACTTTTG TTCATATGCT TTTATTTATC CATGATTTCC AAGACACTGG GCTTCCCATT CTCACTTCCC
CTCATCAATC CCTTTCCTTT CTTTAGAAGG GGGCTTATGT ATGAGACTGG TGAAGTCCAG TGAAGCTAAG TAAAGGGGCA
AGATGG

OVp2-83

AGCAGAGGAG GTTCGATTAA AACTGGAAGA GACCAGAGAG GTACAGAACT TGAGGAAGAG GCCCAACGGG GTGAGTGCTG
TGGCCTTGCT GGTGGGAGAG AAGGTACAAG AGGAGACCAC TCTAGTGGAT GATCCCTTTC AGATGAAGAC AGGTGGTATG
GTGGATATGA AGAAACTGAA GGAAAGGGGC AAAGATAAGA TCAGTGAGGA GGAGGACCTG CACCTGGGGA CATCGTTTTC
TGCA

OVp2-84

CAACAATCTT CTNTAAAATA GACTGTTGAA TTATTCCAAG CCTCCCTAGG TTTGCTCTCA AATGTCATTT ACAGATTGGG
CTAACGACCT AGAATCTATA TATAAAGACT TTCTGAAGAA CTCTGTATTA TAGCAATACC AAACGAGTGC TGTGTGTGCA
AACAGTCTGG CGTTGCTTTT TATGTTGATA TTTATCCTAG AACACTGAAA GAGAATATGC CAGTGATAAC TCACTTTACT
TC

*Fig. 16C*

OVp2-85
ACCAGAACTG AAACAGAGGA CTGTGCTGAA TCTCTAAATC ATGTTGATAG TGATGTACCA CCTTCTAATA CCATGAGTGN
TTTTAACACC TCTGATTACC GCTTTGAGTG TATATGTGGT GAACTTGATC AGATAGATCG TAAGCCTCGT GTTCAATGCC
TGAAGTGTCA CCTGTGGCAA CATGCAAAGT GTGTGAATTA TGATGAGAAA AATCTGAAGA TCAAGCCTTT TTACTGCCCC
C

OVp2-87
AGCGAGAGGA AGAGAGGAGA AGAAAGAGAA ACCAGGGGGG CGAGGCGCCG TCCAATGACA AAGCCCAGGG GTGGGCGCCG
GCCGCCATCT TGTACCGGGC AGCAGGATAT TCGCCCGCGT CCTCCGCCCT CGGAGGGGGA GGGGCGGCGG CGGAGGCGAG
AAAAGTAGCG AGAGACGCCA GCAGCAGCCG CCGCCGCGGA GCCAACGCGG ACTGGGACGG CGGCGGCAGT AGTGGGACCC
GGCGA

OVp2-88
AGCCNAGACT TTAGATTGCC CGGAGGAAGC AAACTCTTCG TATAAAAAAA AGCAGGCCAT CTGCTTAACC CTTGGCTCCA
CCATAAGGCA CTGGGACTCG GATTTCTCTA TCTGATAGAG GTATTTTCTG TGGCCCTGGG AGCTGTCTGT CTTTCCCCTA
CCCCCAAGGA TGCCAGGAAG ACGTCCACCA TTAGCCATGT GGCAACCTTT ACTTCTATGC CTCACAAGTG CCTTTCAGAG
A

OVp2-90
GCATGCCCCT TGGAGTGGAA GGAAGCTGGA CAGGGCAGGC CTCTGGGGAC GGGACACAGG GAAGCCCGAA GGGGCGCCTT
GGCCAGGTCT GCCATCTCCT CCAGCGAGGC TCTGGCCAGC ACTGGGTGAG AGTGGGGAGG GGGCACTGGC CTTTGCAGCA
CAGTAAAACA TGGTCCAGAC AACCTGTGGC CCCGGCCTCA TGAGCACCCC CTGCACAGGC CCAGCCCAAG CCAGGCGCTA
GAAGG

OVp2-93
AAGCGATGCC CCTTGGAGTG GAAGGAAGCT GGACAGGGCA GGCCTCTGGG GACGGGACAC AGGGAAGCCC GAAGGGGCGC
CTTGGCCAGG TCTGCCATCT CCTCCAGCGA GGCTCTGGCC AGCACTGGGT GAGAGTGGGG AGGGGGCACT GGCCTTTGCA
GCACAGTAAA ACATGGTCCA GACAACCTGT GGCCCCGGCC TCATGAGCAC CCCCTGCACA GGCCCAGCCC AAGCCAGGCG
CT

OVp2-94
GCCTTTGCGC ACCGTTTCTT CCCTCCGCAC CCGTTAAGTT CTCCGGTCGG GCGGCAGTCT CTGAACACTT AGCCGCGCCA
TCCGGGGTCA CACCGCCTGG AAGGAGGTGA CGGGGGCGGC GCGGGGCGCG GACACTCCCC GCTGAGAGTC CGCCTGCCAT
GGACTCGGAA TATTACAGCG GCGACCAGTC AGATGATGGT GGTGCTACCC CAGTACAGGA TGAACGGGAT TCAGGGTCAG
ACGGTGA

OVp2-98
AAGCGCCCGC GCACCCTCTC TCGGGGCTGG TGGCCTGCGT GGGCGGCCGG GTGGTCGGCA GAGCCGCCGG GGCCCCCGGG
CTCAGAAAGA GGCCGAAATG GCTGCGAAGC AGGCCCCGGG CAGGAGTCGC TCGGGCGCAG GGAGGAAGTG AACCGGCCGG
AGGTAGCGCC CGGCTGCTGG CCCCACAGTC CCGACACCTT CGGAACTCCT AACTCCTTTA CTTGTCCGG

OVp2-99
CAAACAATAC TATCTTATAA AATAGTACTG TTGAATTATT CCAAGCCTCC CTAGGTTTGC TCTCAAATGT CATTTACAGA
TTGGGCTAAC GACCTAAAAT CTATATATAA AGACTTTCTG AAGAACTCTG TATTATAGCA ATACCAAACG AGTGCTGTGT
GTGCAAACAG TCTGGCGTTG CTTTTTATGT TGATATTTAT CCTAGAACAC TGAAAGAGAA TATGCCA

*Fig. 16D*

OVp2-110

```
AAGCGCCGCC CGGGCCCTGG ATCCTGCACC GAGGCCGCAA AAAGGCCACA GGCAGCGCAG TGTCCATCTT CGTGTATGAT
GTGAAACCGG GAGCTGAAGA GCAGACCCAG GTGGCCAAAG CTGCCTTCAA ACGCCTCAAA ACTCTCCGAC ACCCCAACAT
CCTGGCCTAT ATCGATGGGT TGGAGACAGA AAAGTGCCTC ACATCGTGA CAGAGGCTGT GACCCCCCTG GGAACATACC
TCAAGGGCTG GCGAGTGGAA ACTTGGGGGT CTGGACTACA TGTACTCGGC ACAGGGCAAC GGCGGGGGAC CACCCAGCAA
GGGGATCCCG GAGCTCGAGC AGTATGATCC CCCGGAGCTG GCTGACAGCA GTAGCAGAGC AGTCAGAGAG AAGTGGTCAG
CAGACATGTG GCGCTTGGGC TGCCTCATCT GGGAAGTTTT CAATGGGTCT CTACCTCGGG CAGCTGCCCT GCGCAACCCT
GGGAAGATCC CCAAATCCCT GGTGACCCAT TACTGTGAAC TGGTGGGAGC TAACCCAAAA G
```

OVp3-4

```
AAGCGTCTCT TTTCCACTGT TGCAGTGAGC TGAGACCATG CCACTGTACT CTAGCCTGGG TAACAGCCAG ACCCTGTCTC
AAAAAAAAAA ACAATTTTTT TCATAACATA ATTCCCATTT TTATTTATTT TGAGTCACTC ATAATTAATT GCCAAAAAAG
CATTTTATAC ATTGAGTTGG GGGGTAGTGG ATCTTAGTGT GGTGTTGCAT GGAGGGGCGA GATTTTATAT TTATAATCAA
CACGTGGGTT AACATGTTTT TTTGAAATCC AAGCAATACA CAGGAAATTT AAGTAGAATA
AAAATTGCAG CCCATTTTTG AAATGTCAGC ATGTGC
```

OVp3-8

```
CAGCTGNGAA TCTGACTGGT CCTGNACTTT TTTTGGCTGG NGGGCTATTA ANTATATCCT CAGTTTCAGA GCCTGTTATT
GGTCTATTCA NGGATTCAAC TTCTTCCTTG NTTANTCTTG GGAGGGGGTA TGTGTCCANG AATTTATCCA TTTCTTCTAN
ATTTTCTAGC TTATTTGTGT ACAGATGTTT ATAGTATTCA TTCTCTGATG GGAGNTTGTA TTTCTGTGGG ATCAGNGGTG
ATATCCC
```

OVp3-11

```
CTGGCTGCTT TTTTGCTGNG GGTAGATGGT GGGAATACTT CTGGTCTAGA TATAACTTAC CACTAAGAAA CCCCCAGTAT
GTCACCACTG CCTAAATCTA ACTAGACCAG GGTCCAAATG CCATCCAGGC CAGGCAGGAA ATATACCTCA TGTGAAAGAC
AGTAAGGAGT TGTGGGCAGT GTAACAAACA GGAGAGCTAT GCCCCAACTA AAAGGAGCAG CTGCTACTGC TTAGTTTCAG
CCA
```

OVp3-19

```
CCAAACACCC GAAAGACACA AACCAGAATT GAGCCCTACT CCCCAAAATG TACAAACAGA TGATACGCTT AACTTTTTGG
ACACCTGTGA TTTGCATACT GAGCATATAA AGCCATCTTT ACGCACGTCC ATCGGTGAAA GAAAACGGTC TCTTTCACCA
CTAATTAAGT TTTCTCCAGT GGAACAAAGA TTGAGAACCA CAATAGCATG TAGTCTTGGA GAACTACCTA ATTTAAAGGA
AGAAGACATT TTGAATAAGA GCCTTGATGC AAAAGAACCA CCGTCTGACT TGACAAGATG AAGACGTACC CATTTAATAT
AACTATGATG CACTTAAATT GAAGCTATGC CACAGGATAG AAAATGAATT ACAACTTAAA TACATGTTGG AAGTGTAACA
CTGTTTTTCA AGGGTTAAAA AAATTCCTAA TGCCTTTTAG CCTTCTTTAA TATTTTTAGG TAAGGAAAGT ATGTTTGGAT
TTTTTCCTCT TTGTAGGTAT ATGAGATTGA AATGTGAAGT ATTTGGACAA CAAACGTCAA GCAATGGAA GCCATTTTGA
TTTCTTGAGT AATCTTGTAA GCATTAAGTG AATGACAAAG TAGTAGTGTA ACTTATTTCT TATGTTATAA CTTCAGTCAA
TTAATATAAG GATAGTTTTT GTTGTATGTT CACTAAATGG TTAATATAAT AGCCATTGAA TATACTAATC TTTCATCTTA
GAGAACTATA CAACTTTTAT TGTTTCTTAA TGGAACATTC TGGCTAACCA GAAAAAGTGA GAAAAGTAGT ACCCTTGGGA
TGTGTAGTCA AGATGACAAA TTTTAAGACT GGAAAAGCTC TAAACAGGCT AATGATTCT TCAGGTAGAA TGATCCTGAG
AAGGTGATGT TTGATGGAAT AAAGTGCATG TGATGATTAA GTGAAGACTG GGGCAGAATG ATTT
```

OVp3-31

```
TAAAGATAAT GATTGATAAG CTAGAACTTT CTGATGTAGT CATTACATGA AACCCCTTGT CACTGGTTTG TGTGTTCAGA
GGAAGCCATG GCCGAGATAG CTTTCCTGAA ATAAACCAGT AGCTTTTCAG ATTGACGTTC TTGCTACAAT TGTACCATCT
GGTAATTCCT GAAAATGTCA ATTTTTTTGT GTTAATATTT TTGGTTTCAA ACAATAACAA ATGTCTCTAG
```

*Fig. 16E*

OVp3-38

AAGCGGAAGA AGGAGAAGCA ATTCTATTCC AAGGCCAAGA CCTACTGGAA ACAAATCCCA CCCACGGTGG ACGGCATGCT
TGGGGGGTAT GGCCACATCT CCAGCATCGA CATCAACAGC TCCCGGAAGT TTCTGCAGAG GTTTTTGAGG GAAGGCCCGA
ACAAGACAGG AACGTCCTGT GCCCTGGACT GTGGAGCTGG CATTGGGAGG ATCACCAAGC GGCTGCTCCT GCCGCTGTTC
AGAGAG

OVp3-40

CCAAACACCC GAAAGACACA AACCAGAATT GAGCCCTACT CCCCAAAATG TACAAACAGA TGATACGCTT AACTTTTTGG
ACACCTGTGA TTTGCATACT GAGCATATAA AGCCATCTTT ACGCACGTCC ATCGGTGAAA GAAAACGGTC TCTTTCACCA
CTAATTAAGT TTTCTCCAGT GGAACAAAGA TTGAGAACCA CAATAGCATG TAGTCTTGGA GAACTACCTA ATTTAAAGGA
AGAAGA

OVp3-41

TTTGGAGCTT CAAAGAGGCA AAGTGACTAA GGAGGAAATT AGTAAAGAGT TTATGTTAAG CGCAGATTGT CTTCTCTTTT
TAAGATGCCT TGTGAATATC TCTCCTTGGA TGCAATGGAG AAATGGATCA TCTGTAAGTA ACCGAGCTAG CTAGGGCTGT
CTCTTGTGTT TAAGCTTTAA TGAGGGAATG CCTGTTTCTG CCTTAGCTCT GCCCTTCACC CTGCAATGAC ACCTGTGTGC
T

OVp3-44

CCAAACACCC GAAAGACACA AACCAGAATT GAGCCCTACT CCCCAAAATG TACAAACAGA TGATACGCTT AACTTTTTGG
ACACCTGTGA TTTGCATACT GAGCATATAA AGCCATCTTT ACGCACGTCC ATCGGTGAAA GAAAACGGTC TCTTTCACCA
CTAATTAAGT TTTCTCCAGT GGAACAAAGA TTGAGAACCA CAATAGCATG TAGTCTTGGA GAACTACCTA ATTTAAAGGA
AGAAGA

OVp3-47

ATTGCATCGT TTTCCAACAT ACTTTTAGAT TTACAAAGTA AAACCAACCA TGGATCTGCC TATCTTGGTG TGTCGATCTT
GTAATTTTAT CTTTGTGTGT GTGTGTGTGT GTGTGTGTGC ACTCACTGGG GCCTAAGCTC AGAACCTCAC ACAGGCAGAG
TATACACACG CCCTGCAACT AAACTGCATC TCTAGTCCCT ATACATGTGT CCTACTCATC CTTCAAAGTG AGTCCCTAGG
GGAT

*Fig. 16F*

OVp3-51

AAGCCGGTAT TTGTGAGAGG AGTCGGCGTT TGAAGAGGTG GAACTCCTAG GGCTTTTTTG AGAGTGCTGA TTTAGAAGAA
TACAAATCAT GGCTGAAAAT AGTGTATTAA CATCCACTAC TGGGAGGACT AGCTTGGCAG ACTCTTCCAT TTTTGATTCT
AAAGTTACTG AGATTTCCAA GGAAAACTTA CTTATTGGAT CTACTTCATA TGTAGAAGAA GAGATGCCTC AGATTGAAAC
AAGAGTGATA TTGGTTCAAG AAGCTGGAAA ACAAGAAGAA CTTATAAAAG CCTTAAAGGA CATTAAAGTG GGCTTTGTAA
AGATGGAGTC AGTGGAAGAA TTTGAAGGTT TGGATTCTCC GGAATTTGAA AATGTATTTG TAGTCACGGA CTTTCAGGAT
TCTGTCTTTA ATGACCTCTA CAAGGCTGAT GTAGAGTTA TTGACACAGT TGTATTAAAT TGTTCACAAA AAGGAGAGCC
TTTGCCATTT TCATGTCGCC CGTTGTATTG TACAAGTATG ATGAATCTAG TACTATGCTT TACTGGATTT AGGAAAAAAG
AAGAACTAGT CAGGTTGGTG ACATTGGTCC ATCACATGGG TGGAGTTATT CGAAAAGACT TTAATTCAAA AGTTACACAT
TTGGTGGCAA ATTGTACACA AGGAGAAAAA TTCAGGGTTG CTGTGAGTCT AGGTACTCCA ATTATGAAGC CAGAATGGAT
TTATAAAGCT TGGGAAAGGC GGAATGAACA GGATTTCTAT GCAGCAGTTG ATGACTTTAG AAATGAATTT AAAGTTCCTC
CATTTCAAGA TTGTATTTTA AGTTTCCTGG GATTTTCAGA TGAAGAGAAA ACCAATATAT GGAAGAAATG ACTGAAATGC
AAGGAGGTAA ATATTTACCG CTTGGAGATG AAAGATGCAC TCACCTTGTA GTTGAAGAGA ATATAGTAAA AGATCTTCCC
TTTGAACCTT CAAAGAAACT TTATGTTGTC AAGCAAGAGT GGTTCTGGGG AAGCATTCAA ATGGATGCCC GAGCTGGAGA
AACTATGTAT TTATATGAAA AGGCAAATAC TCCTGAGCTC AAGAAATCAG TGTCAATGCT TTCTCTAAAT ACCCCTAACA
GCAATCGCAA ACGACGTCGT TTAAAAGAAA CACTTGCTCA GCTTTCAAGA GAGACAGACG TGTCACCATT TCCACCCCGT
AAGCGCCCAT CAGCTGAGCA TTCCCTTTCC ATAGGGTCAC TCCTAGATAT CTCCAACACA CCAGAGTCTA GCATTAACTA
TGGAGACACC CCAAAGTCTT GTACTAAGTG TTCTAAAAGC TCCACTCCAG TTCCTTCAAA GCAGTCAGCA AGGTGGCAAG
TTGCAAAAGA GCTTTATCAA ACTGAAAGTA ATTATGTTAA TATATTGGCA ACAATTATTC AGTTATTTCA AGTACCATTG
GAAGAGGAAG GACAACGTGG TGGACCTATC CTTGCACCAG AGGAGATTAA GACTATTTTT GGTAGCATCC CAGATATCTT
TGATGTACAC ACTAAGATAA AGGATGATCT TGAAGACCTT ATAGTTAATT GGGATGAGAG CAAAAGCATT GGTGACATTT
TTCTGAAATA TTCAAAAGAT TTGGTAAAAA CCTACCCTCC CTTTGTAAAC TTCTTTGAAA TGAGCAAGGA AACAATTATT
AAATGTGAAA ACAGAAACC AAGATTTCAT GCTTTTCTCA AGATAAACCA AGCAAAACCA G

OVp3-64

TCAAAAGCAA CAAGATTAAA AAGATTAGAA TGCAGTGGAA TTGTAGCTTT AAGACGCTGA ATGTGATTCT GTATCATTTA
AGAGAGAAAG TAGAATTAAC ACATGTTCAC ACACAGAAAG AATCTACTCT TTGTACAACC TTTGCTGAAA GAACTTTGAA
AGACTTCAGT AAAAACAAAG TTAAATCCAG AAAAGACAAG ATCAAACAAG CAATGGTGAG CAAAAAACCT AGCAAACGTG
GCACTAAAC

OVp3-70

TTGTTTATCA TGGAGCTAAT AATCCTAAAG GATTGCTGGA AGTTCGGGAA GCCCTGGAAA AGGTACACAA AGTAGAAGAC
CTTCTTCCGA TTATGAAGTT TAATACTAAA ACGAAGGATG GGTTCACCGT GAACACAAAA GTTCCCAGCC TTAAAGACCA
AGGGAAGGAA TATGATGGAT TCACAATCAC GATTACAGGA GACAAAGTTG GCAATATATT ATTTTCTGTG GAAACTCAAA
CCA

OVp3-71

AAGCGTTGTT GCCCTGTGAT TAGTTCTGCT TTTTAACCCA CTCCCTGGAT GCATTTTTCC CTCCTTGCAT TTCCCTCTTT
TCCTGGAGTT CATACTAGAG AATCTGCACT ATGTTTTTCC CTTTTTGTCT TGAGATGAAA GTTTTAAAAT AATCCACCTC
TGTCATTTCC ACTCTCTGAA CATCCCAAGC TGTATCCCTG GCCTCTTTTC TCAGACTATG TTTCTTTACT TGGGACCTAG
AACT

OVp3-81

AGCCCNCCTG AAGCGCCGCG GCGCCGCTAT CGAGCTTCCT GCANTGGTGG CCACCCGAGC AAGTGCCGTG GCGGGGGCGG
AGAGCGGCCA CGGCGGCGGC GCCTCCCCAA GTGGCCCGTT GCGTCCGACC CCGCGTGAAA GATATCAAGT TATTCTAGTA
CAACCATATA AATAAATAAT ACCTGAAGTC TCAGTGTAAC ATGGACAATT AACAGTGATG ACAGATAAAT ACAGACGCAT
GGGGA

*Fig. 16G*

OVp3-87

TGCCAGAGCA GCTGGGAAGG TGTGGAAGGA GCAGTTCCGG GTGAGGTGGC CTTCCCTTAT GAAACACTAC AGCCCCACCG
ACTACGTCAA TTGGTTGGAA GAGTATAAAG TTCGGCAAAA AGCTGGGTTA GAAGCGCGGA AGATTGTAGC CTCGTTCTCA
AAGAGGTTCT TTTCAGAGCA CGTTCCTTGT AATGGCTTCA GTGACATTGA GAACCTTGAA GGACCAGAGA TTTTTTTTGA
GGATGAACTG GTGTGTATCC TAAATATGGA AGGAAGAAAA GCTTTGACCT GGAAATACT

OVp3-88

AGCCGGGCCC GAGCTGGGCT CTGCGAGGTG CAAGAAAGCC TTTGAGGTGA AGGTGTATGA AAGTCATCAT AACAGATGTT
TTCCAAAAAC TTGTAGAAGG TTGTGAAAAA ACTACTAGGA TCACGCGGCA TGTATTGAGG TGTGGCATGC AGCATTTTGG
AAGGAAAATT GAAGACGTGT TCAAGAAAAC ATGAACAGAA GCAAATGATG AAAATCAGCA TTTTACTTGA TGTTGATAAC
ATCACA

OVp3-107

AGTCCCTAAA TACATGAGGC TGGGTGAGCA GATGAAACCG GTAGCCACTG TGCTGATGCA TGTGACTCCA TTCAGTTGGG
GATTTTGGTT CCATGTGGAT CCATACTAAG TATTCTTCAG TCAGTGGATT TTAGCAAGGG GAGGTAGGAG TGGAAGAGAG
GTGTGAAGAA ACCTCTCCGA ACAAATGAAC CAGCAGTAAG TTTCTAAAAA TCAGAATCTA GATAGAAGTT CTGCAATATG
AAATGAGCAC ATTCTTTGAT AAGGCGTATC TATTCATGCT TTTGTACCAC TGTTTTGTAC CTGACTCCCT GACCGATTTG
TATTTTTTAT ATACAACTAG AAGGAAGTCA CAAGATTGCC TTCTACAGTG TGCCATTTCC AAATGGATCT GTTGTTGGAG
GAAACTGGTT GCTAGTCAAT GTTCTATATT TAATGAATGT GTGATAAATC ATCCTGTAAT CAGTATGGAG TAACCTGTTT
TTGTAGTTTG GATGAATATG TCCTGAGAAA TTTCCATCCA CTTTGGTT

OVp3-110

AAGCGTTCTG CATCCTCCAG GCTCTGGTTC CCATGCAGCA GCTGTCAGCG TTCAGACAAC CCCTCAGAAC GTGCCCAGCC
GGTCAGGCCT GCCCCACATG CACTCCCAGC TGGAGCATCG CCCCAGCCAG AGGAGCAGCT CCCCTGTGGG CCTTGCCAAA
TGGTTTGGCT CAGATGTGCT ACAGCAACCC CTGCCCTCCA TGCCCGCCAA AGTTATCAGT GTAGATGAAT GGAAATACCG
ACAGTGAGCA GGGCAGGCAG ACTCAACTAA GCCCGGACCT GTGGTGGCAC ACTGGGCAGG ACCCTGCTTC ATCTCGGGTT
GGTTTATGGG CTTTTACTTT GGAGCACTCT GTGTGAAGCT GTTTGGTGGA ACCCATGCAT CTGGTGTGGT CCGCATTATG
ATGGAAGGAT CTTAACCAGT CGAGTGGAGT GTACATTGTC TGAATACAGG ATGCACAATG TTGTCAATCC TGGAAATGGT
CTTTCTTTTT TGTAAGATAT GTGAATGAAG TGTTGGTGTC CTCACCAAGA GGTGGCACCT

*Fig. 16H*

OVp3-127

```
AAGCATTGAT GAACTCCCAG AGGGCCGGCC AGTGCGGGTA GCCCGGATTG ATGAACTCCC AGAGGGCGCT GTGAAGCCTC
CAGCAAACAA GTATCCTATC TTCTTTTTTG GCACCCATGA AACTGCATTT CTAGGTCCCA AAGACCTTTT TCCATATAAG
GAGTACAAAG ACAAGTTTGG AAAGTCAAAC AAACGGAAAG GATTTAACGA AGGATTGTGG GAAATAGAAA ATAACCCAGG
AGTAAAGTTT ACTGGCTACC AGGCAATTCA GCAACAGAGC TCTTCAGAAA CTGAGGGAGA AGGTGGAAAT ACTGCAGATG
CAAGCAGTGA GGAAGAAGGT GATAGAGTAG AAGAAGATGG AAAAGGCAAA AGAAAGAATG AAAAAGCAGG CTCAAAACGG
AAAAAGTCAT ATACTTCAAA GAAATCCTCT AAACAGTCCC GGAAATCTCC AGGAGATGAA GATGACAAAG ACTGCAAAGA
AGAGGAAAAC AAAAGCAGCT CTGAGGGTGG AGATGCGGGC AACGACACAA GAAACACAAC TTCAGACTTG CAGAAAACCA
GTGAAGGGAC CTAACTACCA TAATGAATGC TGCATATTAA GAGAAACCAC AAGAAGGTTA TATGTTTGGT TGTCTAATAT
TCTTGGATTT GATATGAACC AACACATAGT CCTTGTTGTC ATTGACAGAA CCCCAGTTTG TATGTACATT ATTCATATTC
CTCTCTGTTG TGTTTCGGGG GGAAAAGACA TTTTAGCCTT TTTTAAAAGT TACTGATTTA ATTTCATGTT ATTTGGTTGC
ATGAAGTTGC CCTTAACCAC TAAGGATTAT CAAGATTTTT GCGCAGACTT ATACATGTCT AGGATCCTTT TATCAAGGCA
GTTATGATCA TCGTTTTCCT GCCTTGACCC CACCATCATC AAACACTCAG TTAAATATAA ATTAACATTT TTTAGATGAC
CACTCAACAT AATGCTTAAG AATGGAATTT CCTCTCTGTG ACAGAACCCA GGAATTAATT CCTAAATACA TAACGTTGGT
ATATTGAAGA CGAAATTAAA ATTGTCCTTC AGTTTTGAGG CCATGTGTAA AGTTTACCCA TATTGTAAAA TATCTATTCC
GGTATTAGAA ATAGCTAGTT GACAGCTTAT ACTTCTCAAA ATTCATATTG TTATGTACAC AAACTAAGTT TCTATATGTG
AAGTTAGTGA GTCTTTTTGT GTTACTCCAA AATAAAGGCA ATGATTTATT TTTTTCCCAG TGCCAATACA ATTTTGAGCT
AAGCACTCAA GGTGGATACT TTACATTTTA AAGCTGGAAT CAGCAACAGC CCTATGGGAA ACCAGACAAA GCATTGACTT
TTAAATGTAG ACTTTTAAAA TAAACTGTTT TCTTTTGGAA CTACAATTAG AATAGTTAAT ATTCATCCTT AAACCATTAT
TATGTGTACA TTATTGTTGC TATTGTGATA ATAGAGAATT TTATTTATTT TTATGCCAGC TTATATTGTG AGAACACATT
TAGTCAGTTT GGGTTTTATC AATCCTGTTA ATGCTTGTCC TTGGAACATC TTTCGCGTAT TCACGGTTTG TAGTTGAAAA
GTTTACTGTA AAAAAATCAA AAACAAAAAA ATGTATTGTT TTTACAGAAT AAATTTATTG GAATGTGT
```

*Fig. 16I*

OVp2-15
TAATGAGCCA ACCACGTGGG AGCTTAACCA GTGATAGAAC TAGAAATTGG GTTCTTCAAC AGAAAATAGA AGGGAGAAAC
AAAAGAATCA AACTACGCTA AATTGATTGA AATGAATGGA GGAGGAACCG GCTGTAATCA TGAATTAGAA ATGATCAGAC
AAAAGCTTCA ATGTGTAGCT TCAAAACTAC AGGTTCTACC CCAGAAAGCC TCTGAGAG

OVp2-22
AACAAATAAA AAATAAAAAC AACGCCAGTC TCAGTAAATC TGTAGGTGTG TCTAACCGGC AGAATAAGAA AGTAGAAGAA
GAAGAAAAGT TGCTGAAGCT CTTTCAGGGA GTAAATAAAG CCCAAGATGG ATTTACGCAG TGGGTGTGAA CAGATGCTTC
ATGCCCTTAA TACGGCAAAT AACTTGGATG TTCCCACATT TGTTTCTTTC CTGAAAGAAG TAGAATCTCC TTATGAGGTC
C

OVp2-24
AAGCAGACTG ACCACCGGCC TCCCGCCTGC AGGTCAGAGG CTCTGACACT GTCTGGTTTC CAATGCTTCT GGAGACTTCC
TGCCTAGGCC TCATCCTCCT CTTTGCCAGT CACCTGATTA ACCAATTCTC CAGCATTAGG ACTTACCTCC TTCTTTTTGT
AAGGTCTCTT GTATGTTGTT AAATGTTTGG CTTAAACAAT TTATAAAAGC CTTTCTAGAA GGCAGACT

OVp2-47
AAGCGCGATG AGTGCGCCCC CAAAGGGGCA CCCTCGCTGC GGTGCANACA CTGGTGCGTG GCGAGGTTCT CCCCTTTGGG
TGCGATGAGT GCGCACTGGG CGCCACCGTG GATGCCCCCG CCGCCAAGCC CCTGGCCAGC GCGCCTGGCG GACCGGGCTG
CGGCCCAGGA TCCGATCCCG TGGTGCCCCA GCGCGCCCCC TCGGGCGAGC GGTCCTTCTT CTGCCCGGAC TGCGGGCGCG
GCTTCTCCCA TGGG

OVp2-55
TACTTCACTC ACCTAATTGT GATGTTCAAG TCCCCCAGGC CGGCTGCCAT GGTGCTGGAC CGCTCCCAGG ACTTTGGGAA
AACATGGAAG CCTTATAAGT ACTTTGCGAC TAACTGCTCC GCTACATTTG GCCTGGAAGA TGATGTTGTC AAGAAGGGCG
CTATTTGTAC TTCTAAATAC TCCAGTCCTT TTCCATGCAC TGGAGGAGAG GTTATTTTCA AAGCTTT

OVp2-81
ATGCGTNTTC GGCGGCCGCG GCGGACCATG GCCCTGGCCC GGCGTCGCTG GGCTTTCCTC ACGGCGTCCC CGAGCAGCGT
CGCAGAGCGG GCCGACTTCC GGGAAGGAAC TGACCAGCGA CTGAGCGGCG GCCGGCGCGC TTAGCGCCCT GAACATGCGG
CAGTCCCTGC GGGCGACCCC GGGCTCCGGA CAGGCGGCGG CGGAGGCGGC GGCTCGGGAG GGAAGGAGGC GGCGGCGCCG
GCGGAGGTGG CGGCGGAGAC

OVp2-100
AAGCGTGGGG ACCAGGTCTG TGGGCCTCAG GTCTGGCCAG CCAGGGCTGG TGCTGTCCCC GCCTACCTCC ACTTCCTTTC
CCTTGCTCAC TCTGGATCCA GTGACAGCAG GTGTCATGGG TCAAGCATAA ATCATATATA GCATTTTCAG GCATGTTCCT
GGTAGTTCTT TTGAGTCTGA CATTCTAATA AAATAATTTG TAGAAACC

OVp2-104
AACCACACAT TGGAAAAATC AGTTTACCCT AGAATCTAGT TATTGTTGTG GTACAGTTTA ATTTTTGTCA AATAATTCTT
TCTAAAATTT CTAATGTAAG TCTTTAATTT TCAAGATATT TTGCTTAGAA GATGATATGG TTTGGCTGTG TCCCCACCCA
AATCTCACCT TGAATTCCCA CGTGTTGTAG GGGGCAGGTC TTTCCTGTGC TGTTCTTGTG AAAGTGA

*Fig. 17A*

OVp2-108

TAGTACAGCA GCCATGCAGC CACCTTATTT CATAGATGCC ATCTGTGTGT CCTCTTGACT ACCTTCTATT TAGAGGAAGA
ATGAGAGCTT TGTGTGTTTA ACTGAGCTTA TAGTAGGACT TCTTTGCATA TGTATGGTAC TGAAAAATCT TAATATACAT
CTTTAATCCT TTTTAGGTTG TCCTTTAAAG AGTTTTTGAC TAGTTTCTTT TTCTTGACAG CTCTTCTCTT TGGACACATG
GGCCTTCTTA GAGGGTTCAG TCTAGGACCC GGCTCTCCTG GCCCTGTGTT GAGGGTAGCT GGTCCCTCTG TCCCTGTGTC
TGCTAGCACT AGACTTTGTT GCTGCAGATT GATCCAGTGG GTACATAGGC TAATTAATGT GAGTCTTTTT CCTTGTTTAA
AGGAGTCCCT CTTGCTGAAA GTAGAGTGAT TACTATTGCT GTAGTGCTAG GAAAGTATTA AGTTTGTGCT GAAAATCCAT
TGCCATTTGG TACAAATGAC ATTGTTCTTT CTGTGAAAGA GATGCCCT

OVp3-3

AATGCGGGCC GCGTGCGTGC TGTGCGGGGC NGCCGGCGGT CGCCCAGAGC GGAGCATCCG GCCCCCGGCA CTCCCTTCCC
CAGCAGGCCT AGGGAGCTGC GCGCGGGGGC AGTGCGTGAC CTGGAGACCC GGGCCCTGGT GGATTGGGAG TCGGGCNGGG
GGGAGCAGGT CATGCTAGGG TGGTCTCCGG CCAAGGGAGC GATGAAGGTC AGGCGCGGCG AGCGGGGCTG GGAGGCGGGG
C

OVp3-5

AGAATATTAA GAAAATGAAG TAACTGATTT TCTAAAAAAA AAAAAAAAAA AATTTCTACA TTATAACTCA CAGCATTGTT
CCATTGCAGG TTTTGCAATG TTTGGGGGTA AAGACAGTAG AAATATTATT CAGTAAACAA TAATGTGTGA ACTTTTAAGA
TGGATAATAG GGCATGGACT GAGTGCTGCT ATCTTGAAAT GTGCACAGGT ACACTTACCT TTTTTTTTTT TTTTTTTAAC
TTTTTCC

OVp3-9

CTTGTTCCCT CTCCAAGTAT TTCATAGTAA CACTCTACTT GAAGTGACTT GATCCAGACT GAAAAGTGTC CTGCAGTGGA
ATGACCACCA GGCCCAGATC TAGCCTAGCC TGAGCTCTCA CAACCTCTCC TTAACCTTCC CTAGAACAAT TACCTTTAGC
TCAGTAATGG GAAAATCTCT ACCCTAACAT GAGGGCAGGA CACACACACA CACACACACA CCCTTTGATC TCAGTCTTTA
NACAAG

OVp3-23

AAGCGGCTCA GGGCTCCTTC CATTCTAACC TTGAGCCACA GTGTCACTCT TCAGGGCTCT GCTCCTGGCT CTATTTTGTT
AAGGTGTCAT CAGCCTTCAA CCTCCATTTA TATATTTTTA TAATGTTAAG CCACTGACCA ACTTTTTCAT AGAAACAACT
ATCAGATTCG AGGGCTCCCT TTGTCCCCCT GACCTGGGCA CAGGCATGGG CGATGGCTCC CTCTTCC

OVp3-50

AAGCCACCAT CATCAAAGAC CAAAGGTAGA TAAAACCACA AAGATGGGAA AAAAAACAGA GCAGAAAAGC TGAAAATTCT
AAAAATCAGA GCGCCTCTCC TCCTCCAAAG GAACACAGCT CCTTGCCAGC AATGGAACAA AGCTGGACAG AGAATGACTT
TGACAAGTTG AGAGAAGAAG GCTTGAGATG ATCAAACTTC TCCGAGCTAA AGGAGGAAGT TTGAACCCAT AGCAAAGAA

OVp3-66

AAGCTCCGTT TATCACAGTC CACTTAAAAA ATGATGATGA TGATAAAAAC CATGACCCAC CAATCACATG CCTATCATAT
AGTAAAACCC AGCCCATGAC CCCTAACAGG GGCCCTCTCA GCCCTCCTAA TGACCTCCGG CCTAACCATG TGATTTCACT
TCCACTCCAT AACGCTCCTC ATACTAGGCC TACTAACCAA CACACTAACC ATATACCAAT GATGGCGCGA TGTAACACGA
GAAAGCACA

*Fig. 17B*

OVp3-84

```
AGCCAGATGA CCTTTTTCCC CAAGTGATAC TCCAAGAGCA AAAGTATTGA AAATAGAAGA AGTCAGTGAT ACTTCATCCC
TGCAACCTCA AGCCAGTTTG AAGCAGGATG TATGTCAGTC TTACAGCGAG AAAATGCCCA TAGAGATAGA ACAAAAACCT
GCTCAGTTTG CCACAACTGT TCTTCCTCCA ATTCCTGCAA ACTCGTTCCA GCTCGAATCT GATTTCAGAC AATTGAAAAG
TTCT
```

OVp3-104

```
AAGCGTCACT GAGCCTGCCA ACCACGCTGT GGCAGGTACC TCCAGCCCCA GACACCTGCA GCCTCCACTG AAAGCTCAAT
GGCAGCCTCA TGAGACCCTG GACCGGAACC ACCCACTACC TAAAAAATCC CAAACATATA ACTGAACTCC TTATACCCAA
TTGGACCAAT CTATCACCCT ATAGAAGAAC TAATGTTAGT ATAAGTAACA TGAAAACATT CTC
```

*Fig. 17C*

OVp2-1
AGCACGTTCA ACTAATATTT TAGACAATAT GGGCAAATCA TCCAAGAAAT CCACTGCACT TAGTCGAACT ACAAATAATG
AAAAGTCTCC CATTATAAAG CCTCTGATTC CAAAGCCGAA GCCTAAGCAG GCATCTGCAG CATCCTATTT CCAGAAAAGA
AATTCTCAAA CTAATAAAAC TGAGGAAGTG AAAGAAGAAA ATCTTAAAAA TGTATTATCT GAAACCCCAG CTATATGTCC
T

OVp2-4
CCTGCCAAAA CCAAGAATCG CCGCAGAAGG AAGCCATCCA CTTCTGATGA TTCTGACTCT AATTTTGAGA AAATTGTTTC
GAAAGCAGTC ACAAGCACTA ATCCAACGG GGAGAGTGAT GACTTCCATA TGGACTTTGA CTCAGCTGTG GCTCCTCGGG
CAAAATCTGT ACGGGCAAAG AAACCTATAA AGTACCTGGA AGAGTCAGAT GAAGATGATC TGTT

OVp2-5
AAGCAATTCT TCCATCAAGG AGATATAGAA AAAAAATATC ATTTGGGTGT GAGTCCACTT TGCGATCAGT CACACTGAAT
CTATTGCCAA CATCCAGATT GGTTTTATGA CTTACCTAGT GGAGCCTTTA TTTACAGAAT GGGCCAGGTT TTCCAATACA
AGGCTATCCC AGACAATGCT TGGACACGTG GGGCTGAATA AAGCCAGCTG GAAGGGACTG CAGAGAGAAC AGTCGAGCAG
TGAGG

OVp2-6
AAGCGTCCTT CCGAGGAAGC TAAGGCTGCG TTGGGGTGAG GCCCTCACTT CATCCGGCGA CTAGCACCGC GTCCGGCAGC
GCCAGCCCTA CACTCGCCCG CGCCATGGCC TCTGTCTCCG AGCTCGCCTG CATCTACTCG GCCCTCATTC TGCACGACGA
TGAGGTGACA GTCACGGAGG ATAAGATCAA TGCCCTCATT AAAGCAGCCG GTGTAAATGT TGAGCCTTTT TGGCCTGGCT
T

OVp2-9
AATGCAAAAT GCTTGCANGT CACTCCCAAA TATAACCCTA CATTACCTTA TATATAAATC ACAATGAAAA TAAAAGTGCC
TACATTACAG AACTGTGAAA TTTTGTTTAA AAAAATAATA AAAATAAACT GTTGGGTATC ATTGGAATAA TGTAACACAT
AAGGCTGGAA AATACTGAAA TACAGTTAAG ACTCAATACA CAAGTTTACT TTAAAAAAGA AAAGAAAGAA AAGTTTGCCA
GA

OVp2-10
AAGCACAAGA TCATCATTCG TGTGCAGACC ACCCCAGACT ACAGTCCCCA GGAGGCTTTC ACCAACGCCA TCACAGACCT
CATCAGCGAG CTCTCCCTTC TGGAGGAGCG ATTCCGGGTG GCCATCAAGG ACAAGCAAGA AGGAATTGAG TAGCAGCTGA
AAGAAGCGTT GCTTAGTGGC TGGAAGGCTG GCACATACTC CTCAGGGCCC TTCAGTTTAC CACATGGCGA CAGCCACTCT
CAG

OVp2-11
TTTAATGTTG TCTCACCATA ACACAAAAAG CATGAACTTG TATTAATCAT ATATAATAGA TTGATCATGC ACTGTATTCA
CAGGAGGTTG GAAAACCATG CCATTTTCTG GAACTTAAGG TGTTGCATTA TTTCATCAAT CATTTGTTAA AAAAACCAA
AAAAATAAAA ATGTGAACCC TTCAGGTGTA AACACCTTAT CTTGGTATAC AATTGATCTT TTTGTTTTGT TTGAAGTAT
CA

OVp2-16
AAGCGGGAGA ATGTGCACCT GCAGGTACCG GGGAGACTCA CAAGGCACGA GTTCTGACAA GAACGTAAAC AGGAAGACCA
GGGCCTTCTT GCTGCAGCCA TGGTAGCCTC GTGTGCTCCC AAAGGAGGCC TTGAACCAGT CTGCATATGA CAGGAACGCA
GAGGGGCCCT CCAGTGCTGC CTGGCGCACA ACCAGGAACG CAGTGACCAT GCTGTCCAGC TGGCA

*Fig. 18A*

OVp2-17
CACGTCCGCC CCTGCGGCCA AGCCCAAGCG GGCCAAGGGC CTCCAAGAAG TCCACAGACC ACCCCAAGTA TTCAGACATG
ATCGTGGCTG CCATCCAGGC CGAGAAGAAC CGCGCTGGCT CCTCGCGCCA GTCCATTCAG AAGTATATCA AGAGCCACTA
CAAGGTGGGT GAGAACGCTG ACTCGCAGAT CAAGTTGTCC ATCAAGCGCC TGGTCACCAC CGGTGTCCT

OVp2-23
AAGCGCTAGT CAGAACCCTA TACCATGAAG TGTAGTTACC ATACAGATTA ATATGTAGCA AAAATGTATG CTTGATATTT
CTCAACTGTG TTAATTTTTC TGCTGTATTC CAGCTGACCA AAACAATATT AAGAATGCAT CTTTATAAAT GGGTGCTAAT
TGATAATGGA AATAATTTAG TAATGGACTA TACAGGATGT TAATAATGAA GCCATATGTT TATGTCTG

OVp2-39
AGCTCAAGAT ACATGAAATC AATCAAAGGG AAACTTGAAG AACAGAGACC AGAAAGAGTA AAACCTTTTA TGACAGGGGC
TGCAGAACAA ATCAAGCACA TCCCTGCTAA TTTCAAAAAC TACCAGTTCT TTATTGGTGA AAACATGAAT CCAGATGGCA
TGGTTGCTCT ATTGGACTAC CGTGAGGATG GTGTGACCCC ATATATGATT TTCTTTAAGG ATGGTTTAGA AATGGAAAAA
TGTTAACAAA TGTGGCAATT ATTTTGGATC TATCACCTGT CATCATAACT GGCTTCTGCT TGTCATCCAC ACAACACCAG
GACTTAAGAC AAATGGGACT GATGTCATCT TGAGCTCTTC ATTTATTTTG ACTGTGATTT ATTTGGAGTG GAGGCATTGT
TTTTAAGAAA AACATGTCAT GTAGGTTGTC TAAAAATAAA ATGCAT

OVp2-43
AATTCAGCCT TCCTCCCTGC CAGAGATCTC TTTAAGAAAA TAGTTTAAAC AATTTGTTAA AAAATTTTCC GTCTTATTTC
ATTTCTGTAA CAGTTGATAT CTGGCTGTCC TTTTTATAAT GCAGAGTGAG AACTTTCCCT ACCGTGTTTG ATAAATGTTG
TCCAGGTTCT ATTGCCAAGA ATGTGTTGTC CAAAATGCCT GTTTAGTTTT TAAAGATGGA ACTCCACCCT TTGCTTGGTT
TTAAGTATGT ATGGAATGTT ATGATAGGAC ATAGTAGTAG CGGTGGTCAG ACATGGAAAT GGTGGGGAGA CAAAAATATA
CATGTGAAAT AAAACTCAGT ATTTTAATAA AG

OVp2-48
AGCCGGCCGA CAGANCTGAG GCGGAGGGCC TGAGCCCGCG CTTCCACCAG CTGGACATCG ACGATCTGCA GAGCATCCGC
GCCCTGCGCG ACTTCCTGCG CAAGGAGTAC GGGGGCCTGG ACGTGCTGGT CAACAACGCG GGCATCGCCT TCAAGGTTGC
TGATCCCACA CCCTTTCATA TTCAAGCTGA AGTGACGATG AAAACAAATT TCTTTGGTAC CCGAGATGTG TGCACAGAAT
TACTCCCTCT A

OVp2-54
AAGCAGNAAG AGACAATGAA CTCATAGGCC AGACTGTGCG TATCTCCCAG GGACCCTACA AAGGCTACAT TGGTGTGGTG
AAGGATGCCA CAGAGTCCAC GGCCAGAGTA GAACTGCATT CTACCTGCCA GACCATCTCT GTGGATCGCC AGCGGCTCAC
CACGGTCGAC TCCCAGCGTC CAGGTGGCAT GACCTCTACA TATGGACGGA CTCCCATGTA TGGCTCTC

OVp2-58
AAGCCTGTGG CGCTCCGTGA AATTAGACGT TATCAGAAGT NCACTGAACT TCTGATTCGC AAACTTCCCT TCCAGCGTCT
GGNGCGAGAA ATTGCTCAGG ACTTTAAAAC AGATCTGCGC TTCCAGAGCG CAGCTATCGG TGCTTTGCAG GAGGCAAGTG
AGGCCTATCT GGTTGGCCTT TTTGAAGACA CCAACCTGTG TGCTATCCAT GCCAAACGTG TAACAATTAT GCCAAAAGAC

OVp2-59
AAGCCTTCCT GACCTTGGGC TACGGCTGAC CGTTTTTTTG TGGTGTACTC CGTGCCATCA TGTCCGTCCT GACGCCGCTG
CTGCTGCGGG GCTTGACAGG CTCGGCCCGG CGGCTCCCAG TGCCGCGCGC CAAGATCCAT TCGTTGCCGC CGGAGGGGAA
GCTTGGGATC ATGGAATTGG CCGTTGGGCT TACCTCCTGC TTCGTGACCT TCCTCCTGCC AGCGGGCTGG ATCCTGTCAC
ACCTGGA

*Fig. 18B*

OVp2-66
AAGCCCGGAN NCGNCACCGC CGCGCNNTCG CCCCACCCGCC CGCCCGCCGC TCCCGGCCCC GCTCGCCCCC TCCGCCGCCG
CCGCCCGCCC CTGCGACTAC GCTGCGGCCT CCCGCCCGCT CCCGCTCGCT CCCGCGGCCC TCGCTCGCCT CGCGCCGGCA
GTTTTGGGCC TACACCTCCC CTCCCCCCGC CAGCCGCCAA AGACTTGACC ACGTAACGAG CCCAACTCCC CCGAACGC

OVp2-82
CAGCGCCAGC GAGGTCGGAG CGGACAGCGA GGTCGGCAGC GGCACAGCGA GGTCGGCAGC GGCACAGCGA GGTCGGCAGT
GGCAGCGAGG TCGGCAGCGG CACAGCGAGG TCGGCAGCGG CAGCGAGGTC GGCAGCGGCG CGCGCTGTGC TCTTCCGCGG
ACTCTGAATC ATGGCGACCA CGGCCACGAT GGCGACCTCG GGCTCGGCGC GAAAGCGGCT GCTCAAAGAG GAAGACATGA
CTAAAGT

OVp2-91
GATTAACCAC AATTCTCAGA CCCAATCCTG AGTCCTCAGG AGGTTGTATC TTGCAGCCCC TATGCCCAAG GTTGTGATGG
TGGATTCCCA TACCTCATTG CAGGGAAGTA TGCCCAAGAT TTTGGGGTGG TGGAAGAAAG CTGCTTTCCC TACACAGCCA
AAGATTCTCC ATGCAAACCA AGGGAGAATT GCCTCCGTTA CTATTCTTCT GACTACTACT ATGTGGGTGG TTTCTATGGT
GGCTGCA

OVp2-103
AAGCAGAGAA AGAAGAATCT GATGATGAAG CTGCAGTAGA GGAAGAAGAA GAAGAAAAGA AACCAAAGAC TAAAAAAGTT
GAAAAAACTG TCTGGGACTG GGAACTTATG AATGATATCA AACCAATATG GCAGAGACCA TCAAAAGAAG TAGAAGAAGA
TGAATACAAA GCTTTCTACA AATCATTTTC AAAGGAAAGT GATGACCCCA TGGCTTATAT TCACTTTA

OVp2-106
AAGCCGGAGC CGGAGACAAG AGCAGAGGCC GAACTCGGGA TCTGACAAGA TGGCCGGGCT GCCCCGCANG ATCATCAAGG
AAACCCAGCG TTTGCTGGCA GAACCAGTTC CTGGCATTAA AGCAGAACCA GATGAGAGCA ACGCCCGTTA TTTTCATGTG
GTCATTGCTG GCCCCCAGGA TTCCCCCTTT GAGGGAGGGA CTTTTAAACT TGAACTATTC CTTCCAGAAG AATACCCAAT
GGCAGCACCT AAAGTACGTT TCATGACCAA AATTTATCAT CCTAATGTAG ACAAGTTGGG AAGAATATGT TTAGATATTT
TGAAAGGTAA GTGTTGTTTG TCACCCTGTG CTTTATTAAC GTGTCCTTTT TGTCCTAAGC ATTCTACATT TAGAATGTAA
GCATTGGAAT CTCACTGTAT GCTAACAGCC CCAGAGTGTG TGGGAGGGAA GTGCAGCAGT TCTGGGCCTG TTGTCCATGC
TTTATCATAT ACTGGGCCTG TTACCTTCAT AGATAAGTGG TCCCCA

OVp2-109
TTTAATGTTG TCTCACCATA ACACAAAAAG CATGAACTTG TATTAATCAT ATATAATAGA TTGATCATGC ACTGTATTCA
CAGGAGGTTG GAAAACCATG CCATTTTCTG GAACTTAAGG TGTTGCATTA TTTCATCAAT CATTTGTTAA AAAAAAACTA
AAAAATAAAA ATGTGAACCC TTCAGGTGTA AACACCTTAT CTTGGTATAC AATTGATCTT TTTGTTTTGT TTGAAGTAT
CAGATATTAA TTTGGAATAA GGTAAGGTTC TCTTGAAACA TTTGAAAACC CTTTAAGCCA ACTGATCTGA CAGCTTTCCC
ATCAGTAGAA GTGGGAACAT ACCTTCTTAG GTATTTACTA TTAACTACAT GTAGGCAGTT TATAGCTTCT GATCAGTGTA
GTAGACATTA CAAACACTGG TTGTAATGGG GTTTTCTGTA GACTTTACTT GAGAGGTGAG TATAAAGCAT TTTTTAGTCA
TCATCATGAC GATGCTGCTC AAGTGCAGAT CCAGAACAGT ACAGCG

OVp3-2
AATGCCCATC ATGGCAGCGG CGTTCCGCAG AGGCTGCAGG GTCCTGAGAA GTGTTTCTCA TTTTGAGTGT CGAACACAAC
ACTCGAAAGC GGCTCACAAG CAGGAGCCCG GATTAGGGTT TAGTTTTGAG TTGACNGGAA CAGCAGAAAG AGTTTCAAGC
AACTGCCCGC AAGTTTGCCA GAGAGGAGAT TATCCCCGTC GCCCCGGAAT ATGACAAAAG CGGGGAGGTG GGTATCGGGT
TGC

*Fig. 18C*

OVp3-6
AAGCCGNGAA CAACGCCCTA NAAAAAACAA GAAGGTAATC CCTCAACAAA CCTAAAAGAA GACAGCCACA AGAACAGAAT
GCAAGAGATG GAAGAGAGAA TCTCAGGTGC AGAAGATTCC ATAGAAACA TCGGCACAAC AATCAAAGAA AATGGAAAAT
GCAAAAAGAT CCTAACTCAA AATATCCAGG AAATCCAGGA CACAATAAGA AGACCAAACG TACGGATAAT AGGAGTGGAT
GAGAAG

OVp3-7
TTCAGATAAC TACTTGAAAT ATGCAGAGAA ATCCCTGAAT GATATGTTTG TGAAGACATA TGGCCATTTA TACATGCAAA
ATTCTGAGCT ATTTAAAGAT CTCTTCGTAG AGTTGAAACG TTACTACGTG GTGGGAAATG TGAACCTGGA AGAAATGCTA
AATGACTTCT GGGCTCGCCT CCTGGAGCGG ATGTTCCGCC TGGTGAACTC CCAGTACCAC TTTACAGATG AGTATCTGGA
ATGTGT

OVp3-17
AAGCCCAAAA TGGGAAAGGA AAAGACTCAT ATCAACATTG TCGTCATTGG ACACGTAGAT TCGGGCAAGT CCACCACTAC
TGGCCATCTG ATCTATAAAT GCGGTGGCAT CGACAAAAGA ACCATTGAAA AATTTGAGAA GGAGGCTGCT GAGATGGGAA
AGGGCTCCTT CAAGTATGCC TGGGTCTTGG ATAAACTGAA AGCTGAGCGT GAACGTGGTA TCACCATTGA TATCTCCTTG
TG

OVp3-24
AGAGAGGAAG AAGCGANGGG CACGGCGCTG AGACAGAGCT GGAGATGAGG CCAGACCATG GACACTACAC CCAGCAATAG
AGACGGGACT GCGGAGGAAG GAGGACCCAG GACAGGATCC AGGCCGGCTT GCCACACCCC CCACCCCTAG GACTTATTCC
CGCTGACTGA GTCTCTGAGG GGCTACCAGG AAAGCGCCTC CAACCCTAGC AAAAGTGCAA GATGGGGAGT GAGAGGCTGG
GA

OVp3-26
AAGCCGAACG CGGAGAGCAC GCCATGAAGG CCTCGGGCAC GCTACGAGAG TACAAGGTAG TGGGTCGCTG CCTGCCCACC
CCCAAATGCC ACACGCCGCC CCTCTACCGC ATGCGAATCT TTGCGCCTAA TCATGTCGTC GCCAAGTCCC GCTTCTGGTA
CTTTGTATCT CAGTTAAAGA AGATGAAGAA GTCTTCAGGG GAGATTGTCT ACTGTGGGCA GGTGTTTGA

OVp3-28
TCAATGCAGG GTCTAAAAGC TGGTGTTATT GCTGTTATTG TGGTTGTGGT GATAGCAGTT GTTGCTGGAA TTGTTGTGCT
GGTTATTTCC AGAAAGAAGA GAATGGCAAA GTATGAGAAG GCTGAGATAA AGGAGATGGG TGAGATGCAT AGGGAACTCA
ATGCATAACT ATATAATTTG AAGATTATAG AAGAAGGGAA ATAGCAAATG GACACAAATT ACAAATGTGT G

OVp3-29
AAGCGTGCAG CGGGCAGACC CTGTGGCCGT CACGCCCTGC CGCTCCAGGG AAGGGAGCCA GGCTGAGCCT CTGCCACGTG
GGAGAGGGGC TGTTTCCAGC CACCACCCAA AAAAACACCA CAAGGGTCAG TCCTAGCCCA CCCGACAGCT TCCCTTCCCA
AGCAGGGGTT TCGGGACAG TGCACCAGGG AGGGCCACTG ACAGGCTTGG ACATGTGCC CAGCTCTCCT

OVp3-34
TTCTAAGACC CGAGAGAAAA AGTTGGGACT AGGAACTGCA TATATTCATG GAATGAAACA TGCCACAGGA AACTACATCA
TTATTATGGA TGCTGATCTC TCACACCATC CAAAATTTAT TCCTGAATTT ATTAGGAAGC AAAAGGAGGG TAATTTTGAT
ATTGTCTCTG GAACTCGCTA CAAAGGAAAT GGAGGTGTAT ATGGCTGGGA TTTGAAAAGA AAAATAATCA

Fig. 18D

OVp3-36
AAGCTGGTGG TAGGGTGTCA ATTTTAGATC TCTCCTGCTT TCTCTTGTGG GCATTTAGTG CTATACATTT CCCTCTACAC
CCTGCTTTAA ATGTGTCCCA GAGATTCTGG TACATTGTGT CTTTGTTCTC ATTGGTTTCA AAGAACATCT TTATTTCTGC
GTTCATTTCA TTATTTACCC ACTAGTCATT CAGGAGCAGG TTGTTCAGTT TCCATGTAGT TGTGTGGTT

OVp3-37
AAGTGTGATC CCCATGAAGC AACGTGCTAT GACGATGGGG AGACCTACCA TGTAGGAGAA CAGTGGCAGA AAGAATATCT
CGGAGCCATT TGCTCCTGCA CGTGTTTCGG AGGCCAGCGG GGCTGGCGCT GTGACAACTG CCGTAGACCT GGGGCTGCTG
AACCCAGTCC CGATGGCACC ACCGGCCACA CCTACAACCA GTATACACAG AGATACAATC AGAGAACAAA CACTAACGTA
AATTGCC

OVp3-52
AAGCGACCAC CACGCACTTG ATGGCCTGCG ACGGCGCCGT GGGGAAGACA TGCTTGCTGA TCAGCTACAC GACCAACGCC
TTCCCCGGAG AGTACATCCC CACCGTTTTT GACAACTACT CTGCCAACGT GATGGTGGAC GGGAAACCAG TCAACTTGGG
GCTGTGGGAC ACAGCGGGTC AGGAGGACTA CGATCGGCTG CGGCCACTCT CCTACCCCCA AACTGACGTC T

OVp3-53
AAGCCTTTGC CGGCCTGCCG GGCCTGCAGC TCCTGGACCT GTCACAGAAC CAGATCGCCA GCCTGCCCAG CGGGGTCTTC
CAGCCACTCG CCAACCTCAG GAGCACGGAG ATCTCGCCGG CTTTACGTTC ACCTCGGTGT CTGCAGCACC CTCCGCTTCC
TCTCCTAGGC GACGAGACCC AGTGGCTAGA AGTTCACCAT GTCTATTCTC AAGATCCATG CCAGGGAGAT CTTTGACTC

OVp3-54
CTTTGAGGTT CCTTTCTTCT GCAAACACAC TGTCAGATGG TAACAATGCT GTTTTAGGGT TAATAATTTC TGCCCCTTTC
TTCTCCAAGT CACTGTTAAA CATCTGCTGA TTTAAAGCAC ACTCCTCGGC ATTTTCAGTG AATTGTTCAA TACTGACTGA
AGCGGATGCT ACAAGAGGAA TTTCTTCTTT GACCTCCTCT CCTTGAGTTT CAAGCTCCAA AGTTTC

OVp3-83
AGCTCCCACA ACAGGTGGCT AAGGGAAAAG GAGGTAGATG ATGGCAAAAT AAGATTTAGT TGTGTTTTCT CAGAGCCGCC
ACAAGATTGA ACAAAATGTT TTCTGTTTGG GCATCCTGAG GAAGTTGTAT TAGCTGTTAA TGCTCTGTGA GTTTAGAAAA
AGTCTTGATA GTAAATCTAG TTTTTGACAC AGTGCATGAA CTAAGTAGTT AAATATTTAC ATATTCAGAA AGGAATAGTG
GAAAA

OVp3-86
GATTAACCAC AATTCTCAGA CCCAATCCTG AGTCCTCAGG AGGTTGTATC TTGCAGCCCC TATGCCCAAG GTTGTGATGG
TGGATTCCCA TACCTCATTG CAGGGAAGTA TGCCCAAGAT TTTGGGGTGG TGGAAGAAAG CTGCTTTCCC TACACAGCCA
AAGATTCTCC ATGCAAACCA AGGGAGAATT GCCTCCGTTA CTATTCTTCT GACTACTACT ATGTGGGTGG TTTCTATGGT
GGCTGC

OVp3-90
AGCCCAAATG GAAAGGAAAA GACTCATATC AAACATTGTC GTCATTGGAC ACGTAGATTC GGGCAAGTCC ACCACTACTG
GCCATCTGAT CTATAAATGC GGTGGCATCG ACAAAAGAAC CATTGAAAAA TTTGAGAAGG AGGCTGCTGA GATGGGAAAG
GGCTCCTTCA AGTATGCCTG GGTCTTGGAT AAACTGAAAG CTGAGCGTGA ACGTGGTATC ACCATTGATA TCTCCTTGTG
GAAAT

*Fig. 18E*

COMPOSITIONS AND METHODS FOR OVARIAN CANCER THERAPY AND DIAGNOSIS

CROSS-REFERENCE TO RELATED APPLICATIONS

This application is a continuation-in-part of U.S. application Ser. No. 09/246,429, filed Feb. 8, 1999, which is a continuation-in-part of U.S. application Ser. No. 09/159,320 filed Sep. 23, 1998, now abandoned.

TECHNICAL FIELD

The present invention relates generally to ovarian cancer therapy. The invention is more specifically related to polypeptides comprising at least a portion of an ovarian carcinoma protein, and to polynucleotides encoding such polypeptides, as well as antibodies and immune system cells that specifically recognize such polypeptides. Such polypeptides, polynucleotides, antibodies and cells may be used in vaccines and pharmaceutical compositions for treatment of ovarian cancer.

BACKGROUND OF THE INVENTION

Ovarian cancer is a significant health problem for women in the United States and throughout the world. Although advances have been made in detection and therapy of this cancer, no vaccine or other universally successful method for prevention or treatment is currently available. Management of the disease currently relies on a combination of early diagnosis and aggressive treatment, which may include one or more of a variety of treatments such as surgery, radiotherapy, chemotherapy and hormone therapy. The course of treatment for a particular cancer is often selected based on a variety of prognostic parameters, including an analysis of specific tumor markers. However, the use of established markers often leads to a result that is difficult to interpret, and high mortality continues to be observed in many cancer patients.

Immunotherapies have the potential to substantially improve cancer treatment and survival. Such therapies may involve the generation or enhancement of an immune response to an ovarian carcinoma antigen. However, to date, relatively few ovarian carcinoma antigens are known and the generation of an immune response against such antigens has not been shown to be therapeutically beneficial.

Accordingly, there is a need in the art for improved methods for identifying ovarian tumor antigens and for using such antigens in the therapy of ovarian cancer. The present invention fulfills these needs and further provides other related advantages.

SUMMARY OF THE INVENTION

Briefly stated, this invention provides compositions and methods for the therapy of cancer, such as ovarian cancer. In one aspect, the present invention provides polypeptides comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished. Within certain embodiments, the ovarian carcinoma protein comprises a sequence that is encoded by a polynucleotide sequence selected from the group consisting of sequences recited in FIGS. 5, 8, 13, 16A–16I and 17A–17C (SEQ ID NOs:5, 8, 13, 19–68 and 69–85), SEQ ID NOs:130, 133, 135, 137, 138, 140, 142, 144–146, 148, 153, 155, 158, 159, 161, 163, 170, 174, 177, 178, 179, 180–182, 184, 187, 189, 190, 192, 195, 196, 198, 200, 207, 214–216, 220, 221, 222, 227, 228, 230, 231, 232, 234, 240–242, 243, 244–246, 250, 251, 253, 254, 256, 259, 261, 262, 264, 265, 272–275, 276, 278, 280, 281, 282, 283, 287, 288, 291, 292, 296, 297, 299, 301, 304–309, 311, 313, 314, 317, 323, 325 and 333, and complements of such polynucleotides.

The present invention further provides polynucleotides that encode a polypeptide as described above or a portion thereof, expression vectors comprising such polynucleotides and host cells transformed or transfected with such expression vectors.

Within other aspects, the present invention provides pharmaceutical compositions and vaccines. Pharmaceutical compositions may comprise a physiologically acceptable carrier in combination with one or more of: (i) a polypeptide comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished, wherein the ovarian carcinoma protein comprises an amino acid sequence encoded by a polynucleotide that comprises a sequence recited in any one of FIGS. 5, 8, 13, 16A–16I and 17A–17C (SEQ ID NOs: 5, 8, 13, 19–68 and 69–85), SEQ ID NOs:130, 133, 135, 137, 138, 140, 142, 144–146, 148, 153, 155, 158, 159, 161, 163, 170, 174, 177, 178, 179, 180–182, 184, 187, 189, 190, 192, 195, 196, 198, 200, 207, 214–216, 220, 221, 222, 227, 228, 230, 231, 232, 234, 240–242, 243, 244–246, 250, 251, 253, 254, 256, 259, 261, 262, 264, 265, 272–275, 276, 278, 280, 281, 282, 283, 287, 288, 291, 292, 296, 297, 299, 301, 304–309, 311, 313, 314, 317, 323, 325 or 333, or a complement of any of the foregoing sequences; (ii) a polynucleotide encoding at least 5 amino acid residues of such an ovarian carcinoma protein; (iii) an antibody that specifically binds to such an ovarian carcinoma protein; (iv) an antigen-presenting cell that expresses a polypeptide as described above and/or (v) a T cell that specifically reacts with such a polypeptide. Vaccines may comprise a non-specific immune response enhancer in combination with one or more of: (i) a polypeptide comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished, wherein the ovarian carcinoma protein comprises an amino acid sequence encoded by a polynucleotide that comprises a sequence recited in any one of FIGS. 5, 8, 13, 16A–16I and 17A–17C (SEQ ID NOs: 5, 8, 13, 19–68 and 69–85), SEQ ID NOs:130, 133, 135, 137, 138, 140, 142, 144–146, 148, 153, 155, 158, 159, 161, 163, 170, 174, 177, 178, 179, 180–182, 184, 187, 189, 190, 192, 195, 196, 198, 200, 207, 214–216, 220, 221, 222, 227, 228, 230, 231, 232, 234, 240–242, 243, 244–246, 250, 251, 253, 254, 256, 259, 261, 262, 264, 265, 272–275, 276, 278, 280, 281, 282, 283, 287, 288, 291, 292, 296, 297, 299, 301, 304–309, 311, 313, 314, 317, 323, 325 or 333, or a complement of any of the foregoing sequences; (ii) a polynucleotide encoding at least 5 amino acid residues of such an ovarian carcinoma protein; (iii) an anti-idiotypic antibody that is specifically bound by an antibody that specifically binds to such a polypeptide; (iv) an antigen-presenting cell that expresses such a polypeptide and/or (v) a T cell that specifically reacts with such a polypeptide.

The present invention further provides, in other aspects, fusion proteins that comprise at least one polypeptide as described above, as well as polynucleotides encoding such fusion proteins.

Within related aspects, pharmaceutical compositions comprising a fusion protein or polynucleotide encoding a fusion protein in combination with a physiologically acceptable carrier are provided.

Vaccines are further provided, within other aspects, comprising a fusion protein or polynucleotide encoding a fusion protein in combination with a non-specific immune response enhancer.

Within further aspects, the present invention provides methods for inhibiting the development of a cancer in a patient, comprising administering to a patient a pharmaceutical composition or vaccine as recited above.

The present invention further provides, within other aspects, methods for stimulating and/or expanding T cells, comprising contacting T cells with (a) a polypeptide comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished, wherein the ovarian carcinoma protein comprises an amino acid sequence encoded by a polynucleotide that comprises a sequence recited in any one of SEQ ID NOs: 1–334; (b) a polynucleotide encoding such a polypeptide and/or (c) an antigen presenting cell that expresses such a polypeptide under conditions and for a time sufficient to permit the stimulation and/or expansion of T cells. Such polypeptide, polynucleotide and/or antigen presenting cell(s) may be present within a pharmaceutical composition or vaccine, for use in stimulating and/or expanding T cells in a mammal.

Within other aspects, the present invention provides methods for inhibiting the development of ovarian cancer in a patient, comprising administering to a patient T cells prepared as described above.

Within further aspects, the present invention provides methods for inhibiting the development of ovarian cancer in a patient, comprising the steps of: (a) incubating CD4+ and/or CD8+ T cells isolated from a patient with one or more of: (i) a polypeptide comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished, wherein the ovarian carcinoma protein comprises an amino acid sequence encoded by a polynucleotide that comprises a sequence recited in any one of SEQ ID NOs:1–334; (ii) a polynucleotide encoding such a polypeptide; or (iii) an antigen-presenting cell that expresses such a polypeptide; such that T cells proliferate; and (b) administering to the patient an effective amount of the proliferated T cells, and thereby inhibiting the development of ovarian cancer in the patient. The proliferated cells may be cloned prior to administration to the patient.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 1 depicts a partial sequence of a polynucleotide encoding a ovarian carcinoma antigen designated OV2 (SEQ ID NO:1), and the amino acid sequence of the encoded polypeptide (SEQ ID NO:16).

FIG. 2 depicts a partial sequence of a polynucleotide encoding a ovarian carcinoma antigen designated OV3 (SEQ ID NO:2), and the amino acid sequence of the encoded polypeptide (SEQ ID NO:17).

FIG. 3 depicts a partial sequence of a polynucleotide encoding a ovarian carcinoma antigen designated OV6 (SEQ ID NO:3), and the amino acid sequence of the encoded polypeptide (SEQ ID NO:18).

FIG. 4 depicts a partial sequence of a polynucleotide encoding a ovarian carcinoma antigen designated OV9 (SEQ ID NO:4).

FIG. 5 depicts a partial sequence of a polynucleotide encoding a ovarian carcinoma antigen designated OV10 (SEQ ID NO:5).

FIG. 6 depicts a partial sequence of a polynucleotide encoding a ovarian carcinoma antigen designated OV12 (SEQ ID NO:6).

FIG. 7 depicts a partial sequence of a polynucleotide encoding a ovarian carcinoma antigen designated OV14 (SEQ ID NO:7).

FIG. 8 depicts a partial sequence of a polynucleotide encoding a ovarian carcinoma antigen designated OV17 (SEQ ID NO:8).

FIG. 9 depicts a partial sequence of a polynucleotide encoding a ovarian carcinoma antigen designated OV18 (SEQ ID NO:9).

FIG. 10 depicts a partial sequence of a polynucleotide encoding a ovarian carcinoma antigen designated OV23 (SEQ ID NO:10).

FIG. 11 depicts a partial sequence of a polynucleotide encoding a ovarian carcinoma antigen designated OV24 (SEQ ID NO:11).

FIG. 12 depicts a partial sequence of a polynucleotide encoding a ovarian carcinoma antigen designated OV27 (SEQ ID NO:12).

FIG. 13 depicts a partial sequence of a polynucleotide encoding a ovarian carcinoma antigen designated OV41 (SEQ ID NO:13).

FIG. 14 depicts a partial sequence of a polynucleotide encoding a ovarian carcinoma antigen designated OV54 (SEQ ID NO:14).

FIG. 15 depicts a partial sequence of a polynucleotide encoding a ovarian carcinoma antigen designated OV57 (SEQ ID NO:15).

FIGS. 16A–16I depict partial sequences of polynucleotides (SEQ ID NOs: 19–68) encoding further representative ovarian carcinoma antigens.

FIGS. 17A–17C depict partial sequences of polynucleotides (SEQ ID NOs: 69–85) encoding further representative ovarian carcinoma antigens.

FIGS. 18A–18F depict partial sequences of polynucleotides (SEQ ID NOs: 86–129) encoding further representative ovarian carcinoma antigens.

DETAILED DESCRIPTION OF THE INVENTION

As noted above, the present invention is generally directed to compositions and methods for the detection and therapy of cancer, such as ovarian cancer. The compositions described herein may include immunogenic polypeptides, polynucleotides encoding such polypeptides, binding agents such as antibodies that bind to a polypeptide, antigen presenting cells (APCs) and/or immune system cells (e.g., T cells).

Polypeptides of the present invention generally comprise at least an immunogenic portion of an ovarian carcinoma protein or a variant thereof. Certain ovarian carcinoma proteins have been identified using an immunoassay technique, and are referred to herein as ovarian carcinoma antigens. An "ovarian carcinoma antigen" is a protein that is expressed by ovarian tumor cells (preferably human cells) at a level that is at least two fold higher than the level in normal ovarian cells. Certain ovarian carcinoma antigens react detectably (within an immunoassay, such as an ELISA or Western blot) with antisera generated against serum from an immunodeficient animal implanted with a human ovarian tumor. Such ovarian carcinoma antigens are shed or secreted from an ovarian tumor into the sera of the immunodeficient animal. Accordingly, certain ovarian carcinoma antigens provided herein are secreted antigens. Certain nucleic acid sequences of the subject invention generally comprise a DNA or RNA sequence that encodes all or a portion of such a polypeptide, or that is complementary to such a sequence.

The present invention further provides ovarian carcinoma sequences that are identified using techniques to evaluate altered expression within an ovarian tumor. Such sequences may be polynucleotide or protein sequences. Ovarian carcinoma sequences are generally expressed in an ovarian tumor at a level that is at least two fold, and preferably at least five fold, greater than the level of expression in normal ovarian tissue, as determined using a representative assay provided herein. Certain partial ovarian carcinoma polynucleotide sequences are presented herein. Proteins encoded by genes comprising such polynucleotide sequences (or complements thereof) are also considered ovarian carcinoma proteins.

Antibodies are generally immune system proteins, or antigen-binding fragments thereof, that are capable of binding to at least a portion of an ovarian carcinoma polypeptide as described herein. T cells that may be employed within the compositions provided herein are generally T cells (e.g., $CD4^+$ and/or $CD8^+$) that are specific for such a polypeptide. Certain methods described herein further employ antigen-presenting cells (such as dendritic cells or macrophages) that express an ovarian carcinoma polypeptide as provided herein.

Ovarian Carcinoma Polynucleotides

Any polynucleotide that encodes an ovarian carcinoma protein or a portion or other variant thereof as described herein is encompassed by the present invention. Preferred polynucleotides comprise at least 15 consecutive nucleotides, preferably at least 30 consecutive nucleotides, and more preferably at least 45 consecutive nucleotides, that encode a portion of an ovarian carcinoma protein. More preferably, a polynucleotide encodes an immunogenic portion of an ovarian carcinoma protein, such as an ovarian carcinoma antigen. Polynucleotides complementary to any such sequences are also encompassed by the present invention. Polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an ovarian carcinoma protein or a portion thereof) or may comprise a variant of such a sequence. Polynucleotide variants may contain one or more substitutions, additions, deletions and/or insertions such that the immunogenicity of the encoded polypeptide is not diminished, relative to a native ovarian carcinoma protein. The effect on the immunogenicity of the encoded polypeptide may generally be assessed as described herein. Variants preferably exhibit at least about 70% identity, more preferably at least about 80% identity and most preferably at least about 90% identity to a polynucleotide sequence that encodes a native ovarian carcinoma protein or a portion thereof.

The percent identity for two polynucleotide or polypeptide sequences may be readily determined by comparing sequences using computer algorithms well known to those of ordinary skill in the art, such as Megalign, using default parameters. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned. Optimal alignment of sequences for comparison may be conducted, for example, using the Megalign program in the Lasergene suite of bioinformatics software (DNASTAR, Inc., Madison, Wis.), using default parameters. Preferably, the percentage of sequence identity is determined by comparing two optimally aligned sequences over a window of comparison of at least 20 positions, wherein the portion of the polynucleotide or polypeptide sequence in the window may comprise additions or deletions (i.e., gaps) of 20% or less, usually 5 to 15%, or 10 to 12%, relative to the reference sequence (which does not contain additions or deletions). The percent identity may be calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native ovarian carcinoma protein (or a complementary sequence). Suitable moderately stringent conditions include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotides may be prepared using any of a variety of techniques. For example, an ovarian carcinoma polynucleotide may be identified, as described in more detail below, by screening a late passage ovarian tumor expression library with antisera generated against sera of immunocompetent mice after injection of such mice with sera from SCID mice implanted with late passage ovarian tumors. Ovarian carcinoma polynucleotides may also be identified using any of a variety of techniques designed to evaluate differential gene expression. Alternatively, polynucleotides may be amplified from cDNA prepared from ovarian tumor cells. Such polynucleotides may be amplified via polymerase chain reaction (PCR). For this approach, sequence-specific primers may be designed based on the sequences provided herein, and may be purchased or synthesized.

An amplified portion may be used to isolate a full length gene from a suitable library (e.g., an ovarian carcinoma cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences are then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using, for example, software well known in the art. Primers are preferably 22–30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Additional techniques include capture PCR (Lagerstrom et al., *PCR Methods Applic.* 1:111–19, 1991) and walking PCR (Parker et al., *Nucl Acids. Res.* 19:3055–60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence.

Certain nucleic acid sequences of cDNA molecules encoding portions of ovarian carcinoma proteins are provided in FIGS. 1–15, 16A–16I, 17A–17C and 18A–18F (SEQ ID NOs:1–15, 19–68, 69–85 and 86–129). Other such nucleic acid sequences are provided in SEQ ID NOs:130–334. These polynucleotides were isolated by serological screening of an ovarian tumor cDNA expression library. The library was prepared from unamplified cDNA derived from a human ovarian tumor OV9334 grown in a SCID mouse, in the vector pScreen. Sera from human patients with ovarian cancer were pooled for the screen.

The polynucleotides recited herein, as well as full length polynucleotides comprising such sequences, other portions of such full length polynucleotides, and sequences complementary to all or a portion of such full length molecules, are specifically encompassed by the present invention. It will be apparent to those of ordinary skill in the art that this technique can also be applied to the identification of antigens that are secreted from other types of tumors.

Any of a variety of well known techniques may be used to evaluate tumor-associated expression of a cDNA. For example, hybridization techniques using labeled polynucleotide probes may be employed. Alternatively, or in addition, amplification techniques such as real-time PCR may be used (see Gibson et al., *Genome Research* 6:995–1001, 1996; Heid et al., *Genome Research* 6:986–994, 1996). Real-time PCR is a technique that evaluates the level of PCR product accumulation during amplification. This technique permits quantitative evaluation of mRNA levels in multiple samples. Briefly, mRNA is extracted from tumor and normal tissue and cDNA is prepared using standard techniques. Real-time PCR may be performed, for example, using a Perkin Elmer/Applied Biosystems (Foster City, Calif.) 7700 Prism instrument. Matching primers and fluorescent probes may be designed for genes of interest using, for example, the primer express program provided by Perkin Elmer/Applied Biosystems (Foster City, Calif.). Optimal concentrations of primers and probes may be initially determined by those of ordinary skill in the art, and control (e.g., β-actin) primers and probes may be obtained commercially from, for example, Perkin Elmer/Applied Biosystems (Foster City, Calif.). To quantitate the amount of specific RNA in a sample, a standard curve is generated alongside using a plasmid containing the gene of interest. Standard curves may be generated using the Ct values determined in the real-time PCR, which are related to the initial cDNA concentration used in the assay. Standard dilutions ranging from $10–10^6$ copies of the gene of interest are generally sufficient. In addition, a standard curve is generated for the control sequence. This permits standardization of initial RNA content of a tissue sample to the amount of control for comparison purposes.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., *DNA* 2:183, 1983). Alternatively, RNA molecules may be generated by in vitro or in vivo transcription of DNA sequences encoding an ovarian carcinoma antigen, or portion thereof, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo.

A portion of a sequence complementary to a coding sequence (i.e., an antisense polynucleotide) may also be used as a probe or to modulate gene expression. cDNA constructs that can be transcribed into antisense RNA may also be introduced into cells or tissues to facilitate the production of antisense RNA. An antisense polynucleotide may be used, as described herein, to inhibit expression of an ovarian carcinoma protein. Antisense technology can be used to control gene expression through triple-helix formation, which compromises the ability of the double helix to open sufficiently for the binding of polymerases, transcription factors or regulatory molecules (see Gee et al., In Huber and Carr, *Molecular and Immunologic Approaches,* Futura Publishing Co. (Mt. Kisco, N.Y.; 1994). Alternatively, an antisense molecule may be designed to hybridize with a control region of a gene (e.g., promoter, enhancer or transcription initiation site), and block transcription of the gene; or to block translation by inhibiting binding of a transcript to ribosomes.

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Ovarian Carcinoma Polypeptides

Within the context of the present invention, polypeptides may comprise at least an immunogenic portion of an ovarian carcinoma protein or a variant thereof, as described herein. Certain ovarian carcinoma proteins are ovarian carcinoma antigens that are expressed by ovarian tumor cells and react detectably within an immunoassay (such as an ELISA) with antisera generated against serum from an immunodeficient animal implanted with an ovarian tumor. Other ovarian carcinoma proteins are encoded by ovarian carcinoma polynucleotides recited herein. Polypeptides as described herein may be of any length. Additional sequences derived from the native protein and/or heterologous sequences may be present, and such sequences may (but need not) possess further immunogenic or antigenic properties.

An "immunogenic portion," as used herein is a portion of an antigen that is recognized (i.e., specifically bound) by a B-cell and/or T-cell surface antigen receptor. Such immunogenic portions generally comprise at least 5 amino acid residues, more preferably at least 10, and still more preferably at least 20 amino acid residues of an ovarian carcinoma protein or a variant thereof. Preferred immunogenic portions are encoded by cDNA molecules isolated as described herein. Further immunogenic portions may generally be identified using well known techniques, such as those summarized in Paul, *Fundamental Immunology,* 3rd ed., 243–247 (Raven Press, 1993) and references cited therein. Such techniques include screening polypeptides for the ability to react with ovarian carcinoma protein-specific antibodies, antisera and/or T-cell lines or clones. As used herein, antisera and antibodies are "ovarian carcinoma protein-specific" if they specifically bind to an ovarian carcinoma protein (i.e., they react with the ovarian carcinoma protein in an ELISA or other immunoassay, and do not react detectably with unrelated proteins). Such antisera, antibodies and T cells may be prepared as described herein, and using well known techniques. An immunogenic portion of a native ovarian carcinoma protein is a portion that reacts with such antisera, antibodies and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length protein. Such screens may generally be performed using methods well known to those of ordinary skill in the art, such as those described in Harlow and Lane, *Antibodies: A Laboratory Manual,* Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As noted above, a composition may comprise a variant of a native ovarian carcinoma protein. A polypeptide "variant," as used herein, is a polypeptide that differs from a native ovarian carcinoma protein in one or more substitutions, deletions, additions and/or insertions, such that the immunogenicity of the polypeptide is not substantially diminished. In other words, the ability of a variant to react with ovarian carcinoma protein-specific antisera may be enhanced or unchanged, relative to the native ovarian carcinoma protein, or may be diminished by less than 50%, and preferably less than 20%, relative to the native ovarian carcinoma protein. Such variants may generally be identified by modifying one of the above polypeptide sequences and evaluating the reactivity of the modified polypeptide with ovarian carcinoma protein-specific antibodies or antisera as described herein. Preferred variants include those in which one or more portions, such as an N-terminal leader sequence or transmembrane domain, have been removed. Other preferred variants include variants in which a small portion (e.g. 1–30 amino acids, preferably 5–15 amino acids) has been removed from the N- and/or C-terminal of the mature protein.

Polypeptide variants preferably exhibit at least about 70%, more preferably at least about 90% and most preferably at least about 95% identity to the native polypeptide. Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptides may be prepared using any of a variety of well known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast or a mammalian cell line such as COS or CHO. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J Am. Chem. Soc.* 85:2149–2146, 1963. Equipment for automated synthesis of polypeptides is commercially available from suppliers such as Applied BioSystems, Inc. (Foster City, Calif.), and may be operated according to the manufacturer's instructions.

Within certain specific embodiments, a polypeptide may be a fusion protein that comprises multiple polypeptides as described herein, or that comprises one polypeptide as described herein and a known tumor antigen, such as an ovarian carcinoma protein or a variant of such a protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. Nos. 4,935,233 and 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al. *New Engl. J. Med.,* 336:86–91, 1997).

Within preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen present cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae,* which synthesizes an N-acetyl-L-alanine amidase known as amidase LYTA (encoded by the LytA gene; *Gene* 43:265–292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795–798, 1992). Within a preferred embodiment, a repeat portion of LYTA may be incorporated into a fusion protein. A repeat portion is found in the C-terminal region starting at residue 178. A particularly preferred repeat portion incorporates residues 188–305.

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Binding Agents

The present invention further provides agents, such as antibodies and antigen-binding fragments thereof, that specifically bind to an ovarian carcinoma protein. As used herein, an antibody, or antigen-binding fragment thereof, is said to "specifically bind" to an ovarian carcinoma protein if it reacts at a detectable level (within, for example, an ELISA) with an ovarian carcinoma protein, and does not react detectably with unrelated proteins under similar conditions. As used herein, "binding" refers to a noncovalent association between two separate molecules such that a "complex" is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant maybe determined using methods well known in the art.

Binding agents may be further capable of differentiating between patients with and without a cancer, such as ovarian cancer, using the representative assays provided herein. In other words, antibodies or other binding agents that bind to a ovarian carcinoma antigen will generate a signal indicating the presence of a cancer in at least about 20% of patients with the disease, and will generate a negative signal indicating the absence of the disease in at least about 90% of individuals without the cancer. To determine whether a binding agent satisfies this requirement, biological samples (e.g., blood, sera, leukophoresis, urine and/or tumor biopsies) from patients with and without a cancer (as determined using standard clinical tests) may be assayed as described herein for the presence of polypeptides that bind to the binding agent. It will be apparent that a statistically significant number of samples with and without the disease should be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual,* Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual,* Cold Spring Harbor Laboratory, 1988) and digested by papain to yield Fab and Fc fragments. The Fab and Fc fragments may be separated by affinity chromatography on protein A bead columns.

Monoclonal antibodies of the present invention may be coupled to one or more therapeutic agents. Suitable agents in this regard include radionuclides, differentiation inducers, drugs, toxins, and derivatives thereof. Preferred radionuclides include $^{90}$Y, $^{123}$I, $^{125}$I, $^{131}$I, $^{186}$Re, $^{188}$Re, $^{211}$At, and $^{212}$Bi. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No.

4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Also provided herein are anti-idiotypic antibodies that mimic an immunogenic portion of an ovarian carcinoma protein. Such antibodies may be raised against an antibody, or antigen-binding fragment thereof, that specifically binds to an immunogenic portion of an ovarian carcinoma protein, using well known techniques. Anti-idiotypic antibodies that mimic an immunogenic portion of an ovarian carcinoma protein are those antibodies that bind to an antibody, or antigen-binding fragment thereof, that specifically binds to an immunogenic portion of an ovarian carcinoma protein, as described herein.

T Cells

Immunotherapeutic compositions may also, or alternatively, comprise T cells specific for an ovarian carcinoma protein. Such cells may generally be prepared in vitro or ex vivo, using standard procedures. For example, T cells may be present within (or isolated from) bone marrow, peripheral blood or a fraction of bone marrow or peripheral blood of a mammal, such as a patient, using a commercially available cell separation system, such as the CEPRATE™ system, available from CellPro Inc., Bothell Wash. (see also U.S. Pat. Nos. 5,240,856; 5,215,926; WO 89/06280; WO 91/16116 and WO 92/07243). Alternatively, T cells may be derived from related or unrelated humans, non-human animals, cell lines or cultures.

T cells may be stimulated with an ovarian carcinoma polypeptide, polynucleotide encoding an ovarian carcinoma polypeptide and/or an antigen presenting cell (APC) that expresses such a polypeptide. Such stimulation is performed under conditions and for a time sufficient to permit the generation of T cells that are specific for the polypeptide. Preferably, an ovarian carcinoma polypeptide or polynucleotide is present within a delivery vehicle, such as a microsphere, to facilitate the generation of specific T cells.

T cells are considered to be specific for an ovarian carcinoma polypeptide if the T cells kill target cells coated with an ovarian carcinoma polypeptide or expressing a gene encoding such a polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065–1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with an ovarian carcinoma polypeptide (200 ng/ml–100 µg/ml, preferably 100 ng/ml–25 µg/ml) for 3–7 days should result in at least a two fold increase in proliferation of the T cells and/or contact as described above for 2–3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998). T cells that have been activated in response to an ovarian carcinoma polypeptide, polynucleotide or ovarian carcinoma polypeptide-expressing APC may be $CD4^-$ and/or $CD8^+$. Ovarian carcinoma polypeptide-specific T cells may be expanded using standard techniques. Within preferred embodiments, the T cells are derived from a patient or a related or unrelated donor and are administered to the patient following stimulation and expansion.

For therapeutic purposes, $CD4^+$ or $CD8^+$ T cells that proliferate in response to an ovarian carcinoma polypeptide, polynucleotide or APC can be expanded in number either in vitro or in vivo. Proliferation of such T cells in vitro may be accomplished in a variety of ways. For example, the T cells can be re-exposed to an ovarian carcinoma polypeptide, with or without the addition of T cell growth factors, such as interleukin-2, and/or stimulator cells that synthesize an ovarian carcinoma polypeptide. Alternatively, one or more T cells that proliferate in the presence of an ovarian carcinoma polypeptide can be expanded in number by cloning. Methods for cloning cells are well known in the art, and include limiting dilution. Following expansion, the cells may be administered back to the patient as described, for example, by Chang et al., *Crit. Rev. Oncol. Hematol.* 22:213, 1996.

Pharmaceutical Compositions and Vaccines

Within certain aspects, polypeptides, polynucleotides, binding agents and/or immune system cells as described herein may be incorporated into pharmaceutical compositions or vaccines. Pharmaceutical compositions comprise one or more such compounds or cells and a physiologically acceptable carrier. Vaccines may comprise one or more such compounds or cells and a non-specific immune response enhancer. A non-specific immune response enhancer may be any substance that enhances an immune response to an exogenous antigen. Examples of non-specific immune response enhancers include adjuvants, biodegradable microspheres (e.g., polylactic galactide) and liposomes (into which the compound is incorporated; see e.g., Fullerton, U.S. Pat. No. 4,235,877). Vaccine preparation is generally described in, for example, M. F. Powell and M. J. Newman, eds., "Vaccine Design (the subunit and adjuvant approach)," Plenum Press (NY, 1995). Pharmaceutical compositions and vaccines within the scope of the present invention may also contain other compounds, which may be biologically active or inactive. For example, one or more immunogenic portions of other tumor antigens may be present, either incorporated into a fusion polypeptide or as a separate compound within the composition or vaccine.

A pharmaceutical composition or vaccine may contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *PNAS* 86:317–321, 1989;

Flexner et al., *Ann. N.Y. Acad. Sci.* 569:86–103, 1989; Flexner et al., *Vaccine* 8:17–21, 1990; U.S. Pat. Nos. 4,603, 112, 4,769,330, and 5,017,487; WO 89/01973; U.S. Pat. No.4,777,127; GB 2,200,651; EP 0,345,242; WO 91/02805; Berkner, *Biotechniques* 6:616–627, 1988; Rosenfeld et al., *Science* 252:431–434, 1991; Kolls et al., *PNAS* 91:215–219, 1994; Kass-Eisler et al., *PNAS* 90:11498–11502, 1993; Guzman et al., *Circulation* 88:2838–2848, 1993; and Guzman et al., *Cir. Res.* 73:1202–1207, 1993. Techniques for incorporating DNA into such expression systems are well known to those of ordinary skill in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Any of a variety of non-specific immune response enhancers may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.), Merck Adjuvant 65 (Merck and Company, Inc., Rahway, N.J.), alum, biodegradable microspheres, monophosphoryl lipid A and quil A. Cytokines, such as GM-CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-$\gamma$, IL-2 and IL-12) tend to favor the induction of cell mediated immune responses to an administered antigen. In contrast, high levels of Th2-type cytokines (e.g., IL-4, IL-5, IL-6, IL-10 and TNF-$\beta$) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immunol.* 7:145–173, 1989.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Ribi ImmunoChem Research Inc. (Hamilton, Mont.; see U.S. Pat. Nos. 4,436, 727; 4,877,611; 4,866,034 and 4,912,094). Also preferred is AS-2 (SmithKline Beecham). CpG-containing oligonucleotides (in which the CpG dinucleotide is unmethylated) also induce a predominantly Th1 response. Such oligonucleotides are well known and are described, for example, in WO 96/02555. Another preferred adjuvant is a saponin, preferably QS21, which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprises an oil-in-water emulsion and tocopherol. A particularly potent adjuvant formulation involving QS21, 3D-MPL and tocopherol in an oil-in-water emulsion is described in WO 95/17210. Any vaccine provided herein may be prepared using well known methods that result in a combination of antigen, immune response enhancer and a suitable carrier or excipient.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets tumor cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, *Nature* 392:245–251, 1998) and have been shown to be effective as a physiological adjuvant for eliciting prophylactic or therapeutic antitumor immunity (see Timmerman and Levy, *Ann. Rev. Med.* 50:507–529, 1999). In general, dendritic cells may be identified based on their typical shape (stellate in situ, with marked cytoplasmic processes (dendrites) visible in vitro) and based on the lack of differentiation markers of B cells (CD19 and CD20), T cells (CD3), monocytes (CD14) and natural killer cells (CD56), as determined using standard assays. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., *Nature Med.* 4:594–600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor, mannose receptor and DEC-205 marker. The mature phenotype is typically characterized by a lower expression of these markers, but a high expression of cell surface molecules responsible for T cell activation such as class I and class II MIHC, adhesion molecules (e.g., CD54 and CD11) and costimulatory molecules (e.g., CD40, CD80 and CD86).

APCs may generally be transfected with a polynucleotide encoding a ovarian carcinoma antigen (or portion or other variant thereof) such that the antigen, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and cell Biology* 75:456–460, 1997. Antigen loading of dendritic cells may be achieved by incubating dendritic cells or progenitor cells with the polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Cancer Therapy

In further aspects of the present invention, the compositions described herein may be used for immunotherapy of cancer, such as ovarian cancer. Within such methods, pharmaceutical compositions and vaccines are typically administered to a patient. As used herein, a "patient" refers to any warm-blooded animal, preferably a human. A patient may or may not be afflicted with cancer. Accordingly, the above pharmaceutical compositions and vaccines may be used to prevent the development of a cancer or to treat a patient afflicted with a cancer. Within certain preferred embodiments, a patient is afflicted with ovarian cancer. Such cancer may be diagnosed using criteria generally accepted in the art, including the presence of a malignant tumor. Pharmaceutical compositions and vaccines may be administered either prior to or following surgical removal of primary tumors and/or treatment such as administration of radiotherapy or conventional chemotherapeutic drugs.

Within certain embodiments, immunotherapy may be active immunotherapy, in which treatment relies on the in vivo stimulation of the endogenous host immune system to react against tumors with the administration of immuno response-modifying agents (such as tumor vaccines, bacterial adjuvants and/or cytokines).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T lymphocytes (such as CD8$^+$ cytotoxic T lymphocytes and CD4$^-$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

Alternatively, a vector expressing a polypeptide recited herein may be introduced into stem cells taken from a patient and clonally propagated in vitro for autologous transplant back into the same patient.

Routes and frequency of administration, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration), orally or in the bed of a resected tumor. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g. more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 100 µg to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to an ovarian carcinoma antigen generally correlate with an improved clinical outcome. Such immune responses may generally be evaluated using standard proliferation, cytotoxicity or cytokine assays, which may be performed using samples obtained from a patient before and after treatment.

Methods for Detecting Cancer

In general, a cancer may be detected in a patient based on the presence of one or more ovarian carcinoma proteins and/or polynucleotides encoding such proteins in a biological sample (such as blood, sera, urine and/or tumor biopsies) obtained from the patient. In other words, such proteins may be used as markers to indicate the presence or absence of a cancer such as ovarian cancer. In addition, such proteins may be useful for the detection of other cancers. The binding agents provided herein generally permit detection of the level of protein that binds to the agent in the biological sample. Polynucleotide primers and probes may be used to detect the level of mRNA encoding a tumor protein, which is also indicative of the presence or absence of a cancer. In general, an ovarian carcinoma-associated sequence should be present at a level that is at least three fold higher in tumor tissue than in normal tissue.

There are a variety of assay formats known to those of ordinary skill in the art for using a binding agent to detect polypeptide markers in a sample. See, e.g., Harlow and Lane, *Antibodies: A Laboratory Manual,* Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length ovarian carcinoma proteins and portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 µg, and preferably about 100 ng to about 1 µg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with ovarian cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as ovarian cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine,* Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 $\mu$g, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those of ordinary skill in the art that the above protocols may be readily modified to use ovarian carcinoma polypeptides to detect antibodies that bind to such polypeptides in a biological sample. The detection of such ovarian carcinoma protein specific antibodies may correlate with the presence of a cancer.

A cancer may also, or alternatively, be detected based on the presence of T cells that specifically react with an ovarian carcinoma protein in a biological sample. Within certain methods, a biological sample comprising CD4$^+$ and/or CD8$^+$ T cells isolated from a patient is incubated with an ovarian carcinoma protein, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2–9 days (typically 4 days) at 37° C. with an ovarian carcinoma protein (e.g., 5–25 μg/ml). It may be desirable to incubate another aliquot of a T cell sample in the absence of ovarian carcinoma protein to serve as a control. For CD4$^+$ T cells, activation is preferably detected by evaluating proliferation of the T cells. For CD8$^+$ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding an ovarian carcinoma protein in a biological sample. For example, at least two oligonucleotide primers may be employed in a polymerase chain reaction (PCR) based assay to amplify a portion of an ovarian carcinoma protein cDNA derived from a biological sample, wherein at least one of the oligonucleotide primers is specific for (i.e., hybridizes to) a polynucleotide encoding the ovarian carcinoma protein. The amplified cDNA is then separated and detected using techniques well known in the art, such as gel electrophoresis. Similarly, oligonucleotide probes that specifically hybridize to a polynucleotide encoding an ovarian carcinoma protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding an ovarian carcinoma protein that is at least 10 nucleotides, and preferably at least 20 nucleotides, in length. Preferably, oligonucleotide primers and/or probes hybridize to a polynucleotide encoding a polypeptide described herein under moderately stringent conditions, as defined above. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule having a sequence provided herein. Techniques for both PCR based assays and hybridization assays are well known in the art (see, for example, Mullis et al., *Cold Spring Harbor Symp. Quant. Biol.*, 51:263, 1987; Erlich ed., *PCR Technology*, Stockton Press, N.Y., 1989).

One preferred assay employs RT-PCR, in which PCR is applied in conjunction with reverse transcription. Typically, RNA is extracted from a biological sample such as a biopsy tissue and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another embodiment, ovarian carcinoma proteins and polynucleotides encoding such proteins may be used as markers for monitoring the progression of cancer. In this embodiment, assays as described above for the diagnosis of a cancer may be performed over time, and the change in the level of reactive polypeptide(s) evaluated. For example, the assays may be performed every 24–72 hours for a period of 6 months to 1 year, and thereafter performed as needed. In general, a cancer is progressing in those patients in whom the level of polypeptide detected by the binding agent increases over time. In contrast, the cancer is not progressing when the level of reactive polypeptide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple ovarian carcinoma protein markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

Diagnostic Kits

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to an ovarian carcinoma protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding an ovarian carcinoma protein in a biological sample. Such kits generally comprise at least one oligonucleotide probe or primer, as described above, that hybridizes to a polynucleotide encoding an ovarian carcinoma protein. Such an oligonucleotide may be used, for example, within a PCR or hybridization assay. Additional components that may be present within such kits include a second oligonucleotide and/or a diagnostic reagent or container to facilitate the detection of a polynucleotide encoding an ovarian carcinoma protein.

The following Examples are offered by way of illustration and not by way of limitation.

EXAMPLES

Example 1

Identification of Ovarian Tumor Antigen cDNAs

This Example illustrates the identification of cDNA molecules encoding ovarian tumor antigens.

Patient sera (from two human patients with ovarian cancer) was adsorbed against *E. coli* and used at a 1:200 dilution in a serological expression screen performed as described in Sambrook et al., *Molecular Cloning: A Laboratory Manual,* Cold Spring Harbor Laboratories, Cold Spring Harbor, N.Y., 1989. The library screened was made from a SCID-derived human ovarian tumor (OV9334) using a directional RH oligo(dT) priming cDNA library construction kit and the λScreen vector (Novagen). Approximately 600,000 pfu of the amplified OV9334 library were screened.

In a first screen, three novel clones were identified (OV10, OV17 and OV41), and the partial sequences are provided in FIGS. 5, 8 and 13 (SEQ ID NOs: 5, 8 and 13), respectively. Additional sequences matched previously identified genes, which were not previously known to be associated with ovarian carcinoma. These sequences are identified in Table I.

TABLE 1

Additional Ovarian Carcinoma Antigen Partial Sequences

| Sequence | Match |
|---|---|
| OV6 (SEQ ID NO:3) | High Mobility Group Protein 14 |
| OV2 (SEQ ID NO:1) | Hypothetical 33.4 kD Protein |
| OV3 (SEQ ID NO:2) | High Mobility Group Protein 17 |
| OV9 (SEQ ID NO:4) | Integrin Alpha-3 |

TABLE 1-continued

Additional Ovarian Carcinoma Antigen Partial Sequences

| Sequence | Match |
|---|---|
| OV12 (SEQ ID NO:6) | Filamental Protein |
| OV14 (SEQ ID NO:7) | Ubiquitin-Conjugating Enzyme |
| OV18 (SEQ ID NO:9) | Alpha-Glucosidase I |
| OV23 (SEQ ID NO:10) | Ribosomal Protein L10 |
| OV24 (SEQ ID NO:11) | Mitochondrial Gene |
| OV27 (SEQ ID NO:12) | Ribonucleoprotein |
| OV54 (SEQ ID NO:14) | Ribosomal Protein L18 |
| OV57 (SEQ ID NO:15) | Ribosomal Protein S10 |

Within a second screens further clones were identified. Homologies for these clones are provided in Table II. Sequences of novel clones are provided in FIGS. 16A–16I (SEQ ID NOs:19–68). Those clones for which homology was found in the DNA sequence, but not the protein sequence, are provided in FIGS. 17A–17C (SEQ ID NOs:69–85), and those that matched previously identified DNA and protein sequences, which were not previously known to be associated with ovarian carcinoma, are provided in FIGS. 18A–18F (SEQ ID NOs:86–129).

TABLE II

Further Ovarian Carcinoma Antigen Partial Sequences

| Sequence | SEQ ID | DNA Homology | Protein Homology |
|---|---|---|---|
| OVp2-1 | 86 | AND-1 | AND-1 |
| OVp2-2 | 19 | Novel | Novel |
| OVp2-4 | 87 | Topoisom. II | Topoisom. II |
| OVp2-5 | 88 | cAMP phosphodiesterase | cAMP phosphodiesterase |
| OVp2-6 | 89 | P1 | P1 |
| OVp2-9 | 90 | kinase PRKAR1A | kinase PRKAR1A |
| OVp2-10 | 91 | Human RNA polym. II | Human RNA polym. II |
| OVp2-11 | 92 | Mu. p162 | Mu. p162 |
| OVp2-13 | 20 | Novel | Novel |
| OVp2-14 | 21 | Novel | Novel |
| OVp2-15 | 69 | Hu. BAC G5541B18 | Novel |
| OVp2-16 | 93 | Hu. fanconi anemia mRNA | FAA |
| OVp2-17 | 94 | Hu. histone H1 | Histone H1 |
| OVp2-20 | 22 | Novel | Novel |
| OVp2-21 | 23 | Novel | Novel |
| OVp2-22 | 70 | Hu K1AA0642 mRNA | Novel |
| OVp2-23 | 95 | Hu. lysophospholipase mRNA | Hu. lysophospholipase mRNA |
| OVp2-24 | 71 | Hu. Chrom 16 cosmid clone 400D1 | Novel |
| OVp2-25 | 24 | Novel | Novel; similar to PHD finger protein |
| OVp2-27 | 25 | Novel | Novel |
| OVp2-28 | 26 | Novel | Novel |
| OVp2-29 | 27 | Novel | Novel |
| OVp2-31 | 28 | Novel | Novel |
| OVp2-37 | 29 | Novel | Novel |
| OVp2-38 | 30 | Novel | Novel |
| OVp2-39 | 96 | Human Tumor protein | Human Tumor protein |
| OVp2-40 | 31 | Novel | Novel |
| OVp2-42 | 32 | Novel | Novel |
| OVp2-43 | 97 | nucleophosmin | nucleophosmin |
| OVp2-47 | 72 | Hu PAC DJ0751H13 | Novel; zinc finger-like |
| OVp2-48 | 98 | Human Carbonyl Reductase | Carbonyl Reductase |
| OVp2-52 | 33 | Novel | Novel |
| OVp2-54 | 99 | Mu., Hu. chromatin structrl pro. | Mu., Hu. chromatin structrl pro. |
| OVp2-55 | 73 | Hu. mRNA clone A33187 | Novel; similar to laminin |
| OVp2-56 | 34 | Novel | Novel |
| OVp2-58 | 100 | H3.3 Histone | H3.3 Histone |

TABLE II-continued

Further Ovarian Carcinoma Antigen Partial Sequences

| Sequence | SEQ ID | DNA Homology | Protein Homology |
|---|---|---|---|
| OVp2-59 | 101 | cyt.C oxidase subunit | cyt.C oxidase subunit |
| OVp2-60 | 35 | Novel | Novel |
| OVp2-66 | 102 | alpha-CP1; rnp-assoc. | alpha-CP1; rnp-assoc. |
| OVp2-69 | 36 | Novel | Novel |
| OVp2-71 | 37 | Novel | Novel |
| OVp2-81 | 74 | HuCpG DNA clone 11B11 | Novel |
| OVp2-82 | 103 | Human KIAA0111 gene | Euk Init'n Factor 4A-like |
| OVp2-83 | 38 | Novel | Novel |
| OVp2-84 | 39 | Novel | Novel |
| OVp2-85 | 40 | Novel | Novel |
| OVp2-87 | 41 | Novel | Novel |
| OVp2-88 | 42 | Novel | Novel |
| OVp2-90 | 43 | Novel | Novel |
| OVp2-91 | 104 | Mu, Hu cathepsinC | Mu, Hu cathepsinC |
| OVp2-93 | 44 | Novel | Novel |
| OVp2-94 | 45 | Novel | Novel |
| OVp2-98 | 46 | Novel; Carbonyl Reductase (pig) | Novel |
| OVp2-99 | 47 | Novel | Novel |
| OVp2-100 | 75 | Human K1AA0788 | Novel |
| OVp2-103 | 105 | Human tra gp96 | tra gp96 |
| OVp2-104 | 76 | Hu BAC clone 78c6 | Novel |
| OVp2-106 | 106 | Ubiq-conj. enz; carcinoma | Ubiquitin-conjugating enzyme |
| OVp2-108 | 77 | KIAA0249 | Novel |
| OVp2-109 | 107 | Mu.p162 | Mu.p162 |
| OVp2-110 | 48 | Novel | Novel |
| OVp3-2 | 108 | Mu. Acyl-CoA dehydrog. | Mu. Acyl-CoA dehydrog. |
| OVp3-3 | 78 | Hu. Chrom 17, hRPC.117 | Novel |
| OVp3-4 | 49 | Novel | Novel |
| OVp3-5 | 79 | Unkn. Hu. DNA; | Novel |
| OVp3-6 | 109 | Mu. retrotranspsn. | Mu. ORF; carcinoma |
| OVp3-7 | 110 | Hu. glypican4 | Glypican precursor |
| OVp3-8 | 50 | Novel | Novel |
| OVp3-9 | 80 | Mu. entactin | Novel |
| OVp3-11 | 51 | Novel | Novel |
| OVp3-17 | 111 | Elongation Factor 1 alpha | EF-1 alpha |
| OVp3-19 | 52 | Novel | Novel |
| OVp3-23 | 81 | Hu. RES4-4 (brain) | Novel |
| OVp3-24 | 112 | Hu. P8; mitogen | Hu. P8 |
| OVp3-26 | 113 | Hu ribosomal. L18 | Hu ribosomal. L18 |
| OVp3-28 | 114 | Hu KS/14 antigen | Tumor-assoc. glycoprotein |
| OVp3-29 | 115 | Hu. Actin-binding | Hu. Actin-binding |
| OVp3-31 | 53 | Novel | Novel |
| OVp3-34 | 116 | Hu DPM1 | Hu DPM1 |
| OVp3-36 | 117 | Hu PAC DJ269O05 | Hu. Line-1 homolog; putative p150 |
| OVp3-37 | 118 | Mu. fibronectin/precursor (Hu) | fibronectin |
| OVp3-38 | 54 | Novel | Novel |
| OVp3-40 | 55 | Novel | Novel |
| OVp3-41 | 56 | Novel | Novel |
| OVp3-44 | 57 | Novel | Novel |
| OVp3-47 | 58 | Novel | Novel |
| OVp3-50 | 82 | Chrom.; PAC | Novel; similar to p40, 40 kD |
| OVp3-51 | 59 | Novel; 86% Mu. oncogene ect2 | Novel; Mu ect2 |
| OVp3-52 | 119 | RAC3 (Hu Rac3) | Ras-like; G protein; Rac3 |
| OVp3-53 | 120 | (Hu) alpha-enolase | alpha-enolase; carbonate hydratase(Hu) |
| OVp3-54 | 121 | Hu. Nuclr. NP220 | NP220 |
| OVp3-64 | 60 | Novel | Novel |
| OVp3-66 | 83 | Hu. mitochond. DNA | Novel; similar to cyt.C oxidase subunit |
| OVp3-70 | 61 | Novel | Novel |
| OVp3-71 | 62 | Novel | Novel |
| OVp3-81 | 63 | Novel | Novel |
| OVp3-83 | 122 | RNA binding factor | Unknown |
| OVp3-84 | 84 | Hu PAC RPC13-197B17 | Novel |
| OVp3-86 | 123 | Cathepsin C | Cathepsin C |
| OVp3-87 | 64 | Novel | Novel |
| OVp3-88 | 65 | Novel | Novel |
| OVp3-90 | 124 | Human EF-1 alpha | Human EF-1 alpha |
| OVp3-91 | 125 | Human nuclear factor NF-IL6 | similar to Hu. nuclear factor NF-IL6 |
| OVp3-94 | 126 | Hu. polyadenylate-binding PAIP1 | polyadenylate-binding |
| OVp3-95 | 127 | Human TAK1-binding | Unknown |
| OVp3-97 | 128 | Hu ribosomal L27 | Hu ribosomal L27 |

TABLE II-continued

Further Ovarian Carcinoma Antigen Partial Sequences

| Sequence | SEQ ID | DNA Homology | Protein Homology |
|---|---|---|---|
| OVp3-101 | 129 | Human cytoskeletal g-actin | Unknown |
| OVp3-104 | 85 | mitochondrial; Hu. clone 23884 | Novel |
| OVp3-107 | 66 | Novel | Novel |
| OVp3-110 | 67 | Novel | Novel |
| OVp3-127 | 68 | Novel | Novel; 50% homology to human hepatoma-derived growth factor |

Still further ovarian carcinoma sequences are presented in Table III and SEQ ID NOs: 130–334.

TABLE III

Further Ovarian Carcinoma Antigen Partial Sequences

| Clone No. | Sequence | SEQ ID NO | Homology |
|---|---|---|---|
| OVp2-3 | 15674.2 | 130 | Novel |
| OVp2-8 | 15679.2 | 131 | A.t BAC F21E10; ESTs |
| OVp2-26 | 20045.1 | 132 | Human 1-mf; ETS |
| OVp2-33 | 20047.1 | 133 | Novel; ESTs |
| OVp2-34 | 20056.1 | 134 | BiP, GRP; ESTs |
| OVp2-45 | 17295.1 | 135 | Human Chrom 16; ESTs |
| OVp2-49 | 20209.1 | 136 | Human C9ORF3 short isoform; ESTs |
| OVp2-53 | 16111.2 | 137 | Novel; ESTs |
| OVp2-61 | 22421.1 | 138 | Novel |
| OVp2-62 | 22422.1 | 139 | TNF-α stimulated ATP-binding; ESTs |
| OVp2-63 | 22423.1 | 140 | Human.DNA from phage pTELchrom. 16p13.3; ESTs |
| OVp2-64 | 22424.1 | 141 | Human mRNA for fibronectin; ESTs |
| OVp2-65 | 22425.1 | 142 | Novel; ESTs |
| OVp2-74 | 22428.1 | 143 | Human deoxyhypusine synthase mRNA; ESTs |
| OVp2-75 | 22430.1 | 144 | Novel |
| OVp2-76 | 22431.1 | 145 | Novel; ESTs |
| OVp2-77 | 22432.1 | 146 | Novel; ESTs |
| OVp2-78 | 22433.1 | 147 | Human.cDNA DKFZp586E0518; ESTs |
| OVp2-79 | 22434.1 | 148 | Human DNA cosmid U131B10 |
| OVp2-95 | 20213.1 | 149 | Hu. Protective protein; ESTs |
| OVp2-97 | 20214.1 | 150 | Plasma protein S; ESTs |
| OVp2-107 | 20216.1 | 151 | Human epiderm al carcinoma mRNA for E2; ESTs |
| OVp2-113 | 20496.1 | 152 | Human Histone H1'; ESTs |
| OVp2-114 | 20497.1 | 153 | Novel |
| OVp2-116 | 18077.1 | 154 | Human Pyruvate dehydrogenase kinase; EST |
| OVp2-119 | 18078.1 | 155 | Human K1AA0803, BAC clone; ESTs |
| OVp2-121 | 20498.1 | 156 | Murine DNA-binding, Zn Finger; ESTs |
| OVp2-122 | 18085.1 | 157 | Rat trg |
| OVp2-124 | 20500.1 | 158 | Novel; ESTs |
| OVp2-127 | 18084.1 | 159 | Human Cosmid F23149 |
| OVp2-128 | 20501.1 | 160 | Human GlcNac 1-P transferase; ESTs |
| OVp2-129 | 20502.1 | 161 | Novel; EST |
| OVp2-131 | 18573.2 | 162 | Human laminin alpha 5 chain; ESTs |
| OVp2-133 | 18574.1 | 163 | Novel |
| OVp2-134 | 18345.1 | 164 | Human tazarotene-induced gene 2; ESTs |
| OVp2-135 | 18575.1 | 165 | Actin-binding P57, coronin-like; ESTs |
| OVp2-139 | 18728.1 | 166 | Human clone 1033D10; includes BING5; ESTs |
| OVp2-141 | 18577.1 | 167 | Human cosmid F23149; EST |
| OVp2-143 | 18881.1 | 168 | c-myc proto-oncogene; ESTs |
| OVp2-144 | 18882.1 | 169 | Murine, Human nucleic acid-binding protein; ESTs |
| OVp2-146 | 18884.1 | 170 | Novel; ESTs |
| OVp2-147 | 18885.1 | 171 | Human B23 nucleophosmin; ESTs |
| OVp2-148 | 18886.1 | 172 | cation-dependent Human, Murine MP-6R; ESTs |
| OVp2-150 | 18889.1 | 173 | Human FXR1; ESTs |
| OVp2-152 | 18891.1 | 174 | Human KIAA0465; ESTs |
| OVp2-153 | 18892.1 | 175 | Human α-2macroglobin receptor assoc; ESTs |

TABLE III-continued

Further Ovarian Carcinoma Antigen Partial Sequences

| Clone No. | Sequence | SEQ ID NO | Homology |
|---|---|---|---|
| OVp2-158 | 20027.1 | 176 | Topoisomerase II; ESTs |
| OVp2-160 | 20028.1 | 177 | Novel |
| OVp2-162 | 20029.1 | 178 | Novel |
| OVp2-167 | 20035.1 | 179 | K1AA0630; ESTs |
| OVp2-169 | 20037.1 | 180 | Novel |
| OVp2-171 | 20039.1 | 181 | Novel; ESTs |
| OVp2-172 | 20072.1 | 182 | Novel |
| OVp2-174 | 20031.1 | 183 | mig-2; ESTs |
| OVp2-179 | 20040.1 | 184 | Novel; ESTs |
| OVp2-180 | 20041.1 | 185 | Antiquin; turgor protein; ESTs |
| OVp2-184 | 20044.1 | 186 | Human ribosomal P1; ESTs |
| OVp2-185 | 20057.1 | 187 | Novel; ESTs |
| OVp2-187 | 20074.1 | 188 | MuLV env |
| OVp2-188 | 20075.1 | 189 | Novel; EST |
| OVp2-189 | 20058.1 | 190 | Novel; EST |
| OVp2-190 | 20059.1 | 191 | Gonadotropin-Reg Hormone Producing; ESTs |
| OVp2-191 | 21502.1 | 192 | Novel; ESTs |
| OVp2-192 | 21503.1 | 193 | 18S rRNA, DNA; ESTs |
| OVp2-193 | 21504.1 | 194 | Arg-rich Nuclear Protein; ESTs |
| OVp2-194 | 21505.1 | 195 | Novel; ESTs |
| OVp2-195 | 21506.1 | 196 | Novel; ESTs |
| OVp2-196 | 21507.1 | 197 | Human Clone 406A7; ESTs |
| OVp2-197 | 21508.1 | 198 | Novel; ESTs |
| OVp2-204 | 22128.1 | 199 | Human Mitochondrial DNA; ESTs |
| OVp2-206 | 22129.1 | 200 | Human chrom. DNA for RAD23A; ESTs |
| OVp2-207 | 22130.1 | 201 | Human clone 24921 mRNA; ESTs |
| OVp2-208 | 22131.1 | 202 | Human 4F5rel mRNA; ESTs |
| OVp2-209 | 22133.1 | 203 | Human ribosomal pro. S6 kinase.SW1/SNF related; ESTs |
| OVp2-211 | 22134.1 | 204 | Human beta-glucuronidase (BG) mRNA; ESTs |
| OVp2-212 | 22135.1 | 205 | Human DNA for hnRNP protein A2/B1; ESTs |
| OVp2-215 | 22137.1 | 206 | Human translocation protein 1; ESTs |
| OVp2-216 | 22138.1 | 207 | Human chromosone X orf5; ESTs |
| OVp2-217 | 22139.1 | 208 | Human ribosomal protein S19; ESTs |
| OVp2-218 | 22140.1 | 209 | Murine mRNA for histone H3.3A; ESTs |
| OVp2-220 | 22141.1 | 210 | Human PAC 434P1; ESTs |
| OVp2-221 | 22142.1 | 211 | Human AKAP450.K1AA0803.Hyperion; ESTs |
| OVp2-222 | 22144.1 | 212 | Human HRFX2 mRNA, DNA binding |
| OVp2-223 | 22145.1 | 213 | Human NF-kappa-B transcrip'n factor p65; ESTs |
| OVp2-225 | 22146.1 | 214 | Novel |
| OVp2-226 | 22147.1 | 215 | Novel |
| OVp2-228 | 22148.1 | 216 | Novel; ESTs |
| OVp2-229 | 22149.1 | 217 | Human mitochondrial genes; ESTs |
| OVp2-230 | 22150.1 | 218 | O. cuniculus endooligopeptidase A related protein; ESTs |
| OVp2-232 | 22152.1 | 219 | Human clone A9A2BR11; Mu Zfr |
| OVp2-233 | 22153.1 | 220 | Human KIAA0098; Murine chaperonin containg TCP-1; ESTs |
| OVp2-238 | 22154.1 | 221 | human DNA seq. from PAC 93H18; ESTs |
| OVp2-239 | 22155.1 | 222 | Novel |
| OVp2-241 | 22156.1 | 223 | Human glutathione S-transferase theta 1; ESTs |
| OVp2-243 | 22157.1 | 224 | Human TCB.OIP3, pyruvate kinase; ESTs |
| OVp2-244 | 22158.1 | 225 | Human mRNA for KIAA0250 gene; EST |
| OVp2-250 | 22160.1 | 226 | Human complement component C4A mRNA; EST |
| OVp2-251 | 22161.1 | 227 | Novel; EST |
| OVp2-252 | 22162.1 | 228 | Novel; EST |
| OVp2-253 | 22163.1 | 229 | Human. G protein Golf alpha gene; ESTs |
| OVp2-254 | 22164.1 | 230 | Novel; ESTs |
| OVp2-257 | 22897.1 | 231 | Novel; ESTs |
| OVp2-258 | 22440.1 | 232 | Human chrom 16. cosmid clone 399H11; ESTs |
| OVp2-259 | 22441.1 | 233 | human cDNA DKFZp564B112; ESTs |
| OVp2-260 | 22898.1 | 234 | Novel; ESTs |
| OVp2-262 | 22442.1 | 235 | Human mRNA for ribosomal protein L31; ESTs |
| OVp2-265 | 22899.1 | 236 | Human TNF receptor mRNA; ESTs |
| OVp2-266 | 22445.1 | 237 | Human 12q13.1 PAC RPC11-228P16 |
| OVp2-270 | 22447.1 | 238 | Hu. cDNA DKFZp586F1523; ESTs |

TABLE III-continued

Further Ovarian Carcinoma Antigen Partial Sequences

| Clone No. | Sequence | SEQ ID NO | Homology |
|---|---|---|---|
| OVp2-273 | 22450.1 | 239 | Homo sapiens cytochrome b-245; ESTs |
| OVp2-276 | 22451.1 | 240 | Novel; ESTs |
| OVp2-279 | 22454.1 | 241 | Novel; ESTs |
| OVp2-282 | 22903.1 | 242 | Novel; ESTs |
| OVp2-283 | 22904.1 | 243 | Human K1AA9001 mRNA,R1N63; ESTs |
| OVp2-284 | 22905.1 | 244 | Novel; ESTs |
| OVp2-285 | 22906.1 | 245 | Novel; ESTs |
| OVp2-287 | 22907.1 | 246 | Novel |
| OVp3-15 | 20048.1 | 247 | JM26; ESTs |
| OVp3-27 | 20049.1 | 248 | mult. Human BAC; Linel; ESTs |
| OVp3-42 | 20050.1 | 249 | Tyrosine phosphatase; ESTs |
| OVp3-58 | 20052.1 | 250 | Novel; ESTs |
| OVp3-61 | 20060.1 | 251 | Novel; ESTs |
| OVp3-73 | 20064.1 | 252 | glypican-4 |
| OVp3-74 | 20065.1 | 253 | Novel; ESTs |
| OVp3-78 | 20069.1 | 254 | Novel |
| OVp3-80 | 20053.1 | 255 | MLN 50 RNA; EST |
| OVp3-89 | 20217.1 | 256 | Novel |
| OVp3-108 | 20222.1 | 257 | Human parathymosin; ESTs |
| OVp3-109 | 20223.1 | 258 | Human eryth/α-adductin; ESTs |
| OVp3-114 | 18080.1 | 259 | Novel |
| OVp3-115 | 20225.1 | 260 | Human JM26; ESTs |
| OVp3-116 | 20226.1 | 261 | Novel; ESTs |
| OVp3-120 | 20503.1 | 262 | Human K1AA0875; ESTs |
| OVp3-121 | 20227.1 | 263 | Human Guanine-binding; ESTs |
| OVp3-122 | 20228.1 | 264 | Novel; ESTs |
| OVp3-123 | 18086.1 | 265 | Novel |
| OVp3-124 | 18087.1 | 266 | Human transposon L1.2; ESTs |
| OVp3-127 | 18089.1 | 267 | low sim. to Mu. Hepatoma GF; ESTs |
| OVp3-129 | 20504.1 | 268 | Human β spectrin (actin-binding); ESTs |
| OVp3-130 | 18347.1 | 269 | BAC GS083B20; Linel, p150; ESTs |
| OVp3-131 | 18348.1 | 270 | glutathione S-transferase; ESTs |
| OVp3-132 | 18349.1 | 271 | Human mRNA KIAA0710; EST |
| OVp3-136 | 20506.1 | 272 | Novel; ESTs |
| OVp3-137 | 18731.1 | 273 | Novel; ESTs |
| OVp3-142 | 20508.1 | 274 | Novel |
| OVp3-144 | 18735.1 | 275 | Novel; EST |
| OVp3-147 | 18738.1 | 276 | K1AA0941, PGEMEX; ESTs |
| OVp3-148 | 20510.1 | 277 | Polyubiquitin; ESTs |
| OVp3-149 | 18894.1 | 278 | Novel; ESTs |
| OVp3-150 | 18895.1 | 279 | Human SWI/SNF; ESTs |
| OVp4-1 | 20017.1 | 280 | Novel; EST |
| OVp4-2 | 20018.1 | 281 | Human KIAA0241; ESTs |
| OVp4-4 | 20019.1 | 282 | Novel; ESTs |
| OVp4-6 | 20020.1 | 283 | Novel; ESTs |
| OVp4-7 | 20021.1 | 284 | laminin-binding; ESTs |
| OVp4-8 | 20022.1 | 285 | okadaic-acid-inducible; ESTs |
| OVp4-10 | 20023.1 | 286 | MAC25; ESTs |
| OVp4-13 | 20054.1 | 287 | Novel; ESTs |
| OVp4-14 | 20055.1 | 288 | Novel |
| OVp4-15 | 20076.1 | 289 | Human HSP; ESTs |
| OVp4-16 | 20077.1 | 290 | Clathrin; δ3A (AP-3 complex); ESTs |
| OVp4-18 | 20078.1 | 291 | Novel; ESTs |
| OVp4-20 | 20070.1 | 292 | Novel |
| OVp4-22 | 20229.1 | 293 | Human β-Catenin; ESTs |
| OVp4-22A | 20511.1 | 294 | llPPL1 (51C); DNA repair; ESTs |
| OVp4-23 | 20230.1 | 295 | Transcrp'n Fact. AP-1, JUN A, C-JUN; ESTs |
| OVp4-24 | 20231.1 | 296 | Novel; ESTs |
| OVp4-25 | 20512.1 | 297 | Novel; ESTs |
| OVp4-26 | 20232.1 | 298 | ribosomal P0; ESTs |
| OVp4-26A | 20538.1 | 299 | Novel; ESTs |
| OVp4-28 | 20234.1 | 300 | Transcrp'n Factor S-II; ESTs |
| OVp4-29 | 20235.1 | 301 | Novel; ESTs |
| OVp4-30 | 20236.1 | 302 | Human AHNAK; neuroblast diff'n.; ESTs |
| OVp4-31 | 20237.1 | 303 | CD81(TAPA-1) cell surface; ESTs |
| OVp4-33 | 20545.1 | 304 | Novel; ESTs |
| OVp4-34 | 20546.1 | 305 | Novel |
| OVp4-35 | 20547.1 | 306 | Novel; ESTs |
| OVp4-36 | 21510.1 | 307 | Novel |
| OVp4-37 | 20548.1 | 308 | Novel; ESTs |
| OVp4-38 | 22166.1 | 309 | Novel; ESTs |
| OVp4-40 | 20549.1 | 310 | Human Profilin; EST |
| OVp4-43 | 20551.1 | 311 | Novel |
| OVp4-44 | 20552.1 | 312 | Human 30M3; ESTs |

TABLE III-continued

Further Ovarian Carcinoma Antigen Partial Sequences

| Clone No. | Sequence | SEQ ID NO | Homology |
|---|---|---|---|
| OVp4-45 | 20553.1 | 313 | Chrom. 14 specific cosmid |
| OVp4-46 | 20554.1 | 314 | Novel; ESTs |
| OVp4-47 | 20555.1 | 315 | EF-1 α; ESTs |
| OVp4-48 | 20556.1 | 316 | B-CAM mRNA; EST |
| OVp4-49 | 20557.1 | 317 | Novel |
| OVp4-51 | 20559.1 | 318 | Human N-cadherin; ESTs |
| OVp4-52 | 20560.1 | 319 | Human p16INK4/MTS1; ESTs |
| OVp4-53 | 20561.1 | 320 | Human RNA helicase |
| OVp4-54 | 20562.1 | 321 | Murine Fibronectin; ESTs |
| OVp4-55 | 20778.1 | 322 | RibosomalS6(kinase substrate); ESTs |
| OVp4-56 | 20779.1 | 323 | Novel; ESTs |
| OVp4-58 | 20781.1 | 324 | CPG island DNA; EST |
| OVp4-59 | 20782.1 | 325 | Human KIAA 0241; ESTs |
| OVp4-61 | 20784.1 | 326 | Human PAC; EST |
| OVp4-62 | 20785.1 | 327 | Na/H reg. factor; ESTs |
| OVp4-63 | 20786.1 | 328 | Ferritin Heavy Chain; ESTs |
| OVp4-64 | 20787.1 | 329 | MHC -1 H2; ESTs |
| OVp4-66 | 20789.1 | 330 | RNA Helicase-related; ESTs |
| OVp4-70 | 20793.1 | 331 | BC-2protein RNA; ESTs |
| OVp4-72 | 20795.1 | 332 | Phosphorylase Kinase; ESTs |
| OVp4-73 | 20796.1 | 333 | Novel |
| OVp4-74 | 20797.1 | 334 | Human clone 327J16; ESTs |

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for determining the presence or absence of a cancer in a patient, comprising the steps of:

(a) contacting a biological sample obtained from a patient with an oligonucleotide that hybridizes to a polynucleotide sequence selected from the group consisting of:

(i) a polynucleotide recited in SEQ ID NO:87; and
(ii) complement of the foregoing polynucleotide;
(b) detecting in the sample an amount of a polynucleotide that hybridizes to the oligonucleotide; and
(c) comparing the amount of polynucleotide that hybridizes to the oligonucleotide to a predetermined cut-off value, and therefrom determining the presence or absence of a cancer in the patient.

2. A method according to claim 1, wherein the amount of polynucleotide that hybridizes to the oligonucleotide is determined using a polymerase chain reaction.

3. A method according to claim 1, wherein the amount of polynucleotide that hybridizes to the oligonucleotide is determined using a hybridization assay.

* * * * *

```
                        SEQUENCE LISTING

<160> NUMBER OF SEQ ID NOS: 334

<210> SEQ ID NO 1
<211> LENGTH: 514
<212> TYPE: DNA
<213> ORGANISM: Homo sapien

<400> SEQUENCE: 1
ctccttctcg tcacacacca ggtccccgcg gaagccgcgg tgtcggcgcc atggcggagc        60
tgacggctct tgagagtctc atcgagatgg gcttccccag gggacgcgcg gagaaggctc       120
tggccctcac agggaaccag ggcatcgagg ctgcgatgga ctggctgatg gagcacgaag       180
acgaccccga tgtggacgag cctttagaga ctccccttgg acatatcctg ggacgggagc       240
ccacttcctc agagcaaggc ggccttgaag gatctggttc tgctgccgga gaaggcaaac       300
ccgctttgag tgaagaggaa agacaggaac aaactaagag gatgttggag ctggtggccc       360
agaagcagcg ggagcgtgaa gaaagagagg aacgggaggc attggaacgg aacggcagc       420 gcaggagaca agggcaagag ttgtcagcag cacgacagcg gctacaggaa gatgagatgc       480
gccgggctgc tgaggagagg cggagggaaa aggc                                   514

<210> SEQ ID NO 2
<211> LENGTH: 461
<212> TYPE: DNA
<213> ORGANISM: Homo sapien

<400> SEQUENCE: 2
gagaacgacc cccggaccga ccaaagcccg cgcgccgctg catcccgcgt ccagcaccta        60
cgtcccgctg ccgtcgccgc cgccaccatg cccaagagaa aggctgaagg ggatgctaag       120
```

-continued

| | |
|---|---|
| ggagataaag caaaggtgaa ggacgaacca cagagaagat ccgcgaggtt gtctgctaaa | 180 |
| cctgctcctc caaagccaga gcccaagcct aaaaaggccc ctgcaaagaa gggagagaag | 240 |
| gtacccaaag ggaaaaaggg aaaagctgat gctggcaagg aggggaataa ccctgcagaa | 300 |
| aatggagatg ccaaaacaga ccaggcacag aaagctgaag gtgctggaga tgccaagtga | 360 |
| agtgtgtgca ttttgataa ctgtgtactt ctggtgactg tacagtttga aatactattt | 420 |
| tttatcaagt tttataaaaa tgcagaattt tggtttactt t | 461 |

<210> SEQ ID NO 3
<211> LENGTH: 436
<212> TYPE: DNA
<213> ORGANISM: Homo sapien

<400> SEQUENCE: 3

| | |
|---|---|
| gaggagtggc agcggcaagg cagcccagtt tcgcgaaggc tgtcggcgcg ccgcggcccg | 60 |
| caggcacccg gcacgcgcct tccccgcagg caccggcac gcgccttccc cgccgccacg | 120 |
| atgcccaaga ggaaggtcag ctccgccgaa ggcgccgcca aggaagagcc caagaggaga | 180 |
| tcggcgcggt tgtcagctaa acctcctgca aaagtggaag cgaagccgaa aaaggcagca | 240 |
| gcgaaggata aatcttcaga caaaaaagtg caaacaaaag ggaaaagggg agcaaaggga | 300 |
| aaacaggccg aagtggctaa ccaagaaact aaagaagact tacctgcgga aaacggggaa | 360 |
| acgaagactg aggagagtcc agcctctgat gaagcaggag agaaagaagc caagtctgat | 420 |
| taataaccat atacca | 436 |

<210> SEQ ID NO 4
<211> LENGTH: 75
<212> TYPE: DNA
<213> ORGANISM: Homo sapien

<400> SEQUENCE: 4

| | |
|---|---|
| ggaattccct cccctcctt gtgccttctt tgtatatagg cttctcacgg cgaccaataa | 60 |
| acagctccca gtttg | 75 |

<210> SEQ ID NO 5
<211> LENGTH: 222
<212> TYPE: DNA
<213> ORGANISM: Homo sapien

<400> SEQUENCE: 5

| | |
|---|---|
| ccggggctga aaacggtggc agaaagtgag caacttaggg agacagaaag agcgcagaac | 60 |
| tcgaaattcc gaggcagaga gagcggaggg caagccgtgg gtagaaacgc gccgaggcga | 120 |
| ggacgaaggc cttggcccgc ggagacgcag gcacccgcgg agaacgcttc ggatccgtca | 180 |
| cggttttgcc tcatttggaa gatattactt cgcccctgaa aa | 222 |

<210> SEQ ID NO 6
<211> LENGTH: 147
<212> TYPE: DNA
<213> ORGANISM: Homo sapien

<400> SEQUENCE: 6

| | |
|---|---|
| cctgaaagga ccttgggtgg taaagctgta cttggtggga gtgagggcgt ggggaggaac | 60 |
| catgcaaatc gccttccatg gttttaaat gcagtaaata acatttctgg atgagacttg | 120 |
| tttccaaaat aaaccagcta tatctgt | 147 |

<210> SEQ ID NO 7
<211> LENGTH: 952
<212> TYPE: DNA
<213> ORGANISM: Homo sapien

<400> SEQUENCE: 7

```
ggggagcgga gcggggccgc cggggcctct ccagggccgc agcggcagca gttgggcccc      60
ccgccccggc cggcggaccg aagaacgcag aagggggcc gggggaccc gccccggcc       120
ggccgcagcc atgaactcca acgtggagaa cctaccccg cacatcatcc gcctggtgta     180
caaggaggtg acgacactga ccgcagaccc acccgatggc atcaaggtct ttcccaacga    240
ggaggacctc accgacctcc aggtcaccat cgagggccct gaggggaccc catatgctgg    300
aggtctgttc cgcatgaaac tcctgctggg aaggacttc cctgcctccc cacccaaggg     360
ctacttcctg accaagatct ccacccgaa cgtgggcgcc aatggcgaga tctgcgtcaa     420
cgtgctcaag agggactgga cggctgagct gggcatccga cacgtactgc tgaccatcaa    480
gtgcctgctg atccacccta accccgagtc tgcactcaac gaggaggcgg ccgcctgct    540
cttggagaac tacgaggagt atgcggctcg ggcccgtctg ctcacagaga tccacggggg   600
cgccggcggg cccagcggca gggccgaagc cggtcgggcc ctggccagtg gcactgaagc   660
ttcctccacc gaccctgggg ccccagggg cccgggaggg gctgagggtc ccatggccaa    720
gaagcatgct ggcgagcscg ataagaagct ggcggccaac aaaaacacgg acaacaagcg   780
ggcgctgcgg cggctgtagt gggctctctt cctccttcca ccgtgacccc aacctytcct    840
gtcccctccc tccaactctg tctytaagtt atttaaatta tggctggggt cggggagggt   900
acaggggca ctgggacctg gatttgtttt tctaaataaa gttggaaaag ca              952
```

<210> SEQ ID NO 8
<211> LENGTH: 859
<212> TYPE: DNA
<213> ORGANISM: Homo sapien

<400> SEQUENCE: 8

```
ctcatgcctg taatcccagc actttggaag gcaggagcca ccaagcgcag ccatgattta     60
ttagatcact tctaaaagcc ctctctccat ctccaagcca gcaagtgctt ctttgcaccc   120
cagctctaaa acaaagccct tggggacaca atcaaagaca gtagttgcca agaggaatag  180
ggagcatgga aagaaggtgc tggatgtgca tacagctaac ctggtaactc caaactggat  240
gagctcattc cttgagactg gaattacaaa attggaacag ctcactaata attgaagatg  300
atttgggaaa accattatcc ttcctcaggt tttacaaggt ttttatgact catttataag  360
gtcctacagc taaaaaaaat catgctgtat ttcagagaag tttaacttga aaatatttt  420
ttcactaatt aaaaattccc attataccct atagttgcaa ttgtatcctt attgctgaaa  480
gatatccata ctacctacca cttctttaaa atttaaaaaa ttctataaat aaaaaatata   540
acaattgcaa atatgtaaat aacttccaac ataaacaaa atttatagta attataagaa    600
gttcttttat actaaaaatt aagttgtaat tatgatagaa ataatctgta aaaggtattt   660
ttagcaaaat ttattaatac gggtagcaat aataataccc aattatatat gcatattgtt  720
tgtattttag aacctgtgac aaatgaaaat ggttttccta gataagaacg aaactgtgtt  780
gggtggctaa caagatygaa actcatctga ctttgagaaa taaatcaatt tggtttgttt  840
atttaaaaaa aaaaagctt                                                 859
```

<210> SEQ ID NO 9

```
<211> LENGTH: 289
<212> TYPE: DNA
<213> ORGANISM: Homo sapien

<400> SEQUENCE: 9
gaggcatggg ctgccgccct tccacggct ggaccagcct tgtcttactg gccatggctg      60
aagactactg aagggaggga gaggagggga gccaagacac tcatgccact ctggctctga     120
agggacaaag gcttctggct tttgccccca gccccttgga taccagtaat tcaaaccttc    180
ctcatttcat ctcaggtgtc tccttgctgt catcccacat agccctgggg tgaatgtgaa    240
tccagagtct atttttctaa ataaattgga aaaaacaaaa aaaaagctt                  289

<210> SEQ ID NO 10
<211> LENGTH: 328
<212> TYPE: DNA
<213> ORGANISM: Homo sapien

<400> SEQUENCE: 10
tgggttggtg aagattccac atacaaattt tttgaggtta tcctcattga tccattccat     60
aaagctatca gaagaaatcc tgacacccag tggatcacca accagtccaa caagcacagg   120
gagatgcgtg ggctgacatc tgcaggccga agagccgtg gccttggaaa gggccacaag    180
ttccaccaca ctattggtgg ctctcgccgg gcagcttgga gaaggcgcaa tactctccag   240
ctccaccgtt accgctaata taagtaaagt ttgtaaaatt catacttaat aaacaattta   300
ggacagtcaa aaaaaaaaaa aaagcttg                                        328

<210> SEQ ID NO 11
<211> LENGTH: 386
<212> TYPE: DNA
<213> ORGANISM: Homo sapien

<400> SEQUENCE: 11
gcagtacatg ctaagacttc accagtcaaa gcgaactact atactcaatt gatccaataa     60
cttgaccaac ggaacaagtt accctaggga taacagcgca atcctattct agagtccata   120
tcaacaatag ggtttacgac ctcgatgttg gatcaggaca tcccgatggt gcagccgcta   180
ttaaaggttc gtttgttcaa cgattaaagt cctacgtgat ctgagttcag accggagtaa   240
tccaggtcgg tttctatcta cttcaaattc ctccctgtac gaaaggacaa gagaaataag   300
gcctacttca caaagcgcct tccccgtaa atgatatcat ctcaacttag tattataccc    360
acacccaccc aagaacaggg tttgtt                                          386

<210> SEQ ID NO 12
<211> LENGTH: 231
<212> TYPE: DNA
<213> ORGANISM: Homo sapien

<400> SEQUENCE: 12
gacggctacc tggctccgga gaatgggtat tgatggagg ctgcgccgga gtgaagaggt      60
cgtcctctcc atctgctgtg tttggacgcg ttcctgccca gccccttgct gtcatcccct   120
cccccaacct tggccacttg agtttgtcct ccaagggtag gtgtctcatt tgttctggcc   180
ccttggattt aaaaataaaa ttaatttcct gtaaaaaaaa aaaaaagct t               231

<210> SEQ ID NO 13
<211> LENGTH: 84
<212> TYPE: DNA
<213> ORGANISM: Homo sapien
```

<400> SEQUENCE: 13
ctacacacca aatctgctag ttccttgatc tccgacctct caagctctag aactgctaga      60
aataaatttc tatttttata agct                                             84

<210> SEQ ID NO 14
<211> LENGTH: 91
<212> TYPE: DNA
<213> ORGANISM: Homo sapien

<400> SEQUENCE: 14
ccacgcttca ccaccaagag gcccaacacc ttcttctagg tgcagggccc tcgtccgggt      60
gtgccccaaa taaactcagg aacgccccgg t                                     91

<210> SEQ ID NO 15
<211> LENGTH: 168
<212> TYPE: DNA
<213> ORGANISM: Homo sapien

<400> SEQUENCE: 15
gctgacagag atacctacag acggagtgct gtgccacctg gtgccgacaa gaaagccgag      60
gctggggctg ggtcagcaac cgaattccag tttagaggcg gatttggtcg tggacgtggt     120
cagccacctc agtaaaattg gagaggattc ttttgcattg aataaact                  168

<210> SEQ ID NO 16
<211> LENGTH: 154
<212> TYPE: PRT
<213> ORGANISM: Homo sapien

<400> SEQUENCE: 16

Met Ala Glu Leu Thr Ala Leu Glu Ser Leu Ile Glu Met Gly Phe Pro
 1               5                  10                  15

Arg Gly Arg Ala Glu Lys Ala Leu Ala Leu Thr Gly Asn Gln Gly Ile
            20                  25                  30

Glu Ala Ala Met Asp Trp Leu Met Glu His Glu Asp Ala Pro Asp Val
        35                  40                  45

Asp Glu Pro Leu Glu Thr Pro Leu Gly His Ile Leu Gly Arg Glu Pro
    50                  55                  60

Thr Ser Ser Glu Gln Gly Gly Leu Glu Gly Ser Gly Ser Ala Ala Gly
65                  70                  75                  80

Glu Gly Lys Pro Ala Leu Ser Glu Glu Glu Arg Gln Glu Gln Thr Lys
                85                  90                  95

Arg Met Leu Glu Leu Val Ala Gln Lys Gln Arg Glu Arg Glu Glu Arg
            100                 105                 110

Glu Glu Arg Glu Ala Leu Glu Arg Glu Arg Gln Arg Arg Arg Gln Gly
        115                 120                 125

Gln Glu Leu Ser Ala Ala Arg Gln Arg Leu Gln Glu Asp Glu Met Arg
    130                 135                 140

Arg Ala Ala Glu Glu Arg Arg Arg Glu Lys
145                 150

<210> SEQ ID NO 17
<211> LENGTH: 90
<212> TYPE: PRT
<213> ORGANISM: Homo sapien

<400> SEQUENCE: 17

Met Pro Lys Arg Lys Ala Glu Gly Asp Ala Lys Gly Asp Lys Ala Lys
1               5                   10                  15

Val Lys Asp Glu Pro Gln Arg Arg Ser Ala Arg Leu Ser Ala Lys Pro
                20                  25                  30

Ala Pro Pro Lys Pro Glu Pro Lys Pro Lys Lys Ala Pro Ala Lys Lys
            35                  40                  45

Gly Glu Lys Val Pro Lys Gly Lys Gly Lys Ala Asp Ala Gly Lys
    50                  55                  60

Glu Gly Asn Asn Pro Ala Glu Asn Gly Asp Ala Lys Thr Asp Gln Ala
65                  70                  75                  80

Gln Lys Ala Glu Gly Ala Gly Asp Ala Lys
                85                  90

<210> SEQ ID NO 18
<211> LENGTH: 100
<212> TYPE: PRT
<213> ORGANISM: Homo sapien

<400> SEQUENCE: 18

Met Pro Lys Arg Lys Val Ser Ser Ala Glu Gly Ala Ala Lys Glu Glu
1               5                   10                  15

Pro Lys Arg Arg Ser Ala Arg Leu Ser Ala Lys Pro Pro Ala Lys Val
                20                  25                  30

Glu Ala Lys Pro Lys Lys Ala Ala Ala Lys Asp Lys Ser Ser Asp Lys
            35                  40                  45

Lys Val Gln Thr Lys Gly Lys Arg Gly Ala Lys Gly Lys Gln Ala Glu
    50                  55                  60

Val Ala Asn Gln Glu Thr Lys Glu Asp Leu Pro Ala Glu Asn Gly Glu
65                  70                  75                  80

Thr Lys Thr Glu Glu Ser Pro Ala Ser Asp Glu Ala Gly Glu Lys Glu
                85                  90                  95

Ala Lys Ser Asp
            100

<210> SEQ ID NO 19
<211> LENGTH: 244
<212> TYPE: DNA
<213> ORGANISM: Homo sapien

<400> SEQUENCE: 19
caaacaatac tatcttataa aatagtactg ttgaattatt ccaagcctcc ctaggtttgc      60
tctcaaatgt catttacaga ttgggctaac gacctaaaat ctatatataa agactttctg    120
aagaactctg tattatagca ataccaaacg agtgctgtgt gtgcaaacag tctggcgttg    180
ctttttatgt tgatatttat cctagaacac tgaaagagaa tatgccagtg ataactcact    240
ttac                                                                 244

<210> SEQ ID NO 20
<211> LENGTH: 241
<212> TYPE: DNA
<213> ORGANISM: Homo sapien

<400> SEQUENCE: 20
tcaacctcct cctccaagcc ctttctcagt acaagctttc aataaagggg caagttgcag     60
tgcccaagga tttgactatg gcctgggaaa taacaaacgt gacagaggaa ctatctcaac    120
atcttcaaga ccagtgtcca catcagggaa gtcagagctg ccctctaagc acagcaggtc    180

```
agttaaaccc gacgggcatg tgagccggac tcctgctgac cagaagaagc cacgggggac    240
a                                                                    241
```

<210> SEQ ID NO 21
<211> LENGTH: 220
<212> TYPE: DNA
<213> ORGANISM: Homo sapien

<400> SEQUENCE: 21

```
caaaattcta acctgtatca gaggagtgaa atgccccgtg aattgaggca actgtagata    60
ttcgaaatgc ttctaaaaag gctgtgaggt tatgtccttt actgcatgtc attggtaggt   120
catctcaaaa tggcactcga gctttggaag ggtgagaact attgctagat ttggtagggg   180
gtctgcatct atgggcccga gtcctccatc tccacaagct                         220
```

<210> SEQ ID NO 22
<211> LENGTH: 240
<212> TYPE: DNA
<213> ORGANISM: Homo sapien

<400> SEQUENCE: 22

```
atctgcttta agtaactaca tgaaatatct caagccccaa gtaactatac ccagaaccag    60
caccaaccga ggcttctgaa caaaaacaac ctcacaaagc aatttaccca gaaagcaaca   120
tttctaagac aggagactgc ctcctccaaa tggctcactc cattgaaaaa acgccatctg   180
ccagaggcag acaccaaata aaaggcactt ggacatcagg atttgtaaaa aaacaagtac   240
```

<210> SEQ ID NO 23
<211> LENGTH: 221
<212> TYPE: DNA
<213> ORGANISM: Homo sapien

<400> SEQUENCE: 23

```
ggatttttt atacaacctt agaccacctt ctttagcttt aggcgtctgc ggttgccctt    60
ggatctgttc tcaatcctca gtgtgtgtgg cagcatgtga tcatagagag ctgggcaaag   120
ttcactttct ctttgctgac agtctcacct tttctcactg ggaagctgca caggagcctt   180
tgggctggtt cagcccagag gcccctgttc tcctgccttc c                       221
```

<210> SEQ ID NO 24
<211> LENGTH: 248
<212> TYPE: DNA
<213> ORGANISM: Homo sapien

<400> SEQUENCE: 24

```
atggcgcccc gcgcccggag ggccccttct gagcgccccg gccctccct ccgcgctccc     60 cctcctcccc gcggcgcccc cgcccgccc cgccccgcc gagacccga ccccggcccc     120 acgggcggac actcggccgg gcagccgcgg gccgagcgca gccgctccgc accgatgcgc   180
ctggtggcag actccaagtg ggaccggcgg acacgcagcc tcgcgtgtca ggggaagctg   240
atggagaa                                                            248
```

<210> SEQ ID NO 25
<211> LENGTH: 248
<212> TYPE: DNA
<213> ORGANISM: Homo sapien

<400> SEQUENCE: 25

```
tgccggggag gctgaacagg agggttagga ataaaatcag ggcttaagca gagctggtcc    60
```

-continued

```
attcctcagt cctctcacgc ccctgttttc tgagcacggg cgttctgact cagtttttaac    120 tttgaatttta ggagataaca caacatttgt tccttgccca ttaaaaaaaa aaaaaaacaa    180 gtaactttt ttgctccagc tgtactcaac ctggttgact aatgctcact gtagagctag     240
aaaaccaa                                                             248
```

<210> SEQ ID NO 26
<211> LENGTH: 248
<212> TYPE: DNA
<213> ORGANISM: Homo sapien

<400> SEQUENCE: 26

```
gaataggaac taaaatgtaa atctgtctta aacatctgtg aaaagatgg tacttttgac      60 aacatttatc tgcatgtcca gatcagcaat gagtcggcaa ttgacttcta caggaagttt    120
ggcctttgag attattgaga caagaagaa ctactataag aggatagagc ccgcagatgc     180
tcatgtgctg cagaaaaacc tcaaagttcc ttctggtcag aatgcagatg tgcaaaagac    240
agacaact                                                             248
```

<210> SEQ ID NO 27
<211> LENGTH: 178
<212> TYPE: DNA
<213> ORGANISM: Homo sapien

<400> SEQUENCE: 27

```
aaaagatgg tacttttgac aacatttatc tgcatgtcca gatcagcaat gagtcggcaa     60
ttgacttcta caggaagttt ggctttgaga ttattgagac aaagaagaac tactataaga   120
ggatagagcc cgcagatgct catgtgctgc agaaaaacct caaagttcct tctggtca    178
```

<210> SEQ ID NO 28
<211> LENGTH: 240
<212> TYPE: DNA
<213> ORGANISM: Homo sapien

<400> SEQUENCE: 28

```
ccgaggggct gcaagcccgg gagggcccct gtaggagccc agcgcgtggc ggggactgca     60
gcaggaactc ctgcctggcg tggcatcgcg gggcgcccgc tggggagacg ccacccgtgt    120
gtgacccctg tccggagcgg atccagaacc accccggac tcaactgtgt gaggtccaca    180
cggactgttg gccgtgccaa ccagggactg gcgctccgac ctgcccgagg accccaaagc    240
```

<210> SEQ ID NO 29
<211> LENGTH: 443
<212> TYPE: DNA
<213> ORGANISM: Homo sapien

<400> SEQUENCE: 29

```
ctgtttcaaa caaaaccaaa aacctaagta gagcattaca ggcctctgtg gctgctgcgt     60
ttctgtagaa agcaacttat tttattgact tttttttttt aaggaaaaga aataaaaaga    120
ccccagcaag caaaaacatt taaaaaatga tttttttcc tcctacttaa gtggttcttt    180 ctcccttttgc tctactttg gagaatgaac ttaacatccc ggcttctttt gttaagccat    240
agctgacctt aatctgtggt tagtttatta aaataattaa aaatactttc taagaagaga    300
tatttttgat attaggactg atgttgaaac atatagggc aatttataaa aaggtagtta    360
gagaaatata tttttagtgaa ctataaccac agagcacaga tgactcccaa tgagctgatc    420
```

-continued tgtctttagg tttctcccctt tcc                                          443

<210> SEQ ID NO 30
<211> LENGTH: 451
<212> TYPE: DNA
<213> ORGANISM: Homo sapien

<400> SEQUENCE: 30
ttgccgaacc gctttcttac cctccgcacc cgttaagttc tccggtcggg cggcagtctc    60
tgaacactta gccgcgccat ccggggtcac accgcctgga aggaggtgac gggggcggcg   120
cggggcgcgg acactccccg ctgagagtcc gcctgccatg gactcggaat attacagcgg   180
cgaccagtca gatgatggtg gtgctacccc agtacaggat gaacgggatt cagggtcaga   240
cggtgaggat gatgtaaatg agcaacactc cggatcagac actggaagtg tagaacgtca   300
ttcagagaat gaaactagtg atcgagaaga tggcctcccc aaaggacatc atgtgacaga   360
ctctgagaac gatgagccct aaatcttaa tgctagtgac tctgaaagtg aggagcttca   420
caggcaaaag gacagcgact ctgaatctga g                                 451

<210> SEQ ID NO 31
<211> LENGTH: 444
<212> TYPE: DNA
<213> ORGANISM: Homo sapien

<400> SEQUENCE: 31
aaacaatact atcttataaa atagtactgt tgaattattc caagcctccc taggtttgct    60
ctcaaatgtc atttacagat tgggctaacg acctagaatc tatatataaa gactttctga   120
agaactctgt attatagcaa taccaaacga gtgctgtgtg tgcaaacagt ctggcgttgc   180
tttttatgtt gatatttatc ctagaacact gaaagagaat atgccagtga taactcactt   240
tacttcagtc atttcaacac agaaaatgct tctctagcat ttttcttttg tagtgttaac   300
attttgaaat tcatgtttca gaggcttcat catcacagaa tttactcttg ctccatgaaa   360
aaaaattaaa taccttcaga ggaatattta agttgtaaac tatgaaactt gagaaatcct   420
cttgagataa aaggctgcca aatc                                         444

<210> SEQ ID NO 32
<211> LENGTH: 451
<212> TYPE: DNA
<213> ORGANISM: Homo sapien

<400> SEQUENCE: 32
gatccaattc caacaatcta tcttataaaa tagactgttg aattattcca agcctcccta    60
ggtttgctct caaatgtcat ttacagattg gctaacgac ctaaaatcta tatataaaga   120
ctttctgaag aactctgtat tatagcaata ccaaacgagt gctgtgtgtg caaacagtct   180
ggcgttgctt tttatgttga tatttatcct agaacactga aagagaatat gccagtgata   240
actcacttta cttcagtcat ttcaacacag aaaatgcttc tctagcattt ttcttttgta   300
gtgttaacat tttgaaattc atgtttcaga ggcttcatca tcacagaatt tactcttgct   360
ccatgaaaaa aaattaaata ccttcagagg aatatttaag ttgtaaacta tgaaacttga   420
gaaatcctct tgagataaaa ggctgccaaa t                                 451

<210> SEQ ID NO 33
<211> LENGTH: 224
<212> TYPE: DNA
<213> ORGANISM: Homo sapien

<400> SEQUENCE: 33

```
cgcgagtgct gtctccgcag ccgcgcggta gacggccgcg ttccagccct gctggcgacc      60
cccggagttg agcctgcgag ttgggtgcgg gaacaccggc cctgggtggc cgggaaccct     120
aaggccacca ccgcgatccg caggtcaaac gtgacggggc tccctcctgg atagggtcgg    180
tcgggaagtt gatggagact cgacaggcct aagtgtccac catc                      224
```

<210> SEQ ID NO 34
<211> LENGTH: 1231
<212> TYPE: DNA
<213> ORGANISM: Homo sapien

<400> SEQUENCE: 34

```
atccgcggcc aaccagagcg cgcgcgcggc acaacctcat cccaggctcg cgtgcgcagc      60
agctggagca gatccgcagg gacatccgag acttccggtc tagcgcgggg ctggacaaag    120
tcatagtgct gtggacggcg aacacggagc gcttctgtga ggtgattcca ggcctcaacg    180
acacagccga gaacctgctg cgcaccattg agctcggtct ggaggtgtcg ccctccacgc    240
tcttcgccgt ggccagcatc ctggagggct gtgccttcct caatgggtct ccgcagaaca    300
ccctggtgcc cggagctctt gagctcgcgt ggcagcaccg gttttttgtg ggcggagatg    360
acttcaagtc aggccagacc aaagtcaagt ccgtgcttgt ggacttcctc attggctccg    420
gcctcaagac catgtccatc gtgagttaca accacctggg caacaacgat ggggagaacc    480
ctatcggcgc cattgcagtt ccgctctaag gaggtgtcca gagcaacgt ggtggacgac     540
atggtgcaga gcaacccagt gctctatacg cccggcgaag agcctgacca ctgcgtggtc    600
atcaagtatg tgccgtacgt gggtgacagc aagcgcgcgc tggatgagta tacctcggag    660
ctgatgctgg gcggaaccaa cacactggtg ctgcacaaca cgtgtgagga ctcgctgctg    720
gccgcaccca tcatgctgga cctagcgctg ctgaccgagc tgtgccagcg cgtgagcttc    780
tgcactgaca tggaccccga gccgcagacc ttccaccccg tgctgtccct gctcagcttc    840
ctcttcaagg cgccactagt gccgcccggc agcccggtgg tcaatgcgct tttccgccag    900
cgcagctgca tcgagaacat cctcagggcc tgcgtgggc tcccgccaca gaaccacatg     960
ctcctggaac acaaaatgga gcgcccaggg cccagcctca agcgagttgg accgtggct    1020
gccacctacc ctatgttgaa caagaaagga ccggtacccg ctgccaccaa tggctgcacc   1080
ggtgatgcca atgggcatct gcaagaggag cccccaatgc ccaccacctg aggccccggt   1140
cacacagttt ctcggctctt cctccccgct gccccccacg accctacctt gaaggccccc   1200
acaaataaag gcgctgccac tcaaaaaaaa a                                   1231
```

<210> SEQ ID NO 35
<211> LENGTH: 234
<212> TYPE: DNA
<213> ORGANISM: Homo sapien
<220> FEATURE:
<221> NAME/KEY: misc_feature
<222> LOCATION: (1)...(234)
<223> OTHER INFORMATION: n = A,T,C or G

<400> SEQUENCE: 35

```
actgacccca cccaggatca aggctcanga tgcaatgaca ataacgcta ccactaggca      60
gaacttgacc cgtgtgtagg aggatagtgg gaaaagcact tagaggccgg ggtcagtaac    120
aacatcagcc aacagggatg accacgcccg ctgggcttca gcatggaggt gaaacaagca    180
```

-continued gccctggctc ctgccctgcg ggcacctctg tctgggaggg gcaggagggg cttc        234

<210> SEQ ID NO 36
<211> LENGTH: 234
<212> TYPE: DNA
<213> ORGANISM: Homo sapien

<400> SEQUENCE: 36
tcagagccca cccggcatgt acaactgtga aaggccttgg aaaactggag cgatgagagc    60
ggtgaatcgt gttggtctca ttggagaccc gcagattggg agattctgga accaggacga   120
ccttgcccct cacctgcagc agaagccccc ggaaacgccc ggccccgacc cggacctgag   180
ccgcctgggg gcccaaggga agctgaacgc ccggtgggct cccgcgatgg ttct         234

<210> SEQ ID NO 37
<211> LENGTH: 246
<212> TYPE: DNA
<213> ORGANISM: Homo sapien

<400> SEQUENCE: 37
gattcgagag agggaaatct cacttccacc ttatttttcac taaattttct gaaacagaca    60
aaatgtgtag tgttgacagg gccaatctcc gtgacttttg ttcatatgct tttatttatc   120
catgatttcc aagacactgg gcttcccatt ctcacttccc ctcatcaatc cctttccttt   180
ctttagaagg gggcttatgt atgagactgg tgaagtccag tgaagctaag taaaggggca   240
agatgg                                                              246

<210> SEQ ID NO 38
<211> LENGTH: 244
<212> TYPE: DNA
<213> ORGANISM: Homo sapien

<400> SEQUENCE: 38
agcagaggag gttcgattaa aactggaaga gaccagagag gtacagaact tgaggaagag    60
gcccaacggg gtgagtgctg tggccttgct ggtgggagag aagtacaag aggagaccac    120 tctagtggat gatcccttc agatgaagac aggtggtatg gtggatatga agaaactgaa   180
ggaaaggggc aaagataaga tcagtgagga ggaggacctg cacctgggga catcgttttc   240
tgca                                                                244

<210> SEQ ID NO 39
<211> LENGTH: 242
<212> TYPE: DNA
<213> ORGANISM: Homo sapien
<220> FEATURE:
<221> NAME/KEY: misc_feature
<222> LOCATION: (1)...(242)
<223> OTHER INFORMATION: n = A,T,C or G

<400> SEQUENCE: 39
caacaatctt ctntaaaata gactgttgaa ttattccaag cctccctagg tttgctctca    60
aatgtcattt acagattggg ctaacgacct agaatctata tataaagact ttctgaagaa   120
ctctgtatta tagcaatacc aaacgagtgc tgtgtgtgca aacagtctgg cgttgctttt   180
tatgttgata tttatcctag aacactgaaa gagaatatgc cagtgataac tcactttact   240
tc                                                                  242

<210> SEQ ID NO 40
<211> LENGTH: 241

```
<212> TYPE: DNA
<213> ORGANISM: Homo sapien
<220> FEATURE:
<221> NAME/KEY: misc_feature
<222> LOCATION: (1)...(241)
<223> OTHER INFORMATION: n = A,T,C or G

<400> SEQUENCE: 40
accagaactg aaacagagga ctgtgctgaa tctctaaatc atgttgatag tgatgtacca      60
ccttctaata ccatgagtgn ttttaacacc tctgattacc gctttgagtg tatatgtggt    120
gaacttgatc agatagatcg taagcctcgt gttcaatgcc tgaagtgtca cctgtggcaa    180
catgcaaagt gtgtgaatta tgatgagaaa atctgaaga tcaagccttt ttactgcccc     240
c                                                                    241

<210> SEQ ID NO 41
<211> LENGTH: 245
<212> TYPE: DNA
<213> ORGANISM: Homo sapien

<400> SEQUENCE: 41
agcgagagga agagaggaga agaaagagaa accagggggg cgaggcgccg tccaatgaca     60
aagcccaggg gtgggcgccg ccgccatct tgtaccgggc agcaggatat tcgcccgcgt    120
cctccgccct cggaggggga ggggcggcgg cggaggcgag aaaagtagcg agagacgcca    180
gcagcagccg ccgccgcgga gccaacgcgg actgggacgg cggcggcagt agtgggaccc    240
ggcga                                                                245

<210> SEQ ID NO 42
<211> LENGTH: 241
<212> TYPE: DNA
<213> ORGANISM: Homo sapien
<220> FEATURE:
<221> NAME/KEY: misc_feature
<222> LOCATION: (1)...(241)
<223> OTHER INFORMATION: n = A,T,C or G

<400> SEQUENCE: 42
agccnagact ttagattgcc cggaggaagc aaactcttcg tataaaaaaa agcaggccat     60
ctgcttaacc cttggctcca ccataaggca ctgggactcg gatttctcta tctgatagag    120
gtattttctg tggccctggg agctgtctgt cttttcccta cccccaagga tgccaggaag    180
acgtccacca ttagccatgt ggcaaccttt acttctatgc ctcacaagtg cctttcagag    240
a                                                                    241

<210> SEQ ID NO 43
<211> LENGTH: 245
<212> TYPE: DNA
<213> ORGANISM: Homo sapien

<400> SEQUENCE: 43
gcatgcccct tggagtggaa ggaagctgga cagggcaggc ctctgggac gggacacagg      60
gaagcccgaa ggggcgcctt ggccaggtct gccatctcct ccagcgaggc tctggccagc    120
actgggtgag agtggggagg gggcactggc ctttgcagca cagtaaaaca tggtccagac    180
aacctgtggc cccggcctca tgagcacccc ctgcacaggc ccagcccaag ccaggcgcta    240
gaagg                                                                245

<210> SEQ ID NO 44
```

<211> LENGTH: 238
<212> TYPE: DNA
<213> ORGANISM: Homo sapien

<400> SEQUENCE: 44

| | | |
|---|---|---|
| gatgcccctt ggagtggaag gaagctggac agggcaggcc tctggggacg ggacacaggg | | 60 |
| aagcccgaag gggcgccttg gccaggtctg ccatctcctc cagcgaggct ctggccagca | | 120 |
| ctgggtgaga gtgggggaggg ggcactggcc tttgcagcac agtaaaacat ggtccagaca | | 180 |
| acctgtggcc ccggcctcat gagcacccc tgcacaggcc cagcccaagc caggcgct | | 238 |

<210> SEQ ID NO 45
<211> LENGTH: 247
<212> TYPE: DNA
<213> ORGANISM: Homo sapien

<400> SEQUENCE: 45

| | | |
|---|---|---|
| gcctttgcgc accgtttctt ccctccgcac ccgttaagtt ctccggtcgg gcggcagtct | | 60 |
| ctgaacactt agccgcgcca tccggggtca caccgcctgg aaggaggtga cggggggcggc | | 120 |
| gcgggcgcg gacactcccc gctgagagtc cgcctgccat ggactcggaa tattacagcg | | 180 |
| gcgaccagtc agatgatggt ggtgctaccc cagtacagga tgaacgggat tcagggtcag | | 240 |
| acggtga | | 247 |

<210> SEQ ID NO 46
<211> LENGTH: 225
<212> TYPE: DNA
<213> ORGANISM: Homo sapien

<400> SEQUENCE: 46

| | | |
|---|---|---|
| gcccgcgcac cctctctcgg ggctggtggc ctgcgtgggc ggccgggtgg tcggcagagc | | 60 |
| cgccggggcc cccgggctca gaaagaggcc gaaatggctg cgaagcaggc cccgggcagg | | 120 |
| agtcgctcgg gcgcagggag gaagtgaacc ggccggaggt agcgcccggc tgctggcccc | | 180 |
| acagtcccga caccttcgga actcctaact cctttacttg tccgg | | 225 |

<210> SEQ ID NO 47
<211> LENGTH: 227
<212> TYPE: DNA
<213> ORGANISM: Homo sapien

<400> SEQUENCE: 47

| | | |
|---|---|---|
| caaacaatac tatcttataa aatagtactg ttgaattatt ccaagcctcc ctaggtttgc | | 60 |
| tctcaaatgt catttacaga ttgggctaac gacctaaaat ctatatataa agactttctg | | 120 |
| aagaactctg tattatagca ataccaaacg agtgctgtgt gtgcaaacag tctggcgttg | | 180 |
| cttttatgt tgatatttat cctagaacac tgaaagagaa tatgcca | | 227 |

<210> SEQ ID NO 48
<211> LENGTH: 537
<212> TYPE: DNA
<213> ORGANISM: Homo sapien

<400> SEQUENCE: 48

| | | |
|---|---|---|
| gccgcccggg ccctggatcc tgcaccgagg ccgcaaaaag gccacaggca gcgcagtgtc | | 60 |
| catcttcgtg tatgatgtga aaccgggagc tgaagagcag acccaggtgg ccaaagctgc | | 120 |
| cttcaaacgc ctcaaaactc tccgacaccc caacatcctg gcctatatcg atgggttgga | | 180 |
| gacagaaaag tgcctccaca tcgtgacaga ggctgtgacc cccctgggaa catacctcaa | | 240 |

```
gggctggcga gtggaaactt gggggtctgg actacatgta ctcggcacag ggcaacggcg    300
ggggaccacc cagcaagggg atcccggagc tcgagcagta tgatccccg gagctggctg    360 acagcagtag cagagcagtc agagagaagt ggtcagcaga catgtggcgc ttgggctgcc   420
tcatctggga agttttcaat gggtctctac ctcgggcagc tgccctgcgc aaccctggga   480
agatccccaa atccctggtg acccattact gtgaactggt gggagctaac ccaaaag      537
```

<210> SEQ ID NO 49
<211> LENGTH: 336
<212> TYPE: DNA
<213> ORGANISM: Homo sapien

<400> SEQUENCE: 49

```
aagcgtctct tttccactgt tgcagtgagc tgagaccatg ccactgtact ctagcctggg    60
taacagccag accctgtctc aaaaaaaaaa acaattttt tcataacata attcccattt    120
ttatttattt tgagtcactc ataattaatt gccaaaaaag cattttatac attgagttgg   180
ggggtagtgg atcttagtgt ggtgttgcat ggaggggcga gattttatat ttataatcaa   240
cacgtgggtt aacatgtttt tttgaaatcc aagcaataca caggaaattt aagtagaata   300
aaaattgcag cccattttg aaatgtcagc atgtgc                                336
```

<210> SEQ ID NO 50
<211> LENGTH: 247
<212> TYPE: DNA
<213> ORGANISM: Homo sapien
<220> FEATURE:
<221> NAME/KEY: misc_feature
<222> LOCATION: (1)...(247)
<223> OTHER INFORMATION: n = A,T,C or G

<400> SEQUENCE: 50

```
cagctgngaa tctgactggt cctgnacttt ttttggctgg nggctatta antatatcct     60 cagtttcaga gcctgttatt ggtctattca nggattcaac ttcttccttg nttantcttg   120 ggaggggta tgtgtccang aatttatcca tttcttctan attttctagc ttatttgtgt   180
acagatgttt atagtattca ttctctgatg ggagnttgta tttctgtggg atcagnggtg   240
atatccc                                                               247
```

<210> SEQ ID NO 51
<211> LENGTH: 243
<212> TYPE: DNA
<213> ORGANISM: Homo sapien
<220> FEATURE:
<221> NAME/KEY: misc_feature
<222> LOCATION: (1)...(243)
<223> OTHER INFORMATION: n = A,T,C or G

<400> SEQUENCE: 51

```
ctggctgctt ttttgctgng ggtagatggt gggaatactt ctggtctaga tataacttac    60
cactaagaaa cccccagtat gtcaccactg cctaaatcta actagaccag ggtccaaatg   120
ccatccaggc caggcaggaa atataccctca tgtgaaagac agtaaggagt tgtgggcagt   180
gtaacaaaca ggagagctat gccccaacta aaggagcag ctgctactgc ttagtttcag   240
cca                                                                   243
```

<210> SEQ ID NO 52
<211> LENGTH: 944
<212> TYPE: DNA

<213> ORGANISM: Homo sapien

<400> SEQUENCE: 52

| | | | | | |
|---|---|---|---|---|---|
| ccaaacaccc | gaaagacaca | aaccagaatt | gagccctact | ccccaaaatg | tacaaacaga | 60 |
| tgatacgctt | aacttttgg | acacctgtga | tttgcatact | gagcatataa | agccatcttt | 120 |
| acgcacgtcc | atcggtgaaa | gaaaacggtc | tctttcacca | ctaattaagt | tttctccagt | 180 |
| ggaacaaaga | ttgagaacca | caatagcatg | tagtcttgga | gaactaccta | atttaaagga | 240 |
| agaagacatt | tgaataaga | gccttgatgc | aaaagaacca | ccgtctgact | tgacaagatg | 300 |
| aagacgtacc | catttaatat | aactatgatg | cacttaaatt | gaagctatgc | cacaggatag | 360 |
| aaaatgaatt | acaacttaaa | tacatgttgg | aagtgtaaca | ctgttttca | agggttaaaa | 420 |
| aaattcctaa | tgccttttag | ccttctttaa | tatttttagg | taaggaaagt | atgtttggat | 480 |
| tttttcctct | ttgtaggtat | atgagattga | aatgtgaagt | atttggacaa | caaacgtcaa | 540 |
| gcaatgggaa | gccattttga | tttcttgagt | aatcttgtaa | gcattaagtg | aatgacaaag | 600 |
| tagtagtgta | acttatttct | tatgttataa | cttcagtcaa | ttaatataag | gatagttttt | 660 |
| gttgtatgtt | cactaaatgg | ttaatataat | agccattgaa | tatactaatc | tttcatctta | 720 |
| gagaactata | caacttttat | tgtttcttaa | tggaacattc | tggctaacca | gaaaaagtga | 780 |
| gaaaagtagt | acccttggga | tgtgtagtca | agatgacaaa | ttttaagact | ggaaaagctc | 840 |
| taaacaggct | taatgattct | tcaggtagaa | tgatcctgag | aaggtgatgt | ttgatggaat | 900 |
| aaagtgcatg | tgatgattaa | gtgaagactg | gggcagaatg | attt | | 944 |

<210> SEQ ID NO 53
<211> LENGTH: 230
<212> TYPE: DNA
<213> ORGANISM: Homo sapien

<400> SEQUENCE: 53

| | | | | | |
|---|---|---|---|---|---|
| taaagataat | gattgataag | ctagaacttt | ctgatgtagt | cattacatga | aaccccttgt | 60 |
| cactggtttg | tgtgttcaga | ggaagccatg | gccgagatag | ctttcctgaa | ataaaccagt | 120 |
| agcttttcag | attgacgttc | ttgctacaat | tgtaccatct | ggtaattcct | gaaaatgtca | 180 |
| attttttgt | gttaatattt | ttggtttcaa | acaataacaa | atgtctctag | | 230 |

<210> SEQ ID NO 54
<211> LENGTH: 242
<212> TYPE: DNA
<213> ORGANISM: Homo sapien

<400> SEQUENCE: 54

| | | | | | |
|---|---|---|---|---|---|
| ggaagaagga | gaagcaattc | tattccaagg | ccaagaccta | ctggaaacaa | atcccaccca | 60 |
| cggtggacgg | catgcttggg | gggtatggcc | acatctccag | catcgacatc | aacagctccc | 120 |
| ggaagtttct | gcagaggttt | tgagggaag | gcccgaacaa | gacaggaacg | tcctgtgccc | 180 |
| tggactgtgg | agctggcatt | gggaggatca | ccaagcggct | gctcctgccg | ctgttcagag | 240 |
| ag | | | | | | 242 |

<210> SEQ ID NO 55
<211> LENGTH: 246
<212> TYPE: DNA
<213> ORGANISM: Homo sapien

<400> SEQUENCE: 55

| | | | | | |
|---|---|---|---|---|---|
| ccaaacaccc | gaaagacaca | aaccagaatt | gagccctact | ccccaaaatg | tacaaacaga | 60 |

```
tgatacgctt aacttttggg acacctgtga tttgcatact gagcatataa agccatcttt      120
acgcacgtcc atcggtgaaa gaaaacggtc tctttcacca ctaattaagt tttctccagt      180
ggaacaaaga ttgagaacca caatagcatg tagtcttgga gaactaccta atttaaagga      240
agaaga                                                                246

<210> SEQ ID NO 56
<211> LENGTH: 241
<212> TYPE: DNA
<213> ORGANISM: Homo sapien

<400> SEQUENCE: 56
tttggagctt caaagaggca aagtgactaa ggaggaaatt agtaaagagt ttatgttaag       60
cgcagattgt cttctctttt taagatgcct tgtgaatatc tctccttgga tgcaatggag      120
aaatggatca tctgtaagta accgagctag ctagggctgt ctcttgtgtt taagctttaa      180
tgagggaatg cctgtttctg ccttagctct gcccttcacc ctgcaatgac acctgtgtgc      240
t                                                                     241

<210> SEQ ID NO 57
<211> LENGTH: 246
<212> TYPE: DNA
<213> ORGANISM: Homo sapien

<400> SEQUENCE: 57
ccaaacaccc gaaagacaca aaccagaatt gagccctact ccccaaaatg tacaaacaga       60
tgatacgctt aacttttggg acacctgtga tttgcatact gagcatataa agccatcttt      120
acgcacgtcc atcggtgaaa gaaaacggtc tctttcacca ctaattaagt tttctccagt      180
ggaacaaaga ttgagaacca caatagcatg tagtcttgga gaactaccta atttaaagga      240
agaaga                                                                246

<210> SEQ ID NO 58
<211> LENGTH: 244
<212> TYPE: DNA
<213> ORGANISM: Homo sapien

<400> SEQUENCE: 58
attgcatcgt tttccaacat acttttagat ttacaaagta aaaccaacca tggatctgcc       60
tatcttggtg tgtcgatctt gtaatttat ctttgtgtgt gtgtgtgtgt gtgtgtgtgc      120
actcactggg gcctaagctc agaacctcac acaggcagag tatacacacg ccctgcaact      180
aaactgcatc tctagtccct atacatgtgt cctactcatc cttcaaagtg agtccctagg      240
ggat                                                                  244

<210> SEQ ID NO 59
<211> LENGTH: 1737
<212> TYPE: DNA
<213> ORGANISM: Homo sapien

<400> SEQUENCE: 59
cggtatttgt gagaggagtc ggcgtttgaa gaggtggaac tcctagggct tttttgagag       60
tgctgattta gaagaataca aatcatggct gaaaatagtg tattaacatc cactactggg      120
aggactagct tggcagactc ttccattttt gattctaaag ttactgagat ttccaaggaa      180
aacttactta ttggatctac ttcatatgta gaagaagaga tgcctcagat tgaaacaaga      240
```

-continued

```
gtgatattgg ttcaagaagc tggaaaacaa gaaggaactta taaaagcctt aaaggacatt      300
aaagtgggct ttgtaaagat ggagtcagtg gaagaatttg aaggtttgga ttctccggaa      360
tttgaaaatg tatttgtagt cacggacttt caggattctg tctttaatga cctctacaag      420
gctgattgta gagttattga cacagttgta ttaaattgtt cacaaaaagg agagcctttg      480
ccattttcat gtcgcccgtt gtattgtaca agtatgatga atctagtact atgctttact      540
ggatttagga aaaagaaga actagtcagg ttggtgacat tggtccatca catgggtgga      600
gttattcgaa aagactttaa ttcaaaagtt acacatttgg tggcaaattg tacacaagga      660
gaaaaattca gggttgctgt gagtctaggt actccaatta tgaagccaga atggatttat      720
aaagcttggg aaaggcggaa tgaacaggat ttctatgcag cagttgatga ctttagaaat      780
gaatttaaag ttcctccatt tcaagattgt atttttaagtt tcctgggatt ttcagatgaa      840
gagaaaacca atatatggaa gaaatgactg aaatgcaagg aggtaaatat ttaccgcttg      900
gagatgaaag atgcactcac cttgtagttg aagagaatat agtaaaagat cttccctttg      960
aaccttcaaa gaactttatt gttgtcaagc aagagtggtt ctggggaagc attcaaatgg     1020
atgcccgagc tggagaaact atgtatttat atgaaaaggc aaatactcct gagctcaaga     1080
aatcagtgtc aatgctttct ctaaataccc ctaacagcaa tcgcaaacga cgtcgtttaa     1140
aagaaacact tgctcagctt tcaagagaga cagacgtgtc accatttcca ccccgtaagc     1200
gcccatcagc tgagcattcc cttttccatag ggtcactcct agatatctcc aacacaccag     1260
agtctagcat taactatgga gacacccaa agtcttgtac taagtcttct aaaagctcca     1320
ctccagttcc ttcaaagcag tcagcaaggt ggcaagttgc aaaagagctt tatcaaactg     1380
aaagtaatta tgttaatata ttggcaacaa ttattcagtt atttcaagta ccattggaag     1440
aggaaggaca acgtggtgga cctatccttg caccagagga gattaagact atttttggta     1500
gcatcccaga tatctttgat gtacacacta agataaagga tgatcttgaa gacctttatag     1560 ttaattggga tgagagcaaa agcattggtg acatttttct gaaatattca aaagatttgg     1620
taaaaaccta ccctccctttt gtaaacttct ttgaaatgag caaggaaaca attattaaat     1680
gtgaaaaaca gaaaccaaga tttcatgctt ttctcaagat aaaccaagca aaaccag       1737
```

```
<210> SEQ ID NO 60
<211> LENGTH: 249
<212> TYPE: DNA
<213> ORGANISM: Homo sapien

<400> SEQUENCE: 60
tcaaaagcaa caagattaaa aagattagaa tgcagtggaa ttgtagcttt aagacgctga       60
atgtgattct gtatcattta agagagaaag tagaattaac acatgttcac acacagaaag      120
aatctactct ttgtacaacc tttgctgaaa gaactttgaa agacttcagt aaaaacaaag      180
ttaaatccag aaaagacaag atcaaacaag caatggtgag caaaaaacct agcaaacgtg      240
gcactaaac                                                              249

<210> SEQ ID NO 61
<211> LENGTH: 243
<212> TYPE: DNA
<213> ORGANISM: Homo sapien

<400> SEQUENCE: 61
ttgtttatca tggagctaat aatcctaaag gattgctgga agttcgggaa gccctggaaa       60
aggtacacaa agtagaagac cttcttccga ttatgaagtt taatactaaa acgaaggatg      120
```

```
ggttcaccgt gaacacaaaa gttcccagcc ttaaagacca agggaaggaa tatgatggat      180
tcacaatcac gattacagga gacaaagttg gcaatatatt attttctgtg gaaactcaaa      240
cca                                                                   243

<210> SEQ ID NO 62
<211> LENGTH: 240
<212> TYPE: DNA
<213> ORGANISM: Homo sapien

<400> SEQUENCE: 62
gttgttgccc tgtgattagt tctgcttttt aacccactcc ctggatgcat ttttccctcc       60
ttgcatttcc ctcttttcct ggagttcata ctagagaatc tgcactatgt ttttcccttt      120
ttgtcttgag atgaaagttt taaaataatc cacctctgtc atttccactc tctgaacatc      180
ccaagctgta tccctggcct cttttctcag actatgtttc tttacttggg acctagaact      240

<210> SEQ ID NO 63
<211> LENGTH: 245
<212> TYPE: DNA
<213> ORGANISM: Homo sapien
<220> FEATURE:
<221> NAME/KEY: misc_feature
<222> LOCATION: (1)...(245)
<223> OTHER INFORMATION: n = A,T,C or G

<400> SEQUENCE: 63
agcccncctg aagcgccgcg gcgccgctat cgagcttcct gcantggtgg ccacccgagc       60
aagtgccgtg gcgggggcgg agagcggcca cggcggcggc gcctcccccaa gtggcccgtt     120 gcgtccgacc ccgcgtgaaa gatatcaagt tattctagta caaccatata aataaataat      180
acctgaagtc tcagtgtaac atggacaatt aacagtgatg acagataaat acagacgcat      240
gggga                                                                 245

<210> SEQ ID NO 64
<211> LENGTH: 299
<212> TYPE: DNA
<213> ORGANISM: Homo sapien

<400> SEQUENCE: 64
tgccagagca gctgggaagg tgtggaagga gcagttccgg gtgaggtggc cttcccttat       60
gaaacactac agccccaccg actacgtcaa ttggttggaa gagtataaag ttcggcaaaa      120
agctgggtta gaagcgcgga agattgtagc ctcgttctca aagaggttct tttcagagca      180
cgttccttgt aatggcttca gtgacattga gaaccttgaa ggaccagaga ttttttttga      240
ggatgaactg gtgtgtatcc taaatatgga aggaagaaaa gctttgacct ggaaatact      299

<210> SEQ ID NO 65
<211> LENGTH: 246
<212> TYPE: DNA
<213> ORGANISM: Homo sapien

<400> SEQUENCE: 65
agccgggccc gagctgggct ctgcgaggtg caagaaagcc tttgaggtga aggtgtatga       60
aagtcatcat aacagatgtt ttccaaaaac ttgtagaagg ttgtgaaaaa actactagga      120
tcacgcggca tgtattgagg tgtggcatgc agcatttgg aaggaaaatt gaagacgtgt      180
tcaagaaaac atgaacagaa gcaaatgatg aaaatcagca ttttacttga tgttgataac      240
```

-continued atcaca                                                                246

<210> SEQ ID NO 66
<211> LENGTH: 528
<212> TYPE: DNA
<213> ORGANISM: Homo sapien

<400> SEQUENCE: 66
agtccctaaa tacatgaggc tgggtgagca gatgaaaccg gtagccactg tgctgatgca      60
tgtgactcca ttcagttggg gattttggtt ccatgtggat ccatactaag tattcttcag    120
tcagtggatt ttagcaaggg gaggtaggag tggaagagag gtgtgaagaa acctctccga    180
acaaatgaac cagcagtaag tttctaaaaa tcagaatcta gatagaagtt ctgcaatatg    240
aaatgagcac attctttgat aaggcgtatc tattcatgct tttgtaccac tgttttgtac    300
ctgactccct gaccgatttg tatttttat atacaactag aaggaagtca caagattgcc    360
ttctacagtg tgccatttcc aaatggatct gttgttggag gaaactggtt gctagtcaat    420
gttctatatt taatgaatgt gtgataaatc atcctgtaat cagtatggag taacctgttt    480
ttgtagtttg gatgaatatg tcctgagaaa tttccatcca ctttggtt                 528

<210> SEQ ID NO 67
<211> LENGTH: 536
<212> TYPE: DNA
<213> ORGANISM: Homo sapien

<400> SEQUENCE: 67
gttctgcatc ctccaggctc tggttcccat gcagcagctg tcagcgttca gacaacccct     60
cagaacgtgc ccagccggtc aggcctgccc cacatgcact cccagctgga gcatcgcccc    120
agccagagga gcagctcccc tgtgggcctt gccaaatggt ttggctcaga tgtgctacag    180 caaccctgc cctccatgcc cgccaaagtt atcagtgtag atgaattgga ataccgacag    240
tgagcagggc aggcagactc aactaagccc ggacctgtgg tggcacactg gcaggaccc    300 tgcttcatct cggttggtt tatgggcttt tactttggag cactctgtgt gaagctgttt    360
ggtggaaccc atgcatctgg tgtggtccgc attatgatgg aaggatctta accagtcgag    420
tggagtgtac attgtctgaa tacaggatgc acaatgttgt caatcctgga aatggtcttt    480
cttttttgta agatatgtga atgaagtgtt ggtgtcctca ccaagaggtg gcacct        536

<210> SEQ ID NO 68
<211> LENGTH: 1664
<212> TYPE: DNA
<213> ORGANISM: Homo sapien

<400> SEQUENCE: 68
attgatgaac tcccagaggg ccggccagtg cgggtagccc ggattgatga actcccagag      60
ggcgctgtga agcctccagc aaacaagtat cctatcttct ttttttggcac ccatgaaact    120 gcatttctag gtcccaaaga cctttttcca tataaggagt acaaagacaa gtttggaaag    180
tcaaacaaac ggaaaggatt taacgaagga ttgtgggaaa tagaaaataa cccaggagta    240
aagtttactg gctaccaggc aattcagcaa cagagctctt cagaaactga gggagaaggt    300
ggaaatactg cagatgcaag cagtgaggaa gaaggtgata gagtagaaga agatggaaaa    360
ggcaaaagaa agaatgaaaa agcaggctca aacggaaaaa agtcatatac ttcaaagaaa    420
tcctctaaac agtcccggaa atctccagga gatgaagatg acaaagactg caaagaagag    480
gaaaacaaaa gcagctctga gggtggagat gcgggcaacg acacaagaaa cacaacttca    540

-continued

```
gacttgcaga aaaccagtga agggacctaa ctaccataat gaatgctgca tattaagaga      600
aaccacaaga aggttatatg tttggttgtc taatattctt ggatttgata tgaaccaaca      660
catagtcctt gttgtcattg acagaacccc agtttgtatg tacattattc atattcctct     720
ctgttgtgtt tcgggggaa aagacatttt agccttttt aaaagttact gatttaattt        780
catgttattt ggttgcatga agttgccctt aaccactaag gattatcaag attttgcgc       840 agacttatac atgtctagga tccttttatc aaggcagtta tgatcatcgt tttcctgcct      900
tgaccccacc atcatcaaac actcagttaa atataaatta acatttttta gatgaccact     960
caacataatg cttaagaatg gaatttcctc tctgtgacag aacccaggaa ttaattccta    1020
aatacataac gttggtatat tgaagacgaa attaaaattg tccttcagtt ttgaggccat    1080
gtgtaaagtt tacccatatt gtaaaatatc tattccggta ttagaaatag ctagttgaca    1140
gcttatactt ctcaaaattc atattgttat gtacacaaac taagtttcta tatgtgaagt    1200
tagtgagtct ttttgtgtta ctccaaaata aaggcaatga tttatttttt tcccagtgcc    1260
aatacaattt tgagctaagc actcaaggtg gatactttac attttaaagc tggaatcagc    1320
aacagcccta tgggaaacca gacaaagcat tgactttta atgtagactt ttaaaataaa     1380
ctgttttctt ttggaactac aattagaata gttaatattc atccttaaac cattattatg    1440
tgtacattat tgttgctatt gtgataatag agaatttat ttattttat gccagcttat       1500 attgtgagaa cacatttagt cagtttgggt tttatcaatc ctgttaatgc ttgtccttgg    1560
aacatctttc gcgtattcac ggtttgtagt tgaaaagttt actgtaaaaa aatcaaaaac    1620
aaaaaaatgt attgttttta cagaataaat ttattggaat gtgt                     1664
```

<210> SEQ ID NO 69
<211> LENGTH: 218
<212> TYPE: DNA
<213> ORGANISM: Homo sapien

<400> SEQUENCE: 69

```
taatgagcca accacgtggg agcttaacca gtgatagaac tagaaattgg gttcttcaac      60
agaaaataga agggagaaac aaaagaatca aactacgcta aattgattga atgaatgga     120 ggaggaaccg gctgtaatca tgaattagaa atgatcagac aaaagcttca atgtgtagct    180
tcaaaactac aggttctacc ccagaaagcc tctgagag                             218
```

<210> SEQ ID NO 70
<211> LENGTH: 241
<212> TYPE: DNA
<213> ORGANISM: Homo sapien

<400> SEQUENCE: 70

```
aacaaataaa aaataaaaac aacgccagtc tcagtaaatc tgtaggtgtg tctaaccggc      60
agaataagaa agtagaagaa gaagaaaagt tgctgaagct ctttcaggga gtaaataaag    120
cccaagatgg atttacgcag tgggtgtgaa cagatgcttc atgcccttaa tacggcaaat    180
aacttggatg ttcccacatt tgtttctttc ctgaaagaag tagaatctcc ttatgaggtc    240
c                                                                     241
```

<210> SEQ ID NO 71
<211> LENGTH: 224
<212> TYPE: DNA
<213> ORGANISM: Homo sapien

<400> SEQUENCE: 71

```
agactgacca ccggcctccc gcctgcaggt cagaggctct gacactgtct ggtttccaat      60
gcttctggag acttcctgcc taggcctcat cctcctcttt gccagtcacc tgattaacca     120
attctccagc attaggactt acctccttct ttttgtaagg tctcttgtat gttgttaaat     180
gtttggctta aacaatttat aaaagccttt ctagaaggca gact                     224
```

<210> SEQ ID NO 72
<211> LENGTH: 250
<212> TYPE: DNA
<213> ORGANISM: Homo sapien
<220> FEATURE:
<221> NAME/KEY: misc_feature
<222> LOCATION: (1)...(250)
<223> OTHER INFORMATION: n = A,T,C or G

<400> SEQUENCE: 72

```
gcgatgagtg cgcccccaaa ggggcaccct cgctgcggtg canacactgg tgcgtggcga      60
ggttctcccc tttgggtgcg atgagtgcgc actgggcgcc accgtggatg ccccgccgc     120
caagcccctg gccagcgcgc ctggcggacc gggctgcggc ccaggatccg atcccgtggt     180
gccccagcgc gcccctcgg gcgagcggtc cttcttctgc ccggactgcg ggcgcggctt      240
ctcccatggg                                                            250
```

<210> SEQ ID NO 73
<211> LENGTH: 227
<212> TYPE: DNA
<213> ORGANISM: Homo sapien

<400> SEQUENCE: 73

```
tacttcactc acctaattgt gatgttcaag tcccccaggc cggctgccat ggtgctggac      60
cgctcccagg actttgggaa acatggaag ccttataagt actttgcgac taactgctcc     120
gctacatttg gcctggaaga tgatgttgtc aagaagggcg ctatttgtac ttctaaatac     180
tccagtcctt ttccatgcac tggaggagag gttattttca aagcttt                   227
```

<210> SEQ ID NO 74
<211> LENGTH: 260
<212> TYPE: DNA
<213> ORGANISM: Homo sapien
<220> FEATURE:
<221> NAME/KEY: misc_feature
<222> LOCATION: (1)...(260)
<223> OTHER INFORMATION: n = A,T,C or G

<400> SEQUENCE: 74

```
atgcgtnttc ggcggccgcg gcggaccatg gccctggccc ggcgtcgctg ggctttcctc      60
acggcgtccc cgagcagcgt cgcagagcgg gccgacttcc gggaaggaac tgaccagcga     120
ctgagcggcg gccggcgcgc ttagcgccct gaacatgcgg cagtccctgc gggcgacccc     180
gggctccgga caggcggcgg cggaggcggc ggctcgggag ggaaggaggc ggcggcgccg     240
gcggaggtgg cggcggagac                                                 260
```

<210> SEQ ID NO 75
<211> LENGTH: 204
<212> TYPE: DNA
<213> ORGANISM: Homo sapien

<400> SEQUENCE: 75

```
gtggggacca ggtctgtggg cctcaggtct ggccagccag ggctggtgct gtccccgcct      60
```

```
acctccactt cctttcccctt gctcactctg gatccagtga cagcaggtgt catgggtcaa      120
gcataaatca tatatagcat tttcaggcat gttcctggta gttcttttga gtctgacatt      180
ctaataaaat aatttgtaga aacc                                              204
```

<210> SEQ ID NO 76
<211> LENGTH: 227
<212> TYPE: DNA
<213> ORGANISM: Homo sapien

<400> SEQUENCE: 76

```
aaccacacat tggaaaaatc agtttaccct agaatctagt tattgttgtg gtacagttta       60
atttttgtca ataattcctt tctaaaattt ctaatgtaag tctttaattt tcaagatatt      120
ttgcttagaa gatgatatgg tttggctgtg tccccaccca aatctcacct tgaattccca      180
cgtgttgtag ggggcaggtc tttcctgtgc tgttcttgtg aaagtga                    227
```

<210> SEQ ID NO 77
<211> LENGTH: 528
<212> TYPE: DNA
<213> ORGANISM: Homo sapien

<400> SEQUENCE: 77

```
tagtacagca gccatgcagc caccttattt catagatgcc atctgtgtgt cctcttgact       60
accttctatt tagaggaaga atgagagctt tgtgtgttta actgagctta tagtaggact      120
tctttgcata tgtatggtac tgaaaaatct taatatacat ctttaatcct ttttaggttg      180
tcctttaaag agttttgac tagtttcttt ttcttgacag ctcttctctt tggacacatg       240
ggccttctta gagggttcag tctaggaccc ggctctcctg gccctgtgtt gagggtagct      300
ggtccctctg tccctgtgtc tgctagcact agactttgtt gctgcagatt gatccagtgg      360
gtacataggc taattaatgt gagtcttttt ccttgtttaa aggagtccct cttgctgaaa      420
gtagagtgat tactattgct gtagtgctag gaaagtatta agtttgtgct gaaaatccat      480
tgccatttgg tacaaatgac attgttcttt ctgtgaaaga gatgccct                   528
```

<210> SEQ ID NO 78
<211> LENGTH: 241
<212> TYPE: DNA
<213> ORGANISM: Homo sapien
<220> FEATURE:
<221> NAME/KEY: misc_feature
<222> LOCATION: (1)...(241)
<223> OTHER INFORMATION: n = A,T,C or G

<400> SEQUENCE: 78

```
aatgcgggcc gcgtgcgtgc tgtgcggggc ngccggcggt cgcccagagc ggagcatccg       60
gcccccggca ctcccttccc cagcaggcct agggagctgc gcgcggggc agtgcgtgac       120 ctggagaccc gggccctggt ggattgggag tcgggcnggg gggagcaggt catgctaggg      180
tggtctccgg ccaagggagc gatgaaggtc aggcgcggcg agcggggctg ggaggcgggg      240
c                                                                       241
```

<210> SEQ ID NO 79
<211> LENGTH: 247
<212> TYPE: DNA
<213> ORGANISM: Homo sapien

<400> SEQUENCE: 79

-continued

```
agaatattaa gaaaatgaag taactgattt tctaaaaaaa aaaaaaaaaa aatttctaca      60
ttataactca cagcattgtt ccattgcagg ttttgcaatg tttgggggta aagacagtag     120
aaatattatt cagtaaacaa taatgtgtga acttttaaga tggataatag ggcatggact    180
gagtgctgct atcttgaaat gtgcacaggt acacttacct tttttttttt ttttttttaac   240 tttttcc                                                              247
```

<210> SEQ ID NO 80
<211> LENGTH: 246
<212> TYPE: DNA
<213> ORGANISM: Homo sapien
<220> FEATURE:
<221> NAME/KEY: misc_feature
<222> LOCATION: (1)...(246)
<223> OTHER INFORMATION: n = A,T,C or G

<400> SEQUENCE: 80

```
cttgttccct ctccaagtat ttcatagtaa cactctactt gaagtgactt gatccagact      60
gaaaagtgtc ctgcagtgga atgaccacca ggcccagatc tagcctagcc tgagctctca    120
caacctctcc ttaaccttcc ctagaacaat tacctttagc tcagtaatgg gaaaatctct    180
accctaacat gagggcagga cacacacaca cacacacaca ccctttgatc tcagtcttta    240 nacaag                                                              246
```

<210> SEQ ID NO 81
<211> LENGTH: 223
<212> TYPE: DNA
<213> ORGANISM: Homo sapien

<400> SEQUENCE: 81

```
ggctcagggc tccttccatt ctaaccttga gccacagtgt cactcttcag ggctctgctc      60
ctggctctat tttgttaagg tgtcatcagc cttcaacctc catttatata ttttataat     120 gttaagccac tgaccaactt tttcatagaa acaactatca gattcgaggg ctcccttgt     180 cccctgacc tgggcacagg catgggcgat ggctccctct tcc                       223
```

<210> SEQ ID NO 82
<211> LENGTH: 235
<212> TYPE: DNA
<213> ORGANISM: Homo sapien

<400> SEQUENCE: 82

```
caccatcatc aaagaccaaa ggtagataaa accacaaaga tgggaaaaaa aacagagcag      60
aaaagctgaa aattctaaaa atcagagcgc ctctcctcct ccaaaggaac acagctcctt    120
gccagcaatg gaacaaagct ggacagagaa tgactttgac aagttgagag aagaaggctt    180
gagatgatca aacttctccg agctaaagga ggaagtttga acccatagca aagaa        235
```

<210> SEQ ID NO 83
<211> LENGTH: 245
<212> TYPE: DNA
<213> ORGANISM: Homo sapien

<400> SEQUENCE: 83

```
tccgtttatc acagtccact taaaaaatga tgatgatgat aaaaaccatg acccaccaat      60
cacatgccta tcatatagta aaacccagcc catgacccct aacagggcc tctctcagccc    120 tcctaatgac ctccggccta accatgtgat ttcacttcca ctccataacg ctcctcatac    180
taggcctact aaccaacaca ctaaccatat accaatgatg gcgcgatgta acacgagaaa    240
```

```
                                                             gcaca                                             245

<210> SEQ ID NO 84
<211> LENGTH: 244
<212> TYPE: DNA
<213> ORGANISM: Homo sapien

<400> SEQUENCE: 84
agccagatga cctttttccc caagtgatac tccaagagca aaagtattga aaatagaaga    60
agtcagtgat acttcatccc tgcaacctca agccagtttg aagcaggatg tatgtcagtc   120
ttacagcgag aaaatgccca tagagataga acaaaaacct gctcagtttg ccacaactgt   180
tcttcctcca attcctgcaa actcgttcca gctcgaatct gatttcagac aattgaaaag   240
ttct                                                                244

<210> SEQ ID NO 85
<211> LENGTH: 219
<212> TYPE: DNA
<213> ORGANISM: Homo sapien

<400> SEQUENCE: 85
gtcactgagc ctgccaacca cgctgtggca ggtacctcca gccccagaca cctgcagcct    60
ccactgaaag ctcaatggca gcctcatgag accctggacc ggaaccaccc actacctaaa   120
aaatcccaaa catataactg aactccttat acccaattgg accaatctat caccctatag   180
aagaactaat gttagtataa gtaacatgaa aacattctc                          219

<210> SEQ ID NO 86
<211> LENGTH: 241
<212> TYPE: DNA
<213> ORGANISM: Homo sapien

<400> SEQUENCE: 86
agcacgttca actatatttt tagacaatat gggcaaatca tccaagaaat ccactgcact    60
tagtcgaact acaaataatg aaaagtctcc cattataaag cctctgattc caaagccgaa   120
gcctaagcag gcatctgcag catcctattt ccagaaaaga aattctcaaa ctaataaaac   180
tgaggaagtg aaagaagaaa atcttaaaaa tgtattatct gaaacccag ctatatgtcc    240 t                                                                  241

<210> SEQ ID NO 87
<211> LENGTH: 224
<212> TYPE: DNA
<213> ORGANISM: Homo sapien

<400> SEQUENCE: 87
cctgccaaaa ccaagaatcg ccgcagaagg aagccatcca cttctgatga ttctgactct    60
aattttgaga aaattgtttc gaaagcagtc acaagcacta atccaacgg ggagagtgat    120 gacttccata tggactttga ctcagctgtg gctcctcggg caaatctgt acgggcaaag    180 aaacctataa agtacctgga agagtcagat gaagatgatc tgtt                    224

<210> SEQ ID NO 88
<211> LENGTH: 241
<212> TYPE: DNA
<213> ORGANISM: Homo sapien

<400> SEQUENCE: 88
```

-continued

```
aattcttcca tcaaggagat atagaaaaaa aatatcattt gggtgtgagt ccactttgcg      60
atcagtcaca ctgaatctat tgccaacatc cagattggtt ttatgactta cctagtggag    120
cctttattta cagaatgggc caggttttcc aatacaaggc tatcccagac aatgcttgga    180
cacgtggggc tgaataaagc cagctggaag ggactgcaga gagaacagtc gagcagtgag    240
g                                                                    241
```

<210> SEQ ID NO 89
<211> LENGTH: 237
<212> TYPE: DNA
<213> ORGANISM: Homo sapien

<400> SEQUENCE: 89

```
gtccttccga ggaagctaag gctgcgttgg ggtgaggccc tcacttcatc cggcgactag     60
caccgcgtcc ggcagcgcca gccctacact cgcccgcgcc atggcctctg tctccgagct    120
cgcctgcatc tactcggccc tcattctgca cgacgatgag gtgacagtca cggaggataa    180
gatcaatgcc ctcattaaag cagccggtgt aaatgttgag ccttttttggc ctggctt      237
```

<210> SEQ ID NO 90
<211> LENGTH: 242
<212> TYPE: DNA
<213> ORGANISM: Homo sapien
<220> FEATURE:
<221> NAME/KEY: misc_feature
<222> LOCATION: (1)...(242)
<223> OTHER INFORMATION: n = A,T,C or G

<400> SEQUENCE: 90

```
aatgcaaaat gcttgcangt cactcccaaa tataaccta cattaccta tatataaatc       60 acaatgaaaa taaagtgcc tacattacag aactgtgaaa ttttgtttaa aaaaataata    120
aaataaaact gttgggtatc attggaataa tgtaacacat aaggctggaa atactgaaa    180 tacagttaag actcaataca caagtttact ttaaaaaga aagaaagaa agtttgcca      240 ga                                                                   242
```

<210> SEQ ID NO 91
<211> LENGTH: 239
<212> TYPE: DNA
<213> ORGANISM: Homo sapien

<400> SEQUENCE: 91

```
acaagatcat cattcgtgtg cagaccaccc cagactacag tccccaggag ctttcacca      60 acgccatcac agacctcatc agcgagctct cccttctgga ggagcgattc cgggtggcca   120
tcaaggacaa gcaagaagga attgagtagc agctgaaaga agcgttgctt agtggctgga   180
aggctggcac atactcctca gggcccttca gtttaccaca tggcgacagc cactctcag    239
```

<210> SEQ ID NO 92
<211> LENGTH: 242
<212> TYPE: DNA
<213> ORGANISM: Homo sapien

<400> SEQUENCE: 92

```
tttaatgttg tctcaccata acacaaaaag catgaacttg tattaatcat atataataga     60
ttgatcatgc actgtattca caggaggttg gaaaaccatg ccattttctg gaacttaagg   120
tgttgcatta tttcatcaat catttgttaa aaaaaccaa aaaaataaaa atgtgaaccc    180
ttcaggtgta acaccttat cttggtatac aattgatctt tttgtttttgt tttgaagtat   240
```

```
ca                                                                       242

<210> SEQ ID NO 93
<211> LENGTH: 221
<212> TYPE: DNA
<213> ORGANISM: Homo sapien

<400> SEQUENCE: 93
gggagaatgt gcacctgcag gtaccgggga gactcacaag gcacgagttc tgacaagaac         60
gtaaacagga agaccagggc cttcttgctg cagccatggt agcctcgtgt gctcccaaag        120
gaggccttga accagtctgc atatgacagg aacgcagagg ggccctccag tgctgcctgg        180
cgcacaacca ggaacgcagt gaccatgctg tccagctggc a                           221

<210> SEQ ID NO 94
<211> LENGTH: 229
<212> TYPE: DNA
<213> ORGANISM: Homo sapien

<400> SEQUENCE: 94
cacgtccgcc cctgcggcca agcccaagcg ggccaagggc ctccaagaag tccacagacc         60
accccaagta ttcagacatg atcgtggctg ccatccaggc cgagaagaac cgcgctggct        120
cctcgcgcca gtccattcag aagtatatca agagccacta caaggtgggt gagaacgctg        180
actcgcagat caagttgtcc atcaagcgcc tggtcaccac cggtgtcct                   229

<210> SEQ ID NO 95
<211> LENGTH: 224
<212> TYPE: DNA
<213> ORGANISM: Homo sapien

<400> SEQUENCE: 95
gctagtcaga accctatacc atgaagtgta gttaccatac agattaatat gtagcaaaaa         60
tgtatgcttg atatttctca actgtgttaa tttttctgct gtattccagc tgaccaaaac        120
aatattaaga atgcatcttt ataaatgggt gctaattgat aatggaaata atttagtaat        180
ggactataca ggatgttaat aatgaagcca tatgtttatg tctg                        224

<210> SEQ ID NO 96
<211> LENGTH: 446
<212> TYPE: DNA
<213> ORGANISM: Homo sapien

<400> SEQUENCE: 96
agctcaagat acatgaaatc aatcaaaggg aaacttgaag aacagagacc agaaagagta         60 aaaccttta tgacaggggc tgcagaacaa atcaagcaca tccctgctaa tttcaaaaac        120
taccagttct ttattggtga aaacatgaat ccagatggca tggttgctct attggactac        180
cgtgaggatg gtgtgacccc atatatgatt ttctttaagg atggtttaga aatggaaaaa        240
tgttaacaaa tgtggcaatt attttggatc tatcacctgt catcataact ggcttctgct        300
tgtcatccac acaacaccag gacttaagac aaatgggact gatgtcatct tgagctcttc        360
atttattttg actgtgattt atttggagtg gaggcattgt ttttaagaaa aacatgtcat        420
gtaggttgtc taaaataaa atgcat                                             446

<210> SEQ ID NO 97
<211> LENGTH: 352
<212> TYPE: DNA
```

<213> ORGANISM: Homo sapien

<400> SEQUENCE: 97

| aattcagcct | tcctccctgc | cagagatctc | tttaagaaaa | tagtttaaac | aatttgttaa | 60 |
| aaaattttcc | gtcttatttc | atttctgtaa | cagttgatat | ctggctgtcc | tttttataat | 120 |
| gcagagtgag | aactttccct | accgtgtttg | ataaatgttg | tccaggttct | attgccaaga | 180 |
| atgtgttgtc | caaaatgcct | gtttagtttt | taaagatgga | actccaccct | ttgcttggtt | 240 |
| ttaagtatgt | atggaatgtt | atgataggac | atagtagtag | cggtggtcag | acatggaaat | 300 |
| ggtggggaga | caaaatatata | catgtgaaat | aaaactcagt | attttaataa | ag | 352 |

```
<210> SEQ ID NO 98
<211> LENGTH: 248
<212> TYPE: DNA
<213> ORGANISM: Homo sapien
<220> FEATURE:
<221> NAME/KEY: misc_feature
<222> LOCATION: (1)...(248)
<223> OTHER INFORMATION: n = A,T,C or G
```

<400> SEQUENCE: 98

| cggccgacag | anctgaggcg | gagggcctga | gcccgcgctt | ccaccagctg | gacatcgacg | 60 |
| atctgcagag | catccgcgcc | ctgcgcgact | tcctgcgcaa | ggagtacggg | ggcctggacg | 120 |
| tgctggtcaa | caacgcgggc | atcgccttca | aggttgctga | tcccacaccc | tttcatattc | 180 |
| aagctgaagt | gacgatgaaa | acaaatttct | ttggtacccg | agatgtgtgc | acagaattac | 240 |
| tccctcta | | | | | | 248 |

```
<210> SEQ ID NO 99
<211> LENGTH: 224
<212> TYPE: DNA
<213> ORGANISM: Homo sapien
<220> FEATURE:
<221> NAME/KEY: misc_feature
<222> LOCATION: (1)...(224)
<223> OTHER INFORMATION: n = A,T,C or G
```

<400> SEQUENCE: 99

| agnaagagac | aatgaactca | taggccagac | tgtgcgtatc | tcccagggac | cctacaaagg | 60 |
| ctacattggt | gtggtgaagg | atgccacaga | gtccacggcc | agagtagaac | tgcattctac | 120 |
| ctgccagacc | atctctgtgg | atcgccagcg | gctcaccacg | gtcgactccc | agcgtccagg | 180 |
| tggcatgacc | tctacatatg | gacggactcc | catgtatggc | tctc | | 224 |

```
<210> SEQ ID NO 100
<211> LENGTH: 236
<212> TYPE: DNA
<213> ORGANISM: Homo sapien
<220> FEATURE:
<221> NAME/KEY: misc_feature
<222> LOCATION: (1)...(236)
<223> OTHER INFORMATION: n = A,T,C or G
```

<400> SEQUENCE: 100

| ctgtggcgct | ccgtgaaatt | agacgttatc | agaagtncac | tgaacttctg | attcgcaaac | 60 |
| ttcccttcca | gcgtctgggng | cgagaaattg | ctcaggactt | taaaacagat | ctgcgcttcc | 120 |
| agagcgcagc | tatcggtgct | ttgcaggagg | caagtgaggc | ctatctggtt | ggccttttttg | 180 |
| aagacaccaa | cctgtgtgct | atccatgcca | aacgtgtaac | aattatgcca | aaagac | 236 |

```
<210> SEQ ID NO 101
<211> LENGTH: 243
<212> TYPE: DNA
<213> ORGANISM: Homo sapien

<400> SEQUENCE: 101
cttcctgacc ttgggctacg gctgaccgtt tttttgtggt gtactccgtg ccatcatgtc      60
cgtcctgacg ccgctgctgc tgcggggctt gacaggctcg gcccggcggc tcccagtgcc     120
gcgcgccaag atccattcgt tgccgccgga ggggaagctt gggatcatgg aattggccgt     180
tgggcttacc tcctgcttcg tgaccttcct cctgccagcg ggctggatcc tgtcacacct     240
gga                                                                   243

<210> SEQ ID NO 102
<211> LENGTH: 234
<212> TYPE: DNA
<213> ORGANISM: Homo sapien
<220> FEATURE:
<221> NAME/KEY: misc_feature
<222> LOCATION: (1)...(234)
<223> OTHER INFORMATION: n = A,T,C or G

<400> SEQUENCE: 102
ccgganncgn caccgccgcg cnntcgccca ccgcccgcc cgccgctccc ggccccgctc       60
gccccctccg ccgccgccgc ccgcccctgc gactacgctg cggcctcccg cccgctcccg    120
ctcgctcccg cggccctcgc tcgcctcgcg ccggcagttt tgggcctaca cctcccctcc    180
ccccgccagc cgccaaagac ttgaccacgt aacgagccca actccccga acgc            234

<210> SEQ ID NO 103
<211> LENGTH: 247
<212> TYPE: DNA
<213> ORGANISM: Homo sapien

<400> SEQUENCE: 103
cagcgccagc gaggtcggag cggacagcga ggtcggcagc ggcacagcga ggtcggcagc      60
ggcacagcga ggtcggcagt ggcagcgagg tcggcagcgg cacagcgagg tcggcagcgg    120
cagcgaggtc ggcagcggcg cgcgctgtgc tcttccgcgg actctgaatc atggcgacca    180
cggccacgat ggcgacctcg ggctcggcgc gaaagcggct gctcaaagag gaagacatga    240
ctaaagt                                                               247

<210> SEQ ID NO 104
<211> LENGTH: 247
<212> TYPE: DNA
<213> ORGANISM: Homo sapien

<400> SEQUENCE: 104
gattaaccac aattctcaga cccaatcctg agtcctcagg aggttgtatc ttgcagcccc      60
tatgcccaag gttgtgatgg tggattccca tacctcattg cagggaagta tgcccaagat    120
tttggggtgg tggaagaaag ctgctttccc tacacagcca aagattctcc atgcaaacca    180
agggagaatt gcctccgtta ctattcttct gactactact atgtgggtgg tttctatggt    240
ggctgca                                                               247

<210> SEQ ID NO 105
<211> LENGTH: 224
<212> TYPE: DNA
<213> ORGANISM: Homo sapien
```

<400> SEQUENCE: 105

| | | | | | |
|---|---|---|---|---|---|
| agagaaagaa | gaatctgatg | atgaagctgc | agtagaggaa | gaagaagaag | aaaagaaacc | 60 |
| aaagactaaa | aaagttgaaa | aaactgtctg | ggactgggaa | cttatgaatg | atatcaaacc | 120 |
| aatatggcag | agaccatcaa | aagaagtaga | agaagatgaa | tacaaagctt | tctacaaatc | 180 |
| attttcaaag | gaaagtgatg | acccatggc | ttatattcac | ttta | | 224 |

<210> SEQ ID NO 106
<211> LENGTH: 522
<212> TYPE: DNA
<213> ORGANISM: Homo sapien
<220> FEATURE:
<221> NAME/KEY: misc_feature
<222> LOCATION: (1)...(522)
<223> OTHER INFORMATION: n = A,T,C or G

<400> SEQUENCE: 106

| | | | | | |
|---|---|---|---|---|---|
| cggagccgga | gacaagagca | gaggccgaac | tcgggatctg | acaagatggc | cgggctgccc | 60 |
| cgcangatca | tcaaggaaac | ccagcgtttg | ctggcagaac | cagttcctgg | cattaaagca | 120 |
| gaaccagatg | agagcaacgc | ccgttatttt | catgtggtca | ttgctggccc | ccaggattcc | 180 |
| cccttcgagg | gagggacttt | taaacttgaa | ctattccttc | cagaagaata | cccaatggca | 240 |
| gcacctaaag | tacgtttcat | gaccaaaatt | tatcatccta | atgtagacaa | gttgggaaga | 300 |
| atatgtttag | atattttgaa | aggtaagtgt | tgtttgtcac | cctgtgcttt | attaacgtgt | 360 |
| cctttttgtc | ctaagcattc | tacatttaga | atgtaagcat | tggaatctca | ctgtatgcta | 420 |
| acagccccag | agtgtgtggg | agggaagtgc | agcagttctg | ggcctgttgt | ccatgcttta | 480 |
| tcatatactg | ggcctgttac | cttcatagat | aagtggtccc | ca | | 522 |

<210> SEQ ID NO 107
<211> LENGTH: 526
<212> TYPE: DNA
<213> ORGANISM: Homo sapien

<400> SEQUENCE: 107

| | | | | | |
|---|---|---|---|---|---|
| tttaatgttg | tctcaccata | acacaaaaag | catgaacttg | tattaatcat | atataataga | 60 |
| ttgatcatgc | actgtattca | caggaggttg | gaaaaccatg | ccattttctg | gaacttaagg | 120 |
| tgttgcatta | tttcatcaat | catttgttaa | aaaaaaacta | aaaaataaaa | atgtgaaccc | 180 |
| ttcaggtgta | aacaccttat | cttggtatac | aattgatctt | tttgttttgt | ttgaagtat | 240 |
| cagatattaa | tttggaataa | ggtaaggttc | tcttgaaaca | tttgaaaacc | ctttaagcca | 300 |
| actgatctga | cagcttttccc | atcagtagaa | gtgggaacat | accttcttag | gtatttacta | 360 |
| ttaactacat | gtaggcagtt | tatagcttct | gatcagtgta | gtagacatta | caaacactgg | 420 |
| ttgtaatggg | gttttctgta | gactttactt | gagaggtgag | tataaagcat | tttttagtca | 480 |
| tcatcatgac | gatgctgctc | aagtgcagat | ccagaacagt | acagcg | | 526 |

<210> SEQ ID NO 108
<211> LENGTH: 243
<212> TYPE: DNA
<213> ORGANISM: Homo sapien
<220> FEATURE:
<221> NAME/KEY: misc_feature
<222> LOCATION: (1)...(243)
<223> OTHER INFORMATION: n = A,T,C or G

<400> SEQUENCE: 108

| | | | | | |
|---|---|---|---|---|---|
| aatgcccatc | atggcagcgg | cgttccgcag | aggctgcagg | gtcctgagaa | gtgtttctca | 60 |

```
ttttgagtgt cgaacacaac actcgaaagc ggctcacaag caggagcccg gattagggtt      120
tagttttgag ttgacnggaa cagcagaaag agtttcaagc aactgcccgc aagtttgcca      180
gagaggagat tatcccgtc gccccggaat atgacaaaag cggggaggtg ggtatcgggt       240
tgc                                                                   243
```

<210> SEQ ID NO 109
<211> LENGTH: 242
<212> TYPE: DNA
<213> ORGANISM: Homo sapien
<220> FEATURE:
<221> NAME/KEY: misc_feature
<222> LOCATION: (1)...(242)
<223> OTHER INFORMATION: n = A,T,C or G

<400> SEQUENCE: 109

```
cgngaacaac gccctanaaa aaacaagaag gtaatccctc aacaaaccta aaagaagaca      60
gccacaagaa cagaatgcaa gagatggaag agagaatctc aggtgcagaa gattccatag     120
agaacatcgg cacaacaatc aaagaaaatg gaaaatgcaa aaagatccta actcaaaata    180
tccaggaaat ccaggacaca ataagaagac caaacgtacg gataatagga gtggatgaga   240
ag                                                                    242
```

<210> SEQ ID NO 110
<211> LENGTH: 246
<212> TYPE: DNA
<213> ORGANISM: Homo sapien

<400> SEQUENCE: 110

```
ttcagataac tacttgaaat atgcagagaa atccctgaat gatatgtttg tgaagacata      60
tggccattta tacatgcaaa attctgagct atttaaagat ctcttcgtag agttgaaacg     120
ttactacgtg gtgggaaatg tgaacctgga agaaatgcta aatgacttct gggctcgcct    180
cctggagcgg atgttccgcc tggtgaactc ccagtaccac tttacagatg agtatctgga   240
atgtgt                                                                246
```

<210> SEQ ID NO 111
<211> LENGTH: 238
<212> TYPE: DNA
<213> ORGANISM: Homo sapien

<400> SEQUENCE: 111

```
ccaaaatggg aaaggaaaag actcatatca acattgtcgt cattggacac gtagattcgg      60
gcaagtccac cactactggc catctgatct ataaatgcgt tggcatcgac aaaagaacca     120
ttgaaaaatt tgagaaggag gctgctgaga tgggaaaggg ctccttcaag tatgcctggg    180
tcttggataa actgaaagct gagcgtgaac gtggtatcac cattgatatc tccttgtg      238
```

<210> SEQ ID NO 112
<211> LENGTH: 242
<212> TYPE: DNA
<213> ORGANISM: Homo sapien
<220> FEATURE:
<221> NAME/KEY: misc_feature
<222> LOCATION: (1)...(242)
<223> OTHER INFORMATION: n = A,T,C or G

<400> SEQUENCE: 112

```
agagaggaag aagcganggg cacggcgctg agacagagct ggagatgagg ccagaccatg      60
```

```
gacactacac ccagcaatag agacgggact gcggaggaag gaggacccag gacaggatcc    120
aggccggctt gccacacccc ccaccccctag gacttattcc cgctgactga gtctctgagg    180
ggctaccagg aaagcgcctc caaccctagc aaaagtgcaa gatggggagt gagaggctgg    240
ga                                                                   242

<210> SEQ ID NO 113
<211> LENGTH: 225
<212> TYPE: DNA
<213> ORGANISM: Homo sapien

<400> SEQUENCE: 113
cgaacgcgga gagcacgcca tgaaggcctc gggcacgcta cgagagtaca aggtagtggg    60
tcgctgcctg cccaccccca aatgccacac gccgcccctc taccgcatgc gaatctttgc    120
gcctaatcat gtcgtcgcca agtcccgctt ctggtacttt gtatctcagt taaagaagat    180
gaagaagtct tcaggggaga ttgtctactg tgggcaggtg tttga                    225

<210> SEQ ID NO 114
<211> LENGTH: 231
<212> TYPE: DNA
<213> ORGANISM: Homo sapien

<400> SEQUENCE: 114
tcaatgcagg gtctaaaagc tggtgttatt gctgttattg tggttgtggt gatagcagtt    60
gttgctggaa ttgttgtgct ggttatttcc agaaagaaga gaatggcaaa gtatgagaag    120
gctgagataa aggagatggg tgagatgcat agggaactca atgcataact atataatttg    180
aagattatag aagaagggaa atagcaaatg gacacaaatt acaaatgtgt g             231

<210> SEQ ID NO 115
<211> LENGTH: 226
<212> TYPE: DNA
<213> ORGANISM: Homo sapien

<400> SEQUENCE: 115
gtgcagcggg cagaccctgt ggccgtcacg ccctgccgct ccagggaagg gagccaggct    60
gagcctctgc cacgtgggag aggggctgtt tccagccacc acccaaaaaa acaccacaag    120
ggtcagtcct agcccacccg acagcttccc ttcccaagca ggggtttcgg ggacagtgca    180
ccagggaggg ccactgacag gcttgggaca tgtgcccagc tctcct                   226

<210> SEQ ID NO 116
<211> LENGTH: 230
<212> TYPE: DNA
<213> ORGANISM: Homo sapien

<400> SEQUENCE: 116
ttctaagacc cgagagaaaa agttgggact aggaactgca tatattcatg gaatgaaaca    60
tgccacagga aactacatca ttattatgga tgctgatctc tcacaccatc caaaattttat    120 tcctgaattt attaggaagc aaaaggaggg taattttgat attgtctctg gaactcgcta    180
caaaggaaat ggaggtgtat atggctggga tttgaaaaga aaaataatca                230

<210> SEQ ID NO 117
<211> LENGTH: 225
<212> TYPE: DNA
<213> ORGANISM: Homo sapien

<400> SEQUENCE: 117
```

-continued

```
tggtggtagg gtgtcaattt tagatctctc ctgctttctc ttgtgggcat ttagtgctat      60
acatttccct ctacaccctg ctttaaatgt gtcccagaga ttctggtaca ttgtgtcttt     120
gttctcattg gtttcaaaga acatctttat ttctgcgttc atttcattat ttacccacta    180
gtcattcagg agcaggttgt tcagtttcca tgtagttgtg tggtt                     225

<210> SEQ ID NO 118
<211> LENGTH: 247
<212> TYPE: DNA
<213> ORGANISM: Homo sapien

<400> SEQUENCE: 118
aagtgtgatc cccatgaagc aacgtgctat gacgatgggg agacctacca tgtaggagaa     60
cagtggcaga aagaatatct cggagccatt tgctcctgca cgtgtttcgg aggccagcgg    120
ggctggcgct gtgacaactg ccgtagacct ggggctgctg aacccagtcc cgatggcacc    180
accggccaca cctacaacca gtatacacag agatacaatc agagaacaaa cactaacgta    240
aattgcc                                                               247

<210> SEQ ID NO 119
<211> LENGTH: 227
<212> TYPE: DNA
<213> ORGANISM: Homo sapien

<400> SEQUENCE: 119
gaccaccacg cacttgatgg cctgcgacgg cgccgtgggg aagacatgct tgctgatcag     60
ctacacgacc aacgccttcc ccggagagta catccccacc gttttttgaca actactctgc    120 caacgtgatg gtggacggga accagtcaa cttggggctg tgggacacag cgggtcagga    180
ggactacgat cggctgcggc cactctccta cccccaaact gacgtct                   227

<210> SEQ ID NO 120
<211> LENGTH: 235
<212> TYPE: DNA
<213> ORGANISM: Homo sapien

<400> SEQUENCE: 120
ctttgccggc ctgccgggcc tgcagctcct ggacctgtca cagaaccaga tcgccagcct     60
gcccagcggg gtcttccagc cactcgccaa cctcaggagc acggagatct cgccggcttt    120
acgttcacct cggtgtctgc agcaccctcc gcttcctctc ctaggcgacg agacccagtg    180
gctagaagtt caccatgtct attctcaaga tccatgccag ggagatcttt gactc         235

<210> SEQ ID NO 121
<211> LENGTH: 226
<212> TYPE: DNA
<213> ORGANISM: Homo sapien

<400> SEQUENCE: 121
ctttgaggtt cctttcttct gcaaacacac tgtcagatgg taacaatgct gtttttagggt    60 taataatttc tgccccttt c ttctccaagt cactgttaaa catctgctga tttaaagcac    120
actcctcggc attttcagtg aattgttcaa tactgactga agcggatgct acaagaggaa    180
tttcttcttt gacctcctct ccttgagttt caagctccaa agtttc                    226

<210> SEQ ID NO 122
<211> LENGTH: 245
<212> TYPE: DNA
```

<213> ORGANISM: Homo sapien

<400> SEQUENCE: 122

| | | | | |
|---|---|---|---|---|
| agctcccaca | acaggtggct | aagggaaaag | gaggtagatg | atggcaaaat aagatttagt | 60 |
| tgtgttttct | cagagccgcc | acaagattga | acaaaatgtt | ttctgtttgg gcatcctgag | 120 |
| gaagttgtat | tagctgttaa | tgctctgtga | gtttagaaaa | agtcttgata gtaaatctag | 180 |
| tttttgacac | agtgcatgaa | ctaagtagtt | aaatatttac | atattcagaa aggaatagtg | 240 |
| gaaaa | | | | | 245 |

<210> SEQ ID NO 123
<211> LENGTH: 246
<212> TYPE: DNA
<213> ORGANISM: Homo sapien

<400> SEQUENCE: 123

| | | | | |
|---|---|---|---|---|
| gattaaccac | aattctcaga | cccaatcctg | agtcctcagg | aggttgtatc ttgcagcccc | 60 |
| tatgcccaag | gttgtgatgg | tggattccca | tacctcattg | cagggaagta tgcccaagat | 120 |
| tttgggtgg | tggaagaaag | ctgctttccc | tacacagcca | aagattctcc atgcaaacca | 180 |
| agggagaatt | gcctccgtta | ctattcttct | gactactact | atgtgggtgg tttctatggt | 240 |
| ggctgc | | | | | 246 |

<210> SEQ ID NO 124
<211> LENGTH: 245
<212> TYPE: DNA
<213> ORGANISM: Homo sapien

<400> SEQUENCE: 124

| | | | | |
|---|---|---|---|---|
| agcccaaatg | gaaaggaaaa | gactcatatc | aaacattgtc | gtcattggac acgtagattc | 60 |
| gggcaagtcc | accactactg | gccatctgat | ctataaatgc | ggtggcatcg acaaaagaac | 120 |
| cattgaaaaa | tttgagaagg | aggctgctga | gatgggaaag | ggctccttca gtatgcctg | 180 |
| ggtcttggat | aaactgaaag | ctgagcgtga | acgtggtatc | accattgata tctccttgtg | 240 |
| gaaat | | | | | 245 |

<210> SEQ ID NO 125
<211> LENGTH: 242
<212> TYPE: DNA
<213> ORGANISM: Homo sapien

<400> SEQUENCE: 125

| | | | | |
|---|---|---|---|---|
| gttaagcaga | aggtggagag | ctgtcgcgcg | agctcagcac | cctgcggaac ttgttcaagc | 60 |
| agctgcccga | gcccctgctc | gcctcctccg | gccactgcta | gcgcggcccc cgcgcgcgtc | 120 |
| cccctgccgg | ccggggctga | gactccgggg | agcgcccgcg | cccgcgccct cgcccccgcc | 180 |
| cccggcggcg | ccggcaaaac | tttggcactg | gggcacttgg | cagcgcgggg agcccgtcgg | 240 |
| ta | | | | | 242 |

<210> SEQ ID NO 126
<211> LENGTH: 245
<212> TYPE: DNA
<213> ORGANISM: Homo sapien

<400> SEQUENCE: 126

| | | | | |
|---|---|---|---|---|
| agcctggagc | ggcgggtgct | cgggctgcgt | ccgctccgca | gaagcaccga gcagccgagc | 60 |
| cggggcccgc | cgccctcctc | ctccatgagg | cccgagtgag | gcgcggcggc tatagccgac | 120 |

```
ccgcggcgcc ttccccccgc gtcctatcgc gagcgcagcg gcagcggccc ctggaggagg    180
aggcggagga ggaggagcat gtcggacggt ttcgatcggg ccccagagca aacgaggccc    240
ctgag                                                                245

<210> SEQ ID NO 127
<211> LENGTH: 246
<212> TYPE: DNA
<213> ORGANISM: Homo sapien

<400> SEQUENCE: 127
agcccccggt gggctgaggc aggggccgct gtcgtcaggc ctgagccagg gtgagctggt     60
gcctgccttg cattttcctt ctggtgctgt gaagaccata ggctggcagg cagctgagat    120
gaactgtctt taccactgat gaggggcctc tgccggctga gggtagcaag caggggttgt    180
gagtcaggct gggggacttg tttgaaagaa agaggagtgg aaaatggttc caggagggaa    240
gaggtt                                                               246

<210> SEQ ID NO 128
<211> LENGTH: 224
<212> TYPE: DNA
<213> ORGANISM: Homo sapien

<400> SEQUENCE: 128
ccgaaatggg caagttcatg aaacctggga aggtggtgct tgtcctggct ggacgctact     60
ccggacgcaa agctgtcatc gtgaagaaca ttgatgatgg cacctcagat cgcccctaca    120
gccatgctct ggtggctgga attgaccgct accccgcaa agtgacagct gccatgggca     180
agaagaagat cgccaagaga tcaaagataa aatcttttgt gaaa                     224

<210> SEQ ID NO 129
<211> LENGTH: 228
<212> TYPE: DNA
<213> ORGANISM: Homo sapien
<220> FEATURE:
<221> NAME/KEY: misc_feature
<222> LOCATION: (1)...(228)
<223> OTHER INFORMATION: n = A,T,C or G

<400> SEQUENCE: 129
ctttgctttc taaactcttc cagaaaggac tgtgagcaag atgaatttac ttttcttaaa     60
aaaaaaaaaa aacagggttg gaaagtccaa gccgtaggac ccagtttcct ttcttagctg    120
atgtctttgg ccagaacacc gngggctgtt acttgctttg aggnggaagc ggtttgcatt    180
tacgcctgta aatgtattca ttcttaattt atgtaaggtt ttttttgt                 228

<210> SEQ ID NO 130
<211> LENGTH: 443
<212> TYPE: DNA
<213> ORGANISM: Homo sapien

<400> SEQUENCE: 130
cagagcaaga ctccgtccca aaaaaaaaaa aaaaaaaaa tacatatata tatatgtata     60
tgtatgtatg tatgtatgtg agtgaaatcc tcatctttta tggtagagag tcaatgacat    120
tatctaaaag gtgataaatt tggaaataga tatgtaagca tattatatat tatctagagt    180
tactgtcata attcttagta ataatagaga gaaatatgaa agaactaagc aagaattatt    240
tagaagagtt tgtctctggg tataaatagg acagatcttg gttctaatca caccactgat    300
```

-continued

| ttgtcaacca caggcaagta ttaataaaaa ctcataaaaa gtaaatgttc taaaactgct | 360 |
| ctaaaaaata aagtcttaaa aaaaggtaaa tgttttggaa taaacagaca attacaataa | 420 |
| caatgacatt aaccccgaag tct | 443 |

<210> SEQ ID NO 131
<211> LENGTH: 444
<212> TYPE: DNA
<213> ORGANISM: Homo sapien

<400> SEQUENCE: 131

| caaacaatac tatcttataa aatagtactg ttgaattatt ccaagcctcc ctaggtttgc | 60 |
| tctcaaatgt catttacaga ttgggctaac gacctaaaat ctatatataa agactttctg | 120 |
| aagaactctg tattatagca ataccaaacg agtgctgtgt gtgcaaacag tctggcgttg | 180 |
| cttttatgt tgatatttat cctagaacac tgaaagagaa tatgccagtg ataactcact | 240 |
| ttacttcagt catttcaaca cagaaaatgc ttctctagca ttttcttt gtagtgttaa | 300 |
| cattttgaaa ttcatgtttc agaggcttca tcatcacaga atttactctt gctccatgaa | 360 |
| aaaaaattaa ataccttcag aggaatattt aagttgtaaa ctatgaaact tgagaaatcc | 420 |
| tcttgagata aaaggctgcc aaat | 444 |

<210> SEQ ID NO 132
<211> LENGTH: 424
<212> TYPE: DNA
<213> ORGANISM: Homo sapien

<400> SEQUENCE: 132

| aaggaagggg cgaacggcgt gagctggcgc cgaaatggga gaaagcagcg agtgagatgg | 60 |
| gaagggcgc caggcgagca cccgggagcc agcgggacct gggcagggc gcccggagca | 120 |
| ggcgcgcatg gcgggccccg cgcggggatc cggctgaag agagcgtagc acggctcgca | 180 |
| cgagtccggg gccgatgtac caggtgagcg gccagcgccc ctctggctgc gacgcgccct | 240 |
| atggagcccc cagcgcagcc ccgggcccag gccagcctca ggggaacccc ttgggctgca | 300 |
| cccacttct gccgaatgac tctggccacc cctcagagct gggcggcacc agacgggcgg | 360 |
| ggaatggtgc cctgggtggc cccaaggccc accggaagtt gcagacacac ccatctctcg | 420 |
| ccag | 424 |

<210> SEQ ID NO 133
<211> LENGTH: 424
<212> TYPE: DNA
<213> ORGANISM: Homo sapien

<400> SEQUENCE: 133

| tacagtgcgt gttcaggacc cccgattgca gaatgagggc tcctggaact cttatgtgga | 60 |
| ttataagata ttcctccata ccaacagcaa agcctttact gccaagactt cctgtgtgcg | 120 |
| gcgccgctac cgtgagttcg tgtggctgag aaagcagcta cagagaaatg ctggtttggt | 180 |
| gcctgttcct gaacttcctg ggaagtcaac cttcttcggc acctcagatg agttcattga | 240 |
| gaagcgacga caaggtctgc agcacttcct tgaaaaggtc ctgcagagtg tggttctcct | 300 |
| gtcagacagc cagttgcacc tattcctgca aagccagctc tcggtgcctg agatagaagc | 360 |
| ctgtgtccag ggccgaagta ccatgactgt gtctgatgcc attcttcgat atgctatgtc | 420 |
| aaac | 424 |

<210> SEQ ID NO 134
<211> LENGTH: 426
<212> TYPE: DNA
<213> ORGANISM: Homo sapien
<220> FEATURE:
<221> NAME/KEY: misc_feature
<222> LOCATION: (1)...(426)
<223> OTHER INFORMATION: n = A,T,C or G

<400> SEQUENCE: 134

```
gggaagcgcc gcggcctgta tttctnnacc tgcccttcgc ctggttcgtg gcgccttntg      60
accccgggcc cctgccgcct gcaagtcgga aacngcgctg tgctcctgtg ctacggcctg     120
tggctggact gcctgctgct gcccaactgg ctggcaagat gaagctctcc ctggtggccg     180
cgatgctgct gctgctcagc gcggcgcggg ccgaggagga ggacaagaag gaggacgtgg     240
gcacggtggt cggcatcgac ctggggacca cctactcctg cgtcggcgtg ttcaagaacg     300
gccgcgtgga gatcatcgcc aacgatcagg gcaaccgcat cacgccgtcc tatgtcgcct     360
tcactcctga aggggaacgt ctgattggcg atgccgccaa gaaccagctc acctccaacc     420
ccgaga                                                               426
```

<210> SEQ ID NO 135
<211> LENGTH: 422
<212> TYPE: DNA
<213> ORGANISM: Homo sapien

<400> SEQUENCE: 135

```
gactcctgtg aggatgcagc actccctggc aggtcagacc tatgccgtgc ccttcatcca      60
gccagacctg cggcgagagg aggccgtcca gcagatggcg gatgccctgc agtacctgca     120
gaaggtctct ggagacatct tcagcaggta gagcagagcc ggagccaggt gcaggccatt     180
ggagagaagg tctccttggc ccaggccaag attgagaaga tcaagggcag caagaaggcc     240
atcaaggtgt tctccagtgc caagtaccct gctccagggc gcctgcagga atatggctcc     300
atcttcacgg gcgcccagga ccctggcctg cagagacgcc ccgccacag gatccagagc     360
aagcaccgcc ccctggacga gcgggccctg caggagaagc tgaaggactt tcctgtgtgc     420
gt                                                                    422
```

<210> SEQ ID NO 136
<211> LENGTH: 233
<212> TYPE: DNA
<213> ORGANISM: Homo sapien
<220> FEATURE:
<221> NAME/KEY: misc_feature
<222> LOCATION: (1)...(233)
<223> OTHER INFORMATION: n = A,T,C or G

<400> SEQUENCE: 136

```
gctgctctga gattnngagt tcttctgcag agatgattaa atatatccaa gagacattgg      60
aaaacnggnt gaacatttta cattggtctg ctcagcacat ggctggatgc ggatatttct     120
ataattccag aaagtcacac agctcctctg tatgagacca gtgggcgcca tttaaaagaa     180
caggatgaga atctaagata tattattaat aaatgtaatg gatttttttt tgt            233
```

<210> SEQ ID NO 137
<211> LENGTH: 427
<212> TYPE: DNA
<213> ORGANISM: Homo sapien
<220> FEATURE:
<221> NAME/KEY: misc_feature
<222> LOCATION: (1)...(427)

<223> OTHER INFORMATION: n = A,T,C or G

<400> SEQUENCE: 137

| taaagcataa tgattgataa gctagaactt tctgatgtag tcattacatg aaaccccttg | 60 |
| tcactggttt gtgtgttcag aggaagccat ggccgagata gctttcctga aataaaccag | 120 |
| tagcttttca gattgacgtt cttgctacaa ttgtaccatc tggtaattcc tgaaaatgtc | 180 |
| aatttttttg tgttaatatt tttggtttca acaataaca aatgtctcta gaaagaaatt | 240 |
| ttaagaaagc ttaattaata gtaaaaatgc ctttcctgaa ataatcttgg aaaatttttt | 300 |
| aaatggcaaa aatggatgaa gtcatgctta atacattgan gggttggttt tttggtttgg | 360 |
| ttnggttggt tnggttttga aaacagaagt tcgctcttgg tgcccangct ggaagtgcaa | 420 |
| tggcacg | 427 |

<210> SEQ ID NO 138
<211> LENGTH: 456
<212> TYPE: DNA
<213> ORGANISM: Homo sapien

<400> SEQUENCE: 138

| taagttcctg aagtgcagaa ctcccagaca aattatgtta gagcctgatt gttagttcag | 60 |
| gaggagcttc cactgctaac tcccatcctc ctactcagtt ctaggccact ggtacccact | 120 |
| tgagggtaga gttgtattta caaatacttg gagtgatttt atgcaacaaa ctgcacagag | 180 |
| gattatagac tcagttaata ggggagtgga gaatgccagc aagcccctga gttagagtga | 240 |
| atggccttca actgtgctta ccaattgtgg aacaaaagcc agctagaacc ctagcaatat | 300 |
| agtagggtta tgggatcttt ggagtgttgc ttttctggct ggatacctcc gtggacagtg | 360 |
| gggcctttgc ctgagttctt gtcctgtgtc caggaagaat gaggtatgca gacaagtgga | 420 |
| gggtgagcaa gatgaagaga agctttattg agtgtt | 456 |

<210> SEQ ID NO 139
<211> LENGTH: 456
<212> TYPE: DNA
<213> ORGANISM: Homo sapien
<220> FEATURE:
<221> NAME/KEY: misc_feature
<222> LOCATION: (1)...(456)
<223> OTHER INFORMATION: n = A,T,C or G

<400> SEQUENCE: 139

| tancaggagg agagtctaag gcanatgatc cctatgctca tcttagcaaa aaggagaaga | 60 |
| aaagctgaa aaacagatg gagtatgagc gccaagtggc ttcattaaaa gcagccaatg | 120 |
| cagctgaaaa tgacttctcc gtgtcccagg cggagatgtc ctcccgccaa gccatgttag | 180 |
| aaaatgcatc tgacatcaag ctggagaagt tcagcatctc cgctcatggc aaggagctgt | 240 |
| tcgtcaatgc agacctgtac attgtagccg gccgccgcta cgggctggta ggacccaatg | 300 |
| gcaagggcaa gaccacactc ctcaagcaca ttgccaaccg agccctgagc atccctccca | 360 |
| acattgatgt gttgctgtgt gagcaggagg tggtagcaga tgagacacca gcagtccagg | 420 |
| ctgttcttcg agctgacacc aagcgattga agctgc | 456 |

<210> SEQ ID NO 140
<211> LENGTH: 452
<212> TYPE: DNA
<213> ORGANISM: Homo sapien

<400> SEQUENCE: 140

```
ggagcttccg ggagggcggc tcgcaggcac catgactcct gtgaggatgc agcactccct     60
ggcaggtcag acctatgccg tgcccctcat ccagccagac ctgcggcgag aggaggccgt    120
ccagcagatg gcggatgccc tgcagtacct gcagaaggtc tctggagaca tcttcagcag    180
gtagagcaga gccggagcca ggtgcaggcc attggagaga aggtctcctt ggcccaggcc    240
aagattgaga agatcaaggg cagcaagaag gccatcaagg tgttctccag tgccaagtac    300
cctgctccag agcgcctgca ggaatatggc tccatcttca cgggcgccca ggaccctggc    360
ctgcagagac gcccccgcca caggatccag agcaagcacc gcccccctgga cgagcgggcc    420 ctgcaggaga agctgacttt cctgtgtgcg tg                                   452

<210> SEQ ID NO 141
<211> LENGTH: 451
<212> TYPE: DNA
<213> ORGANISM: Homo sapien
<220> FEATURE:
<221> NAME/KEY: misc_feature
<222> LOCATION: (1)...(451)
<223> OTHER INFORMATION: n = A,T,C or G

<400> SEQUENCE: 141
agggtacacn aatagnctat tcgccatcag tagaaggtag cagcacagaa ctcaaccttc     60
ctgaaactgc aaactccgtc accctcagtg acttgcaacc tggtgttcag tataacatca    120
ctatctatgc tgtggaagaa atcaagaaa gtacacctgt tgtcattcaa caagaaacca    180
ctggcacccc acgctcagat acagtgccct ctcccaggga cctgcagttt gtggaagtga    240
cagacgtgaa ggtcaccatc atgtggacac cgcctgagag tgcagtgacc ggctaccgtg    300
tggatgtgat ccccgtcaac ctgcctggcg agcacgggca gaggctgccc atcagcagga    360
acacctttgc agaagtcacc gggctgtccc ctggggtcac ctattacttc aaagtctttg    420
cagtgagcca tgggagggag agcaagcctc t                                    451

<210> SEQ ID NO 142
<211> LENGTH: 463
<212> TYPE: DNA
<213> ORGANISM: Homo sapien

<400> SEQUENCE: 142
gaattccaaa caatactatc ttataaaata gtactgttga attattccaa gcctccctag     60
gtttgctctc aaatgtcatt tacagattgg gctaacgacc taaaatctat atataaagac    120
tttctgaaga actctgtatt atagcaatac caaacgagtg ctgtgtgtgc aaacagtctg    180 gcgttgctttt ttatgttgat atttatccta gaacactgaa agagaatatg ccagtgataa    240
ctcactttac ttcagtcatt tcaacacaga aaatgcttct ctagcatttt tcttttgtag    300
tgttaacatt ttgaaattca tgtttcagag gcttcatcat cacagaattt actcttgctc    360
catgaaaaaa aattaaatac cttcagagga atatttaagt tgtaaactat gaaacttgag    420
aaatcctctt gagataaaag gctgccaaat ccagtattat aaa                      463

<210> SEQ ID NO 143
<211> LENGTH: 368
<212> TYPE: DNA
<213> ORGANISM: Homo sapien

<400> SEQUENCE: 143
caccacattg ccaatgccaa cctcatgcgg aacggggccg actacgctgt ttacatcaac    60
```

```
acagcccagg agtttgatgg ctctgactca ggtgcccgac cagacgaggc tgtctcctgg      120
ggcaagatcc gggtggatgc acagcccgtc aaggtctatg ctgacgcctc cctggtcttc      180
cccctgcttg tggctgaaac ctttgcccag aagatggatg ccttcatgca tgagaagaac      240
gaggactgag cggctgcggt cccaggaagg tcttaccccc tcttctattt attaatttgc      300
agacccagcc cctcccctac ttttggtca gctacgtctc tagaataaga tggtatctga      360
agtccttc                                                              368

<210> SEQ ID NO 144
<211> LENGTH: 452
<212> TYPE: DNA
<213> ORGANISM: Homo sapien

<400> SEQUENCE: 144
cttgattcaa aagaatcaaa atgggtattt tgaagagaga cctgtactgc tagtgttcct       60
tgcagcactg ttcacaatag ccaagtgaac agataaagaa aatgaagtgt atacctgcag      120
taggatgctg tgcgtgcagc ctgaaagaag gaaatcctgc cattcgtgac aacgtgggtg      180
accatgaagg agattatgca aaatgaaata agccagacac agaaagaaac tgcatggttc      240
cacttaaatg tgatatccag catagactca cagaagtaaa gggtggaatg gcggtcatca      300
ggggattggg ggagagggaa atggggagct acttaatcaa tgggatgaaa tttcattaaa      360
caagatgaga atgttctaga gatatgccgt actacatggt acctgtagtc aacaataatg      420
tagacttaga aatgtgttaa gcggtggctc tc                                   452

<210> SEQ ID NO 145
<211> LENGTH: 456
<212> TYPE: DNA
<213> ORGANISM: Homo sapien

<400> SEQUENCE: 145
caaacaatac tatcttataa aatagtactg ttgaattatt ccaagcctcc ctaggtttgc       60
tctcaaatgt catttacaga ttgggctaac gacctaaaat ctatatataa agactttctg      120
aagaactctg tattatagca ataccaaacg agtgctgtgt gtgcaaacag tctggcgttg      180 cttttttatgt tgatatttat cctagaacac tgaaagagaa tatgccagtg ataactcact      240
ttacttcagt catttcaaca cagaaaatgc ttctctagca tttttctttt gtagtgttaa      300
cattttgaaa ttcatgtttc agaggcttca tcatcacaga atttactctt gctccatgaa      360
aaaaaattaa ataccttcag aggaatattt aagttgtaaa ctatgaaact tgagaaatcc      420
tcttgagata aaaggctgcc aaatccagta ttataa                               456

<210> SEQ ID NO 146
<211> LENGTH: 210
<212> TYPE: DNA
<213> ORGANISM: Homo sapien

<400> SEQUENCE: 146
ggagagccca aggtctaac ggttaagggg acccacatac cagtgccaag ggggatgtca       60
agtggtgatg tcgttgtgct cccctccccc agagcgggtg ggcgggggt gaatatggtt      120 ggcctgcatc aggtggcctt cccatttaag tgccttctct gtgactgaga gccctagtgt      180
gatgagaact aaagagaaag ccagaccct                                       210

<210> SEQ ID NO 147
<211> LENGTH: 452
```

<212> TYPE: DNA
<213> ORGANISM: Homo sapien

<400> SEQUENCE: 147

| | | | | | |
|---|---|---|---|---|---|
| atacccaga | gcacagtccc | agcttcacca | acttcagggt | cagcacctcg | agatcaagca | 60 |
| ggcagttgat | tcctttaaat | actgctgaaa | gtctctctct | ccagcatagt | gaatctaaga | 120 |
| gaagaggcag | gaaaagacaa | tctacagagt | catctcctgt | accactgaat | cgaagaagtt | 180 |
| ctggcaggca | aggaggtgtc | catgaactgt | ctgcttttga | acaacttgtc | gtggaactgg | 240 |
| tacggcatga | tgatagctgg | ccctttttga | aactggtttc | taaaatccag | gtcccagact | 300 |
| actatgacat | cattaagaag | cccattgcct | taaatataat | tcgagaaaaa | gtaaataaat | 360 |
| gtgaatataa | attagcatct | gagtttattg | atgatattga | gttaatgttt | tcaaactgct | 420 |
| ttgaatacaa | ccctcggaac | acaagtgaag | ca | | | 452 |

<210> SEQ ID NO 148
<211> LENGTH: 453
<212> TYPE: DNA
<213> ORGANISM: Homo sapien

<400> SEQUENCE: 148

| | | | | | |
|---|---|---|---|---|---|
| caagaggaga | aagggactct | ccctggacta | catgatgact | caatggacaa | gctaagagtt | 60 |
| gaaagcaaca | ggaaagttca | cgaatcttgg | tggtagtaac | agtggcagct | gtgatgttgg | 120 |
| ctatataggc | ctgagtctag | ttctccagtc | cagctggtga | ttttgtgagc | tattcaatat | 180 |
| gctttcaata | tatacgtttt | ctgccaccaa | gaggagaaag | ggactctccc | tggactacat | 240 |
| gatgactcaa | tggacaagct | aagagttgaa | agcaacagga | aagttcacga | atcttgggcc | 300 |
| attaccagat | cacctcccta | gcactagtga | gtgcctacca | ccaccactct | aactgccatc | 360 |
| agtgttaact | cagattctcc | aaggagcaga | tactaagatg | gaattagata | tgcaagagat | 420 |
| tgattgaggg | aaatgcccat | gacagaaagc | gtg | | | 453 |

<210> SEQ ID NO 149
<211> LENGTH: 445
<212> TYPE: DNA
<213> ORGANISM: Homo sapien
<220> FEATURE:
<221> NAME/KEY: misc_feature
<222> LOCATION: (1)...(445)
<223> OTHER INFORMATION: n = A,T,C or G

<400> SEQUENCE: 149

| | | | | | |
|---|---|---|---|---|---|
| ggacactgtt | gtggtccagg | atttgggcaa | catcttcact | cgcctgccac | tcaagcggat | 60 |
| gtggcatnag | gcactgctgc | gctcagggga | taaagtgcgc | atggacccc | cctgaccaac | 120 |
| acaacagctg | cttccaccta | cctcaacaac | ccgtacgtgc | ggaaggccct | caacatcccg | 180 |
| gagcagctgc | cacaatggga | catgtgcaac | tttctggtaa | acttacagta | ccgccgtctc | 240 |
| taccgaagca | tgaactccca | gtatctgaag | ctgcttagct | cacagaaata | ccagatccta | 300 |
| ttatataatg | gagatgtaga | catggcctgc | ttgttcagga | agcgggagaa | catggtgaag | 360 |
| gcagcgaggg | gcttgtcggt | gggaaccatg | tggccggcgc | ccttgatcgt | gagaaagctt | 420 |
| gcggccgcac | tcgagcccgg | gtgaa | | | | 445 |

<210> SEQ ID NO 150
<211> LENGTH: 446
<212> TYPE: DNA
<213> ORGANISM: Homo sapien
<220> FEATURE:

<221> NAME/KEY: misc_feature
<222> LOCATION: (1)...(446)
<223> OTHER INFORMATION: n = A,T,C or G

<400> SEQUENCE: 150

| | | |
|---|---|---|
| tttgtcttttt nncaaactga tggacatgag tgagctctaa tatcattatg tttagaaatg | 60 |
| gcttcatcca gatccaactg tacaccatta atattcactt ccatgcagcc attataaaag | 120 |
| gcattcactg gtgtggcact gaatggaaca tctggaaggc cacccaggta tgtggccact | 180 |
| tttgctttca ttgctttgtc caagacggca agttgtcttt gaaggtcttc atgggagatg | 240 |
| gtttctattt taagtggtgt cgacaactcc agattgtttc tgttgactct aaattccaga | 300 |
| tgagattgtt gatcggaaca tagacttagg gcctgtatcc gatatattac agtattttca | 360 |
| acagataaca gaatatcctg tgattttca gaggtggagt ccaccaagga cacagcaaag | 420 |
| ggcactgtgt tgttaccaga aaccaa | 446 |

<210> SEQ ID NO 151
<211> LENGTH: 444
<212> TYPE: DNA
<213> ORGANISM: Homo sapien
<220> FEATURE:
<221> NAME/KEY: misc_feature
<222> LOCATION: (1)...(444)
<223> OTHER INFORMATION: n = A,T,C or G

<400> SEQUENCE: 151

| | | |
|---|---|---|
| cggagacgag agcagaggcc naactcnnga tctgacaaga tggccgggct gccccgcagg | 60 |
| atcatcnggg aaacccancg tttgctggca gaaccagttc ctggcattaa agcanaacca | 120 |
| gatgagagca acgcccgtta ttttcatgtg gtcattgctg gcccccagga ttccccttt | 180 |
| gagggaggga cttttaaact tgaactattc cttccagaag aatacccaat ggcagcacct | 240 |
| aaagtacgtt tcatgaccaa aatttatcat cctaatgtag acaagttggg aagaatntgn | 300 |
| ttagatnttt ttgaaaggat aagtggtncc cnatnnctgc agatccgcac aggtcttgct | 360 |
| atcaatcnan gctttnttna gtctcctntt ncanatgatc catngncaaa ccatatngnc | 420 |
| gcnccttgt antgggcnca nctn | 444 |

<210> SEQ ID NO 152
<211> LENGTH: 444
<212> TYPE: DNA
<213> ORGANISM: Homo sapien

<400> SEQUENCE: 152

| | | |
|---|---|---|
| ccgtccgccc ctgcggccaa gcccaagcgg gccaaggcct ccaagaagtc cacagaccac | 60 |
| cccaagtatt cagacatgat cgtggctgcc atccaggccg agaagaaccg cgctggctcc | 120 |
| tcgcgccagt ccattcagaa gtatatcaag agccactaca aggtgggtga gaacgctgac | 180 |
| tcgcagatca agttgtccat caagcgcctg gtcaccaccg gtgtcctcaa gcagaccaaa | 240 |
| ggggtgggg cctcggggtc cttccggcta gccaagagcg acgaacccaa gaagtcagtg | 300 |
| gccttcaaga agaccaagaa ggaaatcaag aaggtagcca cgccaaagaa ggcatccaag | 360 |
| cccaagaagg ctgcctccaa agccccaacc aagaaaccca agccaccccc ggtcaagaag | 420 |
| gccaagaaga agctggctgc cacg | 444 |

<210> SEQ ID NO 153
<211> LENGTH: 441
<212> TYPE: DNA
<213> ORGANISM: Homo sapien

```
<220> FEATURE:
<221> NAME/KEY: misc_feature
<222> LOCATION: (1)...(441)
<223> OTHER INFORMATION: n = A,T,C or G

<400> SEQUENCE: 153
tgctggatct ggagtcagga gaaatgtgga taaagttttta gtgataaatt ctgctcaaag      60
ttagggtgaa tgcagacatc ctagactgta ctttgggtgg ggtaagaaga aggggggtga     120
ctagacatat acttgcatcc agaggccaga ggtcaatgct gggtgtcttt cttgaccgtt     180
gtcttgtttt gaatggagtg atggagatta aatttaaggc ttttctacca cagagctaca     240
actccagcct ttagtaacag actttctcat tgaatctgga attggcaaga ttggctggtc     300
cccgggcccc acctgtcccc acctccctag tactgggaat ccaggcacgt gccaccatac     360
ccagcttctt acacggctgc tgaaactcag gccctcacgt ttgtgccacg tggagatgcc     420
tcccnatncc catacactat c                                                441

<210> SEQ ID NO 154
<211> LENGTH: 425
<212> TYPE: DNA
<213> ORGANISM: Homo sapien

<400> SEQUENCE: 154
acaacaccaa ccacgaggct gacgactggt gcgtccccag cagagaaccc aaagacatga      60
cgacgttccg cagtgcctag acacacttgg gacatcggaa aatccaaatg tggcttttgt     120
attaaatttg gaaggtccgt aaaagccctg ggctcagcca gagcagggca gaggatgacg     180
ggatgaccag ctgcagagag gagtactcta ctgataactg gagacgatgg gcgaccacct     240
tcagagagaa actgttagca gagaggagct gccctctgct gagagcttca gagacctgca     300
gacatctgaa tgacttgcct gcagagagga gccactcttt tcagggcctt ctctcagctg     360
agagctgaac acccaatggg ataattgcct acagagagga gccacccact cctctgagct     420
gttcc                                                                  425

<210> SEQ ID NO 155
<211> LENGTH: 428
<212> TYPE: DNA
<213> ORGANISM: Homo sapien

<400> SEQUENCE: 155
tgtatcagaa ccttaatgag ccaaccacgt ggagcttaac cagtgataga actagaaatt      60
gggttcttca acagaaaata gaaggagaaa caaaagaatc aaactacgct aaattgattg     120
aaatgaatgg aggaggaacc ggctgtaatc atgaattaga aatgatcaga caaaagcttc     180
aatgtgtagc ttcaaaacta caggttctac cccagaaagc ctctgagaga ctacagtttg     240
aaacagcaga tgatgaagat ttcatttggg ttcaggaaaa tattgatgaa attattttac     300
aactacagaa attaactggc cagcaaggtg aagagcccag cttggtgtcc ccaagtactt     360
cttgtggctc attgactgaa agactactga gacaaaatgc tgagctgaca gggcatatca     420
gtcaactg                                                               428

<210> SEQ ID NO 156
<211> LENGTH: 440
<212> TYPE: DNA
<213> ORGANISM: Homo sapien

<400> SEQUENCE: 156
```

-continued

```
gaagaagaaa cagatgatag tgacacttgg gaacctccac gacatgtgaa acggaagctg    60
tctaaatcag atgactgaaa tctgcctaaa acgttgaagg agaatcaatt cttcaactca   120
agatgtctga tttactgtga atttgcccaa tctttgatga cattgaaaac gttttggggc   180
atacacactc aaaaagcagg atccaatacc caaagaaat ggaacttaat gttgtgccaa    240
agttaaacta ctgcagttgg tggaagttct gcaatgtaaa tagaacacta attaaaaaac   300
aacttgtaaa aatgcaattt aaattttaat acagtacatt tttcttctaa tatgatggag   360
acattctgaa tcttagactt tctgaggggg tttaatgacc actagagctt gtcctcatat   420
tcagtccagt ttaatactgt                                               440
```

<210> SEQ ID NO 157
<211> LENGTH: 1031
<212> TYPE: DNA
<213> ORGANISM: Homo sapien

<400> SEQUENCE: 157

```
accagattgg cctgttagtt cagtgtagtg cagcacaaat cccagtgact aaacaccttg    60
gaagtaagaa tccttgacct ggatttggaa gacctgggct gtgatctctg gcgttttgct   120
tattggctct tcaaacttca acaggcccct aagttttcca agcattggtt tcttcttaca   180
taaagtaaac catcatcaca agtgccctga agatggctga gatcatggaa tcaagtggtg   240
tgcaacagag tgagctttgt ggtttctttt tgggcttaag ttcctggaag gcagggattg   300
tgagtagctc acgcgaacgg gcttttttagt gcctgcaaac tgaaactgag cagatggtca   360
tggtgatttt cttcctagtg gaactgaaaa tctttgttct ttgtctaggt caatgctggc   420
ccactagcat atgcgcgagc tttcttagat gatacaaaca caaagcgata tcctgacaat   480
aaagtgaagc tgcttaagga agttttcagg caatttgtgg aagcttgcgg tcaagcctta   540
gcggtaaacg aacgtctgat taagaagac cagctcgagt atcaggaaga aatgaaagcc    600
aactacaggg aaatggcgaa ggagctttct gaaatcatgc atgagcaggt gagggccgca   660
ctggctccaa caacttggag ttcttggtta ggggtttcaa gtacaccta tcatgactta    720 ggccgcctga tatccttcca gaactgtgac atctgaagga aatgtagca taccacactc    780 ctgccatgct ctagccccag gtcatttggg aacagctaac agattgccca tatgctgtta   840
tctacggcaa gcaggggaga gcgggcccgc ctcctcgtgg ctctaagagg tggccatgtt   900
tcctaagctt tctctctccc caccccgtc tagccaaaaa gaaagaaag gaaaaactca    960 cacgaaaata tccatactgt tctgacaact ttattccttt aatcctttga aaaaagcagg   1020
acttgccaac c                                                        1031
```

<210> SEQ ID NO 158
<211> LENGTH: 445
<212> TYPE: DNA
<213> ORGANISM: Homo sapien

<400> SEQUENCE: 158

```
caaacaatac tatcttataa aatagtactg ttgaattatt ccaagcctcc ctaggtttgc    60
tctcaaatgt catttacaga ttgggctaac gacctaaaat ctatatataa agactttctg   120
aagaactctg tattatagca ataccaaacg agtgctgtgt gtgcaaacag tctggcgttg   180 cttttttatgt tgatatttat cctagaacac tgaaagagaa tatgccagtg ataactcact   240
ttacttcagt catttcaaca cagaaaatgc ttctctagca ttttttcttt gtagtgttaa   300 catttttgaaa ttcatgtttc agaggcttca tcatcacaga atttactctt gctccatgaa   360
```

| aaaaaattaa ataccttcag aggaatattt aagttgtaaa ctatgaaact tgagaaatcc | 420 |
| tcttgagata aaaggctgcc aaatc | 445 |

<210> SEQ ID NO 159
<211> LENGTH: 1071
<212> TYPE: DNA
<213> ORGANISM: Homo sapien

<400> SEQUENCE: 159

| tcatcaatcc tgacacctac cgcatcgacc ccaatgttct tctagatcca gctgatgaga | 60 |
| aactttggga agaggagatt caggccccca ccagctccaa gagatcccag cagcacgcga | 120 |
| aggtggtgcc atggatgcga aagacagagt acatctccac tgagttcaac cgttatggca | 180 |
| tctccaatga gaagcctgag gtcaagattg gggtttctgt gaagcagcag tttaccgagg | 240 |
| aagaaatata caaagacagg gatagccaga tcacagccat tgagaagact tttgaggatg | 300 |
| cccagaaatc aatctcacag cattacagca accccgagt cacaccggtg gaggtcatgc | 360 |
| ctgtcttccc agactttaag atgtggatca atccatgtgc tcaggtgatc tttgactcag | 420 |
| acccagcccc caaggacacg agtggtgcag ctgcgttgga gatgatgtct caggccatga | 480 |
| ttaggggcat gatggatgag gaagggaacc agtttgtggc ctatttcctg cctgtagaag | 540 |
| agacgttgaa gaaacgaaag cgggaccagg aggaggagat ggactatgca ccagatgatg | 600 |
| tgtatgacta caaaattgct cgggagtaca actggaacgt gaagaacaaa gctagcaagg | 660 |
| gctatgagga aaactacttc ttcatcttcc gagagggtga cggggtttac tacaatgagt | 720 |
| tggaaaccag ggtccgcctt agtaagcgcc gggccaaggc tggggttcag tcaggcacca | 780 |
| acgccctgct tgtggtcaaa catcgggaca tgaatgagaa ggaactggaa gctcaggagg | 840 |
| cacggaaggc ccagctagaa aaccacgaac cggaggagga agaggaagag gagatggaga | 900 |
| cagaagagaa agaagctggg ggctcagatg aggagcagga gaagggcagc agcagtgaga | 960 |
| aggagggcag tgaagatgag cactcgggca gcgagagtga acgggaggaa ggtgacaggg | 1020 |
| acgaggccaa gtgacaagag tggcagtggt gaggacgaga gcagcgagga t | 1071 |

<210> SEQ ID NO 160
<211> LENGTH: 444
<212> TYPE: DNA
<213> ORGANISM: Homo sapien

<400> SEQUENCE: 160

| actgaatgta acaacatgac cctcatcaac ttgctactta aagtccttgg gcccatacat | 60 |
| gagagaaacc tcacattgct cctgctgctg ctgcaggtga ggatgggaat cgagtttata | 120 |
| cctccgtgtc tcccttcctg cgtgattctt actccagtcc atttctcctt gcagatcctg | 180 |
| ggcagtgcca tcaccttctc cattcgatat cagctcgttc gactcttcta tgatgtctga | 240 |
| gtcccttgat cattgtcctt tacctcacag tctctaggat tcctgactca ggctgacctc | 300 |
| tctctctggt cccagactgc ctccttgccc aggcctctct cactcttcat actcctccag | 360 |
| attttgttct cagcattttc ctttctctgt gatcattggc atcctgggcg tttcttgccc | 420 |
| tctgctgact actgattgga tttt | 444 |

<210> SEQ ID NO 161
<211> LENGTH: 444
<212> TYPE: DNA
<213> ORGANISM: Homo sapien

<400> SEQUENCE: 161

| | | |
|---|---|---|
| ccttcaacct gcatttcctc ctcctgcagg gcctccaggg aatccagggt cccaagggct | 60 |
| tggatggagc aaagggagag aagggtgcgt cgggtgagag aggccccagc ggcctgcctg | 120 |
| ggccagttgg cccaccgggc cttattgggc tgccaggaac caaaggagag aagggcagac | 180 |
| ccggggagcc aggactagat ggtttccctg gaccccgagg agagaaaggt gatcggagcg | 240 |
| agcgtggaga aagggagaa cgagggggtcc ccggccggaa aggagtgaag ggccagaagg | 300 |
| gcgagccggg accaccaggc ctggaccagc cgtgtcccgt ggagaatccc acgtgcggag | 360 |
| gccggagagg ggcaccaggc tggcggggcc ctgcgagggg caatgggcca tgccctgcgg | 420 |
| gccccgacgg gctgcctgtg cctg | 444 |

<210> SEQ ID NO 162
<211> LENGTH: 435
<212> TYPE: DNA
<213> ORGANISM: Homo sapien

<400> SEQUENCE: 162

| | | |
|---|---|---|
| caccgacgtg tgtgacagcg actacagcgc cagccgctgg aaggcgtcgt cgggggcgcc | 60 |
| attcctcgaa tgatgtaggg cctgtacggt ctcgcagtgg ccggaatgtt tgaagagtag | 120 |
| aacatgtcca tgttgtacag ggagggggtcc gtggccgcgc agagcaacca caccgtgggc | 180 |
| cccttgctgg cggctgcagc tggtgcccca gccctctgt acctcggggg cctgcctgag | 240 |
| cccatggccg tgcagccctg gcccccgcc tactgcggct gcatgaggag gctggcggtg | 300 |
| aaccggtccc ccgtcgccat gactcgctct gtggaggtcc acggggcagt gggggccagt | 360 |
| ggctgcccag ccgcctagga cacagccaac cccggcccct ggtcaggccc ctgcagctgc | 420 |
| ctcacaccgc ccctt | 435 |

<210> SEQ ID NO 163
<211> LENGTH: 437
<212> TYPE: DNA
<213> ORGANISM: Homo sapien

<400> SEQUENCE: 163

| | | |
|---|---|---|
| ggacagcgag gcgcactggg gcctcccagc gcggggccgg ccgcgccgtc cagcccgagg | 60 |
| tctacggctt tgcgctccga gcccagagga agatgcctgc cggcaccgag ctcgggctgc | 120 |
| ggggctgaac gcctgtcttc caggcgcagc ggcagcactg ccctcggccg gtgtcggtag | 180 |
| cggcactcgg cgtgccccgg gcggacgaag agcgcaggct gggtacacct tgcccgaatc | 240 |
| ggcggagttc gcagctagcg agggcgggcc ggccggcccg gatgggcgcg gggtttgcgg | 300 |
| ccccccgccgg gtgctccgga gcggcccggg caccgggggc acgctgagtg ccggagccgc | 360 |
| ggccgcagag agaacttggg gcgggggcca tgccccggtg cggagtctag agccgagcgg | 420 |
| agcgccccgc gggcccg | 437 |

<210> SEQ ID NO 164
<211> LENGTH: 439
<212> TYPE: DNA
<213> ORGANISM: Homo sapien

<400> SEQUENCE: 164

| | | |
|---|---|---|
| aagatttcag ctgcgggacg gtcaggggag acctccaggc gcagggaagg acggccaggg | 60 |
| tgacacggaa gcatgcgacg gctgctgatc cctctggccc tgtggctggg tgcggtgggc | 120 |
| gtgggcgtcg ccgagctcac ggaagcccag cgccggggcc tgcaggtggc cctggaggaa | 180 |

```
tttcacaagc acccgcccgt gcagtgggcc ttccaggaga ccagtgtgga gagcgccgtg      240
gacacgccct tcccagctgg aatatttgtg aggctggaat ttaagctgca gcagacaagc      300
tgccggaaga gggactggaa gaaacccgag tgcaaagtca ggcccaatgg gaggaaacgg      360
aaatgcctgg cctgcatcaa actgggctct gaggacaaag ttctgggccg gttggtccac      420
tgccccatag agacccaag                                                   439

<210> SEQ ID NO 165
<211> LENGTH: 361
<212> TYPE: DNA
<213> ORGANISM: Homo sapien

<400> SEQUENCE: 165 gctgggggt cgggatgctg ggcccctcct catctccctc aaggatggct acgtacccc       60 aaagagccgg gagctgaggg tcaaccgggg cctggacacc gggcgcagga gggcagcacc    120
agaggccagt ggcactccca gctcggatgc cgtgtctcgg ctggaggagg agatgcggaa    180
gctccaggcc acggtgcagg agctccagaa gcgcttggac aggctggagg agacagtcca    240
ggccaagtag agccccgcag ggcctccagc agggtcagcc attcacaccc atccactcac    300
ctcccattcc cagccacatg gcagagaaaa aaatcataat aaaatggctt tattttctgg    360
t                                                                     361

<210> SEQ ID NO 166
<211> LENGTH: 326
<212> TYPE: DNA
<213> ORGANISM: Homo sapien

<400> SEQUENCE: 166
atcacgaagt gatatccaac tccccaagtt gcagtggttc ctggagccca ggaccacccg     60
ccagcgggcc ctcttcctcc tccatatctg aggtcccagc ccgcaacacc agttcccggg    120
ccgcagccgc catggtcgca gcggcggcca ttccccgcag cctcacttcc ggcaactgtc    180
agtcccggcg agtccgttcc ccggagtgga gctacaagtc ccaaagggtc ttcctcagcg    240
cgaaatcgtt cccagatatt tgagttaagt tgtttgactc cagctgtccc ctttcagctc    300
taaccacttc acccaactgc aaatgg                                          326

<210> SEQ ID NO 167
<211> LENGTH: 471
<212> TYPE: DNA
<213> ORGANISM: Homo sapien

<400> SEQUENCE: 167
caaggccatg gcgatatcgg atccgaattc aagctcatca atcctgacac ctaccgcatc     60
gaccccaatg ttcttctaga tccagctgat gagaaacttt tggaagagga gattcaggcc    120
cccaccagct ccaagagatc ccagcagcac gcgaaggtgg tgccatggat gcgaaagaca    180
gagtacatct ccactgagtt caaccgttat ggcatctcca tgagaagcc tgaggtcaag    240 attggggttt ctgtgaagca gcagtttacc gaggaagaaa tatacaaaga cagggatagc    300
cagatcacac ccattgagaa gacttttgag gatgcccaga atcaatctc acagcattac    360 agcaaacccc gagtcacacc ggtggaggtc atgcctgtct tcccagactt taagatgtgg    420
atcaatccat gtgctcaggt gatctttgac tcagacccag ccccccaagga c             471

<210> SEQ ID NO 168
```

<210> SEQ ID NO 168
<211> LENGTH: 438
<212> TYPE: DNA
<213> ORGANISM: Homo sapien

<400> SEQUENCE: 168

```
caaacctcct cacagcccac tggtcctcaa gaggtgccac gtctccacac atcagcacaa      60
ctacgcagcg cctccctcca ctcggaagga ctatcctgct gccaagaggg tcaagttgga     120
cagtgtcaga gtcctgagac agatcagcaa caaccgaaaa tgcaccagcc ccaggtcctc     180
ggacaccgag gagaatgtca agaggcgaac acacaacgtc ttggagcgcc agaggaggaa     240
cgagctaaaa cggagctttt ttgccctgcg tgaccagatc ccggagttgg aaaacaatga     300
aaaggccccc aagtagttta tccttaaaaa agccacagca tacatcctgt ccgtccaagc     360
agaggagcaa aagctcattt ctgaagagga cttgttgcgg aaacgacgag aacagttgaa     420
acacaaactt gaacagct                                                   438
```

<210> SEQ ID NO 169
<211> LENGTH: 437
<212> TYPE: DNA
<213> ORGANISM: Homo sapien

<400> SEQUENCE: 169

```
ctcgcgcctg cagttttttgg cttttcacccc caaccagtga ccaaagactt gaccactcaa    60
agtccagctc cccagaacac tgctcgacat ggacaccggt gtgattgaag gtggattaaa    120
tgtcactctc accatccggc tacttatgca tggaaaggaa gttggcagta tcatcggaaa    180
gaaaggagaa tcagttaaga agatgcgcga ggagagtggt gcacgtatca acatctcaga    240
agggaattgt cctgagagaa ttatcacttt ggctggaccc actaatgcca tcttcaaagc    300
ctttgctatg atcattgaca aactggaaga ggacataagc agctctatga ccaatagcac    360
agctgccagt agaccccccgg tcaccctgag gctggtggtc cctgctagtc agtgtggctc    420
tctcattgga aaaggtg                                                   437
```

<210> SEQ ID NO 170
<211> LENGTH: 435
<212> TYPE: DNA
<213> ORGANISM: Homo sapien

<400> SEQUENCE: 170

```
ccgtccggcc tccctgacat gcttccctct ggaccccgag gttggaccct actgtgacac     60
acctaccatg cggacactct tcaacctcct ctggcttgcc ctggcctgca gccctgttca    120
cactaccctg tcaaagtcag atgccaaaaa agccgcctca aagacgctgc tggagaagag    180
tcagttttca gataagccgg tgcaagaccg gggtttggtg gtgacggacc tcaaagctga    240
gagtgtggtt cttgagcatc gcagctactg ctcggcaaag gcccgggaca gacactttgc    300
tggggatgta ctgggctatg tcactccatg gaacagccat ggctacgatg tcaccaaggt    360
ctttgggagc aagttcacac agatctcacc cgtctggctg cagctgaaga gacgtggccg    420
tgagatgttt gaggt                                                    435
```

<210> SEQ ID NO 171
<211> LENGTH: 435
<212> TYPE: DNA
<213> ORGANISM: Homo sapien

<400> SEQUENCE: 171

```
cagatgtata gattgtgaag atgtttgctt attctgtggg tgtgaatgtt ataattaagg      60
```

```
agatttgtag ggagattagt atagagaggt agagtttttt tcgtgatagt ggttcactgg      120
ataagtggcg ttggcttgcc atgattgtga ggggtaggag tcaggtagtt agtattagga      180
ggaggatgtg aaactcttaa gtatatctgg aaagcggtct gccctggag gtggtagcaa       240 ggttccacag aaaaagtaa aacttgctgc tgatgaagat gatgacgatg atgatgaaga      300
ggatgatgat gaagatgatg atgatgatga ttttgatgat gaggaagctg aagaaaaagc      360
gccagtgaag aaatctatac gagatactcc agccaaaaat gcacaaagt caaatcagaa       420 tggaaaagac tcaaa                                                      435

<210> SEQ ID NO 172
<211> LENGTH: 435
<212> TYPE: DNA
<213> ORGANISM: Homo sapien

<400> SEQUENCE: 172
gcacagcgag gcgctagggg gaacgctggc ctctgaaact agctctggga ccggggtctg       60
cggccggccc ctagctggcc ccgtctccca tccccagaag ggtattcact ggggattctg      120
agctttggct actccagttt cccacgacac gatgttccct ttctacagct gctggaggac      180
tggactgcta ctactactcc tggctgtggc agtgagagaa tcctggcaga cagaagaaaa      240
aaacttgcga cttggtagga gaaagggta aagagtcaga gaaagagttg gctctagtga      300
agaggctgaa accactgttt aataaaagct ttgagcac tgtgggccag ggttcagaca        360
catacatcta catcttcagg gtgtgccggg aagctggcaa ccacacttct ggggcaggcc      420
tggtgcaaat caaca                                                      435

<210> SEQ ID NO 173
<211> LENGTH: 450
<212> TYPE: DNA
<213> ORGANISM: Homo sapien
<220> FEATURE:
<221> NAME/KEY: misc_feature
<222> LOCATION: (1)...(450)
<223> OTHER INFORMATION: n = A,T,C or G

<400> SEQUENCE: 173
attcaagagc aaatgaccaa nagccatgtg ggnggnggtt ggctaaagtt cggatgatga       60
aaggagaatt ttatgtcatt gaatatgctg cttgtgacgc tacttacaat gagaatagtc      120
acatttgaac gacttcggcc tgtcaatcaa aataaaactg tcaaaaaaaa taccttcttt      180
aaatgcacag tggatgttcc tgaggatttg agagaggcgt gtgctaatga aaatgcacat      240
aaagatttta agaaagcagt aggagcatgc agaattttt accatccaga aacaacacag      300
ctaatgatac tgtctgccag tgaagcaact gtgaagagag taaacatctt aagtgacatg      360
catttgcgaa gtattcgtac gaagttgatg cttatgtcca gaaatgaaga ggccactaag      420
catttagaat gcacaaaaca acttgcagca                                      450

<210> SEQ ID NO 174
<211> LENGTH: 307
<212> TYPE: DNA
<213> ORGANISM: Homo sapien
<220> FEATURE:
<221> NAME/KEY: misc_feature
<222> LOCATION: (1)...(307)
<223> OTHER INFORMATION: n = A,T,C or G

<400> SEQUENCE: 174
```

```
cacgagcctg ttctgaaaat gtggacgtaa nacaaacacg tgctcgtcct ttaatggagt      60
tcaccagcac acttgttaac cagtcctgtt tgctttcgtc tttttttgtg cgtaataaag     120
tcaactgacc aagtgaccat gaaaaggggc tgtctgggc tcctgttttt tagctgctgt     180
tcttcagctc cgaccatgtt gctgtgtgat tatctcaatt ggttttaatt gaggcagaaa     240
ctgaanctnt accaatgaac tgnttanaaa caagacacac ttttgtatta aaattgcttg     300
cagtaac                                                               307
```

<210> SEQ ID NO 175
<211> LENGTH: 449
<212> TYPE: DNA
<213> ORGANISM: Homo sapien

<400> SEQUENCE: 175

```
gtttctgcgc gggctcccgg cgctgctact gctgctgctc ttcctcgggc cctggcccgc      60
tgcgagccac ggcggcaagt actcgcggga aagaaccag cccaagccgt ccccgaaacg     120
cgagtccgga gaggagttcc gcatggagaa gttgaaccag ctgtgggaga aggcccagcg     180
actgcatctt cctcccgtga ggctggccga gctccacgct gatctgaaga tacaggagag     240
ggacgaactc gcctggaaga aactaaagct tgacggcttg gacgaagatg gggagaagga     300
agcgagactc atacgcaacc tcaatgtcat cttggccaag tatggtctgg acggaaagaa     360
ggacgctcgg caggtgacca gcaactccct cagtggcacc caggaagacg ggctggatga     420
ccccaggctg gaaaagctgt ggcacaagg                                       449
```

<210> SEQ ID NO 176
<211> LENGTH: 443
<212> TYPE: DNA
<213> ORGANISM: Homo sapien

<400> SEQUENCE: 176

```
tggtgtctct caaaagcctg atcctgccaa aaccaagaat cgccgcaaaa ggaagccatc      60
cacttctgat gattctgact ctaattttga gaaaattgtt tcgaaagcag tcacaagcaa     120
gaaatccaag ggggagagtg atgacttcca tatggacttt gactcagctg tggctcctcg     180
ggcaaaatct gtacgggcaa agaaacctat aaagtacctg gaagagtcag atgaagatga     240
tctgttttaa aatgtgaggc gattatttta agtaattatc ttaccaagcc caagactggt     300
tttaaagtta cctgaagctc ttaacttcct ccctctgaa tttagtttgg ggaaggtgtt     360
tttagtacaa gacatcaaag tgaagtaaag cccaagtgtt cttagctttt ttataatact     420
gtctaaatag tgaccatctc atg                                             443
```

<210> SEQ ID NO 177
<211> LENGTH: 440
<212> TYPE: DNA
<213> ORGANISM: Homo sapien

<400> SEQUENCE: 177

```
gctgcacccg ccgggaaagt ggcgagagcc acctcggcgc ttgggcgctc agtcgcagga      60
ggcgctcctt ggcggtgcct ggagcccggg cgcaccccac cgctcccggg acctgttggg     120
ggctggcccg aaccgtcgtc gaagggagcc gctcggccac cccgacgtt cctcgccccg     180 cccgacgttc cctcaagtgg ccgaaccagc cggacgagcc aaactcgccg ggcctcccgg     240
cggcagcagg tggccccgtc cttccaggga gggccctgcg ccccgcggcg ctccggagcc     300
ctctcggccg ccccccgccag gcgggatgga ggcggatggg gacggagagg agctggcccg     360
```

```
gctgcgctca gtcttcgccg cctgcgacgc gaaccgctcg gggcgcctgg agcgcgagga    420
gttccgggca ctgtgcacgg                                                440

<210> SEQ ID NO 178
<211> LENGTH: 442
<212> TYPE: DNA
<213> ORGANISM: Homo sapien

<400> SEQUENCE: 178
aggaagaaaa attaaagcca tttgaaaagt tcttgctgaa gctagaaggg caattactgg     60
atggaatgat attccaggcc tgtatagaac aacaatttga ttctctcaat ggaggagtat    120
ctgtgtcaaa aatagtact tttgctgagg aatttgcaca tagtattcgg tcaattttg    180 caaatgtaga agccaaactt ggagaacctt ctgaaattga ccagagagac aagtatgttg    240
gaatttgtgg actctttgta ttgcactttc agattttcg aactattgat aaaaagtttt    300
ataagtcttt attggacatt tgtaagaagg taccagccat cactctaact gctaatatta    360
tttggtttcc tgataatttt ctgatccaga aaataccagc agctgccaaa ctgctagaca    420
gaaaaagtct tcaagccatt aa                                             442

<210> SEQ ID NO 179
<211> LENGTH: 434
<212> TYPE: DNA
<213> ORGANISM: Homo sapien

<400> SEQUENCE: 179
ctcccaggag gtgatattat ttttagtgct cagctgaaat accaacccca ggaataagaa     60
ctccatttca aacagttctg gccattctga gcctgctttt gtgattgctc atccattgtc    120
ctccactaga ggggctaagc ttgactgccc ttagccaggc aagcacagta atgtgtgttt    180
tgttcagcat tattatgcaa aaattcacta gttgagatgg tttgttttag gataggaaat    240
gaaattgcct ctcagtgaca ggagtggccc gagcctgctt cctatttga ttttttttt    300 ttttaactga tagatggtgc agcatgtcta catggttgtt tgttgctaaa ctttatataa    360
tgtgtggttt caattcagct tgaaaaataa tctcactaca gtagcagta cattatatgt    420 acattatatg taat                                                      434

<210> SEQ ID NO 180
<211> LENGTH: 440
<212> TYPE: DNA
<213> ORGANISM: Homo sapien

<400> SEQUENCE: 180
cgcaagcggc ctgggccgag cgccgtttcc aggccctcgc caggtctttg aactgcaggt     60
aaagtggcag gaacgtcttc cgtctgctca gcgtttgggg atttagactc ctaaagccag    120
tacctgcccc gtttcccccc caggttccgt cctgcccgcg cccggtctca gggtggcggc    180
cccggacacg gccgtcccc acagacgagg tctccgcct gagctgtcgc acctggcgcg    240
gaggtcgccc ggggtgccct ggctgggtga gaggtggcct ggcgggcgga gcttgccaag    300
aatcacggcc agtccttaag tggatggtgg ggccagcag ctgctctgtc cccttaaca    360 aaccaggggg catgaggggg cctagggcac cgcccccta ccaggctcag gccctccaag    420
gagaacctgc tgagacccct                                                440

<210> SEQ ID NO 181
```

<211> LENGTH: 438
<212> TYPE: DNA
<213> ORGANISM: Homo sapien
<220> FEATURE:
<221> NAME/KEY: misc_feature
<222> LOCATION: (1)...(438)
<223> OTHER INFORMATION: n = A,T,C or G

<400> SEQUENCE: 181

| | | | | | |
|---|---|---|---|---|---|
| caaacaatac | tatcttataa | aatagtnttg | ttgaattatt | ccaagcctcc | ctaggtttgt | 60 |
| tctcaaatgt | catttacaga | ttgggctaac | gacctggaat | ctatatataa | agactttctg | 120 |
| aagaactctg | tattatagca | ataccaaacg | agtgctgtgt | gtgcaaacag | tctggcgttg | 180 |
| cttttatgt | tgatatttat | cctagaacac | tgaaagagaa | tatgccagtg | ataactcact | 240 |
| ttacttcagt | catttcaaca | cagaaaatgc | ttctctagca | tttttctttt | gtagtgttaa | 300 |
| cattttgaaa | ttcatgtttc | agaggcttca | tcatcacaga | atttactctt | gctccatgaa | 360 |
| aaaaaattaa | ataccttcag | aggaatattt | aagttgtaaa | ctatgaaact | tgagaaatcc | 420 |
| tcttgagata | aaaggctg | | | | | 438 |

<210> SEQ ID NO 182
<211> LENGTH: 423
<212> TYPE: DNA
<213> ORGANISM: Homo sapien
<220> FEATURE:
<221> NAME/KEY: misc_feature
<222> LOCATION: (1)...(423)
<223> OTHER INFORMATION: n = A,T,C or G

<400> SEQUENCE: 182

| | | | | | |
|---|---|---|---|---|---|
| cagagaagga | taaatatttg | aaaggttttt | gaggggaaga | aactctccaa | cactgggttt | 60 |
| accaatttga | caaagggaac | aaggagaaaa | aaantatag | gacaatttac | agcttttgt | 120 |
| ctatgtcatt | aggtagatag | tggtgacatt | caaaataag | gaaataaaag | caggaacaag | 180 |
| actaaaggaa | aattcataat | tcaatttaga | atacattgaa | tttgtagagt | ctatagacat | 240 |
| gcgacttgac | atcaaaaacc | ccgataaatt | accaagaaa | actcttttcc | aactataatg | 300 |
| cgataacttt | ctaacagctt | aatcatgagt | aaaaatcaga | gaaaggcatg | gttatataaa | 360 |
| atattttaca | gaatgaatac | caacaaaact | aagattaaag | tagactatta | tagaattgaa | 420 |
| taa | | | | | | 423 |

<210> SEQ ID NO 183
<211> LENGTH: 437
<212> TYPE: DNA
<213> ORGANISM: Homo sapien

<400> SEQUENCE: 183

| | | | | | |
|---|---|---|---|---|---|
| catggctctg | gacgggataa | ggatgccaga | tggctgctac | gcggacggga | cgtgggaact | 60 |
| gagtgtccat | gtgacggacc | tgaaccgcga | tgtcaccctg | agagtgaccg | gcgaggtgca | 120 |
| cattggaggc | gtgatgctta | agctggtgga | gaaactcgat | gtaaaaaaa | gattggtctg | 180 |
| accatgctct | ctggtgggaa | aagaagagaa | cttggcttct | gaagacacat | tggaccttag | 240 |
| ataagtatgg | tattcaggca | gatgctaagc | ttcagttcac | ccctcagcac | aaactgctcc | 300 |
| gcctgcagct | tcccaacatg | aagtatgtga | aggtgaaagt | gaatttctct | gatagagtct | 360 |
| tcaaagctgt | ttctgacatc | tgtaagactt | ttaatatcag | acaccccgaa | gaactttctc | 420 |
| tcttaaagaa | acccaga | | | | | 437 |

<210> SEQ ID NO 184
<211> LENGTH: 442
<212> TYPE: DNA
<213> ORGANISM: Homo sapien
<220> FEATURE:
<221> NAME/KEY: misc_feature
<222> LOCATION: (1)...(442)
<223> OTHER INFORMATION: n = A,T,C or G

<400> SEQUENCE: 184

| | |
|---|---|
| ccaaccacca gaggatcatt caccaatntc ccgaaaggaa tttgttcgat ttctgctggc | 60 |
| cactccaacc aagtcagagc tgcgctgcca gtgtgcaaat ctccagggag tcaagatgct | 120 |
| ctgctcaaac gcagaaggcg catccctgag gctctgtaat tttgaggatc cttcgggtct | 180 |
| taaagccaac ttagagggtg ctaatctgaa aggtgtggac atggaaggaa gccagatgac | 240 |
| agggattaac ctcagagttg ccaccttaaa aaatgcaaaa ctgaagaact gtaatctcag | 300 |
| aggagcaact ctggcaggaa ccgatttaga aaactgtgat ttgtcggggt gtgacctcca | 360 |
| ggaagccaac ctgagaggct ccaatgtgaa gggtgccata tttgaagaga tgctgacacc | 420 |
| attacatatg tcccagagtg tc | 442 |

<210> SEQ ID NO 185
<211> LENGTH: 433
<212> TYPE: DNA
<213> ORGANISM: Homo sapien

<400> SEQUENCE: 185

| | |
|---|---|
| gaacctgctg tccttcactg ggagcactca ggtgggaaaa caggtgggcc tgatggtgca | 60 |
| ggagaggttt gggagaagtc tgttggaact tggaggaaac aatgccatta ttgcctttga | 120 |
| agatgcagac ctcagcttag ttgttccatc agctctcttc gctgctgtgg aacagctgg | 180 |
| ccagaggtgt accactgcga ggcgactgtt tatacatgaa agcatccatg atgaggttgt | 240 |
| aaacagactt aaaaaggcct atgcacagat ccgagttggg aacccatggg accctaatgt | 300 |
| tctctatggg ccactccaca ccaagcaggc agtgagcatg tttcttggag cagtggaaga | 360 |
| agcaaagaaa gaaggtggca cagtggtcta tgggggcaag gttatggatc gccctggaaa | 420 |
| ttatgtagaa ccg | 433 |

<210> SEQ ID NO 186
<211> LENGTH: 422
<212> TYPE: DNA
<213> ORGANISM: Homo sapien
<220> FEATURE:
<221> NAME/KEY: misc_feature
<222> LOCATION: (1)...(422)
<223> OTHER INFORMATION: n = A,T,C or G

<400> SEQUENCE: 186

| | |
|---|---|
| cttccgagga agctaaggct gcgttngggt gaggccctca cttcatccgg cgactagntc | 60 |
| cgcgtccggc agcgccagcc ctacactcgc ccncgccatg gcctctgtct ccgagctcgc | 120 |
| ctgcatctac tcggccctca ttctgcacga cgatgaggtg acagtcacgg aggataagat | 180 |
| caatgccctc attaaagcag ccggtgtaaa tgttgagcct ttttggcctg cttgtttgc | 240 |
| aaaggccctg gccaacgtca acattgggag cctcatctgc aatgtagggg ccggtggacc | 300 |
| tgctccagca gctggtgctg caccagcagg aggtcctgcc ccctccactg ctgctgctcc | 360 |
| agctgaggag aagaaagtgg aagcaaagaa agaagaatcc gaggagtctg atgatgacat | 420 |
| gg | 422 |

<210> SEQ ID NO 187
<211> LENGTH: 436
<212> TYPE: DNA
<213> ORGANISM: Homo sapien

<400> SEQUENCE: 187

```
attccaaaca atactatctt ataaaatagt actgttgaat tattccaagc ctccctaggt      60
ttgctttcaa atgtcattta cagattgggc taacgaccta aaatctatat ataaagactt     120
tctgaagaac tctgtattat agcaatacca acgagtgct gtgtgtgcaa acagtctggc     180
gttgctttt atgttgatat ttatcctaga acactgaaag agaatatgcc agtgataact     240
cactttactt cagtcatttc aacacagaaa atgcttctct agcatttttc ttttgtagtg     300
ttaacatttt gaaattcatg tttcagaggc ttcatcatca cagaatttac tcttgctcca     360
tgaaaaaaaa ttaaatacct tcagaggaat atttaagttg taaactatga aacttgagaa     420
atcctcttga gataaa                                                    436
```

<210> SEQ ID NO 188
<211> LENGTH: 436
<212> TYPE: DNA
<213> ORGANISM: Homo sapien

<400> SEQUENCE: 188

```
tcaagccctc aacctcacca gtcctgataa aacccaagag tgctggttat gcctagtatc      60
gggacccca tactacgagg gggttgccgt cctaggtacc tactccaacc atacttctgc     120
cccagctaac tgctctgtgg cctctcaaca caaattgacc ttgtccgaag tgaccggaca     180
gggactctgc ataggagcgg tccctaaaac ccatcaagtc ttgtgtaata ccacccaaaa     240
gacaagcgat gggtcctact atttggccgc tcccacagga actacctggg cttgtagtac     300
tggactcact ccctgtatct caaccaccat acttgacctc accaccgatt actgtgtcct     360
ggtcgagctt tggccaaggg tgacctacca ttcccctagt tatgtttacc accaatttga     420
aagacgagcc agatat                                                    436
```

<210> SEQ ID NO 189
<211> LENGTH: 422
<212> TYPE: DNA
<213> ORGANISM: Homo sapien

<400> SEQUENCE: 189

```
ggaagatata acctcatcag atcagggaac ctccaatagc acaagagga catcgctgag      60
ccgagggatc tctgtcacat ccaacctgga agaatggcac gccctgttgg tcgagtccaa     120
aacctaccta gaggaagagg aggatgagga agcctggaa aaaatcattt ccaaactga     180
caagcttcag agcattgaca gccactccat ggaggaagtt ggagaggtgg aaaacaaccc     240
agtgagcaaa gcaatcgctc accacctggg cattgacatt tctgcagaag ccgcctggc     300
caagaaccgg aaaggcatcg ccattatcat tcacgggaca cccttgtcag gaaagtcagc     360
caatgccgtt agcgtggcca agtactacaa cgcagcctgc ctgagcatcg actccattgt     420
gc                                                                   422
```

<210> SEQ ID NO 190
<211> LENGTH: 426
<212> TYPE: DNA
<213> ORGANISM: Homo sapien
<220> FEATURE:
<221> NAME/KEY: misc_feature

```
<222> LOCATION: (1)...(426)
<223> OTHER INFORMATION: n = A,T,C or G

<400> SEQUENCE: 190
ggaagatata acctcatcag atcannttaa cctccaatag cacaaagagg acatcgcttt      60
ccgagggatc tctgtcacat ccaacctgga agaccggcac gccctgttgg tcgagtccaa     120
aacctaccta gaggaagagg aggatgagga aagcctggaa aaaatcattt tccaaactga     180
caagcttcag agcattgaca gccactccat ggaggaagtt ggagaggtgg aaaacaaccc     240
agtgagcaaa gcaatcgctc accacctggg cattgacatt tctgcagaag gccgcctggc     300
caagaaccgg aaaggcatcg ccattatcat tcacgggaca cccttgtcag gaaagtcagc     360
caatgccgtt agcgtggcca agtactacaa cgcagcctgc ctgagcatcg actccattgt     420
gctgga                                                               426

<210> SEQ ID NO 191
<211> LENGTH: 432
<212> TYPE: DNA
<213> ORGANISM: Homo sapien
<220> FEATURE:
<221> NAME/KEY: misc_feature
<222> LOCATION: (1)...(432)
<223> OTHER INFORMATION: n = A,T,C or G

<400> SEQUENCE: 191
ccgagccggg gttctggcgg agcgcttngg ccctgaagga cgccgccgag caccgcgagc      60
tgatggcctg gaaccaggcg gagaaccggc ggctgcacga gctgcggata gcgaggctgc     120
ggcaggagga gcgggagcag gagcagcggc aggcgttgga gcaggcccgc aaggccgaag     180
aggtgcaggc ctgggcgcag cgcaaggagt gggaagtgct gcagctgcag gaagaggtga     240
aaaacttcat cacccgagag aacctggagg cacgggtgga agcagcattg gactcccgga     300
agaactacaa ctgggccatc accagagagg ggctggtggt caggccacaa cgcagggact     360
cctaggggcc cagtaaggac agtgcccgcc agggaccatg tatgtatcat ggcggaagag     420
ttggccctga cc                                                        432

<210> SEQ ID NO 192
<211> LENGTH: 440
<212> TYPE: DNA
<213> ORGANISM: Homo sapien

<400> SEQUENCE: 192
caagagcaga ggccgaactc gggatctgac aagatggccg ggctgccccg caggatcatc      60
aaggaaaccc agcgtttgct ggcagaacca gttcctggca ttaaagcaga accagatgag     120
agcaacgccc gttatttttca tgtggtcatt gctggccccc aggattcccc ctttgaggga     180 gggacttttta aacttgaact attccttcca gaagaatacc caatggcagc acctaaagta     240
cgtttcatga ccaaaattta tcatcctaat gtagacaagt tgggaagaat atgtttagat     300
attttgaaag gtaagtgttg tttgtcaccc tgtgctttat taacgtgtcc tttttgtcct     360
aagcattcta catttagaat gtaagcattg gaatctcact gtatgctaac agccccagag     420
tgtgtgggag ggaagtgcag                                                 440

<210> SEQ ID NO 193
<211> LENGTH: 477
<212> TYPE: DNA
<213> ORGANISM: Homo sapien
<220> FEATURE:
```

<221> NAME/KEY: misc_feature
<222> LOCATION: (1)...(477)
<223> OTHER INFORMATION: n = A,T,C or G

<400> SEQUENCE: 193

```
cggcgacgac ccattcgaac gtctgcccta tcaactttcg atggtagtcg ccgtgcctac      60
catggtgacc acgggtgacg gggaatcagg gttcgattcc ggagagggag cctgagaaac     120
ggctaccaca tccaaggaag gcagcaggcg cgcaaattac ccactcccga cccggggagg     180
tagtgacgaa aaataacaat acaggactct ttcgaggccc tgtaattgga atgagtccac     240
tttaaatcct ttaacgagga tccattggag ggcaagtctg gtgccagcag ccgcggtaat     300
tccagctcca atagcgtata ttaaagttgc tgcagttaaa aagctcgtag ttggatcttg     360
ggagcgggcg ggcggtccgc cgcgaggcga gccaccgccc gtncccgccc cttgcctctc     420
ggngcccccct cgatgctctt agctgagtgt cccgcgggc ccnaancgtt nactttg       477
```

<210> SEQ ID NO 194
<211> LENGTH: 443
<212> TYPE: DNA
<213> ORGANISM: Homo sapien
<220> FEATURE:
<221> NAME/KEY: misc_feature
<222> LOCATION: (1)...(443)
<223> OTHER INFORMATION: n = A,T,C or G

<400> SEQUENCE: 194

```
aagcctcatt ccaganaaag aggtagaagg tcntaggagc acatcaaaaa caagagacaa      60
aaagaaagaa gacaaagaaa agaaacgttc taaaacacca ccaaaaagtt acagcacagc     120
cagacgttct agaagtgcaa gcagagagag acgacgacga agaagcagga gtggcacaag     180
atctcctaaa aagcctcggt ctcctaaaag aaaattgtcc cgctcaccat cccctaggag     240
acataaaaag gagaagaaga aagataaaga caaagaaaga agtagggatg aaagagaacg     300
atcaacaagc aagaagaaga agagtaaaga taaggaaaag gaccgggaaa gaaaatcaga     360
gagtgataaa gatgtaaaac aggttcacgg gattatgtga agaggaacag gggtatgcag     420
tgagaaagag aaaaaagaag aga                                            443
```

<210> SEQ ID NO 195
<211> LENGTH: 428
<212> TYPE: DNA
<213> ORGANISM: Homo sapien

<400> SEQUENCE: 195

```
aattcacatc tctcagaggt tcaccgtaga cagctttgga aactacgctt cctgtggaca      60
aattgacttc tcctgaggtg gatcttggaa agcactagaa actaaacatc ttcaccaggt     120
gctgaagaaa agtgtcttcg ttttaattgc caagcaggga tgtggacatt tggatggtga     180
cttccctggg tggttcccca tagattcacc attgcctcta atggtgtcta cacccgtcat     240
actaccagct gagatggtgg tgggcataag gagaatttgt gtctataacc cttagtgtgt     300
tctggttttt tttcttttaa tttttaaatt gtcgtaaaat actcataaaa catactgtct     360
tcaccatttt taagtgcaca gttcagtaac gttaactgtt aatacattca taatgctgtg     420
tggccgtc                                                             428
```

<210> SEQ ID NO 196
<211> LENGTH: 423
<212> TYPE: DNA
<213> ORGANISM: Homo sapien

<400> SEQUENCE: 196

```
aaaaagatac aagtttataa catcttataa aaactaccat ttaaaagtga tcttgtccat      60
ttgatattcc cctcccccat agcaaaatat tatttaaaaa aaaaaaaaca aaaaacaggg     120
tggagaggag gataggaagg ggacagttga taaaaccccca gggccacagc agaggcaaag    180
ggcatctggg gagagggttc gaagctgtgg cggactccac taatgtaacc ctccaatgtc     240
aagccatggg cgtgatcagt agctaagtga tgacaaggct gttgggggtg gacggaaaag    300
acttggggca aagcagactg tttatagcct gagctggtag ggcctggtgc agcagcctac    360
ccggaactgg cactactctt tcccaggttc cctgactctc tatcctggtc tctgagagcg    420
tgc                                                                  423
```

<210> SEQ ID NO 197
<211> LENGTH: 427
<212> TYPE: DNA
<213> ORGANISM: Homo sapien

<400> SEQUENCE: 197

```
caggcacctt cctggcagta gagttcacca ctttggcgga ctatttgcat ctgttgcagg      60
ctgcggccca ggcactcaat ccgctaggcc cttctgcgat gttttacctg gctgcggctg     120
tgtcagattt ctatgttcct gtctctgaaa tgcctgaaca caagatccag tcatctgggg    180
gcccactgca gataacaatg aagatggtgc caaaactgct ttctcctttg gttaaagatt     240
gggctcccaa agcatttata atttccttta agttggagac tgaccccgcc attgtaatta    300
atcgagctcg gaaggctttg gaaatttatc agcatcaagt ggtggtggct aatatccttg    360
agtcacgaca gtcctttgtg tttattgtaa ccaaagactc ggaaaccaag ttattgctat    420
cagagga                                                              427
```

<210> SEQ ID NO 198
<211> LENGTH: 427
<212> TYPE: DNA
<213> ORGANISM: Homo sapien

<400> SEQUENCE: 198

```
caaacaatac tatcttataa aatagtactg ttgaattatt ccaagcctcc ctaggtttgc      60
tctcaaatgt catttacaga ttgggctaac gacctaaaat ctatatataa agactttctg    120
aagaactctg tattatagca ataccaaacg agtgctgtgt gtgcaaacag tctggcgttg    180
cttttttatgt tgatatttat cctagaacac tgaaagagaa tatgccagtg ataactcact    240
ttacttcagt catttcaaca cagaaaatgc ttctctagca ttttcttt gtagtgttaa      300
cattttgaaa ttcatgtttc agaggcttca tcatcacaga atttactctt gctccatgaa    360
aaaaaaatta ataccttca gaggaatatt taagttgtaa actatgaaac ttgagaaatc     420
ctcttga                                                              427
```

<210> SEQ ID NO 199
<211> LENGTH: 442
<212> TYPE: DNA
<213> ORGANISM: Homo sapien

<400> SEQUENCE: 199

```
actccacctt actaccagac aaccttagcc aaaccatttta cccaaataaa gtataggcga     60
tagaaattga aacctggcgc aatagatata gtaccgcaag ggaaagatga aaaattataa    120
```

```
ccaagcataa tatagcaagg actaacccct ataccttctg cataatgaat taactagaaa    180
taactttgca aggagagcca aagctaagac ccccgaaacc agacgagcta cctaagaaca    240
gctaaaagag cacacccgtc tatgtagcaa aatagtggga agatttatag gtagaggcga    300
caaacctacc gagcctggtg atagctggtt gtccaagata gaatcttagt tcaactttaa    360
atttgcccac agaaccctct aaatcccctt gtaaatttaa ctgttagtcc aaagaggaac    420
agctctttgg acactaggaa aa                                             442
```

<210> SEQ ID NO 200
<211> LENGTH: 353
<212> TYPE: DNA
<213> ORGANISM: Homo sapien
<220> FEATURE:
<221> NAME/KEY: misc_feature
<222> LOCATION: (1)...(353)
<223> OTHER INFORMATION: n = A,T,C or G

<400> SEQUENCE: 200

```
ggcaggactg ggaggcgaca gatgggcccc tcttggcctc tgtcccagct ctctgcagcc    60
agacggaaag gcggctgctt gcctctccat cctccgaaaa acccctgagg accccccccc   120
atcctcttct aggatgaggg gaagctggag ccccaacttt gatcctccat tggagtggcc   180
caaatctttc catctagggc aagtcctgaa aggcccaagg cccctcccc  agnntagcct   240 tggcctccag cctggagaag ggctaacatc agctcattgt caaggccacc cccaccccag   300
aacagaaccg tgtctctgat aaaggttttg aagtgaataa agttttaaaa act          353
```

<210> SEQ ID NO 201
<211> LENGTH: 443
<212> TYPE: DNA
<213> ORGANISM: Homo sapien

<400> SEQUENCE: 201

```
actaagaggt gcttagacaa gggctggtgc ccggcccagg gtgcccagcg gggccatgcc    60
atggcagata aagctcagga cgtcaaaaac tcaccatgga ccccaaggca gaaaccaaga   120
actgtctgca ggcaaataag cacccagcac ccatcctggc tgccggtgcc ccgtaccctg   180
tatttattct tttaacaata acaaaagcca tttatttatt ccatctagaa aggaaaccct   240
gtttcagtcc cctctctctg gctgttctgt tactttcctt ccacctgtgc cctccctggg   300
atatgtatgc ctcgcccgcc ctccctgggc acatgtgcac acgtgcccag gcacaagtat   360
gtctctgggt cccttgccct gcagtttcca gggggctctg ctccaagttc cctagcgggc   420
ccctcaggga gaaatagcct cac                                            443
```

<210> SEQ ID NO 202
<211> LENGTH: 443
<212> TYPE: DNA
<213> ORGANISM: Homo sapien
<220> FEATURE:
<221> NAME/KEY: misc_feature
<222> LOCATION: (1)...(443)
<223> OTHER INFORMATION: n = A,T,C or G

<400> SEQUENCE: 202

```
cccgcggtaa ccagcgtgag ctcgcccncc agaagaatat gaaaaagcag agcgactcgg    60
ttaagggaaa gcgccgagat gacgggcttt ctgctgccgc cgcaagcag  agggactcgg   120 agatcatgca gcagaancag aaaaaggcaa acgagaagaa ggaggaaccc aagtagcttt   180
gtggcttcgt gtccaaccct cttgcccttc gcctgtgtgc ctggagccag tcccaccacg   240
```

```
ctcgcgtttc ctcctgtagt gctcacaggt cccagcaccg atggcattcc ctttgccctg      300
agtctgcagc gggtcccttt tgtgcttcct tccctcagg tagcctctct cccctgggc       360 cactcccggg ggtgagggg ttaccccttc ccagtgnttt tttattcctg gnggggctna      420
ccccnangtn ttaaaagtng ctt                                              443
```

```
<210> SEQ ID NO 203
<211> LENGTH: 432
<212> TYPE: DNA
<213> ORGANISM: Homo sapien

<400> SEQUENCE: 203
taccagaggt aaaggagga gctggtacca ttccttctga aactattcca atcaatagaa       60
aaagagggaa tcctcccta ctcattttt gaggccagca tcatcctgat accaaagctg      120
ggcagagaca caacgaaaaa agagaatttt agacgaaatat ccttcatgaa cattgatgca    180 aaatcctca ataaaatact ggcaaaccga atccagcagc acatcaaaaa gcttttccac     240
catgatcaag tgggcttcat ccctgggatg caaggctggt tcaacatatg caatcaata    300 aatgtaatcc agcatataaa cagaaccaaa gacaaaaacc acatgattat ctcaatagat   360
gcagaaaagg cctttgacaa aattcaacaa aattcatgct aaaaactctc aataaatgag   420
gtattgatgg ga                                                         432
```

```
<210> SEQ ID NO 204
<211> LENGTH: 230
<212> TYPE: DNA
<213> ORGANISM: Homo sapien
<220> FEATURE:
<221> NAME/KEY: misc_feature
<222> LOCATION: (1)...(230)
<223> OTHER INFORMATION: n = A,T,C or G

<400> SEQUENCE: 204
cgagtatgga gcagaaacga ttgcagggtt tnaccaggat ccacctctga tgttcactga     60
agagnaccag aaaagnctgc tagagcagtn ccatctgggt ctngatccca aacgcagaaa    120
atacntggtn ggagagctna nntgaatac tantgatttc atgactgaac agtcaccgac    180
tagagtgctg gggntggcaa acnggatctt cactcggcag agacaacctt               230
```

```
<210> SEQ ID NO 205
<211> LENGTH: 431
<212> TYPE: DNA
<213> ORGANISM: Homo sapien

<400> SEQUENCE: 205
ggaaattaca atgattttgg aaattataac cagcaacctt ctaactacgg tccaatgaag      60
agtggaaact ttggtggtag caggaacatg gggggaccat atggtggagg aaactatggt   120
ccaggaggca gtggaggaag tgggggttat ggtgggagga gccgatactg agcttcttcc    180
tatttgccat gggtaagtag ctttttgagtt ttacaattat tattatcttg ggagacatag    240
ctgcaggagt aaaagcttt taggatcatg ttatctttcc ttaaaatctg gttagatgga    300
taatttcata acctattttt tttttactct ttacttctgt tgaaacaggc ttcactgtat    360
aaataggaga ggatgagagc ccagaggtaa cagaacagct tcaggttatc gaaataacaa   420
tgttaaggaa a                                                          431
```

```
<210> SEQ ID NO 206
```

<211> LENGTH: 427
<212> TYPE: DNA
<213> ORGANISM: Homo sapien

<400> SEQUENCE: 206

```
ggaaagaaga agataaaaag agcaagaaag aaaatataaa ggatgagaag acaaaaaaag      60
aaaagagaa aaaaaaagat ggtgaaaagg aagaatccaa aaaggaggaa actccaggaa     120
ctcctaaaaa gaaggaaact aagaaaaaat tcaaacttga gccacatgat gatcaggttt     180
ttctggatgg aaatgaggtg tatgtatgga tctatgaccc agttcacttt aaaacatttg     240
tcatgggatt aattcttgtg attgcagtaa tagcggccac cctcttcccc ctttggccag     300
cagaaatgag agtaggtgtt tattacctca gtgtgggtgc aggctgtttt gtagccagta     360
ttcttctcct tgctgttgct cgatgcattc tatttctcat catttggctc ataactggag     420
gaaggca                                                              427
```

<210> SEQ ID NO 207
<211> LENGTH: 432
<212> TYPE: DNA
<213> ORGANISM: Homo sapien
<220> FEATURE:
<221> NAME/KEY: misc_feature
<222> LOCATION: (1)...(432)
<223> OTHER INFORMATION: n = A,T,C or G

<400> SEQUENCE: 207

```
acaagcacca agagattgaa acaaagaaa tttatgctca aaggcaactt ttactaaaag       60
atatggattt gctaagagga agagaagcag agctgaagca aagagttgaa gcttttgaat     120
tgaaccagaa gctccaggaa gaaaaacata aaagcataac tgaggcactt aggagacagg     180
agcagaatat aaagagtttt gaggagacct atgaccgaaa gctcaagaat gaacttctaa     240
agtatcaact tgaactgaag gatgactaca tcattagaac taatcgactg attgaagatg     300
aaaggaagaa taaagaaaaa gctgttcatt tgcaagagga gctcatagct attaattcaa     360
aaaaggagga actcaatcaa tctgtaaatc gtgtgaaaga acttgagctt gaattagaag     420
tctgtcaaan cc                                                         432
```

<210> SEQ ID NO 208
<211> LENGTH: 431
<212> TYPE: DNA
<213> ORGANISM: Homo sapien

<400> SEQUENCE: 208

```
cgcggaggcc gcacgatgcc tggagttact gtaaaagacg tgaaccagca ggagttcgtc      60
agagctctgg cagccttcct caaaaagtcc gggaagctga agtccccga atgggtggat      120
accgtcaagc tggccaagca caaagagctt gctccctacg atgagaactg gttctacacg     180
cgagctgctt ccacagcgcg gcacctgtac ctccggggtg gcgctggggt tggctccatg     240
accaagatct atgggggacg tcagagaaac ggcgtcatgc ccagccactt cagccgaggc     300
tccaagagtg tggcccgccg ggtcctccaa gccctggagg ggctgaaaat ggtggaaaag     360
gaccaagatg gcggccgcaa actgacacct cagggacaaa gagatctgga cagaatcgcc     420
ggacaggtgg c                                                          431
```

<210> SEQ ID NO 209
<211> LENGTH: 427
<212> TYPE: DNA
<213> ORGANISM: Homo sapien

<400> SEQUENCE: 209

```
ctggtactgt ggccctccgt gaaatcagac gctatcagaa gtccactgaa cttctgatcc      60
gcaagctccc ctttcagcgt ctggtgcgag aaattgctca ggacttcaaa acagatctgc     120
gcttccagag tgcagctatt ggtgctttgc aggaggcaag tgaggcctat ctggttggcc     180
tttttgaaga taccaatctg tgtgctatcc atgccaaacg tgtaacaatt atgccaaaag     240
atatccagct agcacgccgc atacgcggag aacgtgctta agagtccact atgaggggaa     300
acatttcatt ctcaaaaaaa ttttttttcc tcttcttcct gttatcagta gttctgaatg     360
ttagatattt tttccatggg gtcaaggta cctaagtata tgattgcgag tggaaacata     420
ggggaca                                                               427
```

<210> SEQ ID NO 210
<211> LENGTH: 427
<212> TYPE: DNA
<213> ORGANISM: Homo sapien

<400> SEQUENCE: 210

```
atttatacct acaaaaagaa aacaagatga tggtatcaaa aggacaattt acaaactaag      60
aatagtaaca tagcttttcag catcctgtgc ctgaacatca cacatctaca agtctttcaa     120
gtcttaatgc aacaggaatg tgtctggaga ccagcaagaa catcaataga gagcactgat     180
cccaagcaaa agccactaac cttttagatg agaagtccac acaacgaatt gttagggagg     240
attggggaga agcagcccat tgcttaatac attggaaccc tttccctaag ttgagtttca     300
accatgaatg caataactag cataaaaacga ttcttctgct catgttctga agccaacagc    360
agaacctgaa ttataagtga cagacatgga ggcagaagag ttaaactctg ctagatttca     420
gctgtgc                                                               427
```

<210> SEQ ID NO 211
<211> LENGTH: 429
<212> TYPE: DNA
<213> ORGANISM: Homo sapien

<400> SEQUENCE: 211

```
tgtatcagaa ccttaatgag ccaaccacgt ggagcttaac cagtgataga actagaaatt      60
gggttcttca acagaaaata gaaggagaaa caaaagaatc aaaactacgct aaattgattg    120
aaatgaatgg aggaggaacc ggctgtaatc atgaattaga aatgatcaga caaaagcttc     180
aatgtgtagc ttcaaaacta caggttctac cccagaaagc ctctgagaga ctacagtttg     240
aaacagcaga tgatgaagat ttcatttggg ttcaggaaaa tattgatgaa attattttac     300
aactacagaa attaactggc cagcaaggtg aagagcccag cttggtgtcc ccaagtactt     360
cttgtggctc attgactgaa agactactga gacaaaatgc tgagctgaca gggcatatca     420
gtcaactga                                                             429
```

<210> SEQ ID NO 212
<211> LENGTH: 426
<212> TYPE: DNA
<213> ORGANISM: Homo sapien

<400> SEQUENCE: 212

```
agaacatctg tttctgggcc cccatccacc gtggccttcc agttgtccac ggtgtcctaa      60
gagcctcgcc atttctgatg ttcccgtgtt cctcccccag atgtctccca cgtcttcccc     120
```

| | |
|---|---:|
| gagttcccag cgcccgacct gggcagcttc ctgctgcagg acggcgtcac actgcacgac | 180 |
| gtcaaggccc tgcagctggt gtacagacgg cactgcgagg tgaccgcccc agcccaggca | 240 |
| ggcagctcct gcgtgtccct cccgggaacc gccagcgctc aggccaggcg tccccgggtg | 300 |
| acgctgagga gctggagccc cgagcccccc aacaagcatc ctctctgaag cagcagcccc | 360 |
| tccgcatcca tgtccatcgc ctgctcctct cctctctgtg gcctcccttg ggattccagg | 420 |
| gcaccc | 426 |

<210> SEQ ID NO 213
<211> LENGTH: 430
<212> TYPE: DNA
<213> ORGANISM: Homo sapien
<220> FEATURE:
<221> NAME/KEY: misc_feature
<222> LOCATION: (1)...(430)
<223> OTHER INFORMATION: n = A,T,C or G

<400> SEQUENCE: 213

| | |
|---|---:|
| gctcaagatc tgccgagtaa accggaactc tnggagctgc ctcggtgggg atgagatctt | 60 |
| nttgctgtgc gacaaggtgc anaaagaana cattgangng tatttcacgg gaccaggctg | 120 |
| ggaggcacga ggctcctttt ctcaagctga tgtgcatcgg caagtggcca ttgtgttccg | 180 |
| gactcctccg tacgccgacc ccagcctcca ggctcctgtt cgagtctcca tgcagctacg | 240 |
| gcggccttct gatcgcgagc tcagtgagcc catggagttc cagtacttgc cagacacaga | 300 |
| tgatcgccac cggattgaag agaagcgcaa aaggacctat gagaccttca agagtatcat | 360 |
| gaagaagagt cctttcaatg gaccaactga accccggcct ccaacccggc gtattgctgt | 420 |
| gcctacccga | 430 |

<210> SEQ ID NO 214
<211> LENGTH: 431
<212> TYPE: DNA
<213> ORGANISM: Homo sapien

<400> SEQUENCE: 214

| | |
|---|---:|
| gttccctggg ctccccccat cacatcccag cccctctggg ctgaccctgt ctagagatgc | 60 |
| atctgtcccc tccttggact gggagctcca aggacagggc caggggtcgt ctccccatcc | 120 |
| cagtgattct ggaattgtcc agggcagggc cgggcgcagg acagacgttt tgtggaacta | 180 |
| atgcaggggt gaattagtgg attcatgggg ccaaagatgt ggcgtcagcg cagatgaggg | 240 |
| tggcgcttcc ccacctctgt cctggtcgct ccccaacctg ctcacacctc tctctctctc | 300 |
| tctccctgac agcatttctt cacttccttt ggggcccgtg accgctgctt cctcctcatc | 360 |
| ttccgcctct ggcagaatgc actgcttgaa aagacgctga gtccccgcga gctctggcac | 420 |
| ctggtgcatc a | 431 |

<210> SEQ ID NO 215
<211> LENGTH: 436
<212> TYPE: DNA
<213> ORGANISM: Homo sapien

<400> SEQUENCE: 215

| | |
|---|---:|
| tcatcatagt tgggagccat tggatgcccc agagggtaag ctgcaaggct ctaggtgtga | 60 |
| caacagcagt tgcagcaagc tccctccaca agaaggaaga ggcattgctc aagaacagct | 120 |
| gttccaagaa aagaaggatc ctgctaaccc ctccccggtg atgcctggaa tagccacctc | 180 |
| tgagagggt gatgaacaca gcctaggctg tagtccttca aattcatcag ctcagcccag | 240 |

| | |
|---|---|
| ccttcccctg tatagaacct gccaccccat aatgcctgtt gcttcttcat ttgtgcttca | 300 |
| ctgtcctgat cctgtgcaga aaactaacca atgcctccaa ggccaaagcc tcaaaacttc | 360 |
| attgacttta aaagtggaca gaggcagtga ggagacctat aggccagagt ttcccagcac | 420 |
| aaagggcttt gtccgt | 436 |

<210> SEQ ID NO 216
<211> LENGTH: 427
<212> TYPE: DNA
<213> ORGANISM: Homo sapien

<400> SEQUENCE: 216

| | |
|---|---|
| gatatgttga atacaccttt gtgtccttca cacagcagtt tacatccagt gctgttacct | 60 |
| tcagatgtat ttgaccaacc acaacctgta ggtaacaaaa gaattgaatt ccatatatct | 120 |
| accgacatgc cagctgcatt taagaaagat ttagaaaagg aacaaaattg tgaggaaaaa | 180 |
| aatcatgatt tacctgctac tgaagttgat gcatccaata taggatttgg aaaaatcttc | 240 |
| cccaaaccta atttggacat cacagaggag attaaagaag actctgatga aatgccttca | 300 |
| gaatgtattt ctagaaagga attggaaaag ggcagaattt ctagagaaga aatggaaaca | 360 |
| ctttcagttt tcagaagtta tgaaccgggt gaaccaaact gtagaattta tgtaaagaat | 420 |
| ttagcta | 427 |

<210> SEQ ID NO 217
<211> LENGTH: 399
<212> TYPE: DNA
<213> ORGANISM: Homo sapien

<400> SEQUENCE: 217

| | |
|---|---|
| acccaacctc cgagcagtac atgctaagac ttcaccagtc aaagcgaact actatactca | 60 |
| attgatccaa taacttgacc aacggaacaa gttaccctag ggataacagc gcaatcctat | 120 |
| tctagagtcc atatcaacaa tagggtttac gacctcgatg ttggatcagg acatcccgat | 180 |
| ggtgcagccg ctattaaagg ttcgtttgtt caacgattaa agtcctacgt gatctgagtt | 240 |
| cagaccggag taatccaggt cggttttcta ctacttcaaa ttcctccctg tacgaaagga | 300 |
| caagagaaat aaggcctact tcacaaagcg ccttcccccg taaatgatat catctcaact | 360 |
| tagtattata cccacaccca cccaagaaca gggtttgtt | 399 |

<210> SEQ ID NO 218
<211> LENGTH: 426
<212> TYPE: DNA
<213> ORGANISM: Homo sapien

<400> SEQUENCE: 218

| | |
|---|---|
| cgcggaggta cgctgagtgg agctcgggc tgcgtagggg agctgagccg agcggctggg | 60 |
| cgggcctggc cgggccagcg gaggggagac gtcggttgag cggcggcgaa catgcgcttt | 120 |
| tgacacattg gaggctttct tgatcatgga tggtgaagat ataccagatt tttcaagttt | 180 |
| aaaggaggaa actgcttatt ggaaggaact ttccttgaag tataagcaaa gcttccagga | 240 |
| agctcgggat gagctagttg aattccagga aggaagcaga gaattagaag cagagttgga | 300 |
| ggcacaatta gtacaggctg aacaaagaaa tagagacttg caggctgata accaaagact | 360 |
| gaaatatgaa gtggaggcat taaggagaa gctagagcat caatatgcac agagctataa | 420 |
| gcaggt | 426 |

<210> SEQ ID NO 219
<211> LENGTH: 427
<212> TYPE: DNA
<213> ORGANISM: Homo sapien

<400> SEQUENCE: 219

| | | | | | |
|---|---|---|---|---|---|
| cggcggcggc | tgcggcccaa | tatagccagc | agccagcttc | gggtgtagcc | tattctcatc | 60 |
| caactacagt | tgctagctac | actgtccatc | aggctccagt | agctgctcac | acagttactg | 120 |
| ctgcctatgc | accagcagcc | gccacagttg | cagttgccag | gcctgctcca | gtagctgttg | 180 |
| cagctgctgc | aacagctgct | gcttatggag | gctaccccac | tgcacacaca | gcaactgact | 240 |
| atggttatac | tcagaggcaa | caagaagcac | caccaccacc | accccagct | actacacaaa | 300 |
| actaccagga | ttcatactca | tatgtaaggt | ccacagctcc | tgctgtagct | tatgatagta | 360 |
| agcaatacta | ccaacaacca | acagcagcaa | cagaagcagg | cagcagcagc | agctgctgct | 420 |
| gctgctg | | | | | | 427 |

<210> SEQ ID NO 220
<211> LENGTH: 428
<212> TYPE: DNA
<213> ORGANISM: Homo sapien

<400> SEQUENCE: 220

| | | | | | |
|---|---|---|---|---|---|
| ctctgtcgaa | gattataaag | cccttcagaa | atacgaaaag | gagaaatttg | aagagatgat | 60 |
| tcaacaaatt | aaagagactg | gtgctaacct | agcaatttgt | cagtggggct | ttgatgatga | 120 |
| agcaaatcac | ttacttcttc | agaacaactt | gcctgcggtt | cgctgggtag | gaggacctga | 180 |
| aattgagctg | attgccatcg | caacaggagg | gcggatcgtc | cccaggttct | cagagctcac | 240 |
| agccgagaag | ctgggctttg | ctggtcttgt | acaggagatc | tcatttggga | caactaagga | 300 |
| taaaatgctg | gtcatcgagc | agtgtaagaa | ctccagagct | gtaaccattt | ttattagagg | 360 |
| aggaaataag | atgatcattg | aggaggcgaa | acgatcccctt | cacgatgctt | tgtgtgtcat | 420 |
| ccggaacc | | | | | | 428 |

<210> SEQ ID NO 221
<211> LENGTH: 422
<212> TYPE: DNA
<213> ORGANISM: Homo sapien

<400> SEQUENCE: 221

| | | | | | |
|---|---|---|---|---|---|
| aaaagcctga | agaatacaat | tctgagaaat | ataaaaaaat | tttaatggta | tactcatgtt | 60 |
| gaaagataaa | tgttgctaag | tcctggtatg | atggtgtgag | cttccttggg | gaagtacttc | 120 |
| ttgagttatg | taactaacag | gatgttttac | tacagatctg | gatggctatt | cagataacat | 180 |
| ggcaaaaaat | gatagcagaa | gatcattaaa | aacttaaaat | atattttatt | agaaaacatt | 240 |
| tatctatgaa | tgaatatttc | cttgatgctg | gtctctgcac | acatatgctt | ggttacttgc | 300 |
| atgcattcat | tggttgttca | ataagtgaga | tgattacaga | taacttaata | ctgtatttc | 360 |
| cttatatgga | aaaccgttat | agacccaata | acaactaaac | ctttcaaaag | aaaatatttt | 420 |
| ct | | | | | | 422 |

<210> SEQ ID NO 222
<211> LENGTH: 47
<212> TYPE: DNA
<213> ORGANISM: Homo sapien

<400> SEQUENCE: 222

```
aagccgcccg gccagccgcc ccgtccggga gggaggtggg ggggtca          47
```

<210> SEQ ID NO 223
<211> LENGTH: 432
<212> TYPE: DNA
<213> ORGANISM: Homo sapien

<400> SEQUENCE: 223

```
ctgcaggccc gtgcccgtgt ggatgagtac ctggcatggc agcacacgac tctgcggaga   60
agctgcctcc gggccttgtg cataaggtg atgttccctg ttttcctggg tgagccagta   120
tctccccaga cactggcagc caccctggca gagttggatg tgaccctgca gttgctcgag   180
gacaagttcc tccagaacaa ggccttcctt actggtcctc acatctcctt agctgacctc   240
gtagccatca cggagctgat gcatcccgtg gtgctggct gccaagtctt cgaaggccga    300
cccaagctgg ccacatggcg gcagcgcgtg gaggcagcag tggggagga cctcttccag    360
gaggcccatg aggtcattct gaaggccaag gacttccac ctgcagaccc caccataaag    420
cagaagctga tg                                                       432
```

<210> SEQ ID NO 224
<211> LENGTH: 428
<212> TYPE: DNA
<213> ORGANISM: Homo sapien

<400> SEQUENCE: 224

```
cccagcccat ccattaggct gggggaaggg ggtgggacag gggctggagg aggggctctg    60
gggtccatca cggcacagga acaacacgca tggtgttggt gaagccggag ccagggcgcc   120
atccggtcag cacaatgacc acatctccct tcttgaagaa gcctcgggcc ttgccaacat   180
tcatggcaaa gttcacccgg aggtccacgt cctcagccca tccattaggc cagcaacgct   240
tgtagaactc actctgggct gtaacgtggc actggtaggt tgggacacca gggaagaaga   300
tcaacgcctc actgaaacat ggctgtgttt gcagcctgct ctagtgggac agcccagagc   360
ctggctgccc atcatgtggc cccacccaat caagggaaga aggaggaatg ctggactgga   420
ggcccctg                                                            428
```

<210> SEQ ID NO 225
<211> LENGTH: 428
<212> TYPE: DNA
<213> ORGANISM: Homo sapien

<400> SEQUENCE: 225

```
ggccagcaac gacgaatacg acagcaacgc ttgatctcta taggcaaatg gattgctgat    60
aatcagccaa ggctgattca gtgtgaaaat gaggtaggga aattgttgtt tatcacagaa   120
atcccagaat taatactgga agaccccagt gaagccaaag agaacctcat tctgcaagaa   180
acatctgtga tagagtcgct ggctgcagat gggagcccag gctaaaatc agtgctatct    240
acaagccgaa atttaagcaa caactgtgac acaggagaga agccagtggt taccttcaaa   300
gaaaacatta agacacgaga agtgaacaga gaccaaggaa gaagttttcc tcccaaagag   360
gtaaaatccc agacagaact aagaaagact ccagtgtctg aagccagaaa aacacctgta   420
actcaaac                                                            428
```

<210> SEQ ID NO 226
<211> LENGTH: 249
<212> TYPE: DNA

<213> ORGANISM: Homo sapien

<400> SEQUENCE: 226

| | | | | | |
|---|---|---|---|---|---|
| cttgctgcct | gcagcataca | gagctgtgtc | caaggctccc | agcgccacca | gggctaggga | 60 |
| gtcggtttct | aagtggagct | tcacggactc | cccgttccgg | tactgcttgg | caccgtccac | 120 |
| gctgagctcc | agcttgccct | cgcaggcccc | agcctggaca | tccactcgca | gggagttggc | 180 |
| cactgggtgg | tctccatggt | agtagaaggc | cacaaagtag | aaggagggtg | ccaggtgatg | 240 |
| gtccacccc | | | | | 249 |

<210> SEQ ID NO 227
<211> LENGTH: 433
<212> TYPE: DNA
<213> ORGANISM: Homo sapien

<400> SEQUENCE: 227

| | | | | | |
|---|---|---|---|---|---|
| agcaacagat | gatacgctta | acttttgga | cacctgtgat | ttgcatactg | agcatataaa | 60 |
| gccatcttta | cgcacgtcca | tcggtgaaag | aaaacggtct | ctttcaccac | taattaagtt | 120 |
| ttctccagtg | gaacaaagat | tgagaaccac | aatagcatgt | agtcttggag | aactacctaa | 180 |
| tttaaaggaa | gaagacattt | tgaataagag | ccttgatgca | aaagaaccac | cgtctgactt | 240 |
| gacaagatga | agacgtaccc | atttaatata | actatgatgc | acttaaattg | aagctatgcc | 300 |
| acaggataga | aaatgaatta | caacttaaat | acatgttgga | agtgtaacac | tgtttttcaa | 360 |
| ggtttaaaaa | aattcctaat | gccttttagc | cttctttaat | atttttaggt | aaggaaagta | 420 |
| tgtttggatt ttt | | | | | 433 |

<210> SEQ ID NO 228
<211> LENGTH: 428
<212> TYPE: DNA
<213> ORGANISM: Homo sapien

<400> SEQUENCE: 228

| | | | | | |
|---|---|---|---|---|---|
| cccctttcgcc | cggctgcacg | agtgctatgg | ccaggagatc | cgggccctgc | gtggccagtg | 60 |
| gctcagcagc | cgggtccagc | cctgaggcca | ccagggcgcc | tgttttaggg | ggacacaagc | 120 |
| tctatgccct | ctgggacagg | ccgggtcctg | gagagactgg | gggagcagat | cctgagggaa | 180 |
| atcatgggca | aggctggccc | ccaggccctg | agtggcctgg | ttttggggga | tgcaggctct | 240 |
| gagaaggtgc | tggattctga | gtgggccttt | aggaccatgt | gacccagaag | gcctaccctt | 300 |
| gaggggaacg | tcacgtgcaa | cactaaggag | aatccagggc | ctgaggggga | ggtttcctga | 360 |
| gaactccggc | cccaggctgg | cctgagctgc | cgggcagagg | cctgtgctgg | caacaggcat | 420 |
| tgccgggc | | | | | 428 |

<210> SEQ ID NO 229
<211> LENGTH: 422
<212> TYPE: DNA
<213> ORGANISM: Homo sapien

<400> SEQUENCE: 229

| | | | | | |
|---|---|---|---|---|---|
| gtttcagaaa | atgttcagac | acccaagtca | tgtacagctg | aaggtagttg | ctggaaacca | 60 |
| tgacattggc | ttccattatg | agatgaacac | atacaaagta | gaacgctttg | agaaagtgtt | 120 |
| cagctctgaa | agactgtttt | cttggaaagg | cattaacttt | gtgatggtca | acagcgtggc | 180 |
| gctgaacggg | gatggctgtg | gcatctgctc | tgaaacagaa | gcagagctca | ttgaagtttc | 240 |
| tcacagactg | aactgctccc | gagaggcacg | tggctccagc | cggtgtggac | ctgggcctct | 300 |

```
gctgcccacg tctgccctg tcctcctgca gcattatcct ctgtatcgga gaagtgatgc    360
taactgttct ggggaagacg ctgctcctcc agaggaaagg gacatcccat ttaaggagaa    420
ct                                                                   422
```

<210> SEQ ID NO 230
<211> LENGTH: 431
<212> TYPE: DNA
<213> ORGANISM: Homo sapien

<400> SEQUENCE: 230

```
tccagacatt aataattttg accctaggaa agctatccat ttatggaatg caagaacacc    60
gtcttcaact ggtgacacaa gatctaattc agattgctca tcaaactcag aaaatgaaag    120
tgattagcaa tatgcaaatg ttgacatttt tgttgcttag caatgtagct cttttgcata    180
gtaaaaaata aataaaata aatggtttcc agaagcctgg aatttaaaag taaacagta     240
acttctcttc acatcaaaca aaaggcattt ggcttcttcc aaacatacag agtaaaaagc    300
ccaagattgt ttcttctata gctttctaac ttcacttatg tattcctgtg ttcttttcaca   360
ctcttttggt ggagctgtat gctgctacac aatggtgtta ttttgatgtc atttttttca    420
gttattccta a                                                         431
```

<210> SEQ ID NO 231
<211> LENGTH: 435
<212> TYPE: DNA
<213> ORGANISM: Homo sapien

<400> SEQUENCE: 231

```
gcctttgccg ctaccgcttt cttaccctcc gcacccgtta agttctccgg tcggcggca     60
gtctctgaac acttagccgc gccatccggg gtcacaccgc ctggaaggag gtgacggggg    120
cggcgcgggg cgcggacact ccccgctgag agtccgcctg ccatggactc ggaatattac    180
agcggcgacc agtcagatga tggtggtgct accccagtac aggatgaacg ggattcaggg    240
tcagacggtg aggatgatgt aaatgagcaa cactccggat cagacactgg aagtgtagaa    300
cgtcattcag agaatgaaac tagtgatcga gaagatggcc tccccaaagg acatcatgtg    360
acagactctg agaacgatga gcccttaaat cttaatgcta gtgactctga aagtgaggag    420
cttcacaggc aaaag                                                    435
```

<210> SEQ ID NO 232
<211> LENGTH: 452
<212> TYPE: DNA
<213> ORGANISM: Homo sapien

<400> SEQUENCE: 232

```
gtcccgggat gcctgccc gagcccagcg agcaggaggg tgagagtgtg aaggccagcc      60
aggagccatc ccccaagcca ggcacagaag tcatcccggc agcccccagg aagcccagaa    120
agttctccaa actggtcctg ctcacagcct ccaaagacag caccaaggtg gcggggggcca   180
agcgcaaggg tgtgcactgt gtcatgtccc tgggggtgcc cggccccgcc acccttgcca    240
aggcctcct ccagacccac cccgaggccc agcgggccat tgaggcagcc ctcaggagc     300
ctgagcagaa acggagcagg caggacccag gcacagacag aacagaagac agtggattag    360
cagcgggggcc tcctgaggct gctggggaga actttgcccc ctgctctgtg gcgcccggca   420
agtccctgta accttgacaa caggcgcatc ct                                 452
```

<210> SEQ ID NO 233
<211> LENGTH: 452
<212> TYPE: DNA
<213> ORGANISM: Homo sapien
<220> FEATURE:
<221> NAME/KEY: misc_feature
<222> LOCATION: (1)...(452)
<223> OTHER INFORMATION: n = A,T,C or G

<400> SEQUENCE: 233

| | | | | |
|---|---|---|---|---|
| ggcgcgggag cagctcggcc ggctgggtct tcatcctcat tgtactccct tggcatntca | | | | 60 |
| tggtgacgtg acttaaaagg tggtgcagag acgtttgaaa ctattgcttt gctgaaaaca | | | | 120 |
| tctgactgcc aggctaggat gtgacactta agggaccagg gatcatttac atactgnggn | | | | 180 |
| cttgcattac tgcgatgaaa tcttccacca ctcccaccac ccactacaag agatggaatt | | | | 240 |
| aattgaaact acagccttca agagacattt ggagcaatac tcttccagtt ctttcttcca | | | | 300 |
| cattttatt gtgggtacag cgtctcccag gatgtagtgt gctgtaatta ttcttccacc | | | | 360 |
| cttttatttt ctgggagttt ctctatctga atagcacaga aatattagtg dataggaagg | | | | 420 |
| gaatataata ttctatccat ctgaaaatta ac | | | | 452 |

<210> SEQ ID NO 234
<211> LENGTH: 434
<212> TYPE: DNA
<213> ORGANISM: Homo sapien

<400> SEQUENCE: 234

| | | | | |
|---|---|---|---|---|
| caaacaatac tatcttataa aatagtactg ttgaattatt ccaagcctcc ctaggtttgc | | | | 60 |
| tctcaaatgt catttacaga ttgggctaac gacctagaat ctatatataa agactttctg | | | | 120 |
| aagaactctg tattatagca ataccaaacg agtgctgtgt gtgcaaacag tctggcgttg | | | | 180 |
| cttttatgt tgatatttat cctagaacac tgaaagagaa tatgccagtg ataactcact | | | | 240 |
| ttacttcagt catttcaaca cagaaaatgc ttctctagca ttttctttt gtagtgttaa | | | | 300 |
| cattttgaaa ttcatgtttc agaggcttca tcatcacaga atttactctt gctccatgaa | | | | 360 |
| aaaaaattaa ataccttcag aggaatattt aagttgtaaa ctatgaaact tgagaaatcc | | | | 420 |
| tcttgagata aaag | | | | 434 |

<210> SEQ ID NO 235
<211> LENGTH: 312
<212> TYPE: DNA
<213> ORGANISM: Homo sapien

<400> SEQUENCE: 235

| | | | | |
|---|---|---|---|---|
| tgggcttcaa gaagcgtgca cctcgggcac tcaaagagat tcggaaattt gccatgaagg | | | | 60 |
| agatgggaac tccagatgtg cgcattgaca ccaggctcaa caaagctgtc tgggccaaag | | | | 120 |
| gaataaggaa tgtgccatac cgaatccgtg tgcggctgtc cagaaaacgt aatgaggatg | | | | 180 |
| aagattcacc aaataagcta tatactttgg ttacctatgt acctgttacc actttcaaaa | | | | 240 |
| atctacagac agtcaatgtg gatgagaact aatcgctgat cgtcagatca aataaagtta | | | | 300 |
| taaaattgcc tt | | | | 312 |

<210> SEQ ID NO 236
<211> LENGTH: 427
<212> TYPE: DNA
<213> ORGANISM: Homo sapien

<400> SEQUENCE: 236

```
cgcccacaag ccacagagcc tagacactga tgaccccgcg acgctgtacg ccgtggtgga    60
gaacgtgccc ccgttgcgct ggaaggaatt cgtgcggcgc ctagggctga gcgaccacga   120
gatcgatcgg ctggagctgc agaacgggcg ctgcctgcgc gaggcgcaat acagcatgct   180
ggcgacctgg aggcggcgca cgccgcggcg cgaggccacg ctggagctgc tgggacgcgt   240
gctccgcgac atggacctgc tgggctgcct ggaggacatc gaggaggcgc tttgcggccc   300
cgccgccctc ccgcccgcgc ccagtcttct cagatgaggc tgcgcccctg cgggcagctc   360
taaggaccgt cctgcgagat cgccttccaa ccccactttt ttctggaaag gagggtcct    420 gcagggg                                                            427
```

<210> SEQ ID NO 237
<211> LENGTH: 452
<212> TYPE: DNA
<213> ORGANISM: Homo sapien

<400> SEQUENCE: 237

```
gtgatttttc catcccattc ccccaaaaat gtgcctcata cactggacaa gacttctact    60
gtgactattc ttggcacaag aaaaaaactt caaacaattc ccaaaaaaaa gcactcactc   120
caaaaaaaaa aaaaaaaaaa aaaggatgtc cctcacccct aagctgaaaa gcagtctctc   180
tcttcagctt agggatgtcc ctcacccctt cacagcacc aaagttgaag agagagactg    240
cttttcactt cttcagttct gccatcttgt tttcaaaggg ctccagcctc actcagtccc   300
taattatggg actgagaaaa gcttggaaag aatcttggtt tcatataaat tcttgttgtt   360
aggccttact aagaagtagg aaagggcatg ggcaaaaggt agggataaaa accaccagca   420
tatacatgga catacacaca cacccacaca ca                                 452
```

<210> SEQ ID NO 238
<211> LENGTH: 453
<212> TYPE: DNA
<213> ORGANISM: Homo sapien
<220> FEATURE:
<221> NAME/KEY: misc_feature
<222> LOCATION: (1)...(453)
<223> OTHER INFORMATION: n = A,T,C or G

<400> SEQUENCE: 238

```
agccgaccgt gattccctct actacanata ttatgtcttg taagttagca tttttagcac    60
acaggagaaa tnttatgtaa taaaattact gtatcttttg gatttaacaa atttgtattt   120
gaaacacatt ctatgtctga taattcttaa tggcactttt actaatttat ttggggatct   180
tgggtacatt cttaatttgt gtttattctt cacgcttgac ttgcaagtgg gatattcccc   240
tgccacaagt gtcaaacagt gatattcttc ctgtgttgtg actggacagt tttccagatc   300 tttttttggga gattttccta cagcttggtt gtatgtnttg agataacacc accaaacagc   360
tctcagaaat tctttttttga ttgatcagna gctatgatga ttctcctcca tgacactaag   420
gattagttta tatatnnnag agaaanangg gct                                453
```

<210> SEQ ID NO 239
<211> LENGTH: 453
<212> TYPE: DNA
<213> ORGANISM: Homo sapien
<220> FEATURE:
<221> NAME/KEY: misc_feature
<222> LOCATION: (1)...(453)
<223> OTHER INFORMATION: n = A,T,C or G

<400> SEQUENCE: 239

```
cgtgtttgtg tgcctgctgg agtaccccg ggggaagagg aagaagggct ccaccatgga      60
gcgctgggga cagaagcaca tgaccgccgt ggtgaagctg ttcgggccct ttaccaggaa     120
ttactatgtt cgggccgtcc tgcatctcct gctctcggtg cccgccggct tcctgctggc    180
caccatcctt ggggccgcct gcctggccat tgcgagcggc atctacctac tggcggctgt    240
gcgtggcgag cagtggacgc ccatcgagcc caagccccgg gagcggccgc agatcggagg    300
caccatcaag cagccgccca gcaaccccc gccgcgccc ccggccgagg cccgcaagaa       360
gcccagcgag gaggaggctg cggcggcggc gggggggaccc ccgggaggtc cccaggncaa   420
ccccatcccg gtgaccgacg aggncgtgtg acc                                  453
```

<210> SEQ ID NO 240
<211> LENGTH: 453
<212> TYPE: DNA
<213> ORGANISM: Homo sapien

<400> SEQUENCE: 240

```
ggctcatctt cgcagacggg ctcctctact gtcccgtggc cttcctcagc ttcgcctcca     60
tgctgggcct cttccctgtc acgcccgagg ccgtcaagtc tgtcctgctg gtggtgctgc    120
ccctgcctgc ctgcctcaac ccactgctgt acctgctctt caaccccac ttccgggatg     180
accttcggcg cttcggccc cgcgcagggg actcagggcc cctagcctat gctgcggccg     240
gggagctgga gaagagctcc cgtgattcta cccaggccct ggtagccttc tctgatgtgg    300
atctcattct ggaagcttct gaagctgggc ggcccctgg gctggagacc tatggcttcc     360
cctcagtgac cctcatctcc tgtcagcagc cagggggccc caggctggag ggcaagccat    420
tgtgtagagc cagaggggaa ccactttggg aac                                  453
```

<210> SEQ ID NO 241
<211> LENGTH: 453
<212> TYPE: DNA
<213> ORGANISM: Homo sapien
<220> FEATURE:
<221> NAME/KEY: misc_feature
<222> LOCATION: (1)...(453)
<223> OTHER INFORMATION: n = A,T,C or G

<400> SEQUENCE: 241

```
aagcaacggc aagggccgca gccagcnccg ggcggagagg gctaccatgg ggaaaatcgc      60
gctgcaactc aaagccacgc tggagaacat caccaacctc cggcccgtgg gcgaggactt    120
ccggtggtac ctgaagatga atgtggcaa ctgtggtgag atttcggaca agtggcagta     180
catccggctg atggacagtg tggcactgaa gggggccgt ggcagtgctt ccatggtcca      240
gaagtgcaag ctgtgtgcaa gagaaaattc catcgagatt ttaagcagca ccatcaagcc    300
ttacaatgct gaagacaatg agaacttcaa gacaatagtg gagtttgagt gccggggcct    360
tgaaccagtt gatttccagc cgcaggctgg gtttgctgct gaaggtgtgg agtcagggac    420
agccttcagt gacattaatc tgcaggagaa gga                                  453
```

<210> SEQ ID NO 242
<211> LENGTH: 441
<212> TYPE: DNA
<213> ORGANISM: Homo sapien
<220> FEATURE:
<221> NAME/KEY: misc_feature
<222> LOCATION: (1)...(441)
<223> OTHER INFORMATION: n = A,T,C or G

<400> SEQUENCE: 242

```
tcctatggcn cgncntnnaa gcggcggcgg nnatnagncn aaagcactac cttgaggctg     60
cagcgcgggg actgcacgac agctgcccgg gccaagcccg ntacctnctc tgggcctaca    120
cttngncgca cgatgataag agcacttttg aagaaacgtg tccatactgt ttccagctgt    180
tggttctgga taactctcga gtgcgtctca aacccaaagc caggttgaca cccaaaatac    240
agaaacttct taatcgagaa gcgagaaact atacactcag ttttaaagaa gcaaaaatgg    300
tgaaaaagtt caaagactcc aaaagtgtat tgttgatcac ttgtaaaaca tgcaacagaa    360
cagtgaaaca tcatggtaaa agtagaagct ttgtgtcaac attgaagagc aatcctgcca    420
ctcctgcaag taaactcagc c                                              441
```

<210> SEQ ID NO 243
<211> LENGTH: 429
<212> TYPE: DNA
<213> ORGANISM: Homo sapien

<400> SEQUENCE: 243

```
gaaaaaggaa aaaagaaga acggaaggc agagaaacat cgtggccgaa ttgggatcga      60
tgaagatgat aagggccta gggcacctcg cccacctcag cccaagaaat ctaagaaagc    120
aggtggtggg ggtagcaatg ctactacact cagccatcct ggctttggga cttccggagg    180
aagtagcaac aagctaccta aaaagtctca aaagacagct ccacctgtcc ttcccactgg    240
ctatgattct gaggaggagg aagaaagcag gcccatgagt tatgatgaga agagacagtt    300
aagcctggat atcaataagt tacctgggga aaagctgggt cgagtagtac atatcatcca    360
agccagggaa ccctctctac gtgattcaaa tccagaagaa attgagattg attttgaaac    420
actcaagcc                                                           429
```

<210> SEQ ID NO 244
<211> LENGTH: 433
<212> TYPE: DNA
<213> ORGANISM: Homo sapien
<220> FEATURE:
<221> NAME/KEY: misc_feature
<222> LOCATION: (1)...(433)
<223> OTHER INFORMATION: n = A,T,C or G

<400> SEQUENCE: 244

```
caaacaatac tatcttatan aatagnactg ttgaattatt ccaagcctcc ctaggtttgc     60
tctcaaatgt catttacaga ttgggctaac gacctaaaat ctatatataa agactttctg    120
aagaactctg tattatagca ataccaaacg agtgctgtgt gtgcaaacag tctggcgttg    180
cttttttatgt tgatatttat cctagaacac tgaaagagaa tatgccagtg ataactcact    240
ttacttcagt catttcaaca cagaaaatgc ttctctagca ttttttcttt gtagtgttaa    300
cattttgaaa ttcatgtttc agaggcttca tcatcacaga atttactctt gctccatgaa    360
aaaaaattaa ataccttcag aggaatattt aagttgtaaa ctatgaaact tgagaaatcc    420
tcttgagata aaa                                                       433
```

<210> SEQ ID NO 245
<211> LENGTH: 430
<212> TYPE: DNA
<213> ORGANISM: Homo sapien

<400> SEQUENCE: 245

-continued

| | |
|---|---|
| gatgccccTT ggagtggcaa ggaagctgga cagggcaggc ctctggggac gggacacagg | 60 |
| gaagcccgaa ggggcgcctt ggccaggtct gccatctcct ccagcgaggc tctggccagc | 120 |
| actgggtgag agtggggagg gggcactggc ctttgcagca cagtaaaaca tggtccagac | 180 |
| aacctgtggc cccggcctca tgagcacccc ctgcacaggc ccagcccaag ccaggcgcta | 240 |
| gaagggctgg ttgtggagtg cttatccttg acaggtatgg ggccaggtga gggcagggga | 300 |
| caaggtgcag ctgaggccga gcccaactag gtcctgggca cccctgcagg tgggagtggt | 360 |
| ccttgtcctc ctggtatcca gcagacaccc ccctctcccc accagcccca ttctcaggtc | 420 |
| ctttcctctt | 430 |

<210> SEQ ID NO 246
<211> LENGTH: 428
<212> TYPE: DNA
<213> ORGANISM: Homo sapien

<400> SEQUENCE: 246

| | |
|---|---|
| cctgcccagc aaggacatct gtccaggtg gcacatggac atgttgagcc cccgcagcag | 60 |
| gggatggtgc cccatggcct gcaccagggg gtcatgtccc ctccacaagg cctcatgacc | 120 |
| cagcagaatt tcatgctgat gaagcagcgg ggcgtggggg gcgaggtcta cagccagccg | 180 |
| ccccacatgc tctccccgca gggctccctc atgggccccc cgccccagca gaacctcatg | 240 |
| gtgtcccacc cccttcggca gcgcagtgtg tccctggaca gccagatggg ctacctcccg | 300 |
| gcaccaggcg gcatggccaa cctgcccttc tagaagtcgc tgccagggct ggagccgggg | 360 |
| caatgttgca aatacgataa ccttaacaaa gttcttcccc tcaatgttgg gatggcctgg | 420 |
| gtcgtggg | 428 |

<210> SEQ ID NO 247
<211> LENGTH: 428
<212> TYPE: DNA
<213> ORGANISM: Homo sapien
<220> FEATURE:
<221> NAME/KEY: misc_feature
<222> LOCATION: (1)...(428)
<223> OTHER INFORMATION: n = A,T,C or G

<400> SEQUENCE: 247

| | |
|---|---|
| gacaagtcgg acaggggcca tgacntntcg gaccgcagcc atgagaaact agacaggtgc | 60 |
| cacgacaagt cagaccgggg ccacgacaag tctnacaggg atcgagagcg tggctatgac | 120 |
| aaggtagaca gagagagaga gcgagacagg gaacgggatc gggaccgcgg gtatgacaag | 180 |
| gcagaccggg aagagggcaa agaacggcgc caccatcgcc gggaggagct ggctccctat | 240 |
| cccaagagca agaaggcagt aagccgaaag gatgaagagt tagaccccat ggaccctagc | 300 |
| tcatactcag acgcccccg gggcacgtgg tcaacaggac tccccaagcg gaatgaggcc | 360 |
| aagactggcg ctgacaccac agcagctggg cccctcttcc agcagcggcc gtatccatcc | 420 |
| ccaggggc | 428 |

<210> SEQ ID NO 248
<211> LENGTH: 430
<212> TYPE: DNA
<213> ORGANISM: Homo sapien
<220> FEATURE:
<221> NAME/KEY: misc_feature
<222> LOCATION: (1)...(430)
<223> OTHER INFORMATION: n = A,T,C or G

<400> SEQUENCE: 248

```
ggctgtgaat ccatctggtc ccggactntt tttggttggt aaactattga ttattgccac      60
nttttcagct cctgttattg gtctattcag agatacncct tcttcctggt ttagtcttgg     120
gagagtgtat gtgtcgagga atgtatccat ttcttctaga ttttctagtt tatttgcgta     180
gaggtgtttg tagtattctc tgatggtagt ttgtatttct gtgggatcgg tggtgatatc     240
ccctttatca ttttttattg tgtctatttg attcttctct cttttttcct ttattagtct     300
tgctagcggt ctatcaattt tgttgatcct ttcaaaaaac cagctcctgg attcattgat     360
tttttgaagg gttttttgtgt ctctatttcc ttcagttcct gctctgatnt tagtnatttc     420
ttgccttctg                                                            430

<210> SEQ ID NO 249
<211> LENGTH: 425
<212> TYPE: DNA
<213> ORGANISM: Homo sapien
<220> FEATURE:
<221> NAME/KEY: misc_feature
<222> LOCATION: (1)...(425)
<223> OTHER INFORMATION: n = A,T,C or G

<400> SEQUENCE: 249
gtcgccgccg ccgccaccgc taccgtcgcc gccgccgccg ccgaggtgac tgaggagaga      60
ggcgcctcct cgctcccgcc accgccggac ttcnatgccc agtccccagc tcgccagcgt     120
ttttcgttgg aatatacgtt gcacatttat ggcgattctg agtgtgaggg cagacttctg     180
ccaggctcag cacagcattt tcgctgacaa gtgagcttgg aggttctatg tgccataatt     240
aacattgcct tgaagactcc tggacaccga gactggcctc agaaatagtt ggctttttt      300 ttttttttaat tgcaagcata tttcttttaa tgactccagt aaaattaagc atcaagtaaa     360
caagtggaaa gtgacctaca cttttaactt gtctcactag tgcctaaatg tagtaaaggc     420
tgctt                                                                 425

<210> SEQ ID NO 250
<211> LENGTH: 424
<212> TYPE: DNA
<213> ORGANISM: Homo sapien
<220> FEATURE:
<221> NAME/KEY: misc_feature
<222> LOCATION: (1)...(424)
<223> OTHER INFORMATION: n = A,T,C or G

<400> SEQUENCE: 250
gttctggtcc acaataaaat gccatngatg gctcaagcaa agcacattaa agccttctta      60
agcttttaaa tgcattccac tattcatttt caanttacct ttaaaatttc cattttacc     120 atgttcacac aagtatgaca cttaatcgcc tcaggttata acaagagata ctgtgaaatc     180
attgaaactt taagagggga aaccctaaaa taagtcaaca tacacatttt ccttctcacc     240
tttttcagga tgttctggtt ctggctgatt actactgctt gagctcacac tggcatcaaa     300
acctgctggc gagctattcc cttcagactg gaggtcttgg agctccccag caacactatc     360
cacctcaatt gtgctatcag tttcactctt gatacttcga acctcttctt ggtttggagc     420
cagt                                                                  424

<210> SEQ ID NO 251
<211> LENGTH: 426
<212> TYPE: DNA
<213> ORGANISM: Homo sapien
```

<400> SEQUENCE: 251

```
attttgatct gtatctacac cacccaaagt taggcctcct ataatgtcca aaacattcct      60
tttagccttt ttatttctta ctgtactgtc tcttactgta ctgtctatct gcagtaattg     120
aggacccata aaatttagat aactacatgt ctttgctctt agaattgtca ctcagcataa     180
tgagcattta acatacaaag gcaatgtact gttttgtgtt gatctatgta aaagaataca     240
attcttttt acataattag tgaaatttta ttttttatta ggaaacacta aatagtgtaa      300
tatttctttt gcttttaaaa aaattcctgg tagcaaatca agataaataa ttgcttcatt     360
ttcttgagca atactgaagc aggatgaagt aagaggaatg cattcattta aacatgcttt     420
gcttta                                                                426
```

<210> SEQ ID NO 252
<211> LENGTH: 429
<212> TYPE: DNA
<213> ORGANISM: Homo sapien
<220> FEATURE:
<221> NAME/KEY: misc_feature
<222> LOCATION: (1)...(429)
<223> OTHER INFORMATION: n = A,T,C or G

<400> SEQUENCE: 252

```
ttcaaagaac tacttgaaaa tgcagagant tccctgaatg atatgtttgt gaagacatat     60
ggncatttat acatgcaaaa ttctgagcta tttaaaganc tcttcgtaga gttgaaacgt    120
tactacgtgg tgggaaatgt gaacctggaa gaaatgctaa atgacttctg ggctcgcctc    180
ctggagcgga tgttccgcct ggtgaactcc cagtaccact ttacagatga gtatctggaa    240
tgtgtgagca agtatacgga gcagctgaag cccttcggag atgtccctcg caaattgaag    300
ctccaggtta tcgtgctttt tgtagcagcc cgtactttcg ctcaaggctt agcggttgcg    360
ggagatgtcg tgagcaaggt ctccgtggta accccacag cccagtgtac ccatgccctg     420
ttgaagatg                                                             429
```

<210> SEQ ID NO 253
<211> LENGTH: 436
<212> TYPE: DNA
<213> ORGANISM: Homo sapien
<220> FEATURE:
<221> NAME/KEY: misc_feature
<222> LOCATION: (1)...(436)
<223> OTHER INFORMATION: n = A,T,C or G

<400> SEQUENCE: 253

```
agcgaattgg tagcaaaaag ggtggaggnt ngaactggag aaaaggaagg atgaaattga     60
acnagaagtt ctccgaaggg tggaggaagc caaacgcatc atggaaaagc agttgctcga    120
agaactcgag cgacagagac aagctgagct tgccgcacaa aaagctagag aggaggaaga    180
acgtgcaaaa cgtgaggagc tagagcgaat actggaagag aataaccgaa aaattgcaga    240
agcacaagcc aaactggccg aagaacagtt gagaattgtt gaagaacaaa gaaagattca    300
tgaggaaagg atgaaactag aacaagaacg acaacgtcaa caaaaagaag aacaaaaaat    360
tatcctgggc aagggggaagt ccaggccaaa actgtccttc tcattaaaaa cccaggatta    420
aattgcaaac tctgaa                                                    436
```

<210> SEQ ID NO 254
<211> LENGTH: 430
<212> TYPE: DNA
<213> ORGANISM: Homo sapien

```
<220> FEATURE:
<221> NAME/KEY: misc_feature
<222> LOCATION: (1)...(430)
<223> OTHER INFORMATION: n = A,T,C or G

<400> SEQUENCE: 254
ccaagatggt caactagaag tagctngtgt ttgtggctct cacagaaaca aatggaagga      60
gagagtaaat aacagcacct tcaactgaaa catgccggta gtcactttgg gaataatcaa     120
ggaaacaacc cacaaagaac agagaaaagc aaggcaggaa aatggcccat ctggaagcag     180
cacagagcca agggagcctc ccctgcccag ggaagtggtg aatgagtgtg tcaccccggg     240
aacccacact tctctcacag atctttgcaa cccttgggtt gggagatcct gtcgtgaacc     300
catttcacca gggctttcag tctgactgac acacagagct acagggagtc tcagcagagg     360
ccccacaaag ggacacatgg agacttggga gccttagata ctagatggct ttctgggcat     420
cccagcaaaa                                                            430

<210> SEQ ID NO 255
<211> LENGTH: 436
<212> TYPE: DNA
<213> ORGANISM: Homo sapien
<220> FEATURE:
<221> NAME/KEY: misc_feature
<222> LOCATION: (1)...(436)
<223> OTHER INFORMATION: n = A,T,C or G

<400> SEQUENCE: 255 ttcatccoct ccccgcgcgt tccttcgcac antgtgattt tgcoctcctg cccacgcaga      60 cctgtngcgg gcaaagagct cccgaggaag cacagcttgg gtcaggttct tgcctttctt     120
aattttagag acagctaccg gaaggagggg aacaaggagt tctcttccgc agcccctttc     180
cccacgccca cccccagtct cagggaccc ttgcctgcct cctaggctgg aagccatggt      240
cccgaagtgt agggcaaggg tgcctcagga ccttttggtc ttcagcctcc ctcagccccc     300
aggatctggg ttaggtggcc gctcctccct gctcctcatg ggaagatgtc tcagagcctt     360
ccatgacctc ccctccccag cccaatgcca agtggacttg gagctgcaca aagtcagcag     420
ggaccactaa atctcc                                                    436

<210> SEQ ID NO 256
<211> LENGTH: 442
<212> TYPE: DNA
<213> ORGANISM: Homo sapien
<220> FEATURE:
<221> NAME/KEY: misc_feature
<222> LOCATION: (1)...(442)
<223> OTHER INFORMATION: n = A,T,C or G

<400> SEQUENCE: 256
gaattnccaa ccccacgagc tgctccctct ttccgcaaac ctcctaaccc cggggttttt      60
ccataagggn gtttacttcg tccacgccag cctgcgaagt tccaaaatgg agtctgggcc     120
acgccggcgt tctgggcacg actacggtct cttgaaaaga tttggaattg accatgtaga     180
taatctctga gagcagttct taaagtgtaa tccagaaccg gtggaacttg ctagaaacgc     240
atattcttcg gaccccctcc aaatctgctg aatctgagat tgtggaggcc attcaatgtc     300
ccttcttcag gaatttggaa aaaggatgga gagatctctc tgagctagac tcttcagtgg     360
aggaaatgtt acaactcatg gacagtggca ttaccatctg ccttaggaac ggagcagcct     420
ctgtcttcaa agaaaaaaga at                                             442
```

<210> SEQ ID NO 257
<211> LENGTH: 436
<212> TYPE: DNA
<213> ORGANISM: Homo sapien
<220> FEATURE:
<221> NAME/KEY: misc_feature
<222> LOCATION: (1)...(436)
<223> OTHER INFORMATION: n = A,T,C or G

<400> SEQUENCE: 257

```
gcggccaccc tccgccgtcc agggcccctc cgtctcggcc ccgggacccc ggctccccgc      60
cagccccggc cccggccccg gcaccatgtc ngataaaagc gtggaggcag cggccgagtt     120
gagcgccaag gacctgaagg agaagaagga gaaggtggag gagaaggcaa gccgaaagga     180
gcgaaagaaa gaagtggtgg aggaggagga gaacgggct gaggaggaag aagaagaaac     240
tgccgaggat ggagaggagg aagatgaagg ggaagaagaa gatgaggaag aagaagaaga    300
ggatgatgaa gggcccgcgc tgaagagagc tgccgaagag gaggatgaag cggatcccaa    360
acggcagaag acagaaaatg gggcatcggc gtgagcccct gccaacaggc tggggttggg    420
aggcctctct gggcct                                                     436
```

<210> SEQ ID NO 258
<211> LENGTH: 436
<212> TYPE: DNA
<213> ORGANISM: Homo sapien

<400> SEQUENCE: 258

```
ggccagggga cggggcgga gccggagccg gagccgacgg gcggtggccg cactgggacc      60
ccggaatccc gcgcgctgcc cacgattcgc ttctgaggaa cctataaaga ttgtacaatg     120
aatggtgatt ctcgtgctgc ggtggtgacc tcaccacccc cgaccacagc ccctcacaag    180
gagaggtact tcgaccgagt agatgagaac aacccagagt acttgaggga gaggaacatg    240
gcaccagacc ttcgccagga cttcaacatg atggagcaaa gaagagggt gtccatgatt    300
ctgcaaagcc ctgctttctg tgaagaattg gaatcaatga tacaggagca atttaagaag   360
gggaagaacc ccacaggcct attggcatta cagcagattg cagattttat gaccacgaat    420
gtaccaaatg tctacc                                                     436
```

<210> SEQ ID NO 259
<211> LENGTH: 341
<212> TYPE: DNA
<213> ORGANISM: Homo sapien
<220> FEATURE:
<221> NAME/KEY: misc_feature
<222> LOCATION: (1)...(341)
<223> OTHER INFORMATION: n = A,T,C or G

<400> SEQUENCE: 259

```
aaaaaatcta gagagaatat aaagaaattt aaagattgaa aagtgaaata ctctcaccta      60
ctcntcagtt aacaaatatt aactcatatg agtgaatat tatgtagcac atgttattct     120
gtacactgaa gatataggga tgacaaagaa attagagttc tggcctaaag gagtttacat    180
attttaaaag gatacagata ttaaccattt atacataaac acataagatt tcttgttctg    240
agtgctaaga acaagagtct aaggaggcat ttgactgaga gtggctaatg agagatttct   300
cctttagcta gcgttgtcag gaagataaaa ccctaatgat g                         341
```

<210> SEQ ID NO 260
<211> LENGTH: 313

```
<212> TYPE: DNA
<213> ORGANISM: Homo sapien

<400> SEQUENCE: 260
aaaccaagat ctgggtaccc gacgacgacg acaaggccat ggcgatatcg gatccgaatt    60
caagcgaccc catggaccct agctcatact cagacgcccc ccggggcacg tggtcaacag   120
gactccccaa gcggaatgag gccaagactg gcgctgacac cacagcagct gggcccctct   180
tccagcagcg gccgtatcca tccccagggg ctgtgctccg ggccaatgca gaggcctccc   240
gaaccaagca gcaggattga agcttcggcc tccctggccc tgggttaaaa taaaagcttt   300
ctggtgatcc tgc                                                      313

<210> SEQ ID NO 261
<211> LENGTH: 446
<212> TYPE: DNA
<213> ORGANISM: Homo sapien

<400> SEQUENCE: 261
gaattctgtc cagtctcaga gagttggaaa gtgctttgca acaaatttta gaaaaagtaa    60
aaactcctgc ttcacccatt cctctggccc caaaaactag ttagcagtat gccttgtggg   120
gaggagccaa gatggccgaa taggaacagc tcccgtctgc agctcccagc atgagcgatg   180
cagaagatgg gtgatttctg catttccaac tgagctttga agagagtagt ggttctccca   240
gcatgtagct tgagatctga gaacgggcag actgcctcct caagtgggtc cctgacccga   300
gtagcctaac tgggaggcac cccccagtac gggcggactg acacctcaca cggccgggta   360
ctcctctgag acaaaacttt cagaagaacg atcaggcagc agcatttgcg gttcaccaat   420
atacactatt ctgcagccac cgctgc                                        446

<210> SEQ ID NO 262
<211> LENGTH: 453
<212> TYPE: DNA
<213> ORGANISM: Homo sapien

<400> SEQUENCE: 262
ccggatccga attcaagcgg cggcagcagt cgacagcgcg atggaggtgg tgccggcgct    60
ggcggaggag gccgcgccgg aggtagcggg cctcagctgc ctcgtcaacc tgccgggtga   120
ggtgctggag tacatcctgt gctgcggctc gctgacggcc gccgacatcg gccgtgtctc   180
cagcaactgc cggcggctgc gcgagctgtg ccagagcagc gggaaggtgt ggaaggagca   240
gttccgggtg aggtggcctt cccttatgaa acactacagc cccaccgact acgtcaattg   300
gttggaagag tataaagttc ggcaaaaagc tgggttagaa gcgcggaaga ttgtagcctc   360
gttctcaaag aggttctttt cagagcacgt tccttgtaat ggcttcagtg acattgagaa   420
ccttgaagga ccagagattt tttttgagga tga                                453

<210> SEQ ID NO 263
<211> LENGTH: 403
<212> TYPE: DNA
<213> ORGANISM: Homo sapien

<400> SEQUENCE: 263
gaattcaagc acccacgcgt gacccgggcc aagtacttca ttcgagacga gtttctgagg    60
atcagcactg ccagtggaga tgggcgtcac tactgctacc ctcatttcac ctgcgctgtg   120
gacactgaga acatccgccg tgtgttcaac gactgccgtg acatcattca gcgcatgcac   180
```

| | |
|---|---|
| cttcgtcagt acgagctgct ctaagaaggg aaccccaaa tttaattaaa gccttaagca | 240 |
| caattaatta aaagtgaaac gtaattgtac aagcagttaa tcacccacca tagggcatga | 300 |
| ttaacaaagc aaccttttcc ttcccccgag tgattttgcg aaaccccctt ttcccttcag | 360 |
| cttgcttaga tgttccaaat ttagaaagct taaggcggcc tac | 403 |

<210> SEQ ID NO 264
<211> LENGTH: 446
<212> TYPE: DNA
<213> ORGANISM: Homo sapien

<400> SEQUENCE: 264

| | |
|---|---|
| gaattcattc gtgcacaatt cattaaatga acgtctcaaa aattaaaaaa attataagat | 60 |
| acgtatttct ttaggccttt gtgttttaa attaaaacca acaaaaagaa gtctccctct | 120 |
| ccactccacc cagcagcaag ggcagccgga acgcttcgct ccagctacct ggcctcccgc | 180 |
| aagagggttc ccccatgaga ccgttagtct ctctttgcct ggctgactac ctgcatacag | 240 |
| taggcactca ctgctggagt gaggcactga ctcctccaaa gattgcaggg ggcggaggag | 300 |
| ggaaccacga aggcctggga gggggcatct ttggccccca ctaaccatct ccctatttct | 360 |
| gcatcctggt gaccgtcagc aagagatgag tcggggagac cctctcctgg agttctagcc | 420 |
| cctaattctg ggctttctat atgaga | 446 |

<210> SEQ ID NO 265
<211> LENGTH: 245
<212> TYPE: DNA
<213> ORGANISM: Homo sapien
<220> FEATURE:
<221> NAME/KEY: misc_feature
<222> LOCATION: (1)...(245)
<223> OTHER INFORMATION: n = A,T,C or G

<400> SEQUENCE: 265

| | |
|---|---|
| cagggctccc tcatgggccc cccgcccag cagaacctca tggtgtccca cccccttcgg | 60 |
| cagngcagtg tgtccctgga cagccagatg ggctacctcc cggcaccagg cggcatggcc | 120 |
| aacctgccct tctagaagtc gctgccaggg ctggagccgg ggcaatgttg caaatacgat | 180 |
| aaccttaaca aagttcttcc cctcaatgtt gggatggcct gggtcgtggg gtgggtgga | 240 |
| ggggg | 245 |

<210> SEQ ID NO 266
<211> LENGTH: 1238
<212> TYPE: DNA
<213> ORGANISM: Homo sapien

<400> SEQUENCE: 266

| | |
|---|---|
| caaaaaccca tctgtacatc accatcatca aagaccaaaa gtagataaaa ccacaaagat | 60 |
| ggggaaaaaa cagaacagaa aaactggaaa ctctaaaacg cagagcgcct ctcctcctcc | 120 |
| aaggaacgc agttcctcac cagcaacaga acaaagctgg atgagaatg attttgacga | 180 |
| gctgagagaa gaaggcttca gacgatcaaa ttactctgag ctacgggagg acattcaaac | 240 |
| caaaggcaaa gaagttgaaa actttgaaaa aatttagaa gaatgtataa ctagaataac | 300 |
| caatacagag aagtgcttaa aggagctgat ggagctgaaa accaaggctc gagaactacg | 360 |
| tgaagaatgc ataagcctca ggagccgatg cgatcaactg gaagaagggt atcagcaat | 420 |
| ggaagatgaa atgaatgaaa tgaagcgaga agggaagttt agagaaaaaa gaataaaaag | 480 |
| aaatgagcaa agcctccaag aaatatggga ctatgtgaaa agaccaaatc tacgtctgat | 540 |

```
tggtgtacct gaaagtgatg tggagaatgg aaccaagttg gaaaacactc tgcaggatat    600
tatccaggag aacttcccca atctagcaag gcaggccaac gttcagattc aggaaataca    660
gagaacgcca caaagatact cctcgagaag agcaactcca agacacataa ttgtcagatt    720
caccaaagtt gaaatgaagg aaaaaatgtt aagggcaacc agagagaaag gtcgggttac    780
cctcaaagga aagcccatca gactaacagc ggatctctcg gcagaaaccc tacaagccag    840
aagagagtgg gggccaatat tcaacattct taaagaaaag aattttcaac ccagaatttc    900
atatccagcc aaactaagct tcataagtga aggagaaata aaatacttta tagacaagca    960
aatgctgaga gattttgtca ccaccaggcc tgccctaaaa gagctcctga aggaagcgct   1020
aaacatggaa aggaacaacc ggtaccagcc gctgcaaaat catgccaaaa tgtaaagacc   1080
atcgagacta ggaagaaact gcatcaacta atgagcaaaa tcaccagcta acatcataat   1140
gacaggatca aattcacaca taacaatatt aactttaaat ataaatggac taaattctgc   1200
aattaaaaga cacagactgg caagttggat aaagagtc                          1238

<210> SEQ ID NO 267
<211> LENGTH: 1664
<212> TYPE: DNA
<213> ORGANISM: Homo sapien

<400> SEQUENCE: 267
attgatgaac tcccagaggg ccggccagtg cgggtagccc ggattgatga actcccagag     60
ggcgctgtga agcctccagc aaacaagtat cctatcttct tttttggcac ccatgaaact    120
gcatttctag gtcccaaaga ccttttttcca tataaggagt acaaagacaa gtttggaaag    180
tcaaacaaac ggaaaggatt taacgaagga ttgtgggaaa tagaaaataa cccaggagta    240
aagtttactg gctaccaggc aattcagcaa cagagctctt cagaaactga gggagaaggt    300
ggaaatactg cagatgcaag cagtgaggaa gaaggtgata gagtagaaga gatggaaaaa    360
ggcaaaagaa agaatgaaaa agcaggctca aacggaaaaa agtcatatac ttcaaagaaa    420
tcctctaaac agtcccggaa atctccagga gatgaagatg acaaagactg caagaagag     480 gaaaacaaaa gcagctctga gggtggagat gcgggcaacg cacaagaaa cacaacttca    540 gacttgcaga aaaccagtga agggacctaa ctaccataat gaatgctgca tattaagaga    600
aaccacaaga aggttatatg tttggttgtc taatattctt ggatttgata tgaaccaaca    660
catagtcctt gttgtcattg acagaacccc agtttgtatg tacattattc atattcctct    720
ctgttgtgtt tcggggggaa aagacatttt agcctttttt aaaagttact gatttaattt    780
catgttattt ggttgcatga agttgccctt aaccactaag gattatcaag attttttgcgc    840 agacttatac atgtctagga tcctttatc aaggcagtta tgatcatcgt tttcctgcct    900
tgaccccacc atcatcaaac actcagttaa atataaatta acattttttta gatgaccact    960 caacataatg cttaagaatg gaatttcctc tctgtgacag aacccaggaa ttaattccta   1020
aatacataac gttggtatat tgaagacgaa attaaaattg tccttcagtt ttgaggccat   1080
gtgtaaagtt tacccatatt gtaaaatatc tattccggta ttagaaatag ctagttgaca   1140
gcttatactt ctcaaaattc atattgttat gtacacaaac taagtttcta tatgtgaagt   1200
tagtgagtct ttttgtgtta ctccaaaata aaggcaatga tttattttttt tcccagtgcc   1260 aatacaattt tgagctaagc actcaaggtg gatactttac atttttaaagc tggaatcagc   1320 aacagcccta tgggaaacca gacaaagcat tgacttttaa atgtagactt ttaaaataaa   1380
```

-continued

```
ctgttttctt ttggaactac aattagaata gttaatattc atccttaaac cattattatg      1440
tgtacattat tgttgctatt gtgataatag agaattttat ttatttttat gccagcttat      1500
attgtgagaa cacatttagt cagtttgggt tttatcaatc ctgttaatgc ttgtccttgg      1560
aacatctttc gcgtattcac ggtttgtagt tgaaaagttt actgtaaaaa atcaaaaac       1620 aaaaaaatgt attgttttta cagaataaat ttattggaat gtgt                       1664
```

<210> SEQ ID NO 268
<211> LENGTH: 436
<212> TYPE: DNA
<213> ORGANISM: Homo sapien

<400> SEQUENCE: 268

```
cggtcacccc gtcatccacc acctcttcca cccgtgccac cccagcccct tctgctccag       60
cagctgcctc agcaactagc ccgagccccg cgcccagttc cgggaatgga gccatcacca      120
gcgagtccag tcccggcaag cgggaaaagg acaaagagaa agacaaagag aagcggttca      180 gccttttttgg caaaagaaa tgaactcctt tccttcacct cctgcccttc tcttaccttt      240
tcagtgaaat tccagcatgc aagctcagaa ccaacacatt actctctgtg cctaatgttc      300
ctcaatgtgg ttgatttttt tttttttaa tttatagagc atttcggggg gggtggggga      360
aacacaccta aacactttat ctccaagtta caaaagtttg aggtgcagag ggaaggccag      420 atttttttttt taatga                                                     436
```

<210> SEQ ID NO 269
<211> LENGTH: 439
<212> TYPE: DNA
<213> ORGANISM: Homo sapien
<220> FEATURE:
<221> NAME/KEY: misc_feature
<222> LOCATION: (1)...(439)
<223> OTHER INFORMATION: n = A,T,C or G

<400> SEQUENCE: 269

```
ggctgtgaat ctatctggtc ctggactctt tttggttggt aagctattga ttattgccac       60
aatttcagat cctgttattg gtctattcag agattcaact tcttccttgt ttagtctttg      120
gagggtgtat gtgtcaagga atttatccat ttcttctaga ttttctagtt tatttgcgta      180
gaggtgtttg tagtattctc tgatggtagt ttgtatttct gtgggatcgg tggtgatatc      240 cccttttatca tttttttattg cgtctatttg attcttctct cttttttttct ttattagtct      300 tgctagcggt ctatcaattn tgttgatcct ttcaaaaaac cagctcctgg attcattaat      360 tttttttgaag ggttttttgt gnctctattt ccttcagttc tgctctgatt ttagttattt      420
cttgccttct gctagcttt                                                   439
```

<210> SEQ ID NO 270
<211> LENGTH: 418
<212> TYPE: DNA
<213> ORGANISM: Homo sapien

<400> SEQUENCE: 270

```
ggaggacctc cgctgcaaat acatctccct catctacacc aactatgagg cgggcaagga       60
tgactatgtg aaggcactgc ccgggcaact gaagcctttt gagaccctgc tgtcccagaa      120
ccagggaggc aagaccttca ttgtgggaga ccagatctcc ttcgctgact acaacctgct      180
ggacttgctg ctgatccatg aggtcctagc ccctggctgc ctggatgcgt tcccctgct       240 ctcagcatat gtggggcgcc tcagtgcccg gcccaagctc aaggccttcc tggcctcccc      300
```

```
tgagtacgtg aacctcccca tcaatggcaa cgggaaacag tgagggttgg ggggactctg    360
agcgggaggc agagtttgcc ttcctttctc caggaccaat aaaatttcta agagagct     418
```

<210> SEQ ID NO 271
<211> LENGTH: 438
<212> TYPE: DNA
<213> ORGANISM: Homo sapien

<400> SEQUENCE: 271

```
cctagatggg ctaggatgga gataacccac cctggtcccc catcccccat accccaact     60 ccctgtcctc tgtccccatt ccctcccctt cccatcctt aaacttagct tagcagcctg    120
ggtacccccc tcacagtggg gcccagccag ggcagaggag gagcatggtg tctatgtgta    180
tgacctgatg gctactgtgg tacacatcct ggactcacgc acaggggca gcctggtggc    240 tcacatcaaa gttggagaga cctaccacca gcgcaaggag ggcgttactc accagcagtg    300
gtatctgttc aatgactttc ttattgaacc tattgataag catgaagctg tgcagtttga    360
catgaattgg aaagtacctg caatccttta ttatgtcaaa cggaatctca attccagata    420
caacctgaac atcaagaa                                                 438
```

<210> SEQ ID NO 272
<211> LENGTH: 443
<212> TYPE: DNA
<213> ORGANISM: Homo sapien
<220> FEATURE:
<221> NAME/KEY: misc_feature
<222> LOCATION: (1)...(443)
<223> OTHER INFORMATION: n = A,T,C or G

<400> SEQUENCE: 272

```
taaagataat gattgataag ctagaacttt ctgatgtagt cattacatga aacccttgt     60 cactggtttg tgtgttcaga ggaagccatg gccgagatag ctttcctgaa ataaaccagt    120
agcttttcag attgacgttc ttgctacaat tgtaccatct ggtaattcct gaaaatgtca    180 attttttgt gttaatattt ttggtttcaa acaaataaca aatgtctcta gaaagaaaat    240
tttaagaaag cttaattaat agtaaaaatg cctttcctga ataattctt ggaaaatttt    300 ttaaatgtca aaatgatgag tcatgctaaa tacatttgag gggttggttt tttggttggt    360
tggttggttg gttttttgaga cagagtttcc ntcttggttg cccaggctng gagtggcaat    420
ggggcccgaa ccttnaanng tta                                           443
```

<210> SEQ ID NO 273
<211> LENGTH: 439
<212> TYPE: DNA
<213> ORGANISM: Homo sapien

<400> SEQUENCE: 273

```
gaattggtag caaaaagggt ggaggaagaa ctggagaaaa ggaaggatga aattgaacga    60
gaagttctcc gaagggtgga ggaagccaaa cgcatcatgg aaaagcagtt gctcgaagaa    120
ctcgagcgac agagacaagc tgagcttgcc gcacaaaaag ctagagagga ggaagaacgt    180
gcaaaacgtg aggagctaga gcgaatactg gaagagaata accgaaaaat tgcagaagca    240
caagccaaac tggccgaaga acagttgaga attgttgaag aacaaagaaa gattcatgag    300
gaaaggatga aactagaaca agaacgacaa cgtcaacaaa aagaagaaca aaaaattatc    360
ctgggcaagg ggaagtccag gccaaaactg tccttctcat taaaaaccca ggattaaatt    420
```

```
gcaaactctg aactttta                                              439
```

<210> SEQ ID NO 274
<211> LENGTH: 445
<212> TYPE: DNA
<213> ORGANISM: Homo sapien
<220> FEATURE:
<221> NAME/KEY: misc_feature
<222> LOCATION: (1)...(445)
<223> OTHER INFORMATION: n = A,T,C or G

<400> SEQUENCE: 274

```
aaaggagacg agtcagccaa ccacagctac atttcaggct ttctcccctg cacttttac     60
agttatcttg gacttcgtat attctggcaa actgtctctt actggtcaga atgtcataga   120
agtgatgtcg gctgctagct tccttcagat gactgatgtc ataagtgtat gtaagacttt   180
tattaaatct tccttagaca ttagtgagaa agaaaaagat cgcntatttc agtctctcag   240
ataaagatgc caattctaat ggtgtagaac cgttcctctt tttatagtgg tggctggcaa   300
gaaggaagca gttctccacg ttctcaccta agcccagagc aaggaacagg tataataagt   360
ggaaaatctt ggaataagta taattatcat ccancctccc anaanaatac tcaacaaccc   420
ttggccaagc atgaaccaag gaaag                                        445
```

<210> SEQ ID NO 275
<211> LENGTH: 441
<212> TYPE: DNA
<213> ORGANISM: Homo sapien

<400> SEQUENCE: 275

```
ggctcccaag aacatggcga cttccacacc tgtggctcgt ggtggtggtt tgccagctac    60
gttcaacaaa aacactccta agacctttac tcctgaatgt gaaaatcaga aggacccttt   120
ggtcaacact gttgttgttt atgattgtga tgtttgttcg tttgcaagcc ccaacatgca   180
ttctgtcttg gttcattatc agaagaaaca ccccgaagaa aaggcttcct actttaggat   240
ccagaaaact atgcgaatgg tgtctgtgga caggggctct gcccttttctc aattatcatt   300
tgaggtgggt gctccaatgt ctcccaaaat gtccaacatg ggttccccac cccccccca   360
caaccccgc caccagacct cagtactgag ctttactact gcaaacactg ttcctacagc    420
aatcggtcag ttgtgggagt g                                            441
```

<210> SEQ ID NO 276
<211> LENGTH: 436
<212> TYPE: DNA
<213> ORGANISM: Homo sapien

<400> SEQUENCE: 276

```
gaaacgccca gtattctcag agtgccatat gaaccatcca ggaaagctgg caaattctct    60
aacagttaat aaagccaatt gtattgtatt gataattgga caaagagaga gaaagaaaga   120
aggaaggaag gaaaaacttg ttactgaaag agactacact atcaggtttc attacatatt   180
ctccttcatt gagaatctgg cccatttca atttaagctt gcggccgcac tcgagcccgg   240
gtgaatgatt gagtttaaac cgctgagcaa taactagcat aacccttgg ggcctctaaa    300
cgggtcttga ggggtttttt gctgaaagga ggaactatat ccggataacc tggcgtaata   360
gcgaagaggc ccgcaccgat cgccttccc aacagttgcg cagcctgaat ggcgaatgga   420
cgcgccctgt agcggc                                                  436
```

<210> SEQ ID NO 277
<211> LENGTH: 440
<212> TYPE: DNA
<213> ORGANISM: Homo sapien
<220> FEATURE:
<221> NAME/KEY: misc_feature
<222> LOCATION: (1)...(440)
<223> OTHER INFORMATION: n = A,T,C or G

<400> SEQUENCE: 277

```
caaatcttcg tgaagacact cactggcaag accatcaccc ttgaggtcga gcccagtgac      60
actatcgaga acgtcaaagc aaagatccaa gacaaggaag gcattcctcc tgaccagcag     120
aggttgatct tgccggaaa gcagctggaa gatgggcgca ccctgtctga ctacaacatc      180
cagaaagagt ctaccctgca cctggtgctc ccgtctcaga ggtgggatgc agatcttcgt     240
gaagactctg actggtaaga ccatcaccct cgaggtngag cccagtgaca ccatcgagaa     300
tgtcaaggca aagatccaag ataaggaagg catccctcct gaccagcaga ggctgatctt     360
tgctggaaaa cagctggaag atgggcgcac cctgtctgac tacaacatcc anaaagagtc     420
caccctgcac ctgntnctcc                                                 440
```

<210> SEQ ID NO 278
<211> LENGTH: 306
<212> TYPE: DNA
<213> ORGANISM: Homo sapien
<220> FEATURE:
<221> NAME/KEY: misc_feature
<222> LOCATION: (1)...(306)
<223> OTHER INFORMATION: n = A,T,C or G

<400> SEQUENCE: 278

```
gagcgngcgg ccgcnctaaa gattcnctcg cacacacaat aagnctttct ctccgaaacc      60
ggaagtaaat ntatatctgt tagaaataat gtagccaaaa gaatgtaaat ttgaggattt     120
ttttgccaat agtttataga aatatatga accaaagtga tttgagtttg taaaaatgta      180
aaatagtatg aacaaaattt gcactctacc agatttgaac atctagtgag gttcacattc     240
atactaagtt ttcaacattg tgttctttt gcattcattt tttactttta ttaaaggttc      300
aaaacc                                                                306
```

<210> SEQ ID NO 279
<211> LENGTH: 450
<212> TYPE: DNA
<213> ORGANISM: Homo sapien
<220> FEATURE:
<221> NAME/KEY: misc_feature
<222> LOCATION: (1)...(450)
<223> OTHER INFORMATION: n = A,T,C or G

<400> SEQUENCE: 279

```
gagcgggcgg ccgngctccg ggccggggtc ccgggggagc agatcctcan aatggccctt      60
ggtgctgcag gcgcggtggg ctccgggccc aggcaccgag ggggcactgg atgactctcc     120
aggtgcagga ccctgccatc tatgactcca gtcttcagc acccaccac cgtggtacag       180
cgccccggga tgccgtctgg agcccggatg ccccaccagg gggcgcccat gggcccccg      240
ggctccccgt acatgggcag cccgccgtg cgacccggcc tggcccccgc gggcatggag      300
cccgcccgca gcgagcagc gccccgccc gggcagagcc aggcacagag ccagggccag      360
ccggtgccca ccgcccccgc gcggagccgc agtgccaaga ggaggaagat ggctgacaaa     420
atcctccctc aaaggattcg ggagctggtc                                      450
```

```
<210> SEQ ID NO 280
<211> LENGTH: 435
<212> TYPE: DNA
<213> ORGANISM: Homo sapien

<400> SEQUENCE: 280
gcagctccga gtggcggcgc gcgggccagg gccggggccg gggccggggc cggagccgga      60
gccggggccg ggcggcgcgc ctgtggagcg ctggggggcgg cctgggggctg agcatggagc    120 agcgcggcg aggtcgcctg cgaggccgct ggccaggcct gagcctctgc caccatggcc       180
attgtgcaga ctctgccagt gccactggag cctgctcctg aagctgccac tgccccacaa      240
gctccagtca tgggtagtgt gagcagcctt atctcaggcc ggccctgtcc cggggggcca      300
gctcctcccc gccaccacgg ccctcctggg cccaccttct tccgccagca ggatggcctg      360
ctacggggtg gctatgaggc acaggagccg ctgtgcccag ctgtgccccc taggaaggct      420
gtccctgtca ccagc                                                      435

<210> SEQ ID NO 281
<211> LENGTH: 443
<212> TYPE: DNA
<213> ORGANISM: Homo sapien

<400> SEQUENCE: 281
ttttagaaag ggattagaat tttactctgc tagttacaag ttttaaagtc acgctacggc      60
attatcaccc tggcaggtag gttttgttat tgttttacat tttgtgaaaa aaagtttttgt    120 agaagttaca gctagtggtc ttttccctcc agagccagtg atgagtgtgg gagcacttca      180
gctctgtaag gggccagcgt tctgaccttt aaccacatga actaacctgc gtcagcagtt      240
gcagaaagta gcctgttagg acagcagctg ctaagcgttg cctggtattt tagtggggag      300
aaggctggga ctcttcatgg catcaacact tgcatgctct gaatctttga tcagagatga      360
ggtgccattt ttggcatttc caccccgtct cgtggtagcc tttaaaagtg gtagaagatg      420
ctgccctaat tccccgagga tga                                             443

<210> SEQ ID NO 282
<211> LENGTH: 435
<212> TYPE: DNA
<213> ORGANISM: Homo sapien
<220> FEATURE:
<221> NAME/KEY: misc_feature
<222> LOCATION: (1)...(435)
<223> OTHER INFORMATION: n = A,T,C or G

<400> SEQUENCE: 282
gacactcaag ccgaacatca gacnttaaga tgcagcaggt ctcgggacca caaaaggtca      60
cgaagtagag aaagaaggcg gagcagaagt agagatcgac gaagaagcag aagccatgat     120
cgatcagaaa gaaaacacag atctcgaagt cgggatcgta gaagaattaa agaaaaagtt     180
aaggaaaaga accgaagaac ctgatcgtga tgagcgtcta aaaaaggaga agcaagaaag     240
agaagaaaga gaaaaagaac gggagagaga aaggggaagaa agagaaagga aaagacgaag    300
ggaagaggaa gaaagagaaa aagaaagggc tcgtgacaga gaagaagaa agagaagtcg      360 ttcacgaagt agacactcaa gccgaacatc agacagaaga tgcagcaggt ctcgggacca     420
caaaaggtca cgaag                                                      435

<210> SEQ ID NO 283
<211> LENGTH: 437
```

```
<212> TYPE: DNA
<213> ORGANISM: Homo sapien

<400> SEQUENCE: 283
agaaaaaaat ttaaactgct ttttcggaag aacaacaaca aaaagaggt aaagacgaat       60 ctataaagta ccgagacttc ctgggcaaag aatggacaat cagtttcctt cctgtgtcga    120
tgtcgatgtt gtctgtgcag gagatgcagt ttttgtgtag agaatgtaaa ttttctgtaa    180 cctttttgaaa tctagttact aataagcact actgtaattt agcacagttt aactccaccc   240
tcatttaaac ttcctttgat tctttccgac catgaaatag tgcatagttt gcctggagaa    300
tccactcacg ttcataaaga gaatgttgat ggcgccgtgt agaagccgct ctgtatccat    360
ccacgcgtgc agagctgcca gcagggagct cacagaaggg gagggagcac caggccagct    420
gagctgcacc cacagtc                                                   437

<210> SEQ ID NO 284
<211> LENGTH: 174
<212> TYPE: DNA
<213> ORGANISM: Homo sapien

<400> SEQUENCE: 284
caattcccta ctgaagactg gagcgctcag cctgccacgg aagactggtc tgcagctccc     60
actgctcagg ccactgaatg ggtaggagca accactgact ggtcttaagc tgttcttgca    120
taggctctta agcagcatgg aaaatggtt gatggaaaat aaacatcagt ttct           174

<210> SEQ ID NO 285
<211> LENGTH: 440
<212> TYPE: DNA
<213> ORGANISM: Homo sapien

<400> SEQUENCE: 285
gagaagaaag agaaaaagaa cgggagagag aaagggaaga aagagaaagg aaaagacgaa     60
gggaagagga agaaagagaa aagaaagggg ctcgtgacag agaaagaaga agagaagtc    120 gttcacgaag tagacactca agccgaacat cagacagaag atgcagcagg tctcgggacc   180
acaaaaggtc acgaagtaga gaaagaaggc ggagcagaag tagagatcga cgaagaagca   240
gaagccatga tcgatcagaa agaaaacaca gatctcgaag tcgggatcga agaagatcaa    300
aaagccggga tcgaaagtca tataagcaca ggagcaaaag tcgggacaga gaacaagata    360
gaaaatccaa ggagaaagaa aagagggat ctgatgataa aaaaagtagt gtgaagtccg    420
gtagtcgaga aaagcagagt                                                440

<210> SEQ ID NO 286
<211> LENGTH: 242
<212> TYPE: DNA
<213> ORGANISM: Homo sapien

<400> SEQUENCE: 286
aagcggtaaa aagggtcac tatggagttc aaaggacaga actcctgcct ggtgaccggg       60
acaacctggc cattcagacc cgggtggcc cagaaaagca tgaagtaact ggctgggtgc    120
tggtatctcc tctaagtaag gaagatgctg gagaatatga gtgccatgca tccaattccc    180
aaggacaggc ttcagcatca gcaaaaatta cagtggttga tgccttacat gaaataccag    240
tg                                                                    242

<210> SEQ ID NO 287
```

<211> LENGTH: 429
<212> TYPE: DNA
<213> ORGANISM: Homo sapien

<400> SEQUENCE: 287

```
tttcagggtt gcattatgca accagtaaat gacctcttga aaggacagag tcgtctgatt      60
tttacttacg ggctaaccaa ttcaggaaaa acatatccat ttcaagggac agaagaaaat     120
attggcattc tgcctcgaac tttgaatgta ttatttgata gtcttcaaga aagactgtat     180
acaaagatga accttaaacc acatagatcc agagaatact taaggttatc atcagaacaa     240
gagaaagaag aaattgctag caaaagtgca ttgcttcggc aaattaaaga ggttactgtg     300
cataatgata gtgatgatac tctttatgga agtttaacta actctttgaa tatctcagag     360
tttgaagaat ccataaaaga ttatgaacaa gccaacttga atatggctaa tagtataaaa     420
ttttctgtg                                                              429
```

<210> SEQ ID NO 288
<211> LENGTH: 436
<212> TYPE: DNA
<213> ORGANISM: Homo sapien
<220> FEATURE:
<221> NAME/KEY: misc_feature
<222> LOCATION: (1)...(436)
<223> OTHER INFORMATION: n = A,T,C or G

<400> SEQUENCE: 288

```
tcaagcctca gagcttcaaa gagcaggact antcctaaga actgtctgtg atatttgacc      60
agaggtgcag cctagctgcc attcttcctc accctgtgga agacattaaa gggagaatga     120
aagtagctgt agaattacct ttgggggaag aagccacttg tgtgaacttgg caaacacccg     180
tgtttgaggg gtcacccagg gtgtcatgag ctgggccgga ggggatggat tgattacttg     240
tcttgtttgc ttgtttctgt tgtaagtcag ggcccctcag cagaaggcag aacagaaccg     300
agttcccttta gaatgctggt ttttgtgtgg agtgaggaag gaccgtgagt gtggtcagtt     360
tccaacctga caggacctgc tcccgttggc caggactgca gcttgttact ttgaccctgg     420
gaagaaggta agtgtt                                                      436
```

<210> SEQ ID NO 289
<211> LENGTH: 425
<212> TYPE: DNA
<213> ORGANISM: Homo sapien

<400> SEQUENCE: 289

```
tataagagct tgaccaatga ctgggaagat cacttggcag tgaagcattt ttcagttgaa      60
ggacagttgg aattcagagc ccttctattt gtcccacgac gtgctccttt tgatctgttt     120
gaaaacagaa agaaaaagaa caatatcaaa ttgtatgtac gcagagtttt catcatggat     180
aactgtgagg agctaatccc tgaatatctg aacttcatta gaggggtggt agactcggag     240
gatctccctc taaacatatc ccgtgagatg ttgcaacaaa gcaaaatttt gaaagttatc     300
aggaagaatt tggtcaaaaa atgcttagaa ctctttactg aactggcgga agataaagag     360
aactacaaga aattctatga gcagttctct aaaaacataa agcttggaat acacgaagac     420
tctca                                                                  425
```

<210> SEQ ID NO 290
<211> LENGTH: 426
<212> TYPE: DNA
<213> ORGANISM: Homo sapien

```
<220> FEATURE:
<221> NAME/KEY: misc_feature
<222> LOCATION: (1)...(426)
<223> OTHER INFORMATION: n = A,T,C or G

<400> SEQUENCE: 290
gctcccggag gcgaggctcg cgcgntcgcc cccgccctgg ccccagcgcc cacccggttn      60
gccccggccc agccatgatc aaggccatcc tcancttcaa caaccacggg aagccgcggc     120
tctccaagtt ctaccagccc tatagtgaag acacgcaaca gcaaatcatc agggagactt     180
tccatttggt gtctaagcgc gatgagaacg tttgtaattt cctagaagga ggattattaa     240
ttggaggctc tgacaacaag ctcatttaca gacattatgc aacactatat tttgtcttct     300
gtgtggactc ctcagaaagt gaacttggca ttttagatct aattcaagta tttgtggaaa     360
cattagacaa atgttttgaa aatgtttgtg aactggattt aatattccat gtagacaagg     420
ttcata                                                                426

<210> SEQ ID NO 291
<211> LENGTH: 426
<212> TYPE: DNA
<213> ORGANISM: Homo sapien
<220> FEATURE:
<221> NAME/KEY: misc_feature
<222> LOCATION: (1)...(426)
<223> OTHER INFORMATION: n = A,T,C or G

<400> SEQUENCE: 291
gagaagcaag aaagagaaga aagattttaa gaacgggaga gagaaaggga agaaagantt      60
tggaaaagac gaagggaaga ggaagaaaga gaaancnnaa agggctcgtg acagagaaag     120
aagaaagaga agtcgttcac gaagtagaca ctcaagccga acatcagaca gaagatgcag     180
caggtctcgg gaccacaaaa ggtcacgaag tagagaaaga aggcggagca gaagtagaga     240
tcgacgaaga agcagaagcc atgatcgatc agaaagaaaa cacagatctc gaagtcggga     300
tcgaagaaga tcaaaaagcc gggatcgaaa gtcatataag cacaggagca aaagtcggga     360
cagagaacaa gatagaaaat ccaaggagaa agaaagagg ggatctgatg ataaaaaaag     420
tagtgt                                                                426

<210> SEQ ID NO 292
<211> LENGTH: 426
<212> TYPE: DNA
<213> ORGANISM: Homo sapien
<220> FEATURE:
<221> NAME/KEY: misc_feature
<222> LOCATION: (1)...(426)
<223> OTHER INFORMATION: n = A,T,C or G

<400> SEQUENCE: 292
ctgggacgtg gaagtggcga ggtgcntgct gccccaggaa gcccctcag cactaggcna       60 tgggctgcaa ggggtaaggc gctcttcacc tganaacgtt ccctcaagct gcacagcctt     120
tcagagcagc aggaccctgc ggtgacatcg aaatgaaaca gaaatagaac ttctgcggtg     180
ggtgagtgat gtgctgggcc tgaaggtgga ctggccaggg accccacagt ggactcgtga     240
ggagggctcg acagacactg gcccagaggg ggctcttgcc tggtggtggg ctgcatgcag     300
cgggaggtca cctaggagca gggtggcccc agccaggctg atgccgtaga aaggactgca     360
ggctctaact ttgagcattt tctcgtgctt gggcatgggt gctgattttg cctgtcaatg     420
ctgatg                                                                426
```

<210> SEQ ID NO 293
<211> LENGTH: 436
<212> TYPE: DNA
<213> ORGANISM: Homo sapien

<400> SEQUENCE: 293

| | | | | | |
|---|---|---|---|---|---|
| ggaagaaata | gttgaaggtt | gtaccggagc | ccttcacatc | ctagctcggg | atgttcacaa | 60 |
| ccgaattgtt | atcagaggac | taaataccat | tccattgttt | gtgcagctgc | tttattctcc | 120 |
| cattgaaaac | atccaaagag | tagctgcagg | ggtcctctgt | gaacttgctc | aggacaagga | 180 |
| agctgcagaa | gctattgaag | ctgagggagc | cacagctcct | ctgacagagt | tacttcactc | 240 |
| taggaatgaa | ggtgtggcga | catatgcagc | tgctgttttg | ttccgaatgt | ctgaggacaa | 300 |
| gccacaagat | tacaagaaac | ggctttcagt | tgagctgacc | agctctctct | tcagaacaga | 360 |
| gccaatggct | tggaatgaga | ctgctgatct | tggacttgat | attggtgccc | agggagaacc | 420 |
| ccttggatat | cgccag | | | | | 436 |

<210> SEQ ID NO 294
<211> LENGTH: 439
<212> TYPE: DNA
<213> ORGANISM: Homo sapien
<220> FEATURE:
<221> NAME/KEY: misc_feature
<222> LOCATION: (1)...(439)
<223> OTHER INFORMATION: n = A,T,C or G

<400> SEQUENCE: 294

| | | | | | |
|---|---|---|---|---|---|
| ccggctcaca | agcgcctcct | tctggacacc | ctgcagctca | gcaagtgata | gcggaggcac | 60 |
| cacgaagctg | tgaactcaga | gccctccct | gctaccaagg | cccagctatg | ccccagggt | 120 |
| tgaaaagtta | tgagggtcag | ggcagtatct | ctctgcctat | ttattggggt | gcctatttat | 180 |
| tggggatctg | cattccccgc | tgcccaatca | ntttgcaatg | ccctaattag | ggcatcctgc | 240 |
| ccctcgcctt | ttaggctcag | gacggaaggt | cagttgccat | ggttaccgag | accctggtt | 300 |
| actctggtgc | tgtcctcttt | tactggaccc | cgcctcccag | cccagggt | gcctgtgggg | 360 |
| gtccatntgg | gtacgtctgg | gcccccactt | tcaccagttt | ctgcggcctt | ccaccgggcc | 420 |
| tgaaccacan | cggaggagc | | | | | 439 |

<210> SEQ ID NO 295
<211> LENGTH: 434
<212> TYPE: DNA
<213> ORGANISM: Homo sapien

<400> SEQUENCE: 295

| | | | | | |
|---|---|---|---|---|---|
| cactacaccg | accccccaccc | agttcttgtg | ccccaagaac | gtgaccgacg | agcaggaggg | 60 |
| cttcgccgag | ggcttcgtgc | gcgccctggc | tgaactgcat | agccagaaca | cgcttcccag | 120 |
| tgtcacctcc | gcggcacagc | cggtcagcgg | ggcgggcatg | gtggctcccg | cggtggcctc | 180 |
| agtagcaggc | gctggcggcg | gtggtggcta | cagcgccagc | ctgcacagtg | agcctccggt | 240 |
| ctacgccaac | ctcagcaact | tcaacccggg | tgcgctgagc | agcggcggtg | gggcgccctc | 300 |
| ctatggcgcg | gccgggctgg | cctttccctc | gcagccgcag | cagcagcagc | agccgcctca | 360 |
| gccgccgcac | cacttgcccc | aacagatccc | ggtgcagcac | ccgcggctgc | aagccctgaa | 420 |
| ggaagagccg | caga | | | | | 434 |

<210> SEQ ID NO 296
<211> LENGTH: 433

<212> TYPE: DNA
<213> ORGANISM: Homo sapien

<400> SEQUENCE: 296

```
caaatacgaa atcttaacaa agaaaaacca aactataaaa aaggaccaac tgaaaattct      60
agaaaaagtg caatatctac tattttttaaa aaattggaga gtttaacaac agagtaaaga    120
tggcataaga aaaaaatcag tataagtaaa agtagatcaa gactagttat gcaattaaaa    180
aacagaggaa taaaaagact ttccagaatt gcctgtacaa cagtaatctc ctttctgtcc    240
tggtgtagat ttttttaacca gcttgttggc cctggtcatt ttggccacat ttgtgaccat    300
cataaaagct aagtggtatt tctgtgtagt ttccgtctgg aactgctttc ccattcccgg    360
gaacccatag ccgggccagc cagggtcccg aacacaggcc caaagtttat taaaccccga    420
tcataacctc cag                                                        433
```

<210> SEQ ID NO 297
<211> LENGTH: 440
<212> TYPE: DNA
<213> ORGANISM: Homo sapien
<220> FEATURE:
<221> NAME/KEY: misc_feature
<222> LOCATION: (1)...(440)
<223> OTHER INFORMATION: n = A,T,C or G

<400> SEQUENCE: 297

```
ctgcggcggc gcggggactg tgaggctgcc gagcggacag cgactcccgg ggaagcccgc      60
gctccgggag cgggagcggg agcaggagca ggagcagcgc cgtcccaggc cagaggcgag    120
cgccgggcgc cgggagagcg gagagcccgg gcagctgccg gagcgcgggg gcgcggcccg    180
aggaaaccac agagcgagcc caggcctggg ggagggcgcc gaacatctga ggcggcttcg    240
cgggagacaa agccgcgcgt agagacgcga tgccccgccg atcgcgagcc cggccggcga    300
gggcgcgggg actgcggcgt ctgagcgcgc caagccgtgc gcccgcgggg acgccgagcc    360
ccggggccgg tgcgggcggc ggcgggcggg gcccangtgc gcccggccgc gtcgggcccg    420
tgactgctcg gggggcggnc                                                 440
```

<210> SEQ ID NO 298
<211> LENGTH: 435
<212> TYPE: DNA
<213> ORGANISM: Homo sapien
<220> FEATURE:
<221> NAME/KEY: misc_feature
<222> LOCATION: (1)...(435)
<223> OTHER INFORMATION: n = A,T,C or G

<400> SEQUENCE: 298

```
gctggccaat aaggtgccag ctgctgcccg tgctggtgcc attgccccat gtgaagtcac      60
tgtgccagcc cagaacactg gtctcgggcc cgagaagacc tccttttttcc aggctttagg    120
tatcaccact aaaatctcca ggggcaccat tgaaatcctg agtgatgtgc agctgatcaa    180
gactggagac aaagtgggag ccagcgaagc cacgctgctg aacatgctca acatctcccc    240
cttctccttt gggctggtca tccagcaggt gttcgacaat ggcagcatct acaaccctga    300
agtgcttgat atcacagagg aaactctgca ttctcgcttc ctggagggtg tccgcaatgt    360
tgccagtgtc tgtctgcaga ttggctaccc aactgntgca tcagtacccc attctatcat    420
caacgggtac aaacg                                                      435
```

<210> SEQ ID NO 299

<211> LENGTH: 441
<212> TYPE: DNA
<213> ORGANISM: Homo sapien

<400> SEQUENCE: 299

| aatgaatatg ccaaatcgta cttatttcag agtaagtttt tcattttttt aggttgtagg | 60 |
|---|---|
| gagtttttt cctactgagt gttattagat tattttaatg ttactattgt tattaggcaa | 120 |
| ttaaaatgtt tttaagcaag ctttaaggca ttaacctccc ccttcagata agtatacata | 180 |
| aattggttct aaaagttaat aagaagtttt ctgaaaccag ggaactttt ttttcctgaa | 240 |
| acatttttag tagtttccca aggcatattt tttggaactg agttctttta ggcatctctg | 300 |
| atgttggtga gatgctttat taactgaatg gatgtaggct tccttttacg ttgaagttga | 360 |
| ttacatggag taagttttg ttttctattt gaaattaaat ggaatctgtt ggagggttat | 420 |
| caaaattgtt tgcatcacaa a | 441 |

<210> SEQ ID NO 300
<211> LENGTH: 434
<212> TYPE: DNA
<213> ORGANISM: Homo sapien

<400> SEQUENCE: 300

| aaaagaagaa agaacctgca attacatcgc agaacagccc tgaggcaaga gaagaaagta | 60 |
|---|---|
| cttccagcgg caatgtaagc aacagaaagg atgagacaaa tgctcgagat acttatgttt | 120 |
| catcctttcc tcgggcacca agcacttctg attctgtgcg gttgaagtgt agggagatgc | 180 |
| ttgctgcagc tcttcgaaca ggggatgact acattgcaat tggagctgat gaggaagaat | 240 |
| taggatctca aattgaagaa gctatatatc aagaaataag gaatacagac atgaaataca | 300 |
| aaatagagt acgaagtagg atatcaaatc ttaaagatgc aaaaaatcca aatttaagga | 360 |
| aaaatgtcct ctgtgggaat attcctcctg acttatttgc tagaatgaca gcagaggaaa | 420 |
| tggctagtga tgag | 434 |

<210> SEQ ID NO 301
<211> LENGTH: 434
<212> TYPE: DNA
<213> ORGANISM: Homo sapien

<400> SEQUENCE: 301

| agaaaggaaa agacgaaggg aagaggaaga aagagaaaaa gaaagggctc gtgacagaga | 60 |
|---|---|
| aagaagaaag agaagtcgtt cacgaagtag acactcaagc cgaacatcag acagaagatg | 120 |
| cagcaggtct cgggaccaca aaaggtcacg aagtagagaa agaaggcgga gcagaagtag | 180 |
| agatcgacga agaagcagaa gccatgatcg atcagaaaga aaacacagat ctcgaagtcg | 240 |
| ggatcgaaga agatcaaaaa gccgggatcg aaagtcatat aagcacagga gcaaaagtcg | 300 |
| ggacagagaa caagatagaa aatccaagga gaaagaaaag aggggatctg atgataaaaa | 360 |
| aagtagtgtg aagtccggta gtcgagaaaa gcagagtgaa gacacaaaca ctgaatcgaa | 420 |
| ggaaagtgat acta | 434 |

<210> SEQ ID NO 302
<211> LENGTH: 437
<212> TYPE: DNA
<213> ORGANISM: Homo sapien

<400> SEQUENCE: 302

| caaattctcc ttatttaaaa gtaagaagca tttgcctttc ggtgaagagg cttcggcctc | 60 |

| | |
|---|---|
| tgcctctcct tccagagagc ccaggcaaat tctccttatt taaaagtaag aagccacggc | 120 |
| accgctcaaa ttcattcagt gatgaaagag agttctctgg accttccacc ccgacgggga | 180 |
| cgctggagtt tgaaggtggg gaagtgtctc tggaaggtgg gaaagttaaa gggaaacacg | 240 |
| ggaagctgaa attcggtacc tttggtggat tggggtcaaa gagcaaaggt cattatgagg | 300 |
| tgactgggag cgatgatgag acaggcaagt tacagggagt gggggtgtcc ctggcctcta | 360 |
| agaagtcccg actgtcctcc tcttctagca atgacagtgg gaataaggtt ggcatccagc | 420 |
| ttcccgaggt ggagctg | 437 |

<210> SEQ ID NO 303
<211> LENGTH: 436
<212> TYPE: DNA
<213> ORGANISM: Homo sapien

<400> SEQUENCE: 303

| | |
|---|---|
| agactttcca tgagacgctc aactgttgtg gctccaacgc actgaccaca ctgactacca | 60 |
| ccatactgag gaacagcctg tgtccctcag gcggcaacat actcaccccc ttactgcagc | 120 |
| aagattgtca tcagaaaatc gatgagctct tctctgggaa gctgtacctc attggaattg | 180 |
| cagccattgt ggtagctgtc attatgatct ttgagtgat tctgagcatg gtgctgtgct | 240 |
| gtggcatccg gaacagctcc gtgtactgag gcccttttgca ttgcaccaga ggatccctgg | 300 |
| agtgaccaga ggccaccttg ggggacatgg cctgtgtata taatatttct gtatcactct | 360 |
| gctacactta gtcttttttac ttttgagttt tttgttttgt tttgttttgt ttttgtttta | 420 |
| gtttttttttt tgtcct | 436 |

<210> SEQ ID NO 304
<211> LENGTH: 440
<212> TYPE: DNA
<213> ORGANISM: Homo sapien

<400> SEQUENCE: 304

| | |
|---|---|
| ctcagaggag gttcgattaa aactggaaga gaccagagag gtacagaact tgaggaagag | 60 |
| gcccaacggg gtgagtgctg tggccttgct ggtgggagag aagtacaag aggagaccac | 120 |
| tctagtggat gatccctttc agatgaagac aggtggtatg gtggatatga agaaactgaa | 180 |
| ggaaaggggc aaagataaga tcagtgagga ggaggacctg cacctgggga catcgttttc | 240 |
| tgcagaaacc aaccgaaggg atgaggatgc agacatgatg aagtacattg agacagagct | 300 |
| aaagaagagg aaagggatcg tggaacatga ggaacagaaa gttaagccaa gaatgcaga | 360 |
| ggactgtctt tatgaacttc cagaaaacat ccgtgttttcc tcagcaaaga agaccgagga | 420 |
| gatgctttcc aaccagatgc | 440 |

<210> SEQ ID NO 305
<211> LENGTH: 440
<212> TYPE: DNA
<213> ORGANISM: Homo sapien

<400> SEQUENCE: 305

| | |
|---|---|
| aggagacgag tcagccaacc acagctacat ttcaggcttt ctcccctgac acttttacag | 60 |
| ttatcttgga cttcgtatat tctggcaaac tgtctcttac tggtcagaat gtcatagaag | 120 |
| tgatgtcggc tgctagcttc cttcagatga ctgatgtcat aagtgtatgt aagactttta | 180 |
| ttaaatcttc cttagacatt agtgagaaag aaaaagatcg ctatttcagt ctctcagata | 240 |

```
aagatgccaa ttctaatggt gtagaacgtt cctctttta tagtggtggc tggcaagaag      300
gaagcagttc tccacgttct cacctaagcc cagagcaagg aacaggtata ataagtggaa      360
aatcttggaa taagtataat tatcatccag cctcccagaa gaatactcaa caaccttgg       420 ccaagcatga accaaggaaa                                                   440

<210> SEQ ID NO 306
<211> LENGTH: 437
<212> TYPE: DNA
<213> ORGANISM: Homo sapien

<400> SEQUENCE: 306
ctcagaggag gttcgattaa aactggaaga gaccagagag gtacagaact tgaggaagag       60
gcccaacggg gtgagtgctg tggccttgct ggtgggagag aaggtacaag aggagaccac      120
tctagtggat gatccctttc agatgaagac aggtggtatg gtggatatga agaaactgaa      180 ggaaagggc aaagataaga tcagtgagga ggaggacctg cacctgggga catcgttttc       240
tgcagaaacc aaccgaaggg atgaggatgc agacatgatg aagtacattg agacagagct      300
aaagaagagg aaagggatcg tggaacatga ggaacagaaa gttaagccaa gaatgcaga       360 ggactgtctt tatgaacttc agaaaacat ccgtgtttcc tcagcaaaga gaccgagga       420 gatgctttcc aaccaga                                                     437

<210> SEQ ID NO 307
<211> LENGTH: 426
<212> TYPE: DNA
<213> ORGANISM: Homo sapien

<400> SEQUENCE: 307
cagactgaga aaacccatag ttaaagctct tggggtttct gagagctcag ctggaagtga       60
ctgggtgaca aggcgcacag gctcagccgt ggaagctcca tcatgattcc acaagtagtg      120
accagtgaga ctgtcacagt gatttcacca aatggaatca gctttcccca aacagacaaa      180
ccccagcctt cccaccagag ccaagacaga ctgaagaaac atctaaaggc tgagatcaaa      240
gtgatggcgg caatccagat catgtgtgct gtgatggtgt tgagtctggg aatcattttg      300
gcatctgttc cctccaatct acactttacc tcagtgtttt ccatcctgtt agaatctggc      360
tacccatttg taggagcttt gttttttgcc atctctggaa ttctgtctat tgtcacagag      420
aaaaag                                                                 426

<210> SEQ ID NO 308
<211> LENGTH: 439
<212> TYPE: DNA
<213> ORGANISM: Homo sapien

<400> SEQUENCE: 308
gctgctcgag gagctgctgc ccaaagggag caaggaggaa cagcgggatt acgtcttcta       60
cctggccgtg gggaactacc ggctcaagga atacgaaag gccttaaagt acgtccgcgg       120
gttgctgcag atagagcccc agaacaacca ggccaaggaa ctggagcggc tcattgacaa      180
ggccatgaag aaagatggac tcgtgggcat ggccatcgtg ggaggcatgg ccctgggtgt      240
ggcgggactg gccggactca tcggacttgc tgtgtccaag tccaaatcct gaaggagacg      300
cgggagccca cggagaacgc tccaggaggg cctgtccatc ctcgctgtcc tttccctgtt      360
ctccccctgc ccccgtctc tatcctctgt ggccttcagc taatttctgc tcccctgaga      420
ttcgtccttc agccccatc                                                   439
```

<210> SEQ ID NO 309
<211> LENGTH: 347
<212> TYPE: DNA
<213> ORGANISM: Homo sapien
<220> FEATURE:
<221> NAME/KEY: misc_feature
<222> LOCATION: (1)...(347)
<223> OTHER INFORMATION: n = A,T,C or G

<400> SEQUENCE: 309

| | | | | | |
|---|---|---|---|---|---|
| tcgtgactgg | ccagttttgt | gcacccagcg | aaacttcatc | catgctctgg | caggacagga | 60 |
| aagcacccgg | cccttggga | atatacaaat | atttgccata | ttctctttgc | ttgttacaaa | 120 |
| aaacagttaa | gaaagcttac | agcagattat | ttacaaacag | tatcctggga | tatgatgaag | 180 |
| gcagaggtgg | gctggcttgg | aggataggat | ctgtggggc | agaggagcca | cagcagccca | 240 |
| gagggtccca | ggctgggcct | tctccccagg | cttcaggctc | tgcaaggcac | tggactctgc | 300 |
| tactgagaag | gaggcttaat | tcttcttgtg | gagaaacttc | nttttgt | | 347 |

<210> SEQ ID NO 310
<211> LENGTH: 438
<212> TYPE: DNA
<213> ORGANISM: Homo sapien

<400> SEQUENCE: 310

| | | | | | |
|---|---|---|---|---|---|
| ctccgtctgg | gccgccgtcc | ccgggaaaac | gttcgtcaac | atcacgccag | ctgaggtggg | 60 |
| tgtcctggtt | ggcaaagacc | ggtcaagttt | ttacgtgaat | gggctgacac | ttgggggcca | 120 |
| gaaatgttcg | gtgatccggg | actcactgct | gcaggatggg | gaatttagca | tggatcttcg | 180 |
| taccaagagc | accggtgggg | cccccacctt | caatgtcact | gtcaccaaga | ctgacaagac | 240 |
| gctagtcctg | ctgatgggca | agaaggtgt | ccacggtggt | tgatcaaca | agaaatgtta | 300 |
| tgaaatggcc | tcccaccttc | ggcgttccca | gtactgacct | cgtctgtccc | ttcccttca | 360 |
| ccgctcccca | cagctttgca | ccccttcct | ccccatacac | acacaaacca | ttttattttt | 420 |
| tgggccatta | ccccatac | | | | | 438 |

<210> SEQ ID NO 311
<211> LENGTH: 440
<212> TYPE: DNA
<213> ORGANISM: Homo sapien

<400> SEQUENCE: 311

| | | | | | |
|---|---|---|---|---|---|
| ctcagagctt | caaagagcag | gactagccta | agaactgtct | gtgatatttg | accagaggtg | 60 |
| cagcctagct | gccattcttc | ctcaccctgt | ggaagacatt | aaagggagaa | tgaaagtagc | 120 |
| tgtagaatta | cctttggggg | aagaagccac | ttggtgaact | tggcaaacac | ccgtgtttga | 180 |
| ggggtcaccc | aggtgtcat | gagctgggcc | ggaggggatg | gattgattac | ttgtcttgtt | 240 |
| tgcttgtttc | tgttgtaagt | cagggcccct | cagcagaagg | cagaacagaa | ccgagttcct | 300 |
| ttagaatgct | ggttttgtg | tggagtgagg | aaggaccgtg | agtgtggtca | gtttccaacc | 360 |
| tgacaggacc | tgctcccgtt | ggccaggact | gcagcttgtt | actttgaccc | tgggaagaag | 420 |
| gtaagtgttc | ccaagaaaag | | | | | 440 |

<210> SEQ ID NO 312
<211> LENGTH: 268
<212> TYPE: DNA
<213> ORGANISM: Homo sapien

<400> SEQUENCE: 312

| tgaaaacaca accataaatc atagttggtt tttctgtgac aatgatctag tacattattt | 60 |
| cctccacagc aaacctacct ttccagaagg tggaaattgt atttgcaaca atcagggcaa | 120 |
| aacccacact tgaaaagcat tttacaatat tatatctaag ttgcacagaa gaccccagtg | 180 |
| atcactagga aatctaccac agtccagttt ttctaatcca agaaggtcca aacttcgggg | 240 |
| aataatgtgt ccctcttctg ctgctgct | 268 |

<210> SEQ ID NO 313
<211> LENGTH: 439
<212> TYPE: DNA
<213> ORGANISM: Homo sapien

<400> SEQUENCE: 313

| ctgcccccg tttcccttcg tctataccac cctccacctc ggaagcgagg tcgcagtcgc | 60 |
| ccactggaca gtttgaagga gaccgcagat ttgcacccgt ttcccatggg cccagacacg | 120 |
| gcaggagttg cccaggccac tcctgcagac attggggcgt gggcgtgggg tccctgagcc | 180 |
| aggccatccg ctgggcctcc cgtggggttc cctgtgacct gatcggaggt gcctttgcct | 240 |
| cacaccagcc ccttggccaa ctgggaaggc cccgagtgca tttaatccca ctggctgtgc | 300 |
| gctaacaggt gtgtccagtt tctgttctgt ggattttacc acgataaaaa aaaaattggg | 360 |
| ggagaaaaag aatttttgta atatgacttt catacttaac acgtgttaca gattcgttta | 420 |
| attccctcag tgatagaac | 439 |

<210> SEQ ID NO 314
<211> LENGTH: 439
<212> TYPE: DNA
<213> ORGANISM: Homo sapien

<400> SEQUENCE: 314

| agttgatgag cggcgtgtcc cctctgcagc gcgcacccccg gcggggcttt ggctgtgacg | 60 |
| cggtcgggc gcggggctgg gctgtggccc cgcggcgccg cctcctccct ggtccctcga | 120 |
| aatcgtggca tctcacttct gagaacgaaa tctcgcttca gtcactctgc cgaaggcgct | 180 |
| gacggcatcg cggccggaac ctctgggccc ggccccttccc agggccgccg ctccgtggga | 240 |
| aaaaacagct cctccatttc cttgaaaact gaacgattat taaaaataga ttaaacttcg | 300 |
| ctggaaatga gtagccagga agttcagggg agggtgccgg gtccttcccg ggcctggcgt | 360 |
| gtcggagcca cccaggtccc gcagctgccg ctgagaaaat gcaaatattt gttgtgacaa | 420 |
| gaatcacata catttactt | 439 |

<210> SEQ ID NO 315
<211> LENGTH: 437
<212> TYPE: DNA
<213> ORGANISM: Homo sapien

<400> SEQUENCE: 315

| tcttgaagtc tggtgatgct gccattgttg atatggttcc tggcaagccc atgtgtgttg | 60 |
| agagcttctc agactatcca cctttgggtc gctttgctgt tcgtgatatg agacagacag | 120 |
| ttgcgtgggt gtcatcaaag cagtggacaa gaaggctgct ggagctggca aggtcaccaa | 180 |
| gtctgcccag aaagctcaga aggctaaatg aatattatcc ctaatacctg ccacccact | 240 |
| cttaatcagt ggtggaagaa cggtctcaga actgtttgtt tcaattggcc atttaagttt | 300 |
| agtagtaaaa gactggttaa tgataacaat gcatcgtaaa accttcagaa ggaaaggaga | 360 |

```
atgttttgtg gaccactttg gttttctttt ttgcgtgtgg cagttttaag ttattagttt      420
ttaaaatcag tactttt                                                     437

<210> SEQ ID NO 316
<211> LENGTH: 434
<212> TYPE: DNA
<213> ORGANISM: Homo sapien
<220> FEATURE:
<221> NAME/KEY: misc_feature
<222> LOCATION: (1)...(434)
<223> OTHER INFORMATION: n = A,T,C or G

<400> SEQUENCE: 316
cccggacgca ccggcccagg cgcgcggggc cccgcggctg ctgttgctcg cagtcctgct       60
ggcggcgcac ccagatgccc aggcggaggt gcgcttgtct gtaccccgt ggtggaggtg       120 atcgaggaaa gtctgtcatt ctggactgca cccctacggg aacccacgac cattatatgc      180
tggaatggtt ccttaccgac cgctcggag ctcgccccg cctagcctcg gctgagatgc        240
agggctctga gcgtcggtc acaatgcacg acacccgggg ccgcagtccc cataccagc        300 tggactccca ngggcgcctg gtgctggctg angcccangt gggcgacnag cgagactacn      360
tgtgcgtggt gagggcangg gcngcaggca ctgctgaggc cactgcncgg ctcaacgtgt      420
ttgcaaagcc anan                                                        434

<210> SEQ ID NO 317
<211> LENGTH: 435
<212> TYPE: DNA
<213> ORGANISM: Homo sapien

<400> SEQUENCE: 317
aaagggagta ttatgaccat ttcaacttga gagatcgaaa cttgagaggt ttgataatat       60
cttggttaag attttattt tgtatatgtg ggtgactggg tgggtgtggg tgtccacaga      120
aggagaaaag ggtattagat tcccgagagc tggagttaca ggcagttgtg agccactcgg      180
cattggtgtt gagaactgaa cataggccct ctggaagagc agcaagtact ctgagtgctg      240
agcagtctct ccagaagctt attgggtagc ccaggctggc tcacggctcc tcctcagctt      300
ctcctgtgtg cctccttttt ggttaataca actgaagaac ctttcaagtg tggggggaaa      360
ttacagaaga aaagaaaaat taccacttct aacaaccact gtaccatcgt gattctattc      420
ttagtgtctc tttat                                                      435

<210> SEQ ID NO 318
<211> LENGTH: 436
<212> TYPE: DNA
<213> ORGANISM: Homo sapien

<400> SEQUENCE: 318
gtggagcctg atgccatcaa gcctgtggga atccgacgaa tggatgaaag acccatccac       60
gctgagcccc agtatccggt ccgatctgca gccccacacc ctggagactt ggggacttca      120
ttatgagggc cttaaagcgg ctgacaatga ccccacagct ccaccatatg actccctgtt      180
agtgtttgac tatgaaggca gtggctccac tgctgggtcc ttgagctccc ttaattcctc      240
aagtagtggt ggtgagcagg actatgatta cctgaacgac tgggggccac ggttcaagaa      300
acttgctgac atgtatggtg gaggtgatga ctgaacttca gggtgaactt ggttttgga       360 caagtacaaa caatttcaac tgatattccc aaaaagcatt cagaagctag gctttaactt      420
```

```
tgtagtctac tagcac                                                       436

<210> SEQ ID NO 319
<211> LENGTH: 442
<212> TYPE: DNA
<213> ORGANISM: Homo sapien
<220> FEATURE:
<221> NAME/KEY: misc_feature
<222> LOCATION: (1)...(442)
<223> OTHER INFORMATION: n = A,T,C or G

<400> SEQUENCE: 319
cgccgacccc gccactctca cccgacccgt gcacgacgct gcccgggagg gcttcctgga        60
cacgctggtg gtgctgcacc gggccggggc gcggctggac gtgcgcnatg cctggggccg       120
tctgccgtgg acctggctga ggagctgggc catcgcgatg tcgcacggta cctgcgcgcg       180
gctgcggggg gcaccagagg cagtaaccat gcccgcatag atgccgcgga aggtccctca       240
gacatccccg attgaaagaa ccagagaggc tctgagaaac ctccggaaac ttagatcatc       300
agtcaccgaa ggtcctacag ggccacaant tggccccgcc acaacccacc ccgctttcgt       360
agttttcatt tagaaaatag agcttttaaa aatgtcctgc cttttaacgt agatatatgc       420
cttcccccac taccgtaaat gt                                                442

<210> SEQ ID NO 320
<211> LENGTH: 451
<212> TYPE: DNA
<213> ORGANISM: Homo sapien
<220> FEATURE:
<221> NAME/KEY: misc_feature
<222> LOCATION: (1)...(451)
<223> OTHER INFORMATION: n = A,T,C or G

<400> SEQUENCE: 320
aaccggaaac ccggaaaccc ggnaaaccaa aaggggggncc cccattgggg ggcccggaaa        60
ttaatttccc gggggnaatt ccccggaaaa tttncaaagn aattaatttta aaaccctnca      120 aaaggcccctt tgggtntnaa gnaagngggn ccttttttttt ttaaaaaaaa attananana     180
agggntttgt atntncccgt ggncaaaagn agnagncaag nttacntggc tggctttacc       240
gttcagnaga cttacaggtg cttgcctgca ttgcaataaa ggactcattt attgagcaag       300
acttatattt atctcttcat tttggagagc ctaataaact gttattacag tttctctact       360
gactttcaaa agttttgaag tttgaaagac ctttgcaatt aaaacagcat gagcacggcc       420
agaacagaga accctgttat aatgggtctg t                                      451

<210> SEQ ID NO 321
<211> LENGTH: 440
<212> TYPE: DNA
<213> ORGANISM: Homo sapien

<400> SEQUENCE: 321
aagtgtgatc cccatgaagc aacgtgctat gacgatggga agacctacca tgtaggagaa        60
cagtggcaga aagaatatct cggagccatt tgctcctgca cgtgtttcgg aggcagcggg       120
gctggcgtgt gacaactgcc gtagacctgg ggctgctgaa cccagtcccg atggcaccac       180
cggccacacc tacaaccagt atacacagag atacaatcag agaacaaaca ctaacgtaaa       240
ttgccccatt gagtgcttca tgccgctaga tgtgcaagct gacagagacg attctcgaga       300
gtaatctttc cagccccacc ctacaagtgt ctctctacca aggtcaatcc acaccccagt       360
gatgttagca gaccctccat ctttgagtgg tcctttcacc cttaagcctt tgctctggat       420
```

```
gccatgttct cagcttcagc                                              440

<210> SEQ ID NO 322
<211> LENGTH: 440
<212> TYPE: DNA
<213> ORGANISM: Homo sapien
<220> FEATURE:
<221> NAME/KEY: misc_feature
<222> LOCATION: (1)...(440)
<223> OTHER INFORMATION: n = A,T,C or G

<400> SEQUENCE: 322
aatctcttga cccatggncg ngtccgcctg ctactgagta aggggcattc ctgttacaga    60
ccaaggagaa ctggagaaag aaagagaaaa tcagttcgtg gttgcattgt ggatgcaaat   120
ctgagcgttc tcaacttggt tattgtaaaa aaggagaga aggatattcc tggactgact    180
gatactacag tgcctcgccg cctgggcccc aaaagagcta gcagaatccg caaacttttc   240
aatctctcta agaagatga tgtccgccag tatgttgtaa gaaagccctt aaataaagaa   300
ggtaagaaac ctaggaccaa agcacccaag attcagcgtc ttgttactcc acgtgtcctg   360
cagcacaaac ggcggcgtat tgctctgaag aagcagcgta ccaagaaaaa taagaagag   420 gctgcagaat atgctaaact                                              440

<210> SEQ ID NO 323
<211> LENGTH: 373
<212> TYPE: DNA
<213> ORGANISM: Homo sapien

<400> SEQUENCE: 323
tctgtatact ttaaaggaga agcaaataga aataaagaga gagggtgata aaatctagat    60
tcatagaatt gtggaaacct tacttcattt taagagtgaa gaacccagtc tgattaaagg   120
aagttccgtg tttaaggcaa catgttgctt gtggcagatc tagactcaaa actgagattc   180
ctgcctctgt ccagtgcttt tttcacttca ttacattacg agccatctta actccattca   240
tgcaattctg gggtaagggg ttttgtcaga attccacctg accttcccta gagcagggtt   300
tggacaggat gagagacccc aatctctcag atttgaggct tcttttcaag atatctgttt   360 ttccctttc ctt                                                      373

<210> SEQ ID NO 324
<211> LENGTH: 439
<212> TYPE: DNA
<213> ORGANISM: Homo sapien

<400> SEQUENCE: 324
atacaaaaaa ctaggagcat actaggaact tgaaaggaa gattgtaaga ttatagccat     60
ctttggtagg atcttggaag ctgattgcat ttaagccttg taactactat gtaaatcaag   120
tgtccaactt ggtaaactct gaggttggct ttgttttta aagagcagat tataatagtt    180
ttgtctggga aagtgattta aacggcctct tcgttaagcc aaacgtgtga tttagggtag   240
agggaggctg ccaagcgcgt cgggtaagca ggggccccac gctcggcccc gcccaggtaa   300
cgctgccttc cgggctttgt taactcgcgc gcgctgcgtc gccaactcag cggcgggcag   360
ggggcggagc cgcagggcgg ggcggtgcgc gttgatgtga cgtccctgcg cgcgccgctt   420
tctgttgccg ggcgcaatg                                               439

<210> SEQ ID NO 325
```

<211> LENGTH: 442
<212> TYPE: DNA
<213> ORGANISM: Homo sapien

<400> SEQUENCE: 325

| | | | | | |
|---|---|---|---|---|---|
| tttagaaag | ggattagaat | tttactctgc | tagttacaag | ttttaaagtc | acgctacggc | 60 |
| attatcaccc | tggcaggtag | gttttgttat | tgttttacat | tttgtgaaaa | aaagttttgt | 120 |
| agaagttaca | gctagtggtc | ttttccctcc | agagccagtg | atgagtgtgg | gagcacttca | 180 |
| gctctgtaag | gggccagcgt | tctgaccttt | aaccacatga | actaacctgc | gtcagcagtt | 240 |
| gcagaaagta | gcctgttagg | acagcagctg | ctaagcgttg | cctggtattt | tagtggggag | 300 |
| aaggctggga | ctcttcatgg | catcaacact | tgcatgctct | gaatctttga | tcagagatga | 360 |
| ggtgccattt | ttggcatttc | caccccgtct | cgtggtagcc | tttaaaagtg | gagaagatgc | 420 |
| tgccctaatt | ccccgaggat | ga | | | | 442 |

<210> SEQ ID NO 326
<211> LENGTH: 433
<212> TYPE: DNA
<213> ORGANISM: Homo sapien

<400> SEQUENCE: 326

| | | | | | |
|---|---|---|---|---|---|
| cgacaggcca | gagccccttg | gggaggagcg | gcggctggag | gcgcgaggct | cctccggatg | 60 |
| cccggagagc | cgcttgcgac | ttaactcccg | cctctttccc | agatgccgcg | tcactgctcc | 120 |
| gccgccggct | gctgcacacg | ggacacgcgc | gagacgcgca | accgcggcat | ctccttccac | 180 |
| agacttccca | agaaggacaa | cccgaggcga | ggcttgtggc | tggccaactg | ccagcggctg | 240 |
| gaccccagcg | gccagggcct | gtgggacccg | gcatccgagt | acatctactt | ctgctccaaa | 300 |
| cactttgagg | aggactgctt | tgagctggtg | ggaatcagtg | gatatcacag | gctaaaggag | 360 |
| ggggcagtcc | ccaccatatt | tgagtctttc | tccaagttgc | gccggacaac | caagaccaaa | 420 |
| ggacacagtt | acc | | | | | 433 |

<210> SEQ ID NO 327
<211> LENGTH: 436
<212> TYPE: DNA
<213> ORGANISM: Homo sapien

<400> SEQUENCE: 327

| | | | | | |
|---|---|---|---|---|---|
| cggctgctgg | tcgtggaccc | cgagacagat | gaacacttca | gcggcttcg | ggtcacaccc | 60 |
| accgaggagc | acgtggaagg | tcctctgccg | tcacccgtca | ccaatggaac | cagccctgcc | 120 |
| cagctcaatg | gtggctctgc | gtgctcgtcc | gaagtgacc | tgcctggttc | gacaaggac | 180 |
| actgaggatg | gcagtgcctg | gaagcaagat | cccttccagg | agagcggcct | ccacctgagc | 240 |
| cccacggcgg | ccgaggccaa | ggagaaggct | cgagccatgc | gagtcaacaa | gcgcgcgcca | 300 |
| cagatggact | ggaacaggaa | gcgtgaaatc | ttcagcaact | tctgagcccc | ttcctgcctg | 360 |
| tctcgggacc | ctgggacccc | tcccgcacgg | accttgggcc | tcagcctgcc | ccgagctccc | 420 |
| ccagcctcag | tggact | | | | | 436 |

<210> SEQ ID NO 328
<211> LENGTH: 440
<212> TYPE: DNA
<213> ORGANISM: Homo sapien

<400> SEQUENCE: 328

| | | | | | |
|---|---|---|---|---|---|
| ggtaaacgta | ggaggcgtag | agctccaggt | tgatctggcg | gttgatggcg | gcctctgagt | 60 |

```
cctggtggta gttctggcgc acctgcgagg tggacgcggt cgtcatggcg gcgactaagg    120
agaggcggcg gcggcggcgg tggctgcgcg gcgctggagc ggcggcgggg gccttggggc    180
tttgaagaac tttgccaaat actttcttca ccaatctcat gaggagaggg aacatgctga    240
gaaactgatg aagctgcaga accaacgagg tggccgaatc ttccttcagg atatcaagaa    300
accagactgt gatgactggg agagcgggct gaatgcaatg gagtgtgcat tacatttgga    360
aaaaaatgtg aatcagtcac tactggaact gcacaaactg ccactgaca aaaatgaccc    420 ccatttgtgt gacttcattg                                               440
```

<210> SEQ ID NO 329
<211> LENGTH: 438
<212> TYPE: DNA
<213> ORGANISM: Homo sapien

<400> SEQUENCE: 329

```
cgcgacgctg ctgcgcacag attccccaaa ggcacatgtg acccatcacc ccagatctaa     60
aggtgaagtc accctgaggt gctgggccct gggcttctac cctgctgaca tcaccctgac    120
ctggcagttg aatggggagg agctgaccca ggacatgag cttgtggaga ccaggcctgc     180
aggggatgga accttccaga agtgggcatc tgtggtggtg cctcttggga aggagcagaa    240
ttacacatgc cgtgtgtacc atgagggct gcctgagccc ctcaccctga gatgggagcc    300
tcctccgtcc actgactctt acatggtgat cgttgctgtt ctgggtgtcc ttggagctat    360
ggccatcatt ggagctgtgg tggcttttgt gatgaagaga aggagaaaca caggtggaaa    420 aggagggac tatgctct                                                  438
```

<210> SEQ ID NO 330
<211> LENGTH: 443
<212> TYPE: DNA
<213> ORGANISM: Homo sapien
<220> FEATURE:
<221> NAME/KEY: misc_feature
<222> LOCATION: (1)...(443)
<223> OTHER INFORMATION: n = A,T,C or G

<400> SEQUENCE: 330

```
tgttccaact aactcagcac aacagggcca taacagtcct gacagccccg tcaccagtgc     60
cgccaagggc atcccaggct ttggcaatac tggcaacatc agtggtgccc ctgtgaccta    120
cccgtctgcc ggagcccaag gagtcaacaa cacagcttca gggaataaca gccgagaagg    180
gactgggggc agcaacggga aaagagagag atatactgag aaccggggca gcagccgtca    240
cagtcacgga gagactggca atcggcatag cgatagncca cgtcacggag atggtggtcg    300
ccatggagat ggataccgcc atccagaaag cagcagccgt nntactgatg gncatcggcn    360
cggggagaac agacatggag gaagcgcagg ccggcatggg gagaaccggg gtgcaaatga    420
tggtcggaat ggggaaagca gga                                           443
```

<210> SEQ ID NO 331
<211> LENGTH: 176
<212> TYPE: DNA
<213> ORGANISM: Homo sapien

<400> SEQUENCE: 331

```
gctggtggga aaaaaagcag aggccgcagc ctcagcccta gctgatgctg atgcagacct     60
ggaggaacgg cttaagaacc tgcggaggga ctgagtgccc ctgccactcc gagataacca    120
```

-continued

```
gtggatgccc aggatctttt accacaaccc ctctgtaata aaagagattt gacact        176

<210> SEQ ID NO 332
<211> LENGTH: 437
<212> TYPE: DNA
<213> ORGANISM: Homo sapien

<400> SEQUENCE: 332
tcctgatgtt acgcatgatc atggagggcc agtaccagtt cagttccccc gagtgggatg    60
accgttccag cactgtcaaa gacctgatct ccaggctgct gcaggtggat cctgaggcac   120
gcctgacagc tgagcaggcc ctacagcacc ccttctttga gcgttgtgaa ggcagccaac   180
cctggaacct cacccccgc cagcggttcc gggtggcagt gtggacagtg ctggctgctg    240
gacgagtggc cctaagcacc catcgtgtac ggccactgac caagaatgca ctgttgaggg   300
acccttatgc gctgcggtca gtgcggcacc tcatcgacaa ctgtgccttc cggctctacg   360
ggcactgggt aaagaaaggg gagcagcaga accgggcggc tctctttcag caccggcccc   420
ctgggccttt tcccatc                                                  437

<210> SEQ ID NO 333
<211> LENGTH: 440
<212> TYPE: DNA
<213> ORGANISM: Homo sapien

<400> SEQUENCE: 333
tacaattaca aagaaacaaa caaacaaaat ttgaccaacc caggcggtta aatttaaact    60
cttcaggaaa aatttaagct gttaaaatta ttcttttttct aaatttctaa agtggaggga  120
cagaattttt cagatttaaa agggcctcct aggtgcccag aaaattagtg gaaagaacca   180
cgtctagacg catctttgat gtgtcagagt tccaaggata aaaagaaact tttaaagtct   240
tctatactca gccaggttat caatcaaata tgagggcaaa ataatatttt cagacagatt   300
ttaggcagtt tatcttccat atatccttttt ctttaagggt atttgtagat acactccaga  360
aaaacaaagag tgaaatatga aggaagttgt ggggtccagc aaacagtgct tccaaatcag  420
acccctgata gaggtggaaa                                               440

<210> SEQ ID NO 334
<211> LENGTH: 439
<212> TYPE: DNA
<213> ORGANISM: Homo sapien

<400> SEQUENCE: 334
attcgtgcac aattcattaa atgaacgtct caaaaattaa aaaaattata agatacgtat    60
ttctttaggc ctttgtgttt ttaaattaaa accaacaaaa agaagtctcc ctctccactc   120
cacccagcag caagggcagc cggaacgctt cgctccagct acctggcctc ccgcaagagg   180
gttcccccat gagaccgtta gtctctcttt gcctggctga ctacctgcat acagtaggca   240
ctcactgctg gagtgaggca ctgactcctc caaagattgc aggggcgga ggagggaacc    300
acgaaggcct gggagggggc atctttggcc cccactaacc atctccctat ttctgcatcc   360
tggtgaccgt cagcaagaga tgagtcgggg agaccctctc ctggagttct agcccctaat   420
tctgggcttt ctatatgag                                                439
```